US007381549B2

(12) United States Patent
Kröger et al.

(10) Patent No.: US 7,381,549 B2
(45) Date of Patent: Jun. 3, 2008

(54) METHOD FOR ZYMOTIC PRODUCTION OF FINE CHEMICALS (METY) CONTAINING SULPHUR

(75) Inventors: Burkhard Kröger, Limburgerhof (DE); Oskar Zelder, Speyer (DE); Corinna Klopprogge, Mannheim (DE); Hartwig Schröder, Nussloch (DE); Stefan Häfner, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 308 days.

(21) Appl. No.: 10/525,710

(22) PCT Filed: Aug. 26, 2003

(86) PCT No.: PCT/EP03/09453

§ 371 (c)(1),
(2), (4) Date: Feb. 24, 2005

(87) PCT Pub. No.: WO2004/024933

PCT Pub. Date: Mar. 25, 2004

(65) Prior Publication Data
US 2005/0260721 A1 Nov. 24, 2005

(30) Foreign Application Priority Data
Aug. 26, 2002 (DE) .............................. 102 39 082

(51) Int. Cl.
C12P 13/12 (2006.01)
C12Q 1/34 (2006.01)
(52) U.S. Cl. .................. 435/113; 435/18; 435/195; 536/23.2
(58) Field of Classification Search ................ 435/113, 435/18, 195; 536/23.2
See application file for complete search history.

(56) References Cited

U.S. PATENT DOCUMENTS

| 4,489,160 A | 12/1984 | Katsumata et al. |
| 4,601,893 A | 7/1986 | Cardinal |
| 5,158,891 A | 10/1992 | Takeda et al. |
| 5,175,108 A | 12/1992 | Bachmann et al. |
| 5,965,391 A | 10/1999 | Reinscheid et al. |
| 2003/0170775 A1 | 9/2003 | Pompejus et al. |

FOREIGN PATENT DOCUMENTS

| DE | 10046870 A1 | 3/2002 |
| EP | 0472869 A2 | 3/1992 |
| EP | 1108790 A2 | 6/2001 |
| JP | 10-229891 A | 9/1998 |
| WO | WO-93/17112 | 9/1993 |
| WO | WO-96/15246 A1 | 5/1996 |
| WO | WO-02/10206 | 2/2002 |
| WO | WO-02/10209 | 2/2002 |
| WO | WO-02/18613 | 3/2002 |
| WO | WO-02/097096 | 12/2002 |
| WO | WO-03/087386 A3 | 10/2003 |
| WO | WO-03/100072 A2 | 12/2003 |
| WO | WO-2004/024931 | 3/2004 |
| WO | WO-2004/024932 | 3/2004 |

OTHER PUBLICATIONS

U.S. Appl. No. 10/511,302, Kröger et al.
Kase, H., et al., "$_L$-Methionine Production by Methionine Analog-resistant Mutants of *Corynebacterium glutamicum*", Agr. Biol. Chem., vol. 39, No. 1, 1975, pp. 153-160.
Martin, J. F., et al., "Cloning Systems in Amino Acid-Producing *Corynebacteria*", Biotechnology, vol. 5, 1987, pp. 137-146.
Liebl, W., "High efficiency electroporation of intact *Corynebacterium glutamicum* cells", FEMS Microbiology Letters, vol. 65, 1989, pp. 299-304.
Pearson, W. R., et al., "Improved tools for biological sequence comparison", Proc. Natl. Acad. Sci. USA, vol. 85, 1988, pp. 2444-2448.
Lennox, E.S., "Transduction of Linked Genetic Characters of the Host by Bacteriophage P1", Virology, vol. 1, 1955, pp. 190-206.
Sahin-Toth, M., et al., "Cysteine scanning mutagenesis of the N-terminal 32 amino acid residues in the lactose permease of *Escherichia coli*", Protein Sciences, vol. 3, 1994, pp. 240-247.
Malakhova, I. I., et al., "Thin-Layer Chromatography of Free Amino Acids. Selection of Conditions for the Separation of L-Lysine, L-Homoserine, and L-Threonine", Biotekhnologiya, vol. 11, 1996, pp. 27-32.
Wahl, G. M., et al., "Cosmid vectors for rapid genomic walking, restriction mapping, and gene transfer", Proc. Natl. Acad. Sci. USA, vol. 84, 1987, pp. 2160-2164.
Eikmanns, B. J., "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase", Journal of Bacteriology, vol. 174, No. 19, 1992, pp. 6076-6086.
Ben-Bassat, A., et al., "Processing of the Initiation Methionine from Proteins: Properties of the *Escherichia coli* Methionine Aminopeptidase and Its Gene Structure", Journal of Bacteriology, vol. 169, No. 2, 1987, pp. 751-757.
Tauch, A., et al., "*Corynebacterium glutamicum* DNA is subjected to methylation-restriction in *Escherichia coli*", FEMS Microbiology Letters, vol. 123, 1994, pp. 343-348.
Liebl, W., et al., "Transfer of *Brevibacterium divaricatum* DSM 20297[1], "*Brevibacterium flavum*" DSM 20411, "*Brevibacterium lactofermentum*" DSM 20412 and DSM 1412, and *Corynebacterium lilium* DSM 20137[T] to *Corynebacterium glutamicum* and Their Distinction by rRNA Gene Restriction Patterns", International Journal of Systematic Bacteriology, vol. 41, No. 2, 1991, pp. 255-260.
Thierbach, G., et al., "Transformation of spheroplasts and protoplasts of *Corynebacterium glutamicum*", Appl. Microbiol. Biotechnol., vol. 29, 1988, pp. 356-362.
Butler, B. A., "Sequence Analysis Using GCG", Methods of Biochemical Analysis, vol. 39, 1998, pp. 74-97.
Schrumpf, B., et al., "A Functionally Split Pathway for Lysine Synthesis in *Corynebacterium glutamicum*", Journal of Bacteriology, vol. 173, No. 14, 1991, pp. 4510-4516.

(Continued)

Primary Examiner—Tekchand Saidha
(74) Attorney, Agent, or Firm—Connolly Bove Lodge & Hutz LLP

(57) ABSTRACT

The invention relates to methods for the fermentative production of sulfur-containing fine chemicals, in particular L-methionine, by using bacteria which express a nucleotide sequence coding for a methionine synthase (metH) gene.

21 Claims, 3 Drawing Sheets

OTHER PUBLICATIONS

Eikmanns, B. J., et al., "A family of *Corynebacterium glutamicum/Escherichia coli* shuttle vectors for cloning, controlled gene expression, and promoter probing", Gene, vol. 102, 1991, pp. 93-98.

Schäfer, A., et al., "Small mobilizable multi-purpose cloning vectors derived from the *Escherichia coli* plasmids pK18 and pK19: selection of defined deletions in the chromosome of *Corynebacterium glutamicum*", Gene, vol. 145, 1994, pp. 69-73.

Staden, R., "The current status and portability of our sequence handling software", Nucleic Acids Research, vol. 14, No. 1, 1986, pp. 217-231.

Serwold-Davis, T. M., et al., "Localization of an origin of replication in *Corynebacterium diphtheriae* broad host range plasmid pNG2 that also functions in *Escherichia coli*", FEMS Microbiology Letters, vol. 66, 1990, pp. 119-124.

Sonnen, H., et al., "Characterization of pGA1, a new plasmid from *Corynebacterium glutamicum* LP-6", Gene, vol. 107, 1991, pp. 69-74.

Patek, M., et al., "Promoters from *Corynebacterium glutamicum*: cloning, molecular analysis and search for a consensus motif", Microbiology, 1996, vol. 142, pp. 1297-1309.

Grant, S. G. N., et al., "Differential plasmid rescue from transgenic mouse DNAs into *Escherichia coli* methylation-restriction mutants", Proc. Natl. Acad. Sci. USA, vol. 87, 1990, pp. 4645-4649.

Jensen, P. R., et al., "Artificial Promoters for Metabolic Optimization", Biotechnology and Bioengineering, vol. 58, 1998, pp. 191-195.

Dunican, L. K., et al., "High Frequency Transformation of Whole Cells of Amino Acid Producing Coryneform Bacteria Using High Voltage Electroporation", Biotechnology, vol. 7, 1989, pp. 1067-1070.

Labarre, J., et al., "Gene Replacement, Integration, and Amplification at the *gdhA* Locus of *Corynebacterium glutamicum*", Journal of Bacteriology, 1993, vol. 175, No. 4, pp. 1001-1007.

Bolivar, F., "Molecular Cloning Vectors Derived From The CoLE1 Type Plasmid pMB1", Life Sciences, vol. 25, 1979, pp. 807-818.

Schwarzer, A., et al., "Manipulation of *Corynebacterium glutamicum* by Gene Disruption and Replacement", Biotechnology, vol. 9, 1991, pp. 84-87.

Tauch, A., et al., "The Erythromycin Resistance Gene of the *Corynebacterium xerosis* R-plasmid pTP10 Also Carrying Chloramphenicol, Kanamycin, and Tetracyclin Resistances is Capable of Transposition in *Corynebacterium glutamicum*", Plasmid, vol. 33, 1995, pp. 168-179.

Tsuchiya, M., et al., "Genetic Control Systems of *Escherichia coli* Can Confer Inducible Expression of Cloned Genes in Coryneform Bacteria", Biotechnology, vol. 6, 1988, pp. 428-430.

Kohara, Y., et al., "The Physical Map of the Whole *E. coli* Chromosome: Application of a New Strategy for Rapid Analysis and Sorting of a Large Genomic Library", Cell, vol. 50, 1987, pp. 495-508.

Sahm, H., et al., "Pathway Analysis and Metabolic Engineering in *Corynebacterium glutamicum*", Biol. Chem., vol. 381, 2000, pp. 899-910.

Ike, Y., et al., "Solid phase synthesis of polynucleotides. VIII. Synthesis of mixed oligodeoxyribonucleotides by the phosphotriester solid phase method", Nucleic Acids Research, vol. 11, No. 2, 1983, pp. 477-488.

Delagrave, S., et al., "Recursive ensemble mutagenesis", Protein Engineering, vol. 6, No. 3, 1993, pp. 327-331.

Arkin, A. P., et al., "An algorithm for protein engineering: Simulations of recursive ensemble mutagenesis", Proc. Natl. Acad. Sci., USA, vol. 89, 1992, pp. 7811-7815.

Marck, C., "DNA Strider: a 'C' program for the fast analysis of DNA and protein sequences on the Apple Macintosh family of computers", Nucleic Acids Research, vol. 16, No. 5, 1988, pp. 1829-1836.

Hochuli, E., et al., "Genetic Approach to Facilitate Purfication of Recombinant Proteins With a Novel Metal Chelate Adsorbent", Biotechnology, vol. 6, 1988, pp. 1321-1325.

Guerrero, C., et al., "Directed mutagenesis of a regulatory palindromic sequence upstream from the *Brevibacterium lactofermentum* tryptophan operon", Gene, vol. 138, 1994, pp. 35-41.

Itakura, K., et al., "Expression in *Escherichia coli* of a Chemically Synthesized Gene for the Hormone Somatostatin", Science, vol. 198, 1977, pp. 1056-1063.

Makrides, S. C., "Strategies for Achieving High-Level Expression of Genes in *Escherichia coli*", Microbiological Reviews, vol. 60, No. 3, 1996, pp. 512-538.

Bernard, P., et al., "The F Plasmid CcdB Protein Induces Efficient ATP-dependent DNA Cleavage by Gyrase", J. Mol. Biol., vol. 234, 1993, pp. 534-541.

Spratt, B. G., "Kanamycin-resistant vectors that are analogues of plasmids pUC8, pUC9, pEMBL8 and pEMBL9", Gene, vol. 41, 1986, pp. 337-342.

Narang, S. A., "Tetrahedron Report No. 140—DNA synthesis", Tetrahedron, vol. 39, No. 1, 1983, pp. 3-22.

Schmidt, S., et al., "Near infrared spectroscopy in fermentation and quality control for amino acid production", Bioprocess Engineering, vol. 19, 1998, pp. 67-70.

Itakura, K., et al., "Synthesis and Use of Synthetic Oligonucleotides", Ann. Rev. Biochem., vol. 53, 1984, pp. 323-356.

Eikmanns, B. J., et al., "Molecular Aspects of lysine, threonine, and isoleucine biosynthesis in *Corynebacterium glutamicum*", Atonie van Leeuwenhoek, vol. 64, 1993, pp. 145-163.

O'Regan, M., et al., "Cloning and nucleotide sequence of the phosphoenolpyruvate carboxylase-coding gene of *Corynebacterium glutamicum* ATCC13032", Gene, vol. 77, 1989, pp. 237-251.

Malumbres, M., et al., "Codon preference in Corynebacteria", Gene, vol. 134, 1993, pp. 15-24.

Simon, R., et al., "A Broad Host Range Mobilization System for In Vivo Genetic Engineering: Transposon Mutagenesis in Gram Negative Bacteria", Biotechnology, vol. 1, 1983, pp. 784-791.

Eikmanns, B. J., et al., "Nucleotide sequence, expression and transcriptional analysis of the *Corynebacterium glutamicum gltA* gene encoding citrate synthase", Microbiology, vol. 140, 1994, pp. 1817-1828.

Sanger, F., et al., "DNA sequencing with chain-terminating inhibitors", Proc. Natl. Acad. Sci. USA, vol. 74, No. 12, 1977, pp. 5463-5467.

Reinscheid, D. J., et al., "Stable Expression of *hom-1-thrB* in *Corynebacterium glutamicum* and Its Effect on the Carbon Flux to Threonine and Related Amino Acids", Applied and Environmental Microbiology, vol. 60, No. 1, 1994, pp. 126-132.

Vieira, J., et al., "The pUC plasmids, an M13mp7-derived system for insertion mutagenesis and sequencing with synthetic universal primers", Gene, vol. 19, 1982, pp. 259-268.

Patek, M., et al., "Leucine Synthesis in *Corynebacterium glutamicum*: Enzyme Activities, Structure of *leuA*, the Effect of *leuA* Inactivation on Lysine Synthesis", Applied and Environmental Microbiology, vol. 60, No. 1, 1994, pp. 133-140.

Motoyama, H., et al., "Overproduction of $_L$-Lysine from Methanol by *Methylobacillus glycogenes* Derivatives Carrying a Plasmid with a Mutated *dapA* Gene", Applied and Environmental Microbiology, vol. 67, No. 7, 2001, pp. 3064-3070.

Shimizu, H., et al., "Cloning and overexpression of the *oah1* gene encoding O-acetyl-$_L$-homoserine sulfhydrylase of *Thermus thermophilus* HB8 and characterization of the gene product", Biochimica et Biophysica Acta, vol. 1549, 2001, pp. 61-72.

Yamagata, S., et al., "Overexpression of the *Saccharomyces cerevisiae* MET17/MET25 gene in *Escherichia coli* and comparative characterization of the product with O-acetylserine—O-acetylhomoserine sulfhydrylase of the yeast", Appl. Microbiol. Biotechnol., vol. 42, 1994, pp. 92-99.

Rey, D.A. et al., "The Putative Transcriptional Repressor McbR, Member of the TetR-family, is Involved in the Regulation of the Metabolic Network Directing the Synthesis of Sulfur Containing Amino Acids in *Corynebacterium glutamicum*", Journal of Biotechnology, vol. 103, (2003) pp. 51-65.

Hwang, B.-J., et al., " *Corynebacterium glutamicum*Utilizes both Transsulfuration and Direct Sulfhydrylation Pathways for Methlonine Biosynthesis", Journal of Bacteriology, vol. 184, No. 5, (2002) pp. 1277-1286.

SEQUENCE LISTING

<160> NUMBER OF SEQ ID NOS: 79

<210> SEQ ID NO 1
<211> LENGTH: 1317
<212> TYPE: DNA
<213> ORGANISM: Corynebacterium diphtheriae
<220> FEATURE:
<221> NAME/KEY: CDS

<222> LOCATION: (1)..(1317)

<400> SEQUENCE: 1

```
atg cca aca aaa tac gat aat tcc aat gcc aac aaa tgg ggt ttc gag        48
Met Pro Thr Lys Tyr Asp Asn Ser Asn Ala Asn Lys Trp Gly Phe Glu
1               5                   10                  15 act cgc tcc atc cac gca gga caa agc gtc gat agt gat acc agt gcc        96
Thr Arg Ser Ile His Ala Gly Gln Ser Val Asp Ser Asp Thr Ser Ala
            20                  25                  30 cgc aac cta ccg att tac ctg aca tca tcg tac gtt ttt aat gac gcc       144
Arg Asn Leu Pro Ile Tyr Leu Thr Ser Ser Tyr Val Phe Asn Asp Ala
        35                  40                  45 gaa cac gca gca aac cgc ttc aac ctt tcc gac gcc ggc ccg gtt tac       192
Glu His Ala Ala Asn Arg Phe Asn Leu Ser Asp Ala Gly Pro Val Tyr
    50                  55                  60 tct cgc ctg acc aac cca act gtc gcg gca gtc gaa gaa cgc cta gcc       240
Ser Arg Leu Thr Asn Pro Thr Val Ala Ala Val Glu Glu Arg Leu Ala
65                  70                  75                  80 aat ctt gaa ggt ggc gta cac gcc gta ctt ttc gct tcc gga atg gcc       288
Asn Leu Glu Gly Gly Val His Ala Val Leu Phe Ala Ser Gly Met Ala
                85                  90                  95 gcc gaa acc gcc gca atc ctc aac atc gcc cgc gcg ggt tcc cac atc       336
Ala Glu Thr Ala Ala Ile Leu Asn Ile Ala Arg Ala Gly Ser His Ile
            100                 105                 110 gtg tcc agt cct cgc att tac ggc ggc acc gaa aca ctc ttt gcc gtc       384
Val Ser Ser Pro Arg Ile Tyr Gly Gly Thr Glu Thr Leu Phe Ala Val
        115                 120                 125 aca ttg gca cgc ctg ggc atc gaa acc act ttc gta gaa aat cct gac       432
Thr Leu Ala Arg Leu Gly Ile Glu Thr Thr Phe Val Glu Asn Pro Asp
    130                 135                 140 gac cca gcc tca tgg gag gct gca gtt caa gac aac acg gta gct ctc       480
Asp Pro Ala Ser Trp Glu Ala Ala Val Gln Asp Asn Thr Val Ala Leu
145                 150                 155                 160 tac gga gaa acc ttc gct aat cca caa gca gac gtg ctt gat att ccc       528
Tyr Gly Glu Thr Phe Ala Asn Pro Gln Ala Asp Val Leu Asp Ile Pro
                165                 170                 175 gca atc gca gag gtt gcc cat aaa cat caa gta cca ctg atc gtc gac       576
Ala Ile Ala Glu Val Ala His Lys His Gln Val Pro Leu Ile Val Asp
            180                 185                 190 aac acc ctc gca acc gca gcc ctt gta cgc ccc ctc gaa ctc ggt gca       624
Asn Thr Leu Ala Thr Ala Ala Leu Val Arg Pro Leu Glu Leu Gly Ala
        195                 200                 205 gac gtc gtc gtg gca tcc cta acc aag ttc tac acc gga aat ggc tcc       672
Asp Val Val Val Ala Ser Leu Thr Lys Phe Tyr Thr Gly Asn Gly Ser
    210                 215                 220 gga ctc ggc gga gtg ctt atc gac ggc gga aac ttc gac tgg acc gtc       720
Gly Leu Gly Gly Val Leu Ile Asp Gly Gly Asn Phe Asp Trp Thr Val
225                 230                 235                 240 aca cgc aac ggc gaa ccg atc ttc ccc gac ttt gtc acc cca gat ccc       768
Thr Arg Asn Gly Glu Pro Ile Phe Pro Asp Phe Val Thr Pro Asp Pro
                245                 250                 255 gcc tat cac ggt ctc aag tat tcc gat ctt ggt gcc ccc gcc ttc gga       816
Ala Tyr His Gly Leu Lys Tyr Ser Asp Leu Gly Ala Pro Ala Phe Gly
            260                 265                 270 cta aag gct cgc gtc gga ctc ctg cgc gac acc ggc gca gcc cca tca       864
Leu Lys Ala Arg Val Gly Leu Leu Arg Asp Thr Gly Ala Ala Pro Ser
        275                 280                 285 cca ctc aac gca tgg atc acc gca caa ggg ctc gac acc ctc tcg cta       912
Pro Leu Asn Ala Trp Ile Thr Ala Gln Gly Leu Asp Thr Leu Ser Leu
    290                 295                 300
```

```
cga gta caa cgc cac aac gaa aac gca ctc gca gta gca caa ttc ctc      960
Arg Val Gln Arg His Asn Glu Asn Ala Leu Ala Val Ala Gln Phe Leu
305                 310                 315                 320 gcc aac cac gag aaa gta gcc aag gtt aac tac gca ggc ctt ccc gac     1008
Ala Asn His Glu Lys Val Ala Lys Val Asn Tyr Ala Gly Leu Pro Asp
                325                 330                 335 tcc cct tgg tac cca gtc aaa gaa aaa ctc gga ttc gac tac acc ggc     1056
Ser Pro Trp Tyr Pro Val Lys Glu Lys Leu Gly Phe Asp Tyr Thr Gly
            340                 345                 350 tcc gta ctt tcc ttt gac gtt aaa ggt gga aaa aac gaa gca tgg cgc     1104
Ser Val Leu Ser Phe Asp Val Lys Gly Gly Lys Asn Glu Ala Trp Arg
        355                 360                 365 ttt atc gac gca ctc aaa cta cac tcg aac ctc gcc aac gtc gga gac     1152
Phe Ile Asp Ala Leu Lys Leu His Ser Asn Leu Ala Asn Val Gly Asp
370                 375                 380 gta cgt tcc ctc gta gtc cac cca gcg acc acc acg cac tca caa tcg     1200
Val Arg Ser Leu Val Val His Pro Ala Thr Thr Thr His Ser Gln Ser
385                 390                 395                 400 gaa gaa tcg gca ctt cta gcc gca gga att aat caa gca acc atc cga     1248
Glu Glu Ser Ala Leu Leu Ala Ala Gly Ile Asn Gln Ala Thr Ile Arg
                405                 410                 415 ctc tcc gtc ggc atc gaa tcc atc gac gac atc atc gcc gac ctc aca     1296
Leu Ser Val Gly Ile Glu Ser Ile Asp Asp Ile Ile Ala Asp Leu Thr
            420                 425                 430 gca ggt ttc gac gca atc taa                                         1317
Ala Gly Phe Asp Ala Ile
        435
```

<210> SEQ ID NO 2
<211> LENGTH: 438
<212> TYPE: PRT
<213> ORGANISM: Corynebacterium diphtheriae

<400> SEQUENCE: 2

```
Met Pro Thr Lys Tyr Asp Asn Ser Asn Ala Asn Lys Trp Gly Phe Glu
1               5                   10                  15

Thr Arg Ser Ile His Ala Gly Gln Ser Val Asp

-continued

```
                    180                 185                 190
Asn Thr Leu Ala Thr Ala Ala Leu Val Arg Pro Leu Glu Leu Gly Ala
                195                 200                 205
Asp Val Val Ala Ser Leu Thr Lys Phe Tyr Thr Gly Asn Gly Ser
            210                 215                 220
Gly Leu Gly Gly Val Leu Ile Asp Gly Gly Asn Phe Asp Trp Thr Val
225                 230                 235                 240
Thr Arg Asn Gly Glu Pro Ile Phe Pro Asp Phe Val Thr Pro Asp Pro
                245                 250                 255
Ala Tyr His Gly Leu Lys Tyr Ser Asp Leu Gly Ala Pro Ala Phe Gly
            260                 265                 270
Leu Lys Ala Arg Val Gly Leu Leu Arg Asp Thr Gly Ala Ala Pro Ser
        275                 280                 285
Pro Leu Asn Ala Trp Ile Thr Ala Gln Gly Leu Asp Thr Leu Ser Leu
        290                 295                 300
Arg Val Gln Arg His Asn Glu Asn Ala Leu Ala Val Ala Gln Phe Leu
305                 310                 315                 320
Ala Asn His Glu Lys Val Ala Lys Val Asn Tyr Ala Gly Leu Pro Asp
                325                 330                 335
Ser Pro Trp Tyr Pro Val Lys Glu Lys Leu Gly Phe Asp Tyr Thr Gly
                340                 345                 350
Ser Val Leu Ser Phe Asp Val Lys Gly Gly Lys Asn Glu Ala Trp Arg
            355                 360                 365
Phe Ile Asp Ala Leu Lys Leu His Ser Asn Leu Ala Asn Val Gly Asp
        370                 375                 380
Val Arg Ser Leu Val Val His Pro Ala Thr Thr Thr His Ser Gln Ser
385                 390                 395                 400
Glu Glu Ser Ala Leu Leu Ala Ala Gly Ile Asn Gln Ala Thr Ile Arg
                405                 410                 415
Leu Ser Val Gly Ile Glu Ser Ile Asp Asp Ile Ile Ala Asp Leu Thr
            420                 425                 430
Ala Gly Phe Asp Ala Ile
        435
```

<210> SEQ ID NO 3
<211> LENGTH: 1350
<212> TYPE: DNA
<213> ORGANISM: Mycobacterium tuberculosis
<220> FEATURE:
<221> NAME/KEY: CDS
<222> LOCATION: (1)..(1350)

<400> SEQUENCE: 3

```
atg agc gcc gac agc aat agc acc gac gcc gat ccg acc gcg cat tgg        48
Met Ser Ala Asp Ser Asn Ser Thr Asp Ala Asp Pro Thr Ala His Trp
1               5                   10                  15 tcg ttc gaa acc aaa cag ata cac gct ggt cag cac cct gat ccg acc        96
Ser Phe Glu Thr Lys Gln Ile His Ala Gly Gln His Pro Asp Pro Thr
                20                  25                  30 acc aac gcc cgg gct ctg ccg atc tat gcg acc acg tcg tac acc ttc       144
Thr Asn Ala Arg Ala Leu Pro Ile Tyr Ala Thr Thr Ser Tyr Thr Phe
            35                  40                  45 gac gac acc gcg cac gcc gcc gcc ctg ttc gga ctg gaa att ccg ggc       192
Asp Asp Thr Ala His Ala Ala Ala Leu Phe Gly Leu Glu Ile Pro Gly
        50                  55                  60 aat atc tac acc cgg atc ggc aac ccc acc acc gac gtc gtc gag cag       240
Asn Ile Tyr Thr Arg Ile Gly Asn Pro Thr Thr Asp Val Val Glu Gln
```

-continued

```
                 65                  70                  75                  80 cgc atc gcc gcg ctc gag ggc ggt gtg gcc gcg ctg ttc ctg tcg tcg           288
Arg Ile Ala Ala Leu Glu Gly Gly Val Ala Ala Leu Phe Leu Ser Ser
                     85                  90                  95 ggg cag gcc gcg gag acg ttc gcc atc ttg aac ctg gcc ggc gcg ggc           336
Gly Gln Ala Ala Glu Thr Phe Ala Ile Leu Asn Leu Ala Gly Ala Gly
                100                 105                 110 gat cac atc gtg tcc agc ccg cgc ctg tac ggc ggc acc tac aac ctg           384
Asp His Ile Val Ser Ser Pro Arg Leu Tyr Gly Gly Thr Tyr Asn Leu
            115                 120                 125 ttc cac tat tcg ctg gcc aag ctc ggc atc gag gtc agc ttc gtc gac           432
Phe His Tyr Ser Leu Ala Lys Leu Gly Ile Glu Val Ser Phe Val Asp
        130                 135                 140 gat ccg gac gat ctg gac acc tgg cag gcg gcg gta cgg ccc aac acc           480
Asp Pro Asp Asp Leu Asp Thr Trp Gln Ala Ala Val Arg Pro Asn Thr
    145                 150                 155                 160 aag gcg ttc ttc gcc gag acc atc tcc aac ccg cag atc gac ctg ctg           528
Lys Ala Phe Phe Ala Glu Thr Ile Ser Asn Pro Gln Ile Asp Leu Leu
                    165                 170                 175 gac acc ccg gcg gtt tcc gag gtc gcc cat cgc aac ggg gtg ccg ttg           576
Asp Thr Pro Ala Val Ser Glu Val Ala His Arg Asn Gly Val Pro Leu
                180                 185                 190 atc gtc gac aac acc atc gcc acg cca tac ctg atc caa ccg ttg gcc           624
Ile Val Asp Asn Thr Ile Ala Thr Pro Tyr Leu Ile Gln Pro Leu Ala
            195                 200                 205 cag ggc gcc gac atc gtc gtg cat tcg gcc acc aag tac ctg ggc ggg           672
Gln Gly Ala Asp Ile Val Val His Ser Ala Thr Lys Tyr Leu Gly Gly
        210                 215                 220 cac ggt gcc gcc atc gcg ggt gtg atc gtc gac ggc ggc aac ttc gat           720
His Gly Ala Ala Ile Ala Gly Val Ile Val Asp Gly Gly Asn Phe Asp
225                 230                 235                 240 tgg acc cag ggc cgc ttc ccc ggc ttc acc acc ccc gac ccc agc tac           768
Trp Thr Gln Gly Arg Phe Pro Gly Phe Thr Thr Pro Asp Pro Ser Tyr
                    245                 250                 255 cac ggc gtg gtg ttc gcc gag ctg ggt cca ccg gcg ttt gcg ctc aaa           816
His Gly Val Val Phe Ala Glu Leu Gly Pro Pro Ala Phe Ala Leu Lys
                260                 265                 270 gct cga gtg cag ctg ctc cgt gac tac ggc tcg gcg gct tcg ccg ttc           864
Ala Arg Val Gln Leu Leu Arg Asp Tyr Gly Ser Ala Ala Ser Pro Phe
            275                 280                 285 aac gcg ttc ttg gtg gcg cag ggt ctg gaa acg ctg agc ctg cgg atc           912
Asn Ala Phe Leu Val Ala Gln Gly Leu Glu Thr Leu Ser Leu Arg Ile
        290                 295                 300 gag cgg cac gtc gcc aac gcg cag cgc gtc gcc gag ttc ctg gcc gcc           960
Glu Arg His Val Ala Asn Ala Gln Arg Val Ala Glu Phe Leu Ala Ala
305                 310                 315                 320 cgc gac gac gtg ctt tcg gtc aac tat gcg ggg ctg ccc tcc tcg ccc          1008
Arg Asp Asp Val Leu Ser Val Asn Tyr Ala Gly Leu Pro Ser Ser Pro
                    325                 330                 335 tgg cat gag cgg gcc aag agg ctg gcg ccc aag gga acc ggg gcc gtg          1056
Trp His Glu Arg Ala Lys Arg Leu Ala Pro Lys Gly Thr Gly Ala Val
                340                 345                 350 ctg tcc ttc gag ttg gcc ggc ggc atc gag gcc ggc aag gca ttc gtg          1104
Leu Ser Phe Glu Leu Ala Gly Gly Ile Glu Ala Gly Lys Ala Phe Val
            355                 360                 365 aac gcg ttg aag ctg cac agc cac gtc gcc aac atc ggt gac gtg cgc          1152
Asn Ala Leu Lys Leu His Ser His Val Ala Asn Ile Gly Asp Val Arg
        370                 375                 380 tcg ctg gtg atc cac ccg gca tcg acc act cat gcc cag ctg agc ccg          1200
```

-continued

```
Ser Leu Val Ile His Pro Ala Ser Thr Thr His Ala Gln Leu Ser Pro
385                 390                 395                 400 gcc gag cag ctg gcg acc ggg gtc agc ccg ggc ctg gtg cgt ttg gct      1248
Ala Glu Gln Leu Ala Thr Gly Val Ser Pro Gly Leu Val Arg Leu Ala
                405                 410                 415 gtg ggc atc gaa ggt atc gac gat atc ctg gcc gac ctg gag ctt ggc      1296
Val Gly Ile Glu Gly Ile Asp Asp Ile Leu Ala Asp Leu Glu Leu Gly
            420                 425                 430 ttt gcc gcg gcc cgc aga ttc agc gcc gac ccg cag tcc gtg gcg gcg      1344
Phe Ala Ala Ala Arg Arg Phe Ser Ala Asp Pro Gln Ser Val Ala Ala
        435                 440                 445 ttc tga                                                              1350
Phe
```

<210> SEQ ID NO 4
<211> LENGTH: 449
<212> TYPE: PRT
<213> ORGANISM: Mycobacterium tuberculosis

<400> SEQUENCE: 4

```
Met Ser Ala Asp Ser Asn Ser Thr Asp Ala Asp Pro Thr Ala His Trp
1               5                   10                  15

Ser Phe Glu Thr Lys Gln Ile His Ala Gly Gln His Pro Asp Pro Thr
                20                  25                  30

Thr Asn Ala Arg Ala Leu Pro Ile Tyr Ala Thr Thr Ser Tyr Thr Phe
            35                  40                  45

Asp Asp Thr Ala His Ala Ala Leu Phe Gly Leu Glu Ile Pro Gly
        50                  55                  60

Asn Ile Tyr Thr Arg Ile Gly Asn Pro Thr Thr Asp Val Val Glu Gln
65                  70                  75                  80

Arg Ile Ala Ala Leu Glu Gly Gly Val Ala Ala Leu Phe Leu Ser Ser
                85                  90                  95

Gly Gln Ala Ala Glu Thr Phe Ala Ile Leu Asn Leu Ala Gly Ala Gly
                100                 105                 110

Asp His Ile Val Ser Ser Pro Arg Leu Tyr Gly Gly Thr Tyr Asn Leu
            115                 120                 125

Phe His Tyr Ser Leu Ala Lys Leu Gly Ile Glu Val Ser Phe Val Asp
        130                 135                 140

Asp Pro Asp Asp Leu Asp Thr Trp Gln Ala Ala Val Arg Pro Asn Thr
145                 150                 155                 160

Lys Ala Phe Phe Ala Glu Thr Ile Ser Asn Pro Gln Ile Asp Leu Leu
                165                 170                 175

Asp Thr Pro Ala Val Ser Glu Val Ala His Arg Asn Gly Val Pro Leu
            180                 185                 190

Ile Val Asp Asn Thr Ile Ala Thr Pro Tyr Leu Ile Gln Pro Leu Ala
        195                 200                 205

Gln Gly Ala Asp Ile Val Val His Ser Ala Thr Lys Tyr Leu Gly Gly
    210                 215                 220

His Gly Ala Ala Ile Ala Gly Val Ile Val Asp Gly Gly Asn Phe Asp
225                 230                 235                 240

Trp Thr Gln Gly Arg Phe Pro Gly Phe Thr Thr Pro Asp Pro Ser Tyr
                245                 250                 255

His Gly Val Val Phe Ala Glu Leu Gly Pro Pro Ala Phe Ala Leu Lys
            260                 265                 270

Ala Arg Val Gln Leu Leu Arg Asp Tyr Gly Ser Ala Ala Ser Pro Phe
        275                 280                 285
```

```
Asn Ala Phe Leu Val Ala Gln Gly Leu Glu Thr Leu Ser Leu Arg Ile
    290                 295                 300

Glu Arg His Val Ala Asn Ala Gln Arg Val Ala Glu Phe Leu Ala Ala
305                 310                 315                 320

Arg Asp Asp Val Leu Ser Val Asn Tyr Ala Gly Leu Pro Ser Ser Pro
                325                 330                 335

Trp His Glu Arg Ala Lys Arg Leu Ala Pro Lys Gly Thr Gly Ala Val
            340                 345                 350

Leu Ser Phe Glu Leu Ala Gly Gly Ile Glu Ala Gly Lys Ala Phe Val
        355                 360                 365

Asn Ala Leu Lys Leu His Ser His Val Ala Asn Ile Gly Asp Val Arg
    370                 375                 380

Ser Leu Val Ile His Pro Ala Ser Thr Thr His Ala Gln Leu Ser Pro
385                 390                 395                 400

Ala Glu Gln Leu Ala Thr Gly Val Ser Pro Gly Leu Val Arg Leu Ala
                405                 410                 415

Val Gly Ile Glu Gly Ile Asp Asp Ile Leu Ala Asp Leu Glu Leu Gly
            420                 425                 430

Phe Ala Ala Ala Arg Arg Phe Ser Ala Asp Pro Gln Ser Val Ala Ala
        435                 440                 445

Phe
```

<210> SEQ ID NO 5
<211> LENGTH: 1284
<212> TYPE: DNA
<213> ORGANISM: Clostridium acetobutylicum
<220> FEATURE:
<221> NAME/KEY: CDS
<222> LOCATION: (1)..(1284)

<400> SEQUENCE: 5

```
atg agt gaa gaa aga aaa ttt ggt ttt gaa aca tta cag gtt cat gca      48
Met Ser Glu Glu Arg Lys Phe Gly Phe Glu Thr Leu Gln Val His Ala
1               5                   10                  15 gga caa gtt gct gat cca act aca gga tca aga gct gta cct att tat      96
Gly Gln Val Ala Asp Pro Thr Thr Gly Ser Arg Ala Val Pro Ile Tyr
            20                  25                  30 caa aca aca tca tat gta ttt aaa aat gct gat cat gca gca aat tta     144
Gln Thr Thr Ser Tyr Val Phe Lys Asn Ala Asp His Ala Ala Asn Leu
        35                  40                  45 ttt caa ttg aaa gaa cct gga aat gta tat aca agg ata atg aat cca     192
Phe Gln Leu Lys Glu Pro Gly Asn Val Tyr Thr Arg Ile Met Asn Pro
    50                  55                  60 aca act gat gta ttt gaa caa aga gta gca gct ctt gag ggc gga gtt     240
Thr Thr Asp Val Phe Glu Gln Arg Val Ala Ala Leu Glu Gly Gly Val
65                  70                  75                  80 gct gga ctt gca aca gca tca gga ctt gca gca att acc tat gct att     288
Ala Gly Leu Ala Thr Ala Ser Gly Leu Ala Ala Ile Thr Tyr Ala Ile
                85                  90                  95 tta aat gtg gca agt gct ggg gat gaa att gtt gca gca agt acc tta     336
Leu Asn Val Ala Ser Ala Gly Asp Glu Ile Val Ala Ala Ser Thr Leu
            100                 105                 110 tat ggt gga aca tat gaa tta ttt ggg gtt act ctt aag aag ctt gga     384
Tyr Gly Gly Thr Tyr Glu Leu Phe Gly Val Thr Leu Lys Lys Leu Gly
        115                 120                 125 ata aag gtt gtt ttt gta gat cca gat aat cct gaa aat ata aga aaa     432
Ile Lys Val Val Phe Val Asp Pro Asp Asn Pro Glu Asn Ile Arg Lys
    130                 135                 140
```

```
gca ata aat gat agg aca aaa gct gta tat ggg gaa act att gga aat      480
Ala Ile Asn Asp Arg Thr Lys Ala Val Tyr Gly Glu Thr Ile Gly Asn
145                 150                 155                 160 cca aga ata aat gtt ttg gat ata gag gca gta gct aaa att gcc cat      528
Pro Arg Ile Asn Val Leu Asp Ile Glu Ala Val Ala Lys Ile Ala His
                165                 170                 175 gaa aat aaa ata cca ctt ata atc gat aat aca ttt ggt aca ccg tat      576
Glu Asn Lys Ile Pro Leu Ile Ile Asp Asn Thr Phe Gly Thr Pro Tyr
            180                 185                 190 ctt ata aga cct ata gaa ttt gga gca gat ata gtt gta cat tca gca      624
Leu Ile Arg Pro Ile Glu Phe Gly Ala Asp Ile Val Val His Ser Ala
        195                 200                 205 aca aag ttt ata gga gga cat gga act act ata ggt gga att ata gtt      672
Thr Lys Phe Ile Gly Gly His Gly Thr Thr Ile Gly Gly Ile Ile Val
    210                 215                 220 gat ggt gga aaa ttt gat tgg aga gct agt gga aag ttt cct gat ttt      720
Asp Gly Gly Lys Phe Asp Trp Arg Ala Ser Gly Lys Phe Pro Asp Phe
225                 230                 235                 240 aca aca ccg gat aag agc tat aat gga ctt ata tat gct gat cta ggt      768
Thr Thr Pro Asp Lys Ser Tyr Asn Gly Leu Ile Tyr Ala Asp Leu Gly
                245                 250                 255 gca cct gct ttt gct tta aaa gca aga gtt caa ctt tta aga aat aca      816
Ala Pro Ala Phe Ala Leu Lys Ala Arg Val Gln Leu Leu Arg Asn Thr
            260                 265                 270 ggt gca acg ctt agt cca caa agt gct ttt tat ttc cta caa ggg ttg      864
Gly Ala Thr Leu Ser Pro Gln Ser Ala Phe Tyr Phe Leu Gln Gly Leu
        275                 280                 285 gaa tca ctt tca ctt agg gtt caa aaa cat gtt gat aat aca aga aag      912
Glu Ser Leu Ser Leu Arg Val Gln Lys His Val Asp Asn Thr Arg Lys
    290                 295                 300 gta gtt gaa ttc ttg aag aac cat cca aaa gtt tca tgg ata aat tat      960
Val Val Glu Phe Leu Lys Asn His Pro Lys Val Ser Trp Ile Asn Tyr
305                 310                 315                 320 cct gaa ctt gag gaa agt cct tat aaa gag tta gca aat aaa tat ctt     1008
Pro Glu Leu Glu Glu Ser Pro Tyr Lys Glu Leu Ala Asn Lys Tyr Leu
                325                 330                 335 cca aag ggt gca ggc tca ata ttt aca ttt gga ata aag gga gga ctt     1056
Pro Lys Gly Ala Gly Ser Ile Phe Thr Phe Gly Ile Lys Gly Gly Leu
            340                 345                 350 gaa gct ggt aaa aga ttt ata aat agt gtt aaa cta ttc tct ctt ttg     1104
Glu Ala Gly Lys Arg Phe Ile Asn Ser Val Lys Leu Phe Ser Leu Leu
        355                 360                 365 gca aat gtt gca gat gca aaa tca ctt gtt ata cat cct tca agt aca     1152
Ala Asn Val Ala Asp Ala Lys Ser Leu Val Ile His Pro Ser Ser Thr
    370                 375                 380 act cat gct gaa ctt aat gaa gaa gaa caa aaa gca gct ggt gtt act     1200
Thr His Ala Glu Leu Asn Glu Glu Glu Gln Lys Ala Ala Gly Val Thr
385                 390                 395                 400 cca gat atg ata aga ctt tca ata gga gta gag gat gca gag gat tta     1248
Pro Asp Met Ile Arg Leu Ser Ile Gly Val Glu Asp Ala Glu Asp Leu
                405                 410                 415 ata tgg gac tta aat caa gct ctc gaa caa gct taa                     1284
Ile Trp Asp Leu Asn Gln Ala Leu Glu Gln Ala
            420                 425

<210> SEQ ID NO 6
<211> LENGTH: 427
<212> TYPE: PRT
<213> ORGANISM: Clostridium acetobutylicum
```

-continued

```
<400> SEQUENCE: 6

Met Ser Glu Glu Arg Lys Phe Gly Phe Glu Thr Leu Gln Val His Ala
1               5                   10                  15

Gly Gln Val Ala Asp Pro Thr Thr Gly Ser Arg Ala Val Pro Ile Tyr
            20                  25                  30

Gln Thr Thr Ser Tyr Val Phe Lys Asn Ala Asp His Ala Ala Asn Leu
        35                  40                  45

Phe Gln Leu Lys Glu Pro Gly Asn Val Tyr Thr Arg Ile Met Asn Pro
50                  55                  60

Thr Thr Asp Val Phe Glu Gln Arg Val Ala Ala Leu Glu Gly Gly Val
65                  70                  75                  80

Ala Gly Leu Ala Thr Ala Ser Gly Leu Ala Ala Ile Thr Tyr Ala Ile
                85                  90                  95

Leu Asn Val Ala Ser Ala Gly Asp Glu Ile Val Ala Ala Ser Thr Leu
            100                 105                 110

Tyr Gly Gly Thr Tyr Glu Leu Phe Gly Val Thr Leu Lys Lys Leu Gly
        115                 120                 125

Ile Lys Val Val Phe Val Asp Pro Asp Asn Pro Glu Asn Ile Arg Lys
130                 135                 140

Ala Ile Asn Asp Arg Thr Lys Ala Val Tyr Gly Glu Thr Ile Gly Asn
145                 150                 155                 160

Pro Arg Ile Asn Val Leu Asp Ile Glu Ala Val Ala Lys Ile Ala His
                165                 170                 175

Glu Asn Lys Ile Pro Leu Ile Ile Asp Asn Thr Phe Gly Thr Pro Tyr
            180                 185                 190

Leu Ile Arg Pro Ile Glu Phe Gly Ala Asp Ile Val Val His Ser Ala
        195                 200                 205

Thr Lys Phe Ile Gly Gly His Gly Thr Thr Ile Gly Gly Ile Ile Val
210                 215                 220

Asp Gly Gly Lys Phe Asp Trp Arg Ala Ser Gly Lys Phe Pro Asp Phe
225                 230                 235                 240

Thr Thr Pro Asp Lys Ser Tyr Asn Gly Leu Ile Tyr Ala Asp Leu Gly
                245                 250                 255

Ala Pro Ala Phe Ala Leu Lys Ala Arg Val Gln Leu Leu Arg Asn Thr
            260                 265                 270

Gly Ala Thr Leu Ser Pro Gln Ser Ala Phe Tyr Phe Leu Gln Gly Leu
        275                 280                 285

Glu Ser Leu Ser Leu Arg Val Gln Lys His Val Asp Asn Thr Arg Lys
290                 295                 300

Val Val Glu Phe Leu Lys Asn His Pro Lys Val Ser Trp Ile Asn Tyr
305                 310                 315                 320

Pro Glu Leu Glu Glu Ser Pro Tyr Lys Glu Leu Ala Asn Lys Tyr Leu
                325                 330                 335

Pro Lys Gly Ala Gly Ser Ile Phe Thr Phe Gly Ile Lys Gly Gly Leu
            340                 345                 350

Glu Ala Gly Lys Arg Phe Ile Asn Ser Val Lys Leu Phe Ser Leu Leu
        355                 360                 365

Ala Asn Val Ala Asp Ala Lys Ser Leu Val Ile His Pro Ser Ser Thr
370                 375                 380

Thr His Ala Glu Leu Asn Glu Glu Gln Lys Ala Ala Gly Val Thr
385                 390                 395                 400

Pro Asp Met Ile Arg Leu Ser Ile Gly Val Glu Asp Ala Glu Asp Leu
                405                 410                 415
```

```
Ile Trp Asp Leu Asn Gln Ala Leu Glu Gln Ala
        420                 425
```

```
<210> SEQ ID NO 7
<211> LENGTH: 1293
<212> TYPE: DNA
<213> ORGANISM: Bacillus halodurans
<220> FEATURE:
<221> NAME/KEY: CDS
<222> LOCATION: (1)..(1293)

<400> SEQUENCE: 7
```

| | | | | | | | | | | | | | | | | |
|---|---|---|---|---|---|---|---|---|---|---|---|---|---|---|---|---|
| atg | aat | cat | gaa | aac | caa | tgg | cag | tta | gaa | aca | aag | gcc | gtt | cat | tca | 48 |
| Met | Asn | His | Glu | Asn | Gln | Trp | Gln | Leu | Glu | Thr | Lys | Ala | Val | His | Ser | |
| 1 | | | | 5 | | | | | 10 | | | | | 15 | | |
| gga | cag | gag | atc | gat | ccg | aca | acg | ttg | tcg | cga | gcc | gtc | cca | ttg | tac | 96 |
| Gly | Gln | Glu | Ile | Asp | Pro | Thr | Thr | Leu | Ser | Arg | Ala | Val | Pro | Leu | Tyr | |
| | | | 20 | | | | | 25 | | | | | 30 | | | |
| caa | acg | acg | tcc | tac | gga | ttt | aaa | gat | aca | gac | cat | gcg | gcg | aat | tta | 144 |
| Gln | Thr | Thr | Ser | Tyr | Gly | Phe | Lys | Asp | Thr | Asp | His | Ala | Ala | Asn | Leu | |
| | | 35 | | | | | 40 | | | | | 45 | | | | |
| ttt | tca | cta | agt | gaa | ttt | ggc | aat | atc | tat | acc | cga | ttg | atg | aac | cca | 192 |
| Phe | Ser | Leu | Ser | Glu | Phe | Gly | Asn | Ile | Tyr | Thr | Arg | Leu | Met | Asn | Pro | |
| | 50 | | | | | 55 | | | | | 60 | | | | | |
| acg | aca | gat | gtg | ttt | gaa | aaa | cgt | gtg | gct | gcg | tta | gaa | gga | gga | gcg | 240 |
| Thr | Thr | Asp | Val | Phe | Glu | Lys | Arg | Val | Ala | Ala | Leu | Glu | Gly | Gly | Ala | |
| 65 | | | | | 70 | | | | | 75 | | | | | 80 | |
| gca | gct | tta | gcg | acg | gcc | tca | ggg | cag | gcg | gcc | att | acg | tat | tcg | att | 288 |
| Ala | Ala | Leu | Ala | Thr | Ala | Ser | Gly | Gln | Ala | Ala | Ile | Thr | Tyr | Ser | Ile | |
| | | | | 85 | | | | | 90 | | | | | 95 | | |
| tta | aat | att | gcg | gag | gct | gga | gat | gaa | atc | gtg | tcc | gct | agt | agc | ctt | 336 |
| Leu | Asn | Ile | Ala | Glu | Ala | Gly | Asp | Glu | Ile | Val | Ser | Ala | Ser | Ser | Leu | |
| | | | 100 | | | | | 105 | | | | | 110 | | | |
| tac | ggc | gga | acg | tat | aat | tta | ttt | tcg | att | acg | ttg | cca | aag | cta | ggg | 384 |
| Tyr | Gly | Gly | Thr | Tyr | Asn | Leu | Phe | Ser | Ile | Thr | Leu | Pro | Lys | Leu | Gly | |
| | | 115 | | | | | 120 | | | | | 125 | | | | |
| gta | aac | gtc | cgt | ttc | gtt | gat | cca | tcg | gac | cca | gaa | aac | ttc | aaa | gca | 432 |
| Val | Asn | Val | Arg | Phe | Val | Asp | Pro | Ser | Asp | Pro | Glu | Asn | Phe | Lys | Ala | |
| | 130 | | | | | 135 | | | | | 140 | | | | | |
| gcg | att | act | gaa | aag | acg | aaa | gcc | att | ttc | gct | gag | tcg | att | gga | aac | 480 |
| Ala | Ile | Thr | Glu | Lys | Thr | Lys | Ala | Ile | Phe | Ala | Glu | Ser | Ile | Gly | Asn | |
| 145 | | | | | 150 | | | | | 155 | | | | | 160 | |
| cct | aag | gga | gac | gtg | tta | gat | att | gaa | gcg | gtg | gcg | aaa | gtt | gca | cac | 528 |
| Pro | Lys | Gly | Asp | Val | Leu | Asp | Ile | Glu | Ala | Val | Ala | Lys | Val | Ala | His | |
| | | | | 165 | | | | | 170 | | | | | 175 | | |
| gat | cat | cac | ctt | ccc | ctc | att | gtc | gat | aac | acg | ttt | cca | agc | cca | tat | 576 |
| Asp | His | His | Leu | Pro | Leu | Ile | Val | Asp | Asn | Thr | Phe | Pro | Ser | Pro | Tyr | |
| | | | 180 | | | | | 185 | | | | | 190 | | | |
| ttg | ctt | caa | ccg | ata | aag | cac | ggc | gca | gac | att | gtt | gtg | cat | tca | gca | 624 |
| Leu | Leu | Gln | Pro | Ile | Lys | His | Gly | Ala | Asp | Ile | Val | Val | His | Ser | Ala | |
| | | 195 | | | | | 200 | | | | | 205 | | | | |
| aca | aaa | ttt | atc | ggt | ggt | cat | ggg | acg | tcg | ata | gga | ggg | atc | att | gtc | 672 |
| Thr | Lys | Phe | Ile | Gly | Gly | His | Gly | Thr | Ser | Ile | Gly | Gly | Ile | Ile | Val | |
| | 210 | | | | | 215 | | | | | 220 | | | | | |
| gat | gga | ggg | acg | ttt | gat | tgg | gcg | aaa | acg | gat | cga | tat | cca | ggg | cta | 720 |
| Asp | Gly | Gly | Thr | Phe | Asp | Trp | Ala | Lys | Thr | Asp | Arg | Tyr | Pro | Gly | Leu | |
| 225 | | | | | 230 | | | | | 235 | | | | | 240 | |
| aca | aca | cct | gat | ccg | agt | tac | cac | ggt | gtt | gta | tat | aca | gat | gcg | gtc | 768 |
| Thr | Thr | Pro | Asp | Pro | Ser | Tyr | His | Gly | Val | Val | Tyr | Thr | Asp | Ala | Val | |
| | | | | 245 | | | | | 250 | | | | | 255 | | |

```
ggt cca att gct tat att att aaa gcg cgt gtt cag cta ttg cgt gac       816
Gly Pro Ile Ala Tyr Ile Ile Lys Ala Arg Val Gln Leu Leu Arg Asp
        260                 265                 270 atg ggg gca gcc ata tcg cca ttt aac tcg ttt tta ctg ttg caa ggg       864
Met Gly Ala Ala Ile Ser Pro Phe Asn Ser Phe Leu Leu Leu Gln Gly
            275                 280                 285 ttg gaa acg ttg cat tta cgg atg gag aga cat agt gaa aat gcc tac       912
Leu Glu Thr Leu His Leu Arg Met Glu Arg His Ser Glu Asn Ala Tyr
290                 295                 300 aaa gta gca gag ttc ctt gag caa cat caa gcg gtc gaa tcg gtg agc       960
Lys Val Ala Glu Phe Leu Glu Gln His Gln Ala Val Glu Ser Val Ser
305                 310                 315                 320 tac tct gga ctg cca tcc cat cca tcc tac cca tta gcg aaa aaa tac      1008
Tyr Ser Gly Leu Pro Ser His Pro Ser Tyr Pro Leu Ala Lys Lys Tyr
                325                 330                 335 tta cct aaa ggc caa ggg gct atc tta acg ttc gag gta aag ggc ggc      1056
Leu Pro Lys Gly Gln Gly Ala Ile Leu Thr Phe Glu Val Lys Gly Gly
                340                 345                 350 gtt gaa gca gga aag aaa ctc att cat tcg gtc cag cta ttc tcc cac      1104
Val Glu Ala Gly Lys Lys Leu Ile His Ser Val Gln Leu Phe Ser His
            355                 360                 365 ctt gcc aac gta ggt gat tca aaa tcg ttg atc atc cat cct gca agc      1152
Leu Ala Asn Val Gly Asp Ser Lys Ser Leu Ile Ile His Pro Ala Ser
370                 375                 380 acg acc cac caa cag ctc tcg gaa gca gaa cag cga gac gca gga gtg      1200
Thr Thr His Gln Gln Leu Ser Glu Ala Glu Gln Arg Asp Ala Gly Val
385                 390                 395                 400 aca cct ggg atg atc aga ctt tcg gta gga acc gaa tcg att cat gat      1248
Thr Pro Gly Met Ile Arg Leu Ser Val Gly Thr Glu Ser Ile His Asp
                405                 410                 415 att atc acc gat ctc aaa cag gcg att gag gcg agt caa gcg taa          1293
Ile Ile Thr Asp Leu Lys Gln Ala Ile Glu Ala Ser Gln Ala
            420                 425                 430

<210> SEQ ID NO 8
<211> LENGTH: 430
<212> TYPE: PRT
<213> ORGANISM: Bacillus halodurans

<400> SEQUENCE: 8

Met Asn His Glu Asn Gln Trp Gln Leu Glu Thr Lys Ala Val His Ser
1               5                   10                  15

Gly Gln Glu Ile Asp Pro Thr Thr Leu Ser Arg Ala Val Pro Leu Tyr
            20                  25                  30

Gln Thr Thr Ser Tyr Gly Phe Lys Asp Thr Asp His Ala Ala Asn Leu
        35                  40                  45

Phe Ser Leu Ser Glu Phe Gly Asn Ile Tyr Thr Arg Leu Met Asn Pro
    50                  55                  60

Thr Thr Asp Val Phe Glu Lys Arg Val Ala Ala Leu Glu Gly Gly Ala
65                  70                  75                  80

Ala Ala Leu Ala Thr Ala Ser Gly Gln Ala Ala Ile Thr Tyr Ser Ile
                85                  90                  95

Leu Asn Ile Ala Glu Ala Gly Asp Glu Ile Val Ser Ala Ser Ser Leu
            100                 105                 110

Tyr Gly Gly Thr Tyr Asn Leu Phe Ser Ile Thr Leu Pro Lys Leu Gly
        115                 120                 125

Val Asn Val Arg Phe Val Asp Pro Ser Asp Pro Glu Asn Phe Lys Ala
    130                 135                 140
```

```
Ala Ile Thr Glu Lys Thr Lys Ala Ile Phe Ala Glu Ser Ile Gly Asn
145                 150                 155                 160

Pro Lys Gly Asp Val Leu Asp Ile Glu Ala Val Ala Lys Val Ala His
                165                 170                 175

Asp His His Leu Pro Leu Ile Val Asp Asn Thr Phe Pro Ser Pro Tyr
            180                 185                 190

Leu Leu Gln Pro Ile Lys His Gly Ala Asp Ile Val Val His Ser Ala
        195                 200                 205

Thr Lys Phe Ile Gly Gly His Gly Thr Ser Ile Gly Gly Ile Ile Val
    210                 215                 220

Asp Gly Gly Thr Phe Asp Trp Ala Lys Thr Asp Arg Tyr Pro Gly Leu
225                 230                 235                 240

Thr Thr Pro Asp Pro Ser Tyr His Gly Val Val Tyr Thr Asp Ala Val
                245                 250                 255

Gly Pro Ile Ala Tyr Ile Ile Lys Ala Arg Val Gln Leu Leu Arg Asp
            260                 265                 270

Met Gly Ala Ala Ile Ser Pro Phe Asn Ser Phe Leu Leu Leu Gln Gly
        275                 280                 285

Leu Glu Thr Leu His Leu Arg Met Glu Arg His Ser Glu Asn Ala Tyr
    290                 295                 300

Lys Val Ala Glu Phe Leu Glu Gln His Gln Ala Val Glu Ser Val Ser
305                 310                 315                 320

Tyr Ser Gly Leu Pro Ser His Pro Ser Tyr Pro Leu Ala Lys Lys Tyr
                325                 330                 335

Leu Pro Lys Gly Gln Gly Ala Ile Leu Thr Phe Glu Val Lys Gly Gly
            340                 345                 350

Val Glu Ala Gly Lys Lys Leu Ile His Ser Val Gln Leu Phe Ser His
        355                 360                 365

Leu Ala Asn Val Gly Asp Ser Lys Ser Leu Ile Ile His Pro Ala Ser
    370                 375                 380

Thr Thr His Gln Gln Leu Ser Glu Ala Glu Gln Arg Asp Ala Gly Val
385                 390                 395                 400

Thr Pro Gly Met Ile Arg Leu Ser Val Gly Thr Glu Ser Ile His Asp
                405                 410                 415

Ile Ile Thr Asp Leu Lys Gln Ala Ile Glu Ala Ser Gln Ala
            420                 425                 430
```

<210> SEQ ID NO 9
<211> LENGTH: 1203
<212> TYPE: DNA
<213> ORGANISM: Bacillus stearothermophilus
<220> FEATURE:
<221> NAME/KEY: CDS
<222> LOCATION: (1)..(1203)

<400> SEQUENCE: 9

```
atg tcg tat gta ttc cgc gac agc gag cac gcg gcc aat ttg ttt ggt      48
Met Ser Tyr Val Phe Arg Asp Ser Glu His Ala Ala Asn Leu Phe Gly
1               5                   10                  15 ttg aaa gag gaa ggt ttt att tat acg cgc att atg aat cca acg aac      96
Leu Lys Glu Glu Gly Phe Ile Tyr Thr Arg Ile Met Asn Pro Thr Asn
            20                  25                  30 gac gtg ttc gaa aag cgg atc gcg gcg ctt gaa ggc ggc att ggg gcg     144
Asp Val Phe Glu Lys Arg Ile Ala Ala Leu Glu Gly Gly Ile Gly Ala
        35                  40                  45 ctc gcg ctg tca tcg ggg cag gcg gcg gtg ttt tat tcg atc atc aac     192
Leu Ala Leu Ser Ser Gly Gln Ala Ala Val Phe Tyr Ser Ile Ile Asn
    50                  55                  60
```

```
                50                  55                  60
atc gcc tcg gcg ggc gat gaa atc gtc tcg tct tcg tcc att tac ggc      240
Ile Ala Ser Ala Gly Asp Glu Ile Val Ser Ser Ser Ile Tyr Gly
 65                  70                  75                  80 gga acg tac aac ttg ttc gcc cat acg ctg cgc aag ttc ggc att acg      288
Gly Thr Tyr Asn Leu Phe Ala His Thr Leu Arg Lys Phe Gly Ile Thr
                 85                  90                  95 gtg aag ttt gtc gat ccg tcc gac ccc gaa aac ttt gag cgg gcg atc      336
Val Lys Phe Val Asp Pro Ser Asp Pro Glu Asn Phe Glu Arg Ala Ile
            100                 105                 110 acc gac aaa acg aaa gcc ttg ttt gcg gaa acg atc ggc aac ccg aaa      384
Thr Asp Lys Thr Lys Ala Leu Phe Ala Glu Thr Ile Gly Asn Pro Lys
        115                 120                 125 aac gat gtg ttg gac att gaa gcg gtg gcc gac atc gcc cat cgc cat      432
Asn Asp Val Leu Asp Ile Glu Ala Val Ala Asp Ile Ala His Arg His
    130                 135                 140 gcc att ccg ctc att gtc gac aac acg gtg gcc agt cca tac tta ttg      480
Ala Ile Pro Leu Ile Val Asp Asn Thr Val Ala Ser Pro Tyr Leu Leu
145                 150                 155                 160 cgg ccg att gaa ttc ggc gcc gat atc gtc gtc cac tca gcg acg aag      528
Arg Pro Ile Glu Phe Gly Ala Asp Ile Val Val His Ser Ala Thr Lys
                165                 170                 175 ttc atc ggc ggg cac ggc aat tcg atc ggc ggt gtg att gtg gac agc      576
Phe Ile Gly Gly His Gly Asn Ser Ile Gly Gly Val Ile Val Asp Ser
            180                 185                 190 ggc aag ttt gac tgg aaa ggg agc ggc aag ttt ccg gag ttc acc gag      624
Gly Lys Phe Asp Trp Lys Gly Ser Gly Lys Phe Pro Glu Phe Thr Glu
        195                 200                 205 cca gac cca agc tac cac ggt ttg gtg tat gtg gac gcc gtc ggc gaa      672
Pro Asp Pro Ser Tyr His Gly Leu Val Tyr Val Asp Ala Val Gly Glu
    210                 215                 220 gcg gcg tac atc acg aaa gcg cgc atc cag ctc ttg cgc gat ttg gga      720
Ala Ala Tyr Ile Thr Lys Ala Arg Ile Gln Leu Leu Arg Asp Leu Gly
225                 230                 235                 240 gcg gcg ttg tcg ccg ttt aat gcg ttt ttg ctt ttg caa ggg ttg gag      768
Ala Ala Leu Ser Pro Phe Asn Ala Phe Leu Leu Leu Gln Gly Leu Glu
                245                 250                 255 acg ctc cat ttg cgg atg cag cgc cat agc gaa aac gcc ctt gcc gtc      816
Thr Leu His Leu Arg Met Gln Arg His Ser Glu Asn Ala Leu Ala Val
            260                 265                 270 gcc aag ttt tta gaa gag gaa gaa gcg gtc gaa tcg gtc aat tac cca      864
Ala Lys Phe Leu Glu Glu Glu Glu Ala Val Glu Ser Val Asn Tyr Pro
        275                 280                 285 ggg ctt ccg agc cat ccg tcg cat gaa ctg gcg aaa aaa tat ttg cca      912
Gly Leu Pro Ser His Pro Ser His Glu Leu Ala Lys Lys Tyr Leu Pro
    290                 295                 300 aac ggg caa gga gcg atc gtc acg ttt gaa atc aaa ggc ggc gtc gaa      960
Asn Gly Gln Gly Ala Ile Val Thr Phe Glu Ile Lys Gly Gly Val Glu
305                 310                 315                 320 gcc ggc aaa aaa ctg atc gac tcg gtc aaa ctg ttc tct cat ttg gcc     1008
Ala Gly Lys Lys Leu Ile Asp Ser Val Lys Leu Phe Ser His Leu Ala
                325                 330                 335 aac atc ggc gat tcg aaa tcg ctc atc atc cac ccg gcc agc aca acg     1056
Asn Ile Gly Asp Ser Lys Ser Leu Ile Ile His Pro Ala Ser Thr Thr
            340                 345                 350 cac gag cag ctg agc cca gat gaa cag ctg tcc gcc ggc gtc acc cca     1104
His Glu Gln Leu Ser Pro Asp Glu Gln Leu Ser Ala Gly Val Thr Pro
        355                 360                 365 ggc ctt gtg cgt ctg tcc gtc ggc aca gaa gcg atc gac gac att ttg     1152
Gly Leu Val Arg Leu Ser Val Gly Thr Glu Ala Ile Asp Asp Ile Leu
```

-continued

```
Gly Leu Val Arg Leu Ser Val Gly Thr Glu Ala Ile Asp Asp Ile Leu
        370                 375                 380 gac gac ttg cgc caa gcc att cgc caa agc cag acg gtg ggg gtg aag    1200
Asp Asp Leu Arg Gln Ala Ile Arg Gln Ser Gln Thr Val Gly Val Lys
385                 390                 395                 400 tag                                                                 1203

<210> SEQ ID NO 10
<211> LENGTH: 400
<212> TYPE: PRT
<213> ORGANISM: Bacillus stearothermophilus

<400> SEQUENCE: 10

Met Ser Tyr Val Phe Arg Asp Ser Glu His Ala Ala Asn Leu Phe Gly
1               5                   10                  15

Leu Lys Glu Glu Gly Phe Ile Tyr Thr Arg Ile Met Asn Pro Thr Asn
            20                  25                  30

Asp Val Phe Glu Lys Arg Ile Ala Ala Leu Glu Gly Gly Ile Gly Ala
        35                  40                  45

Leu Ala Leu Ser Ser Gly Gln Ala Ala Val Phe Tyr Ser Ile Ile Asn
    50                  55                  60

Ile Ala Ser Ala Gly Asp Glu Ile Val Ser Ser Ser Ile Tyr Gly
65                  70                  75                  80

Gly Thr Tyr Asn Leu Phe Ala His Thr Leu Arg Lys Phe Gly Ile Thr
                85                  90                  95

Val Lys Phe Val Asp Pro Ser Asp Pro Glu Asn Phe Glu Arg Ala Ile
            100                 105                 110

Thr Asp Lys Thr Lys Ala Leu Phe Ala Glu Thr Ile Gly Asn Pro Lys
        115                 120                 125

Asn Asp Val Leu Asp Ile Glu Ala Val Ala Asp Ile Ala His Arg His
    130                 135                 140

Ala Ile Pro Leu Ile Val Asp Asn Thr Val Ala Ser Pro Tyr Leu Leu
145                 150                 155                 160

Arg Pro Ile Glu Phe Gly Ala Asp Ile Val Val His Ser Ala Thr Lys
                165                 170                 175

Phe Ile Gly Gly His Gly Asn Ser Ile Gly Gly Val Ile Val Asp Ser
            180                 185                 190

Gly Lys Phe Asp Trp Lys Gly Ser Gly Lys Phe Pro Glu Phe Thr Glu
        195                 200                 205

Pro Asp Pro Ser Tyr His Gly Leu Val Tyr Val Asp Ala Val Gly Glu
    210                 215                 220

Ala Ala Tyr Ile Thr Lys Ala Arg Ile Gln Leu Leu Arg Asp Leu Gly
225                 230                 235                 240

Ala Ala Leu Ser Pro Phe Asn Ala Phe Leu Leu Gln Gly Leu Glu
                245                 250                 255

Thr Leu His Leu Arg Met Gln Arg His Ser Glu Asn Ala Leu Ala Val
            260                 265                 270

Ala Lys Phe Leu Glu Glu Glu Ala Val Glu Ser Val Asn Tyr Pro
        275                 280                 285

Gly Leu Pro Ser His Pro Ser His Glu Leu Ala Lys Lys Tyr Leu Pro
    290                 295                 300

Asn Gly Gln Gly Ala Ile Val Thr Phe Glu Ile Lys Gly Gly Val Glu
305                 310                 315                 320

Ala Gly Lys Lys Leu Ile Asp Ser Val Lys Leu Phe Ser His Leu Ala
                325                 330                 335
```

```
Asn Ile Gly Asp Ser Lys Ser Leu Ile Ile His Pro Ala Ser Thr Thr
        340                 345                 350

His Glu Gln Leu Ser Pro Asp Glu Gln Leu Ser Ala Gly Val Thr Pro
        355                 360                 365

Gly Leu Val Arg Leu Ser Val Gly Thr Glu Ala Ile Asp Asp Ile Leu
        370                 375                 380

Asp Asp Leu Arg Gln Ala Ile Arg Gln Ser Gln Thr Val Gly Val Lys
385                 390                 395                 400

<210> SEQ ID NO 11
<211> LENGTH: 1290
<212> TYPE: DNA
<213> ORGANISM: Chlorobium tepidum
<220> FEATURE:
<221> NAME/KEY: CDS
<222> LOCATION: (1)..(1290)

<400> SEQUENCE: 11
```

| | | | | | | | | | | | | | | | | |
|---|---|---|---|---|---|---|---|---|---|---|---|---|---|---|---|---|
| atg | agt | gag | gat | aac | acc | ttc | cgg | ttc | gag | acc | ttg | cag | gtt | cac | gcc | 48 |
| Met | Ser | Glu | Asp | Asn | Thr | Phe | Arg | Phe | Glu | Thr | Leu | Gln | Val | His | Ala | |
| 1 | | | | 5 | | | | | 10 | | | | | 15 | | |
| ggg | cag | gag | cct | gat | ccg | gtg | acc | gga | tcg | cgc | gcc | gtg | ccc | att | tac | 96 |
| Gly | Gln | Glu | Pro | Asp | Pro | Val | Thr | Gly | Ser | Arg | Ala | Val | Pro | Ile | Tyr | |
| | | 20 | | | | | 25 | | | | | 30 | | | | |
| cag | acc | acc | tcc | tac | gtg | ttc | gag | aac | gcc | gag | cac | ggc | gct | gac | ctg | 144 |
| Gln | Thr | Thr | Ser | Tyr | Val | Phe | Glu | Asn | Ala | Glu | His | Gly | Ala | Asp | Leu | |
| | | | 35 | | | | | 40 | | | | | 45 | | | |
| ttc | gcg | ctt | cgc | aag | gcg | ggc | aat | atc | tac | acg | cgc | ctg | atg | aac | ccg | 192 |
| Phe | Ala | Leu | Arg | Lys | Ala | Gly | Asn | Ile | Tyr | Thr | Arg | Leu | Met | Asn | Pro | |
| | 50 | | | | | 55 | | | | | 60 | | | | | |
| acc | acc | gac | gtg | ctc | gaa | aag | cgc | atg | gcg | gcg | ctc | gaa | ggg | ggc | aag | 240 |
| Thr | Thr | Asp | Val | Leu | Glu | Lys | Arg | Met | Ala | Ala | Leu | Glu | Gly | Gly | Lys | |
| 65 | | | | | 70 | | | | | 75 | | | | | 80 | |
| gcg | gcc | ctc | ggc | gtg | gcg | agc | ggc | cac | tcg | gcg | cag | ttc | atc | gct | att | 288 |
| Ala | Ala | Leu | Gly | Val | Ala | Ser | Gly | His | Ser | Ala | Gln | Phe | Ile | Ala | Ile | |
| | | | | 85 | | | | | 90 | | | | | 95 | | |
| gcc | acc | atc | tgc | cag | gct | gga | gac | aac | att | gtg | tca | tcg | agc | tat | ctc | 336 |
| Ala | Thr | Ile | Cys | Gln | Ala | Gly | Asp | Asn | Ile | Val | Ser | Ser | Ser | Tyr | Leu | |
| | | | 100 | | | | | 105 | | | | | 110 | | | |
| tac | ggc | ggc | acc | tac | aac | cag | ttc | aag | gtc | gcc | ttc | aag | cgc | ctc | ggc | 384 |
| Tyr | Gly | Gly | Thr | Tyr | Asn | Gln | Phe | Lys | Val | Ala | Phe | Lys | Arg | Leu | Gly | |
| | | | 115 | | | | | 120 | | | | | 125 | | | |
| atc | gag | gtg | agg | ttc | gtg | gat | ggc | aac | gat | cag | gag | gcg | ttc | cgc | aag | 432 |
| Ile | Glu | Val | Arg | Phe | Val | Asp | Gly | Asn | Asp | Gln | Glu | Ala | Phe | Arg | Lys | |
| 130 | | | | | 135 | | | | | 140 | | | | | | |
| gct | atc | gac | gag | aac | acg | aaa | gcg | ctc | tac | atg | gag | tcc | agc | ggc | aat | 480 |
| Ala | Ile | Asp | Glu | Asn | Thr | Lys | Ala | Leu | Tyr | Met | Glu | Ser | Ser | Gly | Asn | |
| 145 | | | | | 150 | | | | | 155 | | | | | 160 | |
| ccg | gcg | ttc | cat | gtg | ccc | gat | ttc | gac | gct | atc | gcg | aag | att | gcc | cgt | 528 |
| Pro | Ala | Phe | His | Val | Pro | Asp | Phe | Asp | Ala | Ile | Ala | Lys | Ile | Ala | Arg | |
| | | | 165 | | | | | 170 | | | | | 175 | | | |
| gag | aac | ggc | att | ccg | ctg | atc | gtc | gat | aac | acc | ttt | ggc | tgc | gcg | ggc | 576 |
| Glu | Asn | Gly | Ile | Pro | Leu | Ile | Val | Asp | Asn | Thr | Phe | Gly | Cys | Ala | Gly | |
| | | | | 180 | | | | | 185 | | | | | 190 | | |
| tat | ctc | tgc | cgt | ccc | att | gat | cac | ggc | gcg | tcg | atc | gtg | gtc | gag | tcg | 624 |
| Tyr | Leu | Cys | Arg | Pro | Ile | Asp | His | Gly | Ala | Ser | Ile | Val | Val | Glu | Ser | |
| | | | 195 | | | | | 200 | | | | | 205 | | | |
| gcc | acc | aag | tgg | atc | ggc | ggg | cac | ggc | acc | tcg | atg | ggc | ggc | atc | atc | 672 |
| Ala | Thr | Lys | Trp | Ile | Gly | Gly | His | Gly | Thr | Ser | Met | Gly | Gly | Ile | Ile | |
| | | | | 210 | | | | | 215 | | | | | 220 | | |

```
gtc gat gcc gga acg ttc gac tgg ggc aac ggc aag ttt ccg ctc ttt       720
Val Asp Ala Gly Thr Phe Asp Trp Gly Asn Gly Lys Phe Pro Leu Phe
225                 230                 235                 240 acc gag cca tcg gaa ggc tat cac ggc ctg aaa ttc tac gaa gcg gtc       768
Thr Glu Pro Ser Glu Gly Tyr His Gly Leu Lys Phe Tyr Glu Ala Val
            245                 250                 255 ggc gag ctg gcc ttt atc atc cgg gcg cgg gtc gag gga ctg cgg gat       816
Gly Glu Leu Ala Phe Ile Ile Arg Ala Arg Val Glu Gly Leu Arg Asp
        260                 265                 270 ttc ggc ccg gcg atc agc ccg ttc aac tcc ttc atg ctg ttg cag gga       864
Phe Gly Pro Ala Ile Ser Pro Phe Asn Ser Phe Met Leu Leu Gln Gly
    275                 280                 285 ctt gaa acg ctc tcg ctt cgc gtg cag cgc cac ctc gac aac acg ctt       912
Leu Glu Thr Leu Ser Leu Arg Val Gln Arg His Leu Asp Asn Thr Leu
290                 295                 300 gaa ctg gcc cgc tgg ctc gaa agg cac gat gcg gtt gcg tgg gtg aac       960
Glu Leu Ala Arg Trp Leu Glu Arg His Asp Ala Val Ala Trp Val Asn
305                 310                 315                 320 tat cca ggc ctc gaa agc cat ccg aca cac gcc ctg gca aaa aaa tat      1008
Tyr Pro Gly Leu Glu Ser His Pro Thr His Ala Leu Ala Lys Lys Tyr
            325                 330                 335 ctc acg cat ggc ttc ggc tgc gtg ctg act ttc ggc gtg aag ggt ggt      1056
Leu Thr His Gly Phe Gly Cys Val Leu Thr Phe Gly Val Lys Gly Gly
        340                 345                 350 tat gaa aac gcg gtg aag ttc atc gac agc gtg aag ctg gcg agc cac      1104
Tyr Glu Asn Ala Val Lys Phe Ile Asp Ser Val Lys Leu Ala Ser His
    355                 360                 365 ctg gcc aac gtg ggt gat gca aaa acg ctc gtc att cat ccg gca tcg      1152
Leu Ala Asn Val Gly Asp Ala Lys Thr Leu Val Ile His Pro Ala Ser
370                 375                 380 acg acg cac cag cag ctc agc gcc gag gaa cag gta tcg gcg ggc gtc      1200
Thr Thr His Gln Gln Leu Ser Ala Glu Glu Gln Val Ser Ala Gly Val
385                 390                 395                 400 acc gcc gat atg gtg cgc gtg tcg gtt ggt atc gag cat atc gat gac      1248
Thr Ala Asp Met Val Arg Val Ser Val Gly Ile Glu His Ile Asp Asp
            405                 410                 415 atc aag gct gat ttc agc cag gct ttc gag aat tta gca tga              1290
Ile Lys Ala Asp Phe Ser Gln Ala Phe Glu Asn Leu Ala
        420                 425

<210> SEQ ID NO 12
<211> LENGTH: 429
<212> TYPE: PRT
<213> ORGANISM: Chlorobium tepidum

<400> SEQUENCE: 12

Met Ser Glu Asp Asn Thr Phe Arg Phe Glu Thr Leu Gln Val His Ala
1               5                   10                  15

Gly Gln Glu Pro Asp Pro Val Thr Gly Ser Arg Ala Val Pro Ile Tyr
            20                  25                  30

Gln Thr Thr Ser Tyr Val Phe Glu Asn Ala Glu His Gly Ala Asp Leu
        35                  40                  45

Phe Ala Leu Arg Lys Ala Gly Asn Ile Tyr Thr Arg Leu Met Asn Pro
    50                  55                  60

Thr Thr Asp Val Leu Glu Lys Arg Met Ala Ala Leu Glu Gly Gly Lys
65                  70                  75                  80

Ala Ala Leu Gly Val Ala Ser Gly His Ser Ala Gln Phe Ile Ala Ile
                85                  90                  95
```

```
Ala Thr Ile Cys Gln Ala Gly Asp Asn Ile Val Ser Ser Ser Tyr Leu
            100                 105                 110

Tyr Gly Gly Thr Tyr Asn Gln Phe Lys Val Ala Phe Lys Arg Leu Gly
        115                 120                 125

Ile Glu Val Arg Phe Val Asp Gly Asn Asp Gln Glu Ala Phe Arg Lys
    130                 135                 140

Ala Ile Asp Glu Asn Thr Lys Ala Leu Tyr Met Glu Ser Ser Gly Asn
145                 150                 155                 160

Pro Ala Phe His Val Pro Asp Phe Asp Ala Ile Ala Lys Ile Ala Arg
                165                 170                 175

Glu Asn Gly Ile Pro Leu Ile Val Asp Asn Thr Phe Gly Cys Ala Gly
            180                 185                 190

Tyr Leu Cys Arg Pro Ile Asp His Gly Ala Ser Ile Val Val Glu Ser
        195                 200                 205

Ala Thr Lys Trp Ile Gly Gly His Gly Thr Ser Met Gly Gly Ile Ile
    210                 215                 220

Val Asp Ala Gly Thr Phe Asp Trp Gly Asn Gly Lys Phe Pro Leu Phe
225                 230                 235                 240

Thr Glu Pro Ser Glu Gly Tyr His Gly Leu Lys Phe Tyr Glu Ala Val
                245                 250                 255

Gly Glu Leu Ala Phe Ile Ile Arg Ala Arg Val Glu Gly Leu Arg Asp
            260                 265                 270

Phe Gly Pro Ala Ile Ser Pro Phe Asn Ser Phe Met Leu Leu Gln Gly
        275                 280                 285

Leu Glu Thr Leu Ser Leu Arg Val Gln Arg His Leu Asp Asn Thr Leu
    290                 295                 300

Glu Leu Ala Arg Trp Leu Glu Arg His Asp Ala Val Ala Trp Val Asn
305                 310                 315                 320

Tyr Pro Gly Leu Glu Ser His Pro Thr His Ala Leu Ala Lys Lys Tyr
                325                 330                 335

Leu Thr His Gly Phe Gly Cys Val Leu Thr Phe Gly Val Lys Gly Gly
            340                 345                 350

Tyr Glu Asn Ala Val Lys Phe Ile Asp Ser Val Lys Leu Ala Ser His
        355                 360                 365

Leu Ala Asn Val Gly Asp Ala Lys Thr Leu Val Ile His Pro Ala Ser
    370                 375                 380

Thr Thr His Gln Gln Leu Ser Ala Glu Glu Val Ser Ala Gly Val
385                 390                 395                 400

Thr Ala Asp Met Val Arg Val Ser Val Gly Ile Glu His Ile Asp Asp
                405                 410                 415

Ile Lys Ala Asp Phe Ser Gln Ala Phe Glu Asn Leu Ala
            420                 425
```

<210> SEQ ID NO 13
<211> LENGTH: 1281
<212> TYPE: DNA
<213> ORGANISM: Lactococcus lactis
<220> FEATURE:
<221> NAME/KEY: CDS
<222> LOCATION: (1)..(1281)

<400> SEQUENCE: 13

```
atg act aat cac aat tat aaa ttc gac act ttg caa gtc cat gca gga    48
Met Thr Asn His Asn Tyr Lys Phe Asp Thr Leu Gln Val His Ala Gly
1               5                   10                  15 caa gtc cct gat cct gtc acg ggt tca cgc gcc gtt ccg ctc tat caa    96
```

-continued

| | | |
|---|---|---|
| Gln Val Pro Asp Pro Val Thr Gly Ser Arg Ala Val Pro Leu Tyr Gln<br>20 25 30 | | |
| aca act tct ttc gtt ttt aac aat tca gac cat gcc gaa gct cgt ttt<br>Thr Thr Ser Phe Val Phe Asn Asn Ser Asp His Ala Glu Ala Arg Phe<br>35 40 45 | 144 | |
| gct tta caa gat cct gga gct att tat tca cgt tta gga aat cca acc<br>Ala Leu Gln Asp Pro Gly Ala Ile Tyr Ser Arg Leu Gly Asn Pro Thr<br>50 55 60 | 192 | |
| aac gat gtt ttt gaa gca cgc atc gca gct ctt gaa ggt gga agt gca<br>Asn Asp Val Phe Glu Ala Arg Ile Ala Ala Leu Glu Gly Gly Ser Ala<br>65 70 75 80 | 240 | |
| gcc ctt ggt gtt ggt tct ggc tca gcc gct att acc tat gcc atc ttg<br>Ala Leu Gly Val Gly Ser Gly Ser Ala Ala Ile Thr Tyr Ala Ile Leu<br>85 90 95 | 288 | |
| aat atc gct aca gtc ggt gat aat att gtt tcc gca agt acc ctt tat<br>Asn Ile Ala Thr Val Gly Asp Asn Ile Val Ser Ala Ser Thr Leu Tyr<br>100 105 110 | 336 | |
| ggt gga acc tat cac ctt ttt tct ggg act tta cca aaa tat gga att<br>Gly Gly Thr Tyr His Leu Phe Ser Gly Thr Leu Pro Lys Tyr Gly Ile<br>115 120 125 | 384 | |
| aca act aaa ttt gtc aat cca gat gac ccg aag aat ttt gaa gag gcg<br>Thr Thr Lys Phe Val Asn Pro Asp Asp Pro Lys Asn Phe Glu Glu Ala<br>130 135 140 | 432 | |
| att gat gaa aaa acc aaa gct att tat tat gaa act ttg ggc aat ccg<br>Ile Asp Glu Lys Thr Lys Ala Ile Tyr Tyr Glu Thr Leu Gly Asn Pro<br>145 150 155 160 | 480 | |
| gga aat aat gtg att gat tat gat gcc att ggt caa att gct aaa aaa<br>Gly Asn Asn Val Ile Asp Tyr Asp Ala Ile Gly Gln Ile Ala Lys Lys<br>165 170 175 | 528 | |
| cat gga att ccc gtt att gtt gat gca acg ttt act acc cct gtg acc<br>His Gly Ile Pro Val Ile Val Asp Ala Thr Phe Thr Thr Pro Val Thr<br>180 185 190 | 576 | |
| ttt aaa cca ttt gaa cat ggt gct aat gta att gtt cat tca gca acg<br>Phe Lys Pro Phe Glu His Gly Ala Asn Val Ile Val His Ser Ala Thr<br>195 200 205 | 624 | |
| aaa ttc att ggc ggt cat ggt act tct att ggt gga gtc atc gtt gat<br>Lys Phe Ile Gly Gly His Gly Thr Ser Ile Gly Gly Val Ile Val Asp<br>210 215 220 | 672 | |
| ggc gga aac ttt gat tgg gca aat ggt aat ttt cct gat ttt aca caa<br>Gly Gly Asn Phe Asp Trp Ala Asn Gly Asn Phe Pro Asp Phe Thr Gln<br>225 230 235 240 | 720 | |
| gct gat gaa agc tac aat ggg att aaa ttt gcc gaa ttg ggt gaa att<br>Ala Asp Glu Ser Tyr Asn Gly Ile Lys Phe Ala Glu Leu Gly Glu Ile<br>245 250 255 | 768 | |
| gct ttt gtg act cgg gtt aga gct att tta tta cgt gat acg ggt gcg<br>Ala Phe Val Thr Arg Val Arg Ala Ile Leu Leu Arg Asp Thr Gly Ala<br>260 265 270 | 816 | |
| gct tta tca cct ttt cat tct tgg ctt ttc tta cag ggg cta gaa aca<br>Ala Leu Ser Pro Phe His Ser Trp Leu Phe Leu Gln Gly Leu Glu Thr<br>275 280 285 | 864 | |
| ctc tca ctc cgg gta gaa cgt cac atc tcc aat act aaa aag att gta<br>Leu Ser Leu Arg Val Glu Arg His Ile Ser Asn Thr Lys Lys Ile Val<br>290 295 300 | 912 | |
| gaa ttt tta gac aat cat cct aag gtg gaa ctt gtt aac cat cct ctg<br>Glu Phe Leu Asp Asn His Pro Lys Val Glu Leu Val Asn His Pro Leu<br>305 310 315 320 | 960 | |
| ctt gaa agt aat tcc tat cat gcg ctc tat cag aaa tat tat cca aaa<br>Leu Glu Ser Asn Ser Tyr His Ala Leu Tyr Gln Lys Tyr Tyr Pro Lys<br>325 330 335 | 1008 | |

-continued

```
gat gct gga tct atc ttt acc ttt gaa ctc aaa gac aaa gat gag aaa    1056
Asp Ala Gly Ser Ile Phe Thr Phe Glu Leu Lys Asp Lys Asp Glu Lys
        340                 345                 350 aaa gcg cgt gat ttg att gat cat ctt gaa att ttc tca ctt cta gcc    1104
Lys Ala Arg Asp Leu Ile Asp His Leu Glu Ile Phe Ser Leu Leu Ala
355                 360                 365 aac gtt gga gat acc aaa tca ttg gcc att cat cct gct tcg acc act    1152
Asn Val Gly Asp Thr Lys Ser Leu Ala Ile His Pro Ala Ser Thr Thr
    370                 375                 380 cac cag cag ctg aat gcc gaa gaa ctt gct agt gca ggg att tcc aaa    1200
His Gln Gln Leu Asn Ala Glu Glu Leu Ala Ser Ala Gly Ile Ser Lys
385                 390                 395                 400 gga acc att cga tta tcg gtt ggt att gaa gat gta act gac ttg att    1248
Gly Thr Ile Arg Leu Ser Val Gly Ile Glu Asp Val Thr Asp Leu Ile
                405                 410                 415 gct gat tta gag caa gca tta gaa aaa ata taa                        1281
Ala Asp Leu Glu Gln Ala Leu Glu Lys Ile
            420                 425

<210> SEQ ID NO 14
<211> LENGTH: 426
<212> TYPE: PRT
<213> ORGANISM: Lactococcus lactis

<400> SEQUENCE: 14

Met Thr Asn His Asn Tyr Lys Phe Asp Thr Leu Gln Val His Ala Gly
1               5                   10                  15

Gln Val Pro Asp Pro Val Thr Gly Ser Arg Ala Val Pro Leu Tyr Gln
            20                  25                  30

Thr Thr Ser Phe Val Phe Asn Asn Ser Asp His Ala Glu Ala Arg Phe
        35                  40                  45

Ala Leu Gln Asp Pro Gly Ala Ile Tyr Ser Arg Leu Gly Asn Pro Thr
    50                  55                  60

Asn Asp Val Phe Glu Ala Arg Ile Ala Ala Leu Glu Gly Gly Ser Ala
65                  70                  75                  80

Ala Leu Gly Val Gly Ser Gly Ser Ala Ala Ile Thr Tyr Ala Ile Leu
                85                  90                  95

Asn Ile Ala Thr Val Gly Asp Asn Ile Val Ser Ala Ser Thr Leu Tyr
            100                 105                 110

Gly Gly Thr Tyr His Leu Phe Ser Gly Thr Leu Pro Lys Tyr Gly Ile
        115                 120                 125

Thr Thr Lys Phe Val Asn Pro Asp Asp Pro Lys Asn Phe Glu Glu Ala
    130                 135                 140

Ile Asp Glu Lys Thr Lys Ala Ile Tyr Tyr Glu Thr Leu Gly Asn Pro
145                 150                 155                 160

Gly Asn Asn Val Ile Asp Tyr Asp Ala Ile Gly Gln Ile Ala Lys Lys
                165                 170                 175

His Gly Ile Pro Val Ile Val Asp Ala Thr Phe Thr Pro Val Thr
            180                 185                 190

Phe Lys Pro Phe Glu His Gly Ala Asn Val Ile Val His Ser Ala Thr
        195                 200                 205

Lys Phe Ile Gly Gly His Gly Thr Ser Ile Gly Gly Val Ile Val Asp
    210                 215                 220

Gly Gly Asn Phe Asp Trp Ala Asn Gly Asn Phe Pro Asp Phe Thr Gln
225                 230                 235                 240

Ala Asp Glu Ser Tyr Asn Gly Ile Lys Phe Ala Glu Leu Gly Glu Ile
                245                 250                 255
```

```
Ala Phe Val Thr Arg Val Arg Ala Ile Leu Leu Arg Asp Thr Gly Ala
            260                 265                 270

Ala Leu Ser Pro Phe His Ser Trp Leu Phe Leu Gln Gly Leu Glu Thr
        275                 280                 285

Leu Ser Leu Arg Val Glu Arg His Ile Ser Asn Thr Lys Lys Ile Val
    290                 295                 300

Glu Phe Leu Asp Asn His Pro Lys Val Glu Leu Val Asn His Pro Leu
305                 310                 315                 320

Leu Glu Ser Asn Ser Tyr His Ala Leu Tyr Gln Lys Tyr Tyr Pro Lys
                325                 330                 335

Asp Ala Gly Ser Ile Phe Thr Phe Glu Leu Lys Asp Lys Asp Glu Lys
            340                 345                 350

Lys Ala Arg Asp Leu Ile Asp His Leu Glu Ile Phe Ser Leu Leu Ala
        355                 360                 365

Asn Val Gly Asp Thr Lys Ser Leu Ala Ile His Pro Ala Ser Thr Thr
    370                 375                 380

His Gln Gln Leu Asn Ala Glu Glu Leu Ala Ser Ala Gly Ile Ser Lys
385                 390                 395                 400

Gly Thr Ile Arg Leu Ser Val Gly Ile Glu Asp Val Thr Asp Leu Ile
                405                 410                 415

Ala Asp Leu Glu Gln Ala Leu Glu Lys Ile
            420                 425

<210> SEQ ID NO 15
<211> LENGTH: 1173
<212> TYPE: DNA
<213> ORGANISM: Synechococcus sp.
<220> FEATURE:
<221> NAME/KEY: CDS
<222> LOCATION: (1)..(1173)

<400> SEQUENCE: 15 atg tct cag cgt ttc gaa acc ctc cag ctg cat gcc ggc cag tct cca      48
Met Ser Gln Arg Phe Glu Thr Leu Gln Leu His Ala Gly Gln Ser Pro
1               5                   10                  15 gac tcg gcc acc aat gcc aga gcg gtg ccg att tat cag acc agc tcc      96
Asp Ser Ala Thr Asn Ala Arg Ala Val Pro Ile Tyr Gln Thr Ser Ser
            20                  25                  30 tac gtc ttc aac gac gcc gag cac ggc gcc aac ctg ttt gga ctg aag     144
Tyr Val Phe Asn Asp Ala Glu His Gly Ala Asn Leu Phe Gly Leu Lys
        35                  40                  45 gaa ttc ggc aac atc tac acc cgt ctg atg aac ccg acg acg gat gtg     192
Glu Phe Gly Asn Ile Tyr Thr Arg Leu Met Asn Pro Thr Thr Asp Val
    50                  55                  60 ttc gag aag cgg gtg gcg gcc ctg gaa ggg ggt gtg gcc gcg ctg gcc     240
Phe Glu Lys Arg Val Ala Ala Leu Glu Gly Gly Val Ala Ala Leu Ala
65                  70                  75                  80 aca gcc tcc ggt cag tcg gct cag ttc ctg gcg atc acg aat tgc atg     288
Thr Ala Ser Gly Gln Ser Ala Gln Phe Leu Ala Ile Thr Asn Cys Met
                85                  90                  95 cag gca ggg gat aac ttt gtg tcc acg tcg ttc ctt tac ggc ggc acc     336
Gln Ala Gly Asp Asn Phe Val Ser Thr Ser Phe Leu Tyr Gly Gly Thr
            100                 105                 110 tac aac cag ttc aaa gtg caa ttc ccc cgg ctg ggc atc gac gtg cgc     384
Tyr Asn Gln Phe Lys Val Gln Phe Pro Arg Leu Gly Ile Asp Val Arg
        115                 120                 125 ttc gct gat ggc gac gac gtg gag agc ttt gct gcg cag atc gac gac     432
Phe Ala Asp Gly Asp Asp Val Glu Ser Phe Ala Ala Gln Ile Asp Asp
```

| | | | | | | | | | | | | | | | | |
|---|---|---|---|---|---|---|---|---|---|---|---|---|---|---|---|---|
| | | 130 | | | | 135 | | | | 140 | | | | | | |
| aaa | acc | aaa | ggc | ctc | tac | gtc | gaa | gcg | atg | ggc | aat | cca | cgc | ttc | aac | 480 |
| Lys | Thr | Lys | Gly | Leu | Tyr | Val | Glu | Ala | Met | Gly | Asn | Pro | Arg | Phe | Asn | |
| 145 | | | | 150 | | | | | 155 | | | | | 160 | | |
| atc | ccc | gat | ttc | gag | ggc | ctc | tca | gcc | ctg | gct | aaa | gag | cgc | ggc | atc | 528 |
| Ile | Pro | Asp | Phe | Glu | Gly | Leu | Ser | Ala | Leu | Ala | Lys | Glu | Arg | Gly | Ile | |
| | | | | 165 | | | | | 170 | | | | | 175 | | |
| cca | ttg | atc | gtg | gac | aac | acc | ttg | gga | gct | tgc | ggt | gcc | ctg | atg | cgt | 576 |
| Pro | Leu | Ile | Val | Asp | Asn | Thr | Leu | Gly | Ala | Cys | Gly | Ala | Leu | Met | Arg | |
| | 180 | | | | | 185 | | | | | 190 | | | | | |
| ccg | atc | gat | cat | ggc | gcg | gat | gtg | gtg | gtg | gaa | agc | gcc | acc | aag | tgg | 624 |
| Pro | Ile | Asp | His | Gly | Ala | Asp | Val | Val | Val | Glu | Ser | Ala | Thr | Lys | Trp | |
| | | | 195 | | | | | 200 | | | | | 205 | | | |
| att | ggc | ggc | cat | ggc | acc | agc | ctc | ggt | ggc | gtg | atc | gtt | gat | gcc | ggc | 672 |
| Ile | Gly | Gly | His | Gly | Thr | Ser | Leu | Gly | Gly | Val | Ile | Val | Asp | Ala | Gly | |
| | | 210 | | | | | 215 | | | | | 220 | | | | |
| aca | ttt | aac | tgg | ggc | aat | ggc | aaa | ttc | ccg | ctg | ctg | agc | caa | ccc | agt | 720 |
| Thr | Phe | Asn | Trp | Gly | Asn | Gly | Lys | Phe | Pro | Leu | Leu | Ser | Gln | Pro | Ser | |
| 225 | | | | | 230 | | | | | 235 | | | | | 240 | |
| gcg | gct | tat | cac | ggc | ctt | gtg | cac | tgg | gat | gcc | ttc | ggc | ttc | ggc | agc | 768 |
| Ala | Ala | Tyr | His | Gly | Leu | Val | His | Trp | Asp | Ala | Phe | Gly | Phe | Gly | Ser | |
| | | | | 245 | | | | | 250 | | | | | 255 | | |
| gac | gtc | tgc | aag | atg | ctg | gga | gtg | ccg | gac | aac | cgc | aac | gtc | gcc | ttt | 816 |
| Asp | Val | Cys | Lys | Met | Leu | Gly | Val | Pro | Asp | Asn | Arg | Asn | Val | Ala | Phe | |
| | | | 260 | | | | | 265 | | | | | 270 | | | |
| gcc | ctg | cga | gcc | cgg | gtc | gag | ggt | cta | cgg | gac | tgg | ggt | ccg | gcg | gtt | 864 |
| Ala | Leu | Arg | Ala | Arg | Val | Glu | Gly | Leu | Arg | Asp | Trp | Gly | Pro | Ala | Val | |
| | | 275 | | | | | 280 | | | | | 285 | | | | |
| agt | ccc | ttc | aat | agc | ttc | ctg | ctg | ctg | caa | ggt | cta | gaa | acc | ctc | agc | 912 |
| Ser | Pro | Phe | Asn | Ser | Phe | Leu | Leu | Leu | Gln | Gly | Leu | Glu | Thr | Leu | Ser | |
| 290 | | | | | 295 | | | | | 300 | | | | | | |
| ctg | cgg | gtg | gag | cgc | cac | acg | gag | aac | gcc | atg | gcg | ctg | gcc | acc | tgg | 960 |
| Leu | Arg | Val | Glu | Arg | His | Thr | Glu | Asn | Ala | Met | Ala | Leu | Ala | Thr | Trp | |
| 305 | | | | 310 | | | | | 315 | | | | | 320 | | |
| cta | gca | acg | cac | ccc | aat | gtg | gag | cat | gtg | agc | tac | cca | ggc | ctg | agc | 1008 |
| Leu | Ala | Thr | His | Pro | Asn | Val | Glu | His | Val | Ser | Tyr | Pro | Gly | Leu | Ser | |
| | | | | 325 | | | | | 330 | | | | | 335 | | |
| agc | gat | ccg | tat | cac | gca | gct | gcc | aag | aaa | tac | ctg | acg | ggc | cgg | ggc | 1056 |
| Ser | Asp | Pro | Tyr | His | Ala | Ala | Ala | Lys | Lys | Tyr | Leu | Thr | Gly | Arg | Gly | |
| | | | 340 | | | | | 345 | | | | | 350 | | | |
| atg | gga | tgc | atg | ctg | atg | ttc | tcg | ctc | aag | ggc | ggt | tac | gac | gat | gca | 1104 |
| Met | Gly | Cys | Met | Leu | Met | Phe | Ser | Leu | Lys | Gly | Gly | Tyr | Asp | Asp | Ala | |
| | 355 | | | | | 360 | | | | | 365 | | | | | |
| gtc | cgt | ttc | atc | aac | agc | ctt | caa | ctg | gcc | agt | cac | ctc | gcc | aat | gtg | 1152 |
| Val | Arg | Phe | Ile | Asn | Ser | Leu | Gln | Leu | Ala | Ser | His | Leu | Ala | Asn | Val | |
| 370 | | | | | 375 | | | | | 380 | | | | | | |
| ggg | gat | gcc | aaa | acc | tgg | tga | | | | | | | | | | 1173 |
| Gly | Asp | Ala | Lys | Thr | Trp | | | | | | | | | | | |
| 385 | | | | 390 | | | | | | | | | | | | |

<210> SEQ ID NO 16
<211> LENGTH: 390
<212> TYPE: PRT
<213> ORGANISM: Synechococcus sp.

<400> SEQUENCE: 16

| | | | | | | | | | | | | | | | |
|---|---|---|---|---|---|---|---|---|---|---|---|---|---|---|---|
| Met | Ser | Gln | Arg | Phe | Glu | Thr | Leu | Gln | Leu | His | Ala | Gly | Gln | Ser | Pro |
| 1 | | | | 5 | | | | | 10 | | | | | 15 | |
| Asp | Ser | Ala | Thr | Asn | Ala | Arg | Ala | Val | Pro | Ile | Tyr | Gln | Thr | Ser | Ser |
| | | | 20 | | | | | 25 | | | | | 30 | | |

```
Tyr Val Phe Asn Asp Ala Glu His Gly Ala Asn Leu Phe Gly Leu Lys
             35                  40                  45

Glu Phe Gly Asn Ile Tyr Thr Arg Leu Met Asn Pro Thr Thr Asp Val
 50                  55                  60

Phe Glu Lys Arg Val Ala Ala Leu Glu Gly Val Ala Ala Leu Ala
 65                  70                  75                  80

Thr Ala Ser Gly Gln Ser Ala Gln Phe Leu Ala Ile Thr Asn Cys Met
                 85                  90                  95

Gln Ala Gly Asp Asn Phe Val Ser Thr Ser Phe Leu Tyr Gly Gly Thr
            100                 105                 110

Tyr Asn Gln Phe Lys Val Gln Phe Pro Arg Leu Gly Ile Asp Val Arg
        115                 120                 125

Phe Ala Asp Gly Asp Val Glu Ser Phe Ala Ala Gln Ile Asp Asp
    130                 135                 140

Lys Thr Lys Gly Leu Tyr Val Glu Ala Met Gly Asn Pro Arg Phe Asn
145                 150                 155                 160

Ile Pro Asp Phe Glu Gly Leu Ser Ala Leu Ala Lys Glu Arg Gly Ile
                165                 170                 175

Pro Leu Ile Val Asp Asn Thr Leu Gly Ala Cys Gly Ala Leu Met Arg
            180                 185                 190

Pro Ile Asp His Gly Ala Asp Val Val Glu Ser Ala Thr Lys Trp
        195                 200                 205

Ile Gly Gly His Gly Thr Ser Leu Gly Gly Val Ile Val Asp Ala Gly
    210                 215                 220

Thr Phe Asn Trp Gly Asn Gly Lys Phe Pro Leu Leu Ser Gln Pro Ser
225                 230                 235                 240

Ala Ala Tyr His Gly Leu Val His Trp Asp Ala Phe Gly Phe Gly Ser
                245                 250                 255

Asp Val Cys Lys Met Leu Gly Val Pro Asp Asn Arg Asn Val Ala Phe
            260                 265                 270

Ala Leu Arg Ala Arg Val Glu Gly Leu Arg Asp Trp Gly Pro Ala Val
        275                 280                 285

Ser Pro Phe Asn Ser Phe Leu Leu Gln Gly Leu Glu Thr Leu Ser
    290                 295                 300

Leu Arg Val Glu Arg His Thr Glu Asn Ala Met Ala Leu Ala Thr Trp
305                 310                 315                 320

Leu Ala Thr His Pro Asn Val Glu His Val Ser Tyr Pro Gly Leu Ser
                325                 330                 335

Ser Asp Pro Tyr His Ala Ala Lys Lys Tyr Leu Thr Gly Arg Gly
            340                 345                 350

Met Gly Cys Met Leu Met Phe Ser Leu Lys Gly Gly Tyr Asp Asp Ala
        355                 360                 365

Val Arg Phe Ile Asn Ser Leu Gln Leu Ala Ser His Leu Ala Asn Val
    370                 375                 380

Gly Asp Ala Lys Thr Trp
385                 390

<210> SEQ ID NO 17
<211> LENGTH: 1314
<212> TYPE: DNA
<213> ORGANISM: Emericella nidulans
<220> FEATURE:
<221> NAME/KEY: CDS
<222> LOCATION: (1)..(1314)
```

<400> SEQUENCE: 17

```
atg tcc gac cct tca ccg aaa cgt ttc gag acc ctc cag ctc cat gcg      48
Met Ser Asp Pro Ser Pro Lys Arg Phe Glu Thr Leu Gln Leu His Ala
1               5                   10                  15 ggc cag gag cct gac cct gca act aat tcc cgg gct gtc cca atc tat      96
Gly Gln Glu Pro Asp Pro Ala Thr Asn Ser Arg Ala Val Pro Ile Tyr
            20                  25                  30 gcg aca acg tcc tac acc ttc aat gac tcc gca cac ggc gcc agg ctt     144
Ala Thr Thr Ser Tyr Thr Phe Asn Asp Ser Ala His Gly Ala Arg Leu
        35                  40                  45 ttt ggc ctc aaa gag ttt ggc aat att tac agc cga att atg aat ccc     192
Phe Gly Leu Lys Glu Phe Gly Asn Ile Tyr Ser Arg Ile Met Asn Pro
    50                  55                  60 aca gtc gat gtc ttc gaa aaa cgt att gct gca ctc gag gga ggt gtc     240
Thr Val Asp Val Phe Glu Lys Arg Ile Ala Ala Leu Glu Gly Gly Val
65                  70                  75                  80 gct gcg gtg gct gcc tca tct ggc cag gca gcc cag ttc atg gcc atc     288
Ala Ala Val Ala Ala Ser Ser Gly Gln Ala Ala Gln Phe Met Ala Ile
                85                  90                  95 tct gct cta gcc cat gct ggt gac aat atc gtt tcc aca agt aat ttg     336
Ser Ala Leu Ala His Ala Gly Asp Asn Ile Val Ser Thr Ser Asn Leu
            100                 105                 110 tat ggt ggt aca tac aat cag ttt aag gtc ctt ttc cca cga ctg gga     384
Tyr Gly Gly Thr Tyr Asn Gln Phe Lys Val Leu Phe Pro Arg Leu Gly
        115                 120                 125 att acc aca aaa ttc gtg cag gga gac aaa gca gag gac att gcc gcc     432
Ile Thr Thr Lys Phe Val Gln Gly Asp Lys Ala Glu Asp Ile Ala Ala
    130                 135                 140 gct atc gat gac cgt acc aag gcc gtc tac gtc gag aca ata gga aac     480
Ala Ile Asp Asp Arg Thr Lys Ala Val Tyr Val Glu Thr Ile Gly Asn
145                 150                 155                 160 cct cgc tac aat gtg ccc gac ttt gag gtc att gca aaa gta gcc cat     528
Pro Arg Tyr Asn Val Pro Asp Phe Glu Val Ile Ala Lys Val Ala His
                165                 170                 175 gag aag gga att ccc ctt gtg gtt gac aac acc ttc ggt gcc gga ggc     576
Glu Lys Gly Ile Pro Leu Val Val Asp Asn Thr Phe Gly Ala Gly Gly
            180                 185                 190 tac ttt gtt cga ccc att gaa cat ggc gcc gac att gtc gtg cac agt     624
Tyr Phe Val Arg Pro Ile Glu His Gly Ala Asp Ile Val Val His Ser
        195                 200                 205 gca act aaa tgg att gga ggt cat ggc aca acc atc gga ggc gtt gtc     672
Ala Thr Lys Trp Ile Gly Gly His Gly Thr Thr Ile Gly Gly Val Val
    210                 215                 220 gtg gac agc ggc aaa ttc gac tgg ggc aag aac gcc gcg cgg ttt cct     720
Val Asp Ser Gly Lys Phe Asp Trp Gly Lys Asn Ala Ala Arg Phe Pro
225                 230                 235                 240 cag ttc acg cag cct tct gaa ggt tac cac ggg ttg aac ttc tgg gag     768
Gln Phe Thr Gln Pro Ser Glu Gly Tyr His Gly Leu Asn Phe Trp Glu
                245                 250                 255 acc ttc ggc ccc att gcc ttc gcg att cgt gtc cgg gtc gaa atc ctg     816
Thr Phe Gly Pro Ile Ala Phe Ala Ile Arg Val Arg Val Glu Ile Leu
            260                 265                 270 cgc gac ctc ggg tcc gcg ctg aac cct ttc gcc gcg cag cag ctc atc     864
Arg Asp Leu Gly Ser Ala Leu Asn Pro Phe Ala Ala Gln Gln Leu Ile
        275                 280                 285 ctg ggt ctg gaa acc cta agc ttg cgc gct gag cgt cat gct tcc aac     912
Leu Gly Leu Glu Thr Leu Ser Leu Arg Ala Glu Arg His Ala Ser Asn
    290                 295                 300 gct ctg gcc ctc gcc aac tgg cta aag aag aat gat cac gtc agc tgg     960
Ala Leu Ala Leu Ala Asn Trp Leu Lys Lys Asn Asp His Val Ser Trp
```

-continued

```
Ala Leu Ala Leu Ala Asn Trp Leu Lys Lys Asn Asp His Val Ser Trp
305                 310                 315                 320 gtt tct tac gtg ggc cta gaa gag cac tcc agc cac gaa gtt gca aag      1008
Val Ser Tyr Val Gly Leu Glu Glu His Ser Ser His Glu Val Ala Lys
                325                 330                 335 aag tac ctc aag cgt ggg ttc ggc ggt gtc cta tcc ttt ggt gtc aag      1056
Lys Tyr Leu Lys Arg Gly Phe Gly Gly Val Leu Ser Phe Gly Val Lys
            340                 345                 350 ggt gag gca gcc gtc ggt agc cag gtt gtc gac aac ttt aag ctc atc      1104
Gly Glu Ala Ala Val Gly Ser Gln Val Val Asp Asn Phe Lys Leu Ile
        355                 360                 365 tcc aat cta gca aat gtt gga gac tcc aag acc ctc gcg att cac ccc      1152
Ser Asn Leu Ala Asn Val Gly Asp Ser Lys Thr Leu Ala Ile His Pro
    370                 375                 380 tgg agc acc act cac gag cag ttg acc gac cag gag cga atc gat tct      1200
Trp Ser Thr Thr His Glu Gln Leu Thr Asp Gln Glu Arg Ile Asp Ser
385                 390                 395                 400 ggt gtt acg gaa gat gcc atc cgc atc tct gtc ggc act gag cac atc      1248
Gly Val Thr Glu Asp Ala Ile Arg Ile Ser Val Gly Thr Glu His Ile
                405                 410                 415 gac gac atc atc gcc gac ttt gaa cag tca ttt gca gcg acc ttc aaa      1296
Asp Asp Ile Ile Ala Asp Phe Glu Gln Ser Phe Ala Ala Thr Phe Lys
            420                 425                 430 gtt gtc cgg agt gct tag                                              1314
Val Val Arg Ser Ala
        435
```

<210> SEQ ID NO 18
<211> LENGTH: 437
<212> TYPE: PRT
<213> ORGANISM: Emericella nidulans

<400> SEQUENCE: 18

```
Met Ser Asp Pro Ser Pro Lys Arg Phe Glu Thr Leu Gln Leu His Ala
1               5                   10                  15

Gly Gln Glu Pro Asp Pro Ala Thr Asn Ser Arg Ala Val Pro Ile Tyr
            20                  25                  30

Ala Thr Thr Ser Tyr Thr Phe Asn Asp Ser Ala His Gly Ala Arg Leu
        35                  40                  45

Phe Gly Leu Lys Glu Phe Gly Asn Ile Tyr Ser Arg Ile Met Asn Pro
    50                  55                  60

Thr Val Asp Val Phe Glu Lys Arg Ile Ala Ala Leu Glu Gly Gly Val
65                  70                  75                  80

Ala Ala Val Ala Ala Ser Ser Gly Gln Ala Ala Gln Phe Met Ala Ile
                85                  90                  95

Ser Ala Leu Ala His Ala Gly Asp Asn Ile Val Ser Thr Ser Asn Leu
            100                 105                 110

Tyr Gly Gly Thr Tyr Asn Gln Phe Lys Val Leu Phe Pro Arg Leu Gly
        115                 120                 125

Ile Thr Thr Lys Phe Val Gln Gly Asp Lys Ala Glu Asp Ile Ala Ala
    130                 135                 140

Ala Ile Asp Asp Arg Thr Lys Ala Val Tyr Val Glu Thr Ile Gly Asn
145                 150                 155                 160

Pro Arg Tyr Asn Val Pro Asp Phe Glu Val Ile Ala Lys Val Ala His
                165                 170                 175

Glu Lys Gly Ile Pro Leu Val Val Asp Asn Thr Phe Gly Ala Gly Gly
            180                 185                 190
```

```
Tyr Phe Val Arg Pro Ile Glu His Gly Ala Asp Ile Val His Ser
            195                 200                 205

Ala Thr Lys Trp Ile Gly Gly His Gly Thr Thr Ile Gly Gly Val Val
    210                 215                 220

Val Asp Ser Gly Lys Phe Asp Trp Gly Lys Asn Ala Ala Arg Phe Pro
225                 230                 235                 240

Gln Phe Thr Gln Pro Ser Glu Gly Tyr His Gly Leu Asn Phe Trp Glu
                245                 250                 255

Thr Phe Gly Pro Ile Ala Phe Ala Ile Arg Val Arg Val Glu Ile Leu
            260                 265                 270

Arg Asp Leu Gly Ser Ala Leu Asn Pro Phe Ala Ala Gln Gln Leu Ile
        275                 280                 285

Leu Gly Leu Glu Thr Leu Ser Leu Arg Ala Glu Arg His Ala Ser Asn
    290                 295                 300

Ala Leu Ala Leu Ala Asn Trp Leu Lys Lys Asn Asp His Val Ser Trp
305                 310                 315                 320

Val Ser Tyr Val Gly Leu Glu Glu His Ser Ser His Glu Val Ala Lys
                325                 330                 335

Lys Tyr Leu Lys Arg Gly Phe Gly Gly Val Leu Ser Phe Gly Val Lys
            340                 345                 350

Gly Glu Ala Ala Val Gly Ser Gln Val Val Asp Asn Phe Lys Leu Ile
        355                 360                 365

Ser Asn Leu Ala Asn Val Gly Asp Ser Lys Thr Leu Ala Ile His Pro
    370                 375                 380

Trp Ser Thr Thr His Glu Gln Leu Thr Asp Gln Glu Arg Ile Asp Ser
385                 390                 395                 400

Gly Val Thr Glu Asp Ala Ile Arg Ile Ser Val Gly Thr Glu His Ile
                405                 410                 415

Asp Asp Ile Ile Ala Asp Phe Glu Gln Ser Phe Ala Ala Thr Phe Lys
            420                 425                 430

Val Val Arg Ser Ala
            435
```

<210> SEQ ID NO 19
<211> LENGTH: 1287
<212> TYPE: DNA
<213> ORGANISM: Bacteroides fragilis
<220> FEATURE:
<221> NAME/KEY: CDS
<222> LOCATION: (1)..(1287)

<400> SEQUENCE: 19

```
atg gaa acg aaa aaa tta cat ttt gag act tta caa ctc cat gtt gga      48
Met Glu Thr Lys Lys Leu His Phe Glu Thr Leu Gln Leu His Val Gly
1               5                   10                  15 cag gag act ccc gac ccg gca acc gat gcg cgt gcc gta cct att tat     96
Gln Glu Thr Pro Asp Pro Ala Thr Asp Ala Arg Ala Val Pro Ile Tyr
                20                  25                  30 cag aca act tcc tat gtg ttc cgg gat tcg gcc cat gcc gcc gca cga    144
Gln Thr Thr Ser Tyr Val Phe Arg Asp Ser Ala His Ala Ala Ala Arg
            35                  40                  45 ttt gga ttg caa gac cct ggg aat att tat gga cga ctg acc aat tcc    192
Phe Gly Leu Gln Asp Pro Gly Asn Ile Tyr Gly Arg Leu Thr Asn Ser
        50                  55                  60 act cag gga gta ttg gag gaa cgc atc gca gca ctt gaa ggg gga gta    240
Thr Gln Gly Val Leu Glu Glu Arg Ile Ala Ala Leu Glu Gly Gly Val
65                  70                  75                  80
```

```
                                                              -continued
ggt ggg ctt gcc gtg gct tcc gga gct gct gcc gtg acc tat gct atc     288
Gly Gly Leu Ala Val Ala Ser Gly Ala Ala Ala Val Thr Tyr Ala Ile
             85                  90                  95 gag aat atc acc cgt tcc ggt gat cat att gtg gct gcc aag acc att     336
Glu Asn Ile Thr Arg Ser Gly Asp His Ile Val Ala Ala Lys Thr Ile
                100                 105                 110 tat ggg ggc aca tat aac ttg ctg gcg cat act ctg cct gct tat gga     384
Tyr Gly Gly Thr Tyr Asn Leu Leu Ala His Thr Leu Pro Ala Tyr Gly
            115                 120                 125 gta acg acc act ttt gta gat ccg tcc gat ctt ttt aat ttc gaa cgg     432
Val Thr Thr Thr Phe Val Asp Pro Ser Asp Leu Phe Asn Phe Glu Arg
130                 135                 140 gcg att cgt gaa aat aca aag gcg ata ttc att gaa act ctg gga aac     480
Ala Ile Arg Glu Asn Thr Lys Ala Ile Phe Ile Glu Thr Leu Gly Asn
145                 150                 155                 160 ccc aat tcc aat att atc gat atg gat gcc gta gct gcc att gcc cat     528
Pro Asn Ser Asn Ile Ile Asp Met Asp Ala Val Ala Ala Ile Ala His
                165                 170                 175 aaa tat cgg att ccg ctg att gtg gat aat act ttc ggt acg cct tac     576
Lys Tyr Arg Ile Pro Leu Ile Val Asp Asn Thr Phe Gly Thr Pro Tyr
            180                 185                 190 ctt atc cgt ccc att gag cac ggg gca gac att gtg gta cat tct gcc     624
Leu Ile Arg Pro Ile Glu His Gly Ala Asp Ile Val Val His Ser Ala
            195                 200                 205 aca aaa ttc att ggc gga cac ggc agt tcg ttg gga gga gtt att gtc     672
Thr Lys Phe Ile Gly Gly His Gly Ser Ser Leu Gly Gly Val Ile Val
            210                 215                 220 gat tcc ggt aaa ttt gac tgg gtt gct tcc ggt aaa ttc ccg caa ctg     720
Asp Ser Gly Lys Phe Asp Trp Val Ala Ser Gly Lys Phe Pro Gln Leu
225                 230                 235                 240 acc gag ccg gat gca agt tat cat ggg gta cgg ttt gtc gat gct gcc     768
Thr Glu Pro Asp Ala Ser Tyr His Gly Val Arg Phe Val Asp Ala Ala
                245                 250                 255 ggg gct gct gcc tac att gtc cgt ata cgt gcc gtg ttg ctg cgc gat     816
Gly Ala Ala Ala Tyr Ile Val Arg Ile Arg Ala Val Leu Leu Arg Asp
            260                 265                 270 acg ggt gct gcc atc agc ccg ttc aat gct ttt atc ttg ctg caa ggg     864
Thr Gly Ala Ala Ile Ser Pro Phe Asn Ala Phe Ile Leu Leu Gln Gly
            275                 280                 285 ttg gag act ttg tct ttg cgt gta gaa cgg cat gtg gcc aat gct ttg     912
Leu Glu Thr Leu Ser Leu Arg Val Glu Arg His Val Ala Asn Ala Leu
            290                 295                 300 aag gtt att gat ttt ctg gtg aac cat ccg aag gta gcg gct gtt aat     960
Lys Val Ile Asp Phe Leu Val Asn His Pro Lys Val Ala Ala Val Asn
305                 310                 315                 320 cat cca tca ttg ccc ggt cat ccg gat cat gcc atc tat caa cgt tat    1008
His Pro Ser Leu Pro Gly His Pro Asp His Ala Ile Tyr Gln Arg Tyr
                325                 330                 335 ttt cct ggc ggg gca ggt tct atc ttc act ttc gag gta aag gga gga    1056
Phe Pro Gly Gly Ala Gly Ser Ile Phe Thr Phe Glu Val Lys Gly Gly
            340                 345                 350 acg gag gaa gcg cag aag ttt atc gat agt ctg cag ata ttc tct ttg    1104
Thr Glu Glu Ala Gln Lys Phe Ile Asp Ser Leu Gln Ile Phe Ser Leu
            355                 360                 365 ctg gcc aat gtg gcc gat gtg aag tcg ctg gtg att cat ccg ggc act    1152
Leu Ala Asn Val Ala Asp Val Lys Ser Leu Val Ile His Pro Gly Thr
            370                 375                 380 acc aca cac tcg cag ttg aat gcg cag gag ctg gag gaa cag ggg att    1200
Thr Thr His Ser Gln Leu Asn Ala Gln Glu Leu Glu Glu Gln Gly Ile
385                 390                 395                 400
```

```
aaa ccc gga acg gtc aga ctt tcg ata ggt acg gag cat att gag gac    1248
Lys Pro Gly Thr Val Arg Leu Ser Ile Gly Thr Glu His Ile Glu Asp
            405                 410                 415 att att gat gac tta cgt cag gca tta gag aaa att taa                1287
Ile Ile Asp Asp Leu Arg Gln Ala Leu Glu Lys Ile
        420                 425

<210> SEQ ID NO 20
<211> LENGTH: 428
<212> TYPE: PRT
<213> ORGANISM: Bacteroides fragilis

<400> SEQUENCE: 20

Met Glu Thr Lys Lys Leu His Phe Glu Thr Leu Gln Leu His Val Gly
1               5                   10                  15

Gln Glu Thr Pro Asp Pro Ala Thr Asp Ala Arg Ala Val Pro Ile Tyr
            20                  25                  30

Gln Thr Thr Ser Tyr Val Phe Arg Asp Ser Ala His Ala Ala Ala Arg
        35                  40                  45

Phe Gly Leu Gln Asp Pro Gly Asn Ile Tyr Gly Arg Leu Thr Asn Ser
50                  55                  60

Thr Gln Gly Val Leu Glu Glu Arg Ile Ala Ala Leu Glu Gly Gly Val
65                  70                  75                  80

Gly Gly Leu Ala Val Ala Ser Gly Ala Ala Ala Val Thr Tyr Ala Ile
                85                  90                  95

Glu Asn Ile Thr Arg Ser Gly Asp His Ile Val Ala Ala Lys Thr Ile
            100                 105                 110

Tyr Gly Gly Thr Tyr Asn Leu Leu Ala His Thr Leu Pro Ala Tyr Gly
        115                 120                 125

Val Thr Thr Thr Phe Val Asp Pro Ser Asp Leu Phe Asn Phe Glu Arg
130                 135                 140

Ala Ile Arg Glu Asn Thr Lys Ala Ile Phe Ile Glu Thr Leu Gly Asn
145                 150                 155                 160

Pro Asn Ser Asn Ile Ile Asp Met Asp Ala Val Ala Ala Ile Ala His
                165                 170                 175

Lys Tyr Arg Ile Pro Leu Ile Val Asp Asn Thr Phe Gly Thr Pro Tyr
            180                 185                 190

Leu Ile Arg Pro Ile Glu His Gly Ala Asp Ile Val Val His Ser Ala
        195                 200                 205

Thr Lys Phe Ile Gly Gly His Gly Ser Ser Leu Gly Gly Val Ile Val
210                 215                 220

Asp Ser Gly Lys Phe Asp Trp Val Ala Ser Gly Lys Phe Pro Gln Leu
225                 230                 235                 240

Thr Glu Pro Asp Ala Ser Tyr His Gly Val Arg Phe Val Asp Ala Ala
                245                 250                 255

Gly Ala Ala Ala Tyr Ile Val Arg Ile Arg Ala Val Leu Leu Arg Asp
            260                 265                 270

Thr Gly Ala Ala Ile Ser Pro Phe Asn Ala Phe Ile Leu Leu Gln Gly
        275                 280                 285

Leu Glu Thr Leu Ser Leu Arg Val Glu Arg His Val Ala Asn Ala Leu
290                 295                 300

Lys Val Ile Asp Phe Leu Val Asn His Pro Lys Val Ala Ala Val Asn
305                 310                 315                 320

His Pro Ser Leu Pro Gly His Pro Asp His Ala Ile Tyr Gln Arg Tyr
                325                 330                 335
```

```
Phe Pro Gly Gly Ala Gly Ser Ile Phe Thr Phe Glu Val Lys Gly Gly
            340                 345                 350

Thr Glu Glu Ala Gln Lys Phe Ile Asp Ser Leu Gln Ile Phe Ser Leu
            355                 360                 365

Leu Ala Asn Val Ala Asp Val Lys Ser Leu Val Ile His Pro Gly Thr
            370                 375                 380

Thr Thr His Ser Gln Leu Asn Ala Gln Glu Leu Glu Glu Gln Gly Ile
385                 390                 395                 400

Lys Pro Gly Thr Val Arg Leu Ser Ile Gly Thr Glu His Ile Glu Asp
                405                 410                 415

Ile Ile Asp Asp Leu Arg Gln Ala Leu Glu Lys Ile
                420                 425

<210> SEQ ID NO 21
<211> LENGTH: 1278
<212> TYPE: DNA
<213> ORGANISM: Pseudomonas aeruginosa
<220> FEATURE:
<221> NAME/KEY: CDS
<222> LOCATION: (1)..(1278)

<400> SEQUENCE: 21 atg aaa ctg gaa acc ctg gcc gtc cac gcc ggc tac agc cct gac ccg      48
Met Lys Leu Glu Thr Leu Ala Val His Ala Gly Tyr Ser Pro Asp Pro
1               5                   10                  15 acc acc cgc gcg gtg gcg gtg ccg atc tac cag acc acc tcc tac gcc      96
Thr Thr Arg Ala Val Ala Val Pro Ile Tyr Gln Thr Thr Ser Tyr Ala
                20                  25                  30 ttc gac gac acc cag cat ggc gcc gac ctg ttc gac ctg aag gta ccg     144
Phe Asp Asp Thr Gln His Gly Ala Asp Leu Phe Asp Leu Lys Val Pro
            35                  40                  45 ggc aac atc tac aca cgg atc atg aac ccc acc aac gac gta ctg gaa     192
Gly Asn Ile Tyr Thr Arg Ile Met Asn Pro Thr Asn Asp Val Leu Glu
        50                  55                  60 cag cgc gtc gcg gcg ctg gaa ggc ggg gtc ggg gcg ctg gcg gtg gcc     240
Gln Arg Val Ala Ala Leu Glu Gly Gly Val Gly Ala Leu Ala Val Ala
65                  70                  75                  80 tcg ggg atg gcg gcc atc acc tac gcg atc cag acc gtc gcc gag gcc     288
Ser Gly Met Ala Ala Ile Thr Tyr Ala Ile Gln Thr Val Ala Glu Ala
                85                  90                  95 ggc gac aac atc gtc tcg gtg gcc aag ctc tac ggc ggc acc tac aac     336
Gly Asp Asn Ile Val Ser Val Ala Lys Leu Tyr Gly Gly Thr Tyr Asn
            100                 105                 110 ctg ctg gcc cac acc ctg cca cgc atc ggc atc cag gcg cgc ttc gcc     384
Leu Leu Ala His Thr Leu Pro Arg Ile Gly Ile Gln Ala Arg Phe Ala
        115                 120                 125 gcc cac gac gac gtc gcc gcc ctg gaa gcg ctg atc gac gag cgg acc     432
Ala His Asp Asp Val Ala Ala Leu Glu Ala Leu Ile Asp Glu Arg Thr
    130                 135                 140 aag gcc gtg ttc tgc gaa acc atc ggc aac ccg gcg ggc aac atc atc     480
Lys Ala Val Phe Cys Glu Thr Ile Gly Asn Pro Ala Gly Asn Ile Ile
145                 150                 155                 160 gac ctg cag gca ctg gcc gac gcc gct cac cgc cac ggc gtg cca ctg     528
Asp Leu Gln Ala Leu Ala Asp Ala Ala His Arg His Gly Val Pro Leu
                165                 170                 175 atc gtc gac aac acg gta gcc acc ccg gtg ctc tgc cgg ccg ttc gag     576
Ile Val Asp Asn Thr Val Ala Thr Pro Val Leu Cys Arg Pro Phe Glu
            180                 185                 190 cac ggc gcc gac atc gtc gtg cac tcg ctg acc aag tac atg ggc ggc     624
```

```
cac ggc acc agc atc ggc ggg atc gtg gtc gac tcc ggc aaa ttc gac      672
His Gly Thr Ser Ile Gly Gly Ile Val Val Asp Ser Gly Lys Phe Asp
        210                 215                 220 tgg gcg gcg aac aag tcg cgc ttc ccg ctg ctg aac acg ccc gat ccg      720
Trp Ala Ala Asn Lys Ser Arg Phe Pro Leu Leu Asn Thr Pro Asp Pro
225                 230                 235                 240 tcc tac cac ggc gtc acc tac acc gag gcc ttc gga ccc gcc gcc ttc      768
Ser Tyr His Gly Val Thr Tyr Thr Glu Ala Phe Gly Pro Ala Ala Phe
                245                 250                 255 atc ggc cgc tgc cgg gtg gta ccg ctg cgc aac atg ggc gcg gcg ctc      816
Ile Gly Arg Cys Arg Val Val Pro Leu Arg Asn Met Gly Ala Ala Leu
            260                 265                 270 tcg ccg ttc aac gcc ttc ctc atc ctc caa ggc ctg gag acc ctg gcg      864
Ser Pro Phe Asn Ala Phe Leu Ile Leu Gln Gly Leu Glu Thr Leu Ala
        275                 280                 285 ctg cgc atg gag cgc cac tgc gac aac gcc ctc gcc gtg gcc cgc tac      912
Leu Arg Met Glu Arg His Cys Asp Asn Ala Leu Ala Val Ala Arg Tyr
    290                 295                 300 ctg cag cag cat ccg cag gtg gcc tgg gtg aaa tac gcc ggc ctc gcc      960
Leu Gln Gln His Pro Gln Val Ala Trp Val Lys Tyr Ala Gly Leu Ala
305                 310                 315                 320 gac aac ccc gag cac gcc ctg gcc cgg cgc tac ctg ggg ggc cgc ccg     1008
Asp Asn Pro Glu His Ala Leu Ala Arg Arg Tyr Leu Gly Gly Arg Pro
                325                 330                 335 gcg gcg atc ctg tct ttc ggc atc cag ggc ggc agc gcc gcc ggc gcg     1056
Ala Ala Ile Leu Ser Phe Gly Ile Gln Gly Gly Ser Ala Ala Gly Ala
            340                 345                 350 cgc ttc atc gac gcc ttg aag ctg gtg gtg cgg ctg gtc aac atc ggc     1104
Arg Phe Ile Asp Ala Leu Lys Leu Val Val Arg Leu Val Asn Ile Gly
        355                 360                 365 gac gcc aag tcc ctg gcc tgc cac ccg gcg agc acc acc cac cgc cag     1152
Asp Ala Lys Ser Leu Ala Cys His Pro Ala Ser Thr Thr His Arg Gln
    370                 375                 380 ttg aac gcg gag gaa ctg gcc cgc gcc gga gtc tcc gac gac atg gtg     1200
Leu Asn Ala Glu Glu Leu Ala Arg Ala Gly Val Ser Asp Asp Met Val
385                 390                 395                 400 cgg ctg tcg atc ggc atc gag cac atc gac gac atc ctc gcc gac ctc     1248
Arg Leu Ser Ile Gly Ile Glu His Ile Asp Asp Ile Leu Ala Asp Leu
                405                 410                 415 gac cag gcc ctg gcc gcc gcc gca cgc tga                             1278
Asp Gln Ala Leu Ala Ala Ala Ala Arg
            420                 425

<210> SEQ ID NO 22
<211> LENGTH: 425
<212> TYPE: PRT
<213> ORGANISM: Pseudomonas aeruginosa

<400> SEQUENCE: 22

Met Lys Leu Glu Thr Leu Ala Val His Ala Gly Tyr Ser Pro Asp Pro
1               5                   10                  15

Thr Thr Arg Ala Val Ala Val Pro Ile Tyr Gln Thr Thr Ser Tyr Ala
                20                  25                  30

Phe Asp Asp Thr Gln His Gly Ala Asp Leu Phe Asp Leu Lys Val Pro
            35                  40                  45

Gly Asn Ile Tyr Thr Arg Ile Met Asn Pro Thr Asn Asp Val Leu Glu
        50                  55                  60
```

```
Gln Arg Val Ala Ala Leu Glu Gly Gly Val Gly Ala Leu Ala Val Ala
 65                  70                  75                  80

Ser Gly Met Ala Ala Ile Thr Tyr Ala Ile Gln Thr Val Ala Glu Ala
             85                  90                  95

Gly Asp Asn Ile Val Ser Val Ala Lys Leu Tyr Gly Gly Thr Tyr Asn
            100                 105                 110

Leu Leu Ala His Thr Leu Pro Arg Ile Gly Ile Gln Ala Arg Phe Ala
            115                 120                 125

Ala His Asp Asp Val Ala Ala Leu Glu Ala Leu Ile Asp Glu Arg Thr
        130                 135                 140

Lys Ala Val Phe Cys Glu Thr Ile Gly Asn Pro Ala Gly Asn Ile Ile
145                 150                 155                 160

Asp Leu Gln Ala Leu Ala Asp Ala Ala His Arg His Gly Val Pro Leu
                165                 170                 175

Ile Val Asp Asn Thr Val Ala Thr Pro Val Leu Cys Arg Pro Phe Glu
            180                 185                 190

His Gly Ala Asp Ile Val Val His Ser Leu Thr Lys Tyr Met Gly Gly
        195                 200                 205

His Gly Thr Ser Ile Gly Gly Ile Val Val Asp Ser Gly Lys Phe Asp
    210                 215                 220

Trp Ala Ala Asn Lys Ser Arg Phe Pro Leu Leu Asn Thr Pro Asp Pro
225                 230                 235                 240

Ser Tyr His Gly Val Thr Tyr Thr Glu Ala Phe Gly Pro Ala Ala Phe
                245                 250                 255

Ile Gly Arg Cys Arg Val Val Pro Leu Arg Asn Met Gly Ala Ala Leu
            260                 265                 270

Ser Pro Phe Asn Ala Phe Leu Ile Leu Gln Gly Leu Glu Thr Leu Ala
        275                 280                 285

Leu Arg Met Glu Arg His Cys Asp Asn Ala Leu Ala Val Ala Arg Tyr
    290                 295                 300

Leu Gln Gln His Pro Gln Val Ala Trp Val Lys Tyr Ala Gly Leu Ala
305                 310                 315                 320

Asp Asn Pro Glu His Ala Leu Ala Arg Arg Tyr Leu Gly Gly Arg Pro
                325                 330                 335

Ala Ala Ile Leu Ser Phe Gly Ile Gln Gly Gly Ser Ala Ala Gly Ala
            340                 345                 350

Arg Phe Ile Asp Ala Leu Lys Leu Val Val Arg Leu Val Asn Ile Gly
        355                 360                 365

Asp Ala Lys Ser Leu Ala Cys His Pro Ala Ser Thr Thr His Arg Gln
    370                 375                 380

Leu Asn Ala Glu Glu Leu Ala Arg Ala Gly Val Ser Asp Asp Met Val
385                 390                 395                 400

Arg Leu Ser Ile Gly Ile Glu His Ile Asp Asp Ile Leu Ala Asp Leu
                405                 410                 415

Asp Gln Ala Leu Ala Ala Ala Arg
            420                 425

<210> SEQ ID NO 23
<211> LENGTH: 1296
<212> TYPE: DNA
<213> ORGANISM: Bordetella bronchiseptica
<220> FEATURE:
<221> NAME/KEY: CDS
<222> LOCATION: (1)..(1296)

<400> SEQUENCE: 23
```

```
atg agc gaa ccg aac caa ccc atc tgg cgg ctg gag acc atc gcc gta      48
Met Ser Glu Pro Asn Gln Pro Ile Trp Arg Leu Glu Thr Ile Ala Val
1               5                   10                  15 cat ggg ggc tac cgg ccc gac ccg acc acg cgc gcg gtg gcg gtg ccg      96
His Gly Gly Tyr Arg Pro Asp Pro Thr Thr Arg Ala Val Ala Val Pro
                20                  25                  30 atc tac cag acc gtg gcc tat gcg ttc gac gac acc cag cat ggc gcg     144
Ile Tyr Gln Thr Val Ala Tyr Ala Phe Asp Asp Thr Gln His Gly Ala
        35                  40                  45 gac ctg ttc gac ctg aag gtg ccg ggc aat atc tac acc cgc atc atg     192
Asp Leu Phe Asp Leu Lys Val Pro Gly Asn Ile Tyr Thr Arg Ile Met
50                  55                  60 aac ccc acc acc gac gtg ctg gag cag cgc gtg gcg gcg ctg gaa tgc     240
Asn Pro Thr Thr Asp Val Leu Glu Gln Arg Val Ala Ala Leu Glu Cys
65                  70                  75                  80 ggc gtg gcc gcg ctg gcg ctg gcc tcc ggc cag gcg gcg gtg acc tat     288
Gly Val Ala Ala Leu Ala Leu Ala Ser Gly Gln Ala Ala Val Thr Tyr
                85                  90                  95 gcg atc ctg acc atc gcc gag gcg ggc gac aac atc gtg tcg tcc agc     336
Ala Ile Leu Thr Ile Ala Glu Ala Gly Asp Asn Ile Val Ser Ser Ser
        100                 105                 110 acg ctg tat ggc ggc acg tac aac ctg ttc gcc cac acg ctg ccg cag     384
Thr Leu Tyr Gly Gly Thr Tyr Asn Leu Phe Ala His Thr Leu Pro Gln
                115                 120                 125 tac ggc atc acg acc cgc ttc gcc gat ccg cgc aac ctg gct tcg ttc     432
Tyr Gly Ile Thr Thr Arg Phe Ala Asp Pro Arg Asn Leu Ala Ser Phe
130                 135                 140 gag gcg ctg atc gac gag cgc acc aag gcc att ttc gcc gag tcg gtg     480
Glu Ala Leu Ile Asp Glu Arg Thr Lys Ala Ile Phe Ala Glu Ser Val
145                 150                 155                 160 ggc aat ccg ctg ggc aac gtc acc gac atc gcc gcg ctg gcc gag atc     528
Gly Asn Pro Leu Gly Asn Val Thr Asp Ile Ala Ala Leu Ala Glu Ile
                165                 170                 175 gcg cac cgc cat ggc gtg ccg ctg atc gtc gac aac acg gtg ccg tcg     576
Ala His Arg His Gly Val Pro Leu Ile Val Asp Asn Thr Val Pro Ser
        180                 185                 190 ccc tac ctg ctg cgc ccc atc gag cac ggc gcc gac atc gtg gtg cag     624
Pro Tyr Leu Leu Arg Pro Ile Glu His Gly Ala Asp Ile Val Val Gln
                195                 200                 205 tcg ctc acc aag tac ctg ggc ggg cac ggc acc agc ctg ggc ggg gcc     672
Ser Leu Thr Lys Tyr Leu Gly Gly His Gly Thr Ser Leu Gly Gly Ala
210                 215                 220 atc atc gat tcg ggc aag ttt ccc tgg gcc gag cac aag gcg cgc ttc     720
Ile Ile Asp Ser Gly Lys Phe Pro Trp Ala Glu His Lys Ala Arg Phe
225                 230                 235                 240 aag cgc ctg aac gag ccc gac gtg agc tac cac ggc gtg gtc tac acc     768
Lys Arg Leu Asn Glu Pro Asp Val Ser Tyr His Gly Val Val Tyr Thr
                245                 250                 255 gag gcg ttc ggc gcg gcg gcc tat atc ggc cgc gcc cgc gtg gtg ccg     816
Glu Ala Phe Gly Ala Ala Ala Tyr Ile Gly Arg Ala Arg Val Val Pro
        260                 265                 270 ctg cgc aat acc ggc gcg gcc att tcg ccg ttc aac gcc ttc cag atc     864
Leu Arg Asn Thr Gly Ala Ala Ile Ser Pro Phe Asn Ala Phe Gln Ile
                275                 280                 285 ctg cag ggc atc gag acg ctg gcg ctg cgc gtg gac cgc atc gtc gag     912
Leu Gln Gly Ile Glu Thr Leu Ala Leu Arg Val Asp Arg Ile Val Glu
290                 295                 300 aac tcg gtc aag gtg gcc ggg ttc ctg cgc gac cat ccc aag gtc gaa     960
Asn Ser Val Lys Val Ala Gly Phe Leu Arg Asp His Pro Lys Val Glu
```

```
                    305                 310                 315                 320
tgg gtc aac tat gcc ggc ctg ccc gac cat gcc gac cat gcg ctg gtg    1008
Trp Val Asn Tyr Ala Gly Leu Pro Asp His Ala Asp His Ala Leu Val
                    325                 330                 335 cgc aag tac atg ggc ggc aag gcc ccc ggc ctg ttc act ttc ggc gtg    1056
Arg Lys Tyr Met Gly Gly Lys Ala Pro Gly Leu Phe Thr Phe Gly Val
                340                 345                 350 aag ggc ggc cgc gag gcc ggc gcg cgc ttc cag gac gcc ttg cag ctg    1104
Lys Gly Gly Arg Glu Ala Gly Ala Arg Phe Gln Asp Ala Leu Gln Leu
            355                 360                 365 ttc acc cgc ctg gtg aac atc ggc gac gcc aag tcg ctg gcc acg cac    1152
Phe Thr Arg Leu Val Asn Ile Gly Asp Ala Lys Ser Leu Ala Thr His
370                 375                 380 ccg gct tcc acc acg cac cgc cag ctc aac ccc gaa gag ctc gaa aag    1200
Pro Ala Ser Thr Thr His Arg Gln Leu Asn Pro Glu Glu Leu Glu Lys
385                 390                 395                 400 gcc ggc gtg cgc gag gaa acg gtg cgc ctg tcg atc ggg atc gag cat    1248
Ala Gly Val Arg Glu Glu Thr Val Arg Leu Ser Ile Gly Ile Glu His
                405                 410                 415 atc gac gac ctg atc gcc gac ctg gaa cag gcg ctg gcg caa gtc tga    1296
Ile Asp Asp Leu Ile Ala Asp Leu Glu Gln Ala Leu Ala Gln Val
            420                 425                 430

<210> SEQ ID NO 24
<211> LENGTH: 431
<212> TYPE: PRT
<213> ORGANISM: Bordetella bronchiseptica

<400> SEQUENCE: 24

Met Ser Glu Pro Asn Gln Pro Ile Trp Arg Leu Glu Thr Ile Ala Val
1               5                   10                  15

His Gly Gly Tyr Arg Pro Asp Pro Thr Thr Arg Ala Val Ala Val Pro
            20                  25                  30

Ile Tyr Gln Thr Val Ala Tyr Ala Phe Asp Asp Thr Gln His Gly Ala
        35                  40                  45

Asp Leu Phe Asp Leu Lys Val Pro Gly Asn Ile Tyr Thr Arg Ile Met
    50                  55                  60

Asn Pro Thr Thr Asp Val Leu Glu Gln Arg Val Ala Ala Leu Glu Cys
65                  70                  75                  80

Gly Val Ala Ala Leu Ala Leu Ala Ser Gly Gln Ala Ala Val Thr Tyr
                85                  90                  95

Ala Ile Leu Thr Ile Ala Glu Ala Gly Asp Asn Ile Val Ser Ser Ser
            100                 105                 110

Thr Leu Tyr Gly Gly Thr Tyr Asn Leu Phe Ala His Thr Leu Pro Gln
        115                 120                 125

Tyr Gly Ile Thr Thr Arg Phe Ala Asp Pro Arg Asn Leu Ala Ser Phe
    130                 135                 140

Glu Ala Leu Ile Asp Glu Arg Thr Lys Ala Ile Phe Ala Glu Ser Val
145                 150                 155                 160

Gly Asn Pro Leu Gly Asn Val Thr Asp Ile Ala Ala Leu Ala Glu Ile
                165                 170                 175

Ala His Arg His Gly Val Pro Leu Ile Val Asp Asn Thr Val Pro Ser
            180                 185                 190

Pro Tyr Leu Leu Arg Pro Ile Glu His Gly Ala Asp Ile Val Val Gln
        195                 200                 205

Ser Leu Thr Lys Tyr Leu Gly Gly His Gly Thr Ser Leu Gly Gly Ala
    210                 215                 220
```

```
Ile Ile Asp Ser Gly Lys Phe Pro Trp Ala Glu His Lys Ala Arg Phe
225                 230                 235                 240

Lys Arg Leu Asn Glu Pro Asp Val Ser Tyr His Gly Val Val Tyr Thr
            245                 250                 255

Glu Ala Phe Gly Ala Ala Ala Tyr Ile Gly Arg Ala Arg Val Val Pro
                260                 265                 270

Leu Arg Asn Thr Gly Ala Ala Ile Ser Pro Phe Asn Ala Phe Gln Ile
            275                 280                 285

Leu Gln Gly Ile Glu Thr Leu Ala Leu Arg Val Asp Arg Ile Val Glu
        290                 295                 300

Asn Ser Val Lys Val Ala Gly Phe Leu Arg Asp His Pro Lys Val Glu
305                 310                 315                 320

Trp Val Asn Tyr Ala Gly Leu Pro Asp His Ala Asp His Ala Leu Val
                325                 330                 335

Arg Lys Tyr Met Gly Gly Lys Ala Pro Gly Leu Phe Thr Phe Gly Val
                340                 345                 350

Lys Gly Gly Arg Glu Ala Gly Ala Arg Phe Gln Asp Ala Leu Gln Leu
            355                 360                 365

Phe Thr Arg Leu Val Asn Ile Gly Asp Ala Lys Ser Leu Ala Thr His
370                 375                 380

Pro Ala Ser Thr Thr His Arg Gln Leu Asn Pro Glu Glu Leu Glu Lys
385                 390                 395                 400

Ala Gly Val Arg Glu Glu Thr Val Arg Leu Ser Ile Gly Ile Glu His
                405                 410                 415

Ile Asp Asp Leu Ile Ala Asp Leu Glu Gln Ala Leu Ala Gln Val
                420                 425                 430

<210> SEQ ID NO 25
<211> LENGTH: 1269
<212> TYPE: DNA
<213> ORGANISM: Nitrosomonas europaea
<220> FEATURE:
<221> NAME/KEY: CDS
<222> LOCATION: (1)..(1269)

<400> SEQUENCE: 25 atg aaa cgg gaa aca ctc gcc att cat ggc ggt ttt gcc ggc gat ccg      48
Met Lys Arg Glu Thr Leu Ala Ile His Gly Gly Phe Ala Gly Asp Pro
1               5                   10                  15 cag act cat gca gtc gcg gtc ccc att tac cag acc acc agc tac tat      96
Gln Thr His Ala Val Ala Val Pro Ile Tyr Gln Thr Thr Ser Tyr Tyr
            20                  25                  30 ttt gat gat act cag cac ggg gct gat ttg ttt gat ctg aag gtg cag     144
Phe Asp Asp Thr Gln His Gly Ala Asp Leu Phe Asp Leu Lys Val Gln
        35                  40                  45 ggt aac atc tac aca cgc atc atg aac ccg act act gct gtc ctg gaa     192
Gly Asn Ile Tyr Thr Arg Ile Met Asn Pro Thr Thr Ala Val Leu Glu
    50                  55                  60 gaa aga gtg gcg tta ctg gaa gga gga gtg gga gcg ctg gcc atg gct     240
Glu Arg Val Ala Leu Leu Glu Gly Gly Val Gly Ala Leu Ala Met Ala
65                  70                  75                  80 tcc ggc atg gcc gcc att aca gcc tgt gtg cag act ctg gcc agg gcg     288
Ser Gly Met Ala Ala Ile Thr Ala Cys Val Gln Thr Leu Ala Arg Ala
                85                  90                  95 ggc gac aac att atc tcc acc agc cag gtt tac ggt ggc acc tat aat     336
Gly Asp Asn Ile Ile Ser Thr Ser Gln Val Tyr Gly Gly Thr Tyr Asn
            100                 105                 110
```

-continued

| | | |
|---|---|---|
| ttc ttt tgc cat acg ttg ccc aat ctg ggt att gaa gtt cgc atg gtg<br>Phe Phe Cys His Thr Leu Pro Asn Leu Gly Ile Glu Val Arg Met Val<br>115                             120                        125 | | 384 |
| gat ggt cgt aat ccg gcc gct ttt gcc gat gcc atc gat gac aat acc<br>Asp Gly Arg Asn Pro Ala Ala Phe Ala Asp Ala Ile Asp Asp Asn Thr<br>      130                          135                        140 | | 432 |
| aga atg att tat tgc gag tcg atc gga aat ccg gcc ggt aat gtg gtg<br>Arg Met Ile Tyr Cys Glu Ser Ile Gly Asn Pro Ala Gly Asn Val Val<br>145                             150                        155                        160 | | 480 |
| gat atc gcc gca ctg gct gaa gtg gcg cat gca gcg ggc gtg ccg ctg<br>Asp Ile Ala Ala Leu Ala Glu Val Ala His Ala Ala Gly Val Pro Leu<br>                    165                        170                        175 | | 528 |
| gta gtg gac aat acc gta cca acc ccg gtg ctt tgt cgt cct ttc gaa<br>Val Val Asp Asn Thr Val Pro Thr Pro Val Leu Cys Arg Pro Phe Glu<br>                180                        185                        190 | | 576 |
| cat ggt gcc gat atc gtc gtc cat gcg ctg acc aaa tac atg ggt ggt<br>His Gly Ala Asp Ile Val Val His Ala Leu Thr Lys Tyr Met Gly Gly<br>                    195                        200                        205 | | 624 |
| cac ggc acc agc atc ggc gga atc atc gtg gat tcc ggc aag ttc ccc<br>His Gly Thr Ser Ile Gly Gly Ile Ile Val Asp Ser Gly Lys Phe Pro<br>      210                          215                        220 | | 672 |
| tgg gaa ggc aac tcg cgt ttt cca caa ttc aac caa cct gat ccc agc<br>Trp Glu Gly Asn Ser Arg Phe Pro Gln Phe Asn Gln Pro Asp Pro Ser<br>225                             230                        235                        240 | | 720 |
| tat cac ggt gtg gtt tat gtg gat gca ttt ggt ccg gct gcg ttt atc<br>Tyr His Gly Val Val Tyr Val Asp Ala Phe Gly Pro Ala Ala Phe Ile<br>                    245                        250                        255 | | 768 |
| ggc cgt gcg cgt gtg gta ccg ttg cgc aac atg gga gcg gca att tca<br>Gly Arg Ala Arg Val Val Pro Leu Arg Asn Met Gly Ala Ala Ile Ser<br>                  260                        265                        270 | | 816 |
| cct ttc aat tct ttt ctg att ctg caa ggt atc gaa acc ctg ccg ttg<br>Pro Phe Asn Ser Phe Leu Ile Leu Gln Gly Ile Glu Thr Leu Pro Leu<br>            275                        280                        285 | | 864 |
| agg atg gaa cgg cat tgc acc aat gcg ctg gcg att gca cgt tat ctg<br>Arg Met Glu Arg His Cys Thr Asn Ala Leu Ala Ile Ala Arg Tyr Leu<br>                290                        295                        300 | | 912 |
| caa agg cat ccc aaa gtc agc tgg gtc aat ttt gcc ggc ctt gaa gat<br>Gln Arg His Pro Lys Val Ser Trp Val Asn Phe Ala Gly Leu Glu Asp<br>305                             310                        315                        320 | | 960 |
| aac cgt gat tac gca ctg gtg cag aaa tac atg gat ggc ggt att ccc<br>Asn Arg Asp Tyr Ala Leu Val Gln Lys Tyr Met Asp Gly Gly Ile Pro<br>                    325                        330                        335 | | 1008 |
| tca tcg att ctg agt ttt ggc atc aag ggc ggg cgc gag gct tgt gct<br>Ser Ser Ile Leu Ser Phe Gly Ile Lys Gly Gly Arg Glu Ala Cys Ala<br>                340                        345                        350 | | 1056 |
| cgc ttt atg gac aga ctg atg ctg atc aaa cgg ctg gtc aac atc ggg<br>Arg Phe Met Asp Arg Leu Met Leu Ile Lys Arg Leu Val Asn Ile Gly<br>            355                        360                        365 | | 1104 |
| gat gcc aaa acg ctg gcc tgc cac ccg gcg acg acc acc cac cgt cag<br>Asp Ala Lys Thr Leu Ala Cys His Pro Ala Thr Thr Thr His Arg Gln<br>      370                          375                        380 | | 1152 |
| ctc aat gat gaa gaa ctg gca aaa gcc ggt gtc agt gct gat ctg gtg<br>Leu Asn Asp Glu Glu Leu Ala Lys Ala Gly Val Ser Ala Asp Leu Val<br>385                             390                        395                        400 | | 1200 |
| cgt tta tgt gtc ggc atc gag cat att gac gat ctg att gcc gat gta<br>Arg Leu Cys Val Gly Ile Glu His Ile Asp Asp Leu Ile Ala Asp Val<br>                    405                        410                        415 | | 1248 |
| gag cag gct ttc cag gat tag<br>Glu Gln Ala Phe Gln Asp<br>                    420 | | 1269 |

<210> SEQ ID NO 26
<211> LENGTH: 422
<212> TYPE: PRT
<213> ORGANISM: Nitrosomonas europaea

<400> SEQUENCE: 26

Met Lys Arg Glu Thr Leu Ala Ile His Gly Gly Phe Ala Gly Asp Pro
1               5                   10                  15

Gln Thr His Ala Val Ala Val Pro Ile Tyr Gln Thr Thr Ser Tyr Tyr
                20                  25                  30

Phe Asp Asp Thr Gln His Gly Ala Asp Leu Phe Asp Leu Lys Val Gln
            35                  40                  45

Gly Asn Ile Tyr Thr Arg Ile Met Asn Pro Thr Thr Ala Val Leu Glu
        50                  55                  60

Glu Arg Val Ala Leu Leu Glu Gly Gly Val Gly Ala Leu Ala Met Ala
65                  70                  75                  80

Ser Gly Met Ala Ala Ile Thr Ala Cys Val Gln Thr Leu Ala Arg Ala
                85                  90                  95

Gly Asp Asn Ile Ile Ser Thr Ser Gln Val Tyr Gly Gly Thr Tyr Asn
            100                 105                 110

Phe Phe Cys His Thr Leu Pro Asn Leu Gly Ile Glu Val Arg Met Val
        115                 120                 125

Asp Gly Arg Asn Pro Ala Ala Phe Ala Asp Ala Ile Asp Asp Asn Thr
    130                 135                 140

Arg Met Ile Tyr Cys Glu Ser Ile Gly Asn Pro Ala Gly Asn Val Val
145                 150                 155                 160

Asp Ile Ala Ala Leu Ala Glu Val Ala His Ala Ala Gly Val Pro Leu
                165                 170                 175

Val Val Asp Asn Thr Val Pro Thr Pro Val Leu Cys Arg Pro Phe Glu
            180                 185                 190

His Gly Ala Asp Ile Val Val His Ala Leu Thr Lys Tyr Met Gly Gly
        195                 200                 205

His Gly Thr Ser Ile Gly Gly Ile Ile Val Asp Ser Gly Lys Phe Pro
    210                 215                 220

Trp Glu Gly Asn Ser Arg Phe Pro Gln Phe Asn Gln Pro Asp Pro Ser
225                 230                 235                 240

Tyr His Gly Val Val Tyr Val Asp Ala Phe Gly Pro Ala Ala Phe Ile
                245                 250                 255

Gly Arg Ala Arg Val Val Pro Leu Arg Asn Met Gly Ala Ala Ile Ser
            260                 265                 270

Pro Phe Asn Ser Phe Leu Ile Leu Gln Gly Ile Glu Thr Leu Pro Leu
        275                 280                 285

Arg Met Glu Arg His Cys Thr Asn Ala Leu Ala Ile Ala Arg Tyr Leu
    290                 295                 300

Gln Arg His Pro Lys Val Ser Trp Val Asn Phe Ala Gly Leu Glu Asp
305                 310                 315                 320

Asn Arg Asp Tyr Ala Leu Val Gln Lys Tyr Met Asp Gly Gly Ile Pro
                325                 330                 335

Ser Ser Ile Leu Ser Phe Gly Ile Lys Gly Gly Arg Glu Ala Cys Ala
            340                 345                 350

Arg Phe Met Asp Arg Leu Met Leu Ile Lys Arg Leu Val Asn Ile Gly
        355                 360                 365

Asp Ala Lys Thr Leu Ala Cys His Pro Ala Thr Thr Thr His Arg Gln

```
              370                 375                 380
Leu Asn Asp Glu Glu Leu Ala Lys Ala Gly Val Ser Ala Asp Leu Val
385                 390                 395                 400

Arg Leu Cys Val Gly Ile Glu His Ile Asp Asp Leu Ile Ala Asp Val
                405                 410                 415

Glu Gln Ala Phe Gln Asp
            420

<210> SEQ ID NO 27
<211> LENGTH: 1281
<212> TYPE: DNA
<213> ORGANISM: Sinorhizobium meliloti
<220> FEATURE:
<221> NAME/KEY: CDS
<222> LOCATION: (1)..(1281)

<400> SEQUENCE: 27 atg aaa gcc gga ccc gga ttc agc acg ctt gca att cac gcc ggg gcc     48
Met Lys Ala Gly Pro Gly Phe Ser Thr Leu Ala Ile His Ala Gly Ala
1               5                   10                  15 cag ccc gat ccg acg acc ggt gcg cgg gcg acg ccg atc tat cag acg     96
Gln Pro Asp Pro Thr Thr Gly Ala Arg Ala Thr Pro Ile Tyr Gln Thr
            20                  25                  30 acc agc ttc gtc ttc aac gac acg gat cat gcg gcc gca ctc ttc ggc    144
Thr Ser Phe Val Phe Asn Asp Thr Asp His Ala Ala Ala Leu Phe Gly
        35                  40                  45 ctc cag caa ttc ggc aat atc tat acc cgc atc atg aat ccg acg cag    192
Leu Gln Gln Phe Gly Asn Ile Tyr Thr Arg Ile Met Asn Pro Thr Gln
    50                  55                  60 gcg gtg ctg gag gag cgg atc gcg gcg ctc gaa ggc ggg acc gcc ggg    240
Ala Val Leu Glu Glu Arg Ile Ala Ala Leu Glu Gly Gly Thr Ala Gly
65                  70                  75                  80 ctg gcc gtt tcc tcg ggg cat gcg gcc cag ctg ctg gtt ttc cat acg    288
Leu Ala Val Ser Ser Gly His Ala Ala Gln Leu Leu Val Phe His Thr
                85                  90                  95 atc atg agg ccg ggt gac aat ttc gtt tcc gcc aga cag ctt tac ggc    336
Ile Met Arg Pro Gly Asp Asn Phe Val Ser Ala Arg Gln Leu Tyr Gly
            100                 105                 110 ggg tcg gcc aat cag ttc ggc cat gcc ttc aag gcc ttc gac tgg cag    384
Gly Ser Ala Asn Gln Phe Gly His Ala Phe Lys Ala Phe Asp Trp Gln
        115                 120                 125 gtc cgc tgg gcc gat tcg gcg gag ccc gaa agc ttc gat gcg cag atc    432
Val Arg Trp Ala Asp Ser Ala Glu Pro Glu Ser Phe Asp Ala Gln Ile
    130                 135                 140 gac gaa cgc acc aag gcg atc ttc atc gaa agc ctc gcc aat ccg ggc    480
Asp Glu Arg Thr Lys Ala Ile Phe Ile Glu Ser Leu Ala Asn Pro Gly
145                 150                 155                 160 ggc acc ttc gtc gac ata gcc gca atc gct gac gtt gcg cgg cga cac    528
Gly Thr Phe Val Asp Ile Ala Ala Ile Ala Asp Val Ala Arg Arg His
                165                 170                 175 gga ctg ccg ctc atc gtc gac aat acg atg gcg acg ccc tat ctg atg    576
Gly Leu Pro Leu Ile Val Asp Asn Thr Met Ala Thr Pro Tyr Leu Met
            180                 185                 190 cgg ccg ctc gaa cac ggc gcc gat atc gtc gtc cat tcg ctc acc aag    624
Arg Pro Leu Glu His Gly Ala Asp Ile Val Val His Ser Leu Thr Lys
        195                 200                 205 ttc atc ggc ggt cac ggc aat tcg atg ggc ggc atc atc gtc gac ggc    672
Phe Ile Gly Gly His Gly Asn Ser Met Gly Gly Ile Ile Val Asp Gly
    210                 215                 220 ggt acg ttc gac tgg tcg aaa tcc ggc aag tat ccg ctg ctg tcg gag    720
```

```
Gly Thr Phe Asp Trp Ser Lys Ser Gly Lys Tyr Pro Leu Leu Ser Glu
225                 230                 235                 240 ccg agg ccc gaa tat ggc ggc gtc gtc ctg cac cag gcc ttc ggc aac    768
Pro Arg Pro Glu Tyr Gly Gly Val Val Leu His Gln Ala Phe Gly Asn
                245                 250                 255 ttc gcc ttc gcc atc gcc gca cgg gta ttg ggt ctg agg gac ttc ggt    816
Phe Ala Phe Ala Ile Ala Ala Arg Val Leu Gly Leu Arg Asp Phe Gly
            260                 265                 270 ccg gcc att tcg ccc ttc aac gcc ttc ctg atc cag acc ggc gtc gag    864
Pro Ala Ile Ser Pro Phe Asn Ala Phe Leu Ile Gln Thr Gly Val Glu
        275                 280                 285 acg ctg ccg ctg agg atg cag cgc cat tgc gac aac gcg ctg gag gtc    912
Thr Leu Pro Leu Arg Met Gln Arg His Cys Asp Asn Ala Leu Glu Val
    290                 295                 300 gcc aaa tgg ctg aag gga cat gaa aag gtc tcc tgg gtc cgc tat tcc    960
Ala Lys Trp Leu Lys Gly His Glu Lys Val Ser Trp Val Arg Tyr Ser
305                 310                 315                 320 ggg ctc gaa gac gat ccg aac cac gca ctg cag aaa cgc tac tcg ccg   1008
Gly Leu Glu Asp Asp Pro Asn His Ala Leu Gln Lys Arg Tyr Ser Pro
                325                 330                 335 aag ggg gcg gga gcc gtt ttc acc ttc ggg ctc gcg ggc gga tac gag   1056
Lys Gly Ala Gly Ala Val Phe Thr Phe Gly Leu Ala Gly Gly Tyr Glu
            340                 345                 350 gcg gga aag cgc ttt gtc gag gca ctg gaa atg ttc tcc cat ctt gcc   1104
Ala Gly Lys Arg Phe Val Glu Ala Leu Glu Met Phe Ser His Leu Ala
        355                 360                 365 aat atc ggc gac acg cgt tcg ctc gtc atc cac ccc gca tcg acc acg   1152
Asn Ile Gly Asp Thr Arg Ser Leu Val Ile His Pro Ala Ser Thr Thr
    370                 375                 380 cac cgg cag ctc acg ccg gag cag cag gtc gcc gca ggc gcc gga ccc   1200
His Arg Gln Leu Thr Pro Glu Gln Gln Val Ala Ala Gly Ala Gly Pro
385                 390                 395                 400 gac gtc atc cgg ttg tcg gtc ggc atc gag gat gtg gcc gac atc att   1248
Asp Val Ile Arg Leu Ser Val Gly Ile Glu Asp Val Ala Asp Ile Ile
                405                 410                 415 gcc gat ctc gaa cag gcg ctg ggc aag gcc tga                        1281
Ala Asp Leu Glu Gln Ala Leu Gly Lys Ala
            420                 425

<210> SEQ ID NO 28
<211> LENGTH: 426
<212> TYPE: PRT
<213> ORGANISM: Sinorhizobium meliloti

<400> SEQUENCE: 28

Met Lys Ala Gly Pro Gly Phe Ser Thr Leu Ala Ile His Ala Gly Ala
1               5                   10                  15

Gln Pro Asp Pro Thr Thr Gly Ala Arg Ala Thr Pro Ile Tyr Gln Thr
                20                  25                  30

Thr Ser Phe Val Phe Asn Asp Thr Asp His Ala Ala Ala Leu Phe Gly
            35                  40                  45

Leu Gln Gln Phe Gly Asn Ile Tyr Thr Arg Ile Met Asn Pro Thr Gln
        50                  55                  60

Ala Val Leu Glu Glu Arg Ile Ala Ala Leu Glu Gly Gly Thr Ala Gly
65                  70                  75                  80

Leu Ala Val Ser Ser Gly His Ala Ala Gln Leu Leu Val Phe His Thr
                85                  90                  95

Ile Met Arg Pro Gly Asp Asn Phe Val Ser Ala Arg Gln Leu Tyr Gly
            100                 105                 110
```

```
Gly Ser Ala Asn Gln Phe Gly His Ala Phe Lys Ala Phe Asp Trp Gln
            115                 120                 125

Val Arg Trp Ala Asp Ser Ala Glu Pro Glu Ser Phe Asp Ala Gln Ile
        130                 135                 140

Asp Glu Arg Thr Lys Ala Ile Phe Ile Glu Ser Leu Ala Asn Pro Gly
145                 150                 155                 160

Gly Thr Phe Val Asp Ile Ala Ala Ile Ala Asp Val Ala Arg Arg His
                165                 170                 175

Gly Leu Pro Leu Ile Val Asp Asn Thr Met Ala Thr Pro Tyr Leu Met
            180                 185                 190

Arg Pro Leu Glu His Gly Ala Asp Ile Val Val His Ser Leu Thr Lys
        195                 200                 205

Phe Ile Gly Gly His Gly Asn Ser Met Gly Gly Ile Val Asp Gly
210                 215                 220

Gly Thr Phe Asp Trp Ser Lys Ser Gly Lys Tyr Pro Leu Leu Ser Glu
225                 230                 235                 240

Pro Arg Pro Glu Tyr Gly Gly Val Val Leu His Gln Ala Phe Gly Asn
                245                 250                 255

Phe Ala Phe Ala Ile Ala Ala Arg Val Leu Gly Leu Arg Asp Phe Gly
            260                 265                 270

Pro Ala Ile Ser Pro Phe Asn Ala Phe Leu Ile Gln Thr Gly Val Glu
        275                 280                 285

Thr Leu Pro Leu Arg Met Gln Arg His Cys Asp Asn Ala Leu Glu Val
290                 295                 300

Ala Lys Trp Leu Lys Gly His Glu Lys Val Ser Trp Val Arg Tyr Ser
305                 310                 315                 320

Gly Leu Glu Asp Asp Pro Asn His Ala Leu Gln Lys Arg Tyr Ser Pro
                325                 330                 335

Lys Gly Ala Gly Ala Val Phe Thr Phe Gly Leu Ala Gly Gly Tyr Glu
            340                 345                 350

Ala Gly Lys Arg Phe Val Glu Ala Leu Glu Met Phe Ser His Leu Ala
        355                 360                 365

Asn Ile Gly Asp Thr Arg Ser Leu Val Ile His Pro Ala Ser Thr Thr
370                 375                 380

His Arg Gln Leu Thr Pro Glu Gln Gln Val Ala Ala Gly Ala Gly Pro
385                 390                 395                 400

Asp Val Ile Arg Leu Ser Val Gly Ile Glu Asp Val Ala Asp Ile Ile
                405                 410                 415

Ala Asp Leu Glu Gln Ala Leu Gly Lys Ala
            420                 425

<210> SEQ ID NO 29
<211> LENGTH: 1293
<212> TYPE: DNA
<213> ORGANISM: Thermotoga maritima
<220> FEATURE:
<221> NAME/KEY: CDS
<222> LOCATION: (1)..(1293)

<400> SEQUENCE: 29 atg gac tgg aag aaa tac ggt tac aac aca agg gct ctt cac gca ggt     48
Met Asp Trp Lys Lys Tyr Gly Tyr Asn Thr Arg Ala Leu His Ala Gly
1               5                   10                  15 tat gaa cca ccc gag cag gcc aca gga tcg aga gcg gtc cct ata tat    96
Tyr Glu Pro Pro Glu Gln Ala Thr Gly Ser Arg Ala Val Pro Ile Tyr
            20                  25                  30
```

```
caa acg act tct tac gtt ttc aga gac tct gat cac gcg gcg aga ctc      144
Gln Thr Thr Ser Tyr Val Phe Arg Asp Ser Asp His Ala Ala Arg Leu
        35                  40                  45 ttc gca ctg gaa gaa cct ggg ttc atc tat aca agg att gga aat cct      192
Phe Ala Leu Glu Glu Pro Gly Phe Ile Tyr Thr Arg Ile Gly Asn Pro
 50                  55                  60 acc gtc tca gtt ctt gaa gaa aga ata gcc gcc ctg gaa gaa ggg gtg      240
Thr Val Ser Val Leu Glu Glu Arg Ile Ala Ala Leu Glu Glu Gly Val
 65                  70                  75                  80 gga gcc tta gcg gtt gcc agt gga caa gcc gct ata act tac gcc att      288
Gly Ala Leu Ala Val Ala Ser Gly Gln Ala Ala Ile Thr Tyr Ala Ile
                 85                  90                  95 ttg aac atc gcg ggc cca gga gat gag atc gtc agc ggg agc gcg ctg      336
Leu Asn Ile Ala Gly Pro Gly Asp Glu Ile Val Ser Gly Ser Ala Leu
            100                 105                 110 tat ggg gga acg tac aat ctg ttc aga cac act ctc tat aaa aaa tcc      384
Tyr Gly Gly Thr Tyr Asn Leu Phe Arg His Thr Leu Tyr Lys Lys Ser
        115                 120                 125 ggc atc atc gtg aag ttt gtg gat gag aca gat cca aag aac ata gaa      432
Gly Ile Ile Val Lys Phe Val Asp Glu Thr Asp Pro Lys Asn Ile Glu
130                 135                 140 gag gcc atc acc gag aaa aca aag gcg gtg tac ctt gaa act atc ggg      480
Glu Ala Ile Thr Glu Lys Thr Lys Ala Val Tyr Leu Glu Thr Ile Gly
145                 150                 155                 160 aat ccc ggt ctc aca gtg ccg gac ttt gaa gcg ata gcg gag atc gct      528
Asn Pro Gly Leu Thr Val Pro Asp Phe Glu Ala Ile Ala Glu Ile Ala
                165                 170                 175 cac aga cac ggt gtt cct ttg ata gtg gac aat acg gta gct ccg tac      576
His Arg His Gly Val Pro Leu Ile Val Asp Asn Thr Val Ala Pro Tyr
            180                 185                 190 ata ttc agg ccc ttc gaa cac ggt gcc gac atc gtt gtt tat tcg gcc      624
Ile Phe Arg Pro Phe Glu His Gly Ala Asp Ile Val Val Tyr Ser Ala
        195                 200                 205 acg aaa ttc atc gga gga cac gga aca tcg ata ggc ggt ctc atc gta      672
Thr Lys Phe Ile Gly Gly His Gly Thr Ser Ile Gly Gly Leu Ile Val
    210                 215                 220 gac agc gga aaa ttc gac tgg acg aac gga aag ttt cca gaa ctc gtg      720
Asp Ser Gly Lys Phe Asp Trp Thr Asn Gly Lys Phe Pro Glu Leu Val
225                 230                 235                 240 gaa cca gat ccc agc tac cac ggt gtg agt tat gtg gag acg ttc aaa      768
Glu Pro Asp Pro Ser Tyr His Gly Val Ser Tyr Val Glu Thr Phe Lys
                245                 250                 255 gaa gca gcc tac ata gca aaa tgt aga acc cag ctt ttg agg gac ctg      816
Glu Ala Ala Tyr Ile Ala Lys Cys Arg Thr Gln Leu Leu Arg Asp Leu
            260                 265                 270 gga agc tgt atg agc ccg ttc aac gcg ttt ctg ttc atc ctc gga ctt      864
Gly Ser Cys Met Ser Pro Phe Asn Ala Phe Leu Phe Ile Leu Gly Leu
        275                 280                 285 gaa acc ctc agc ttg agg atg aag aaa cac tgt gaa aac gca ctg aag      912
Glu Thr Leu Ser Leu Arg Met Lys Lys His Cys Glu Asn Ala Leu Lys
    290                 295                 300 atc gtt gaa ttt ctg aaa tcg cat ccc gcc gtg agc tgg gtc aac tat      960
Ile Val Glu Phe Leu Lys Ser His Pro Ala Val Ser Trp Val Asn Tyr
305                 310                 315                 320 ccg ata gct gaa ggc aat aaa acc aga gaa aat gcg ctg aaa tac ctc     1008
Pro Ile Ala Glu Gly Asn Lys Thr Arg Glu Asn Ala Leu Lys Tyr Leu
                325                 330                 335 aaa gaa gga tac ggt gcg att gta acg ttc ggt gtg aaa ggc gga aaa     1056
Lys Glu Gly Tyr Gly Ala Ile Val Thr Phe Gly Val Lys Gly Gly Lys
```

-continued

```
              340                 345                 350
gag gcg gga aag aag ttc ata gac agt ctc aca ctc att tcc cac ctc     1104
Glu Ala Gly Lys Lys Phe Ile Asp Ser Leu Thr Leu Ile Ser His Leu
            355                 360                 365 gcc aac att ggt gat gca aga act ctg gct att cat ccc gct tcg aca     1152
Ala Asn Ile Gly Asp Ala Arg Thr Leu Ala Ile His Pro Ala Ser Thr
        370                 375                 380 acc cat cag cag ctc acg gaa gaa gag cag ttg aaa acg ggt gtt act     1200
Thr His Gln Gln Leu Thr Glu Glu Glu Gln Leu Lys Thr Gly Val Thr
385                 390                 395                 400 ccg gat atg ata aga ttg tct gtt gga ata gaa gat gtg gaa gat atc     1248
Pro Asp Met Ile Arg Leu Ser Val Gly Ile Glu Asp Val Glu Asp Ile
                405                 410                 415 ata gcc gat ctg gat cag gct ctc aga aaa tct cag gag gga tga         1293
Ile Ala Asp Leu Asp Gln Ala Leu Arg Lys Ser Gln Glu Gly
            420                 425                 430
```

<210> SEQ ID NO 30
<211> LENGTH: 430
<212> TYPE: PRT
<213> ORGANISM: Thermotoga maritima

<400> SEQUENCE: 30

```
Met Asp Trp Lys Lys Tyr Gly Tyr Asn Thr Arg Ala Leu His Ala Gly
1               5                   10                  15

Tyr Glu Pro Pro Glu Gln Ala Thr Gly Ser Arg Ala Val Pro Ile Tyr
                20                  25                  30

Gln Thr Thr Ser Tyr Val Phe Arg Asp Ser Asp His Ala Ala Arg Leu
            35                  40                  45

Phe Ala Leu Glu Glu Pro Gly Phe Ile Tyr Thr Arg Ile Gly Asn Pro
        50                  55                  60

Thr Val Ser Val Leu Glu Glu Arg Ile Ala Ala Leu Glu Glu Gly Val
65                  70                  75                  80

Gly Ala Leu Ala Val Ala Ser Gly Gln Ala Ala Ile Thr Tyr Ala Ile
                85                  90                  95

Leu Asn Ile Ala Gly Pro Gly Asp Glu Ile Val Ser Gly Ser Ala Leu
            100                 105                 110

Tyr Gly Gly Thr Tyr Asn Leu Phe Arg His Thr Leu Tyr Lys Lys Ser
        115                 120                 125

Gly Ile Ile Val Lys Phe Val Asp Glu Thr Asp Pro Lys Asn Ile Glu
    130                 135                 140

Glu Ala Ile Thr Glu Lys Thr Lys Ala Val Tyr Leu Glu Thr Ile Gly
145                 150                 155                 160

Asn Pro Gly Leu Thr Val Pro Asp Phe Glu Ala Ile Ala Glu Ile Ala
                165                 170                 175

His Arg His Gly Val Pro Leu Ile Val Asp Asn Thr Val Ala Pro Tyr
            180                 185                 190

Ile Phe Arg Pro Phe Glu His Gly Ala Asp Ile Val Val Tyr Ser Ala
        195                 200                 205

Thr Lys Phe Ile Gly Gly His Gly Thr Ser Ile Gly Gly Leu Ile Val
    210                 215                 220

Asp Ser Gly Lys Phe Asp Trp Thr Asn Gly Lys Phe Pro Glu Leu Val
225                 230                 235                 240

Glu Pro Asp Pro Ser Tyr His Gly Val Ser Tyr Val Glu Thr Phe Lys
                245                 250                 255

Glu Ala Ala Tyr Ile Ala Lys Cys Arg Thr Gln Leu Leu Arg Asp Leu
```

```
                260                 265                 270
Gly Ser Cys Met Ser Pro Phe Asn Ala Phe Leu Phe Ile Leu Gly Leu
            275                 280                 285
Glu Thr Leu Ser Leu Arg Met Lys Lys His Cys Glu Asn Ala Leu Lys
        290                 295                 300
Ile Val Glu Phe Leu Lys Ser His Pro Ala Val Ser Trp Val Asn Tyr
305                 310                 315                 320
Pro Ile Ala Glu Gly Asn Lys Thr Arg Glu Asn Ala Leu Lys Tyr Leu
                325                 330                 335
Lys Glu Gly Tyr Gly Ala Ile Val Thr Phe Gly Val Lys Gly Gly Lys
            340                 345                 350
Glu Ala Gly Lys Lys Phe Ile Asp Ser Leu Thr Leu Ile Ser His Leu
        355                 360                 365
Ala Asn Ile Gly Asp Ala Arg Thr Leu Ala Ile His Pro Ala Ser Thr
        370                 375                 380
Thr His Gln Gln Leu Thr Glu Glu Gln Leu Lys Thr Gly Val Thr
385                 390                 395                 400
Pro Asp Met Ile Arg Leu Ser Val Gly Ile Glu Asp Val Glu Asp Ile
                405                 410                 415
Ile Ala Asp Leu Asp Gln Ala Leu Arg Lys Ser Gln Glu Gly
            420                 425                 430
```

<210> SEQ ID NO 31
<211> LENGTH: 1314
<212> TYPE: DNA
<213> ORGANISM: Streptococcus mutans
<220> FEATURE:
<221> NAME/KEY: CDS
<222> LOCATION: (1)..(1314)

<400> SEQUENCE: 31

```
atg gag cta att aat aat aaa agg aga gct tcc atg act cga gaa ttt      48
Met Glu Leu Ile Asn Asn Lys Arg Arg Ala Ser Met Thr Arg Glu Phe
1               5                   10                  15 tct ttt gaa act tta caa tta cat gcg gga caa agt gtt gat cct aca      96
Ser Phe Glu Thr Leu Gln Leu His Ala Gly Gln Ser Val Asp Pro Thr
            20                  25                  30 aca aaa tcg cgt gca gta cca atc tat cag acg act tcc tat gtg ttt     144
Thr Lys Ser Arg Ala Val Pro Ile Tyr Gln Thr Thr Ser Tyr Val Phe
        35                  40                  45 aat gat gca caa gat gct gaa gat tct ttt gca ctt cgt aca ccc ggc     192
Asn Asp Ala Gln Asp Ala Glu Asp Ser Phe Ala Leu Arg Thr Pro Gly
    50                  55                  60 aat att tat acg cgg atc act aat ccg act aca gcc gtt ttt gaa gaa     240
Asn Ile Tyr Thr Arg Ile Thr Asn Pro Thr Thr Ala Val Phe Glu Glu
65                  70                  75                  80 cgg atg gcc gct ctt gaa ggt ggt gtc ggt gca ctg gca aca gct tct     288
Arg Met Ala Ala Leu Glu Gly Gly Val Gly Ala Leu Ala Thr Ala Ser
                85                  90                  95 ggt atg gca gca gta act tat att gcc ttg gct ctt gct cat gca ggt     336
Gly Met Ala Ala Val Thr Tyr Ile Ala Leu Ala Leu Ala His Ala Gly
            100                 105                 110 gat cat att gtg tca gca gcg aca gtt tac ggt ggc act ttt aat ctt     384
Asp His Ile Val Ser Ala Ala Thr Val Tyr Gly Gly Thr Phe Asn Leu
        115                 120                 125 ctt aag gaa act tta cct cgc tat ggc att act aca agt ttt gtt gat     432
Leu Lys Glu Thr Leu Pro Arg Tyr Gly Ile Thr Thr Ser Phe Val Asp
    130                 135                 140
```

```
gtt gct aat ttc gct gaa att gaa gcg gct att aca gac aag act aag    480
Val Ala Asn Phe Ala Glu Ile Glu Ala Ala Ile Thr Asp Lys Thr Lys
145                 150                 155                 160 ttt att atc gct gaa acg tta gga aat cct ctt gga aat atc gct gat    528
Phe Ile Ile Ala Glu Thr Leu Gly Asn Pro Leu Gly Asn Ile Ala Asp
                165                 170                 175 ctt gaa aaa tta gct gag att gcc cat cga cat gct att ccc ttg gtt    576
Leu Glu Lys Leu Ala Glu Ile Ala His Arg His Ala Ile Pro Leu Val
            180                 185                 190 att gat aat acc ttt ggt act cct tat ttg ctt aat gtc ttc tct tac    624
Ile Asp Asn Thr Phe Gly Thr Pro Tyr Leu Leu Asn Val Phe Ser Tyr
        195                 200                 205 ggt gtt gat att gct gtt cat tct gcc act aaa ttt atc ggt gga cat    672
Gly Val Asp Ile Ala Val His Ser Ala Thr Lys Phe Ile Gly Gly His
210                 215                 220 ggg aca tct att ggc ggt gtc att gtt gat tct gga aac ttt gat tgg    720
Gly Thr Ser Ile Gly Gly Val Ile Val Asp Ser Gly Asn Phe Asp Trp
225                 230                 235                 240 gaa aaa tct gga aaa ttc cca caa ttt gta gaa cca gat cct tcc tat    768
Glu Lys Ser Gly Lys Phe Pro Gln Phe Val Glu Pro Asp Pro Ser Tyr
                245                 250                 255 cat gac att agt tat aca cgt gat att gga aaa gca gct ttt gta act    816
His Asp Ile Ser Tyr Thr Arg Asp Ile Gly Lys Ala Ala Phe Val Thr
            260                 265                 270 gcg gtg cgt acg caa ctg ctg cgt gat aca ggc gcc tgc ctt tca cct    864
Ala Val Arg Thr Gln Leu Leu Arg Asp Thr Gly Ala Cys Leu Ser Pro
        275                 280                 285 ttc aat gcc ttt ctt ttg cta caa ggt cta gaa acc tta tca ctt cgt    912
Phe Asn Ala Phe Leu Leu Leu Gln Gly Leu Glu Thr Leu Ser Leu Arg
    290                 295                 300 gtt gag cgt cat gtg gaa aat gct aag aaa att gcg tac tat ctg gaa    960
Val Glu Arg His Val Glu Asn Ala Lys Lys Ile Ala Tyr Tyr Leu Glu
305                 310                 315                 320 aat cat cct aaa gtc aca aaa gtt aat tat gct agt ttg cca tca agt    1008
Asn His Pro Lys Val Thr Lys Val Asn Tyr Ala Ser Leu Pro Ser Ser
                325                 330                 335 cct tat tat gac ttg gct caa aaa tac ttg cca aaa gga gct agt tct    1056
Pro Tyr Tyr Asp Leu Ala Gln Lys Tyr Leu Pro Lys Gly Ala Ser Ser
            340                 345                 350 atc ttt act ttt aat gtt gca ggc agt gcg aaa gcc gct cgc gag gtc    1104
Ile Phe Thr Phe Asn Val Ala Gly Ser Ala Lys Ala Ala Arg Glu Val
        355                 360                 365 att gac agt ctt gaa atc ttt tct gat ttg gcg aat gtt gct gat gcc    1152
Ile Asp Ser Leu Glu Ile Phe Ser Asp Leu Ala Asn Val Ala Asp Ala
    370                 375                 380 aaa tca cta gtt gtt cat ccg gca aca acc act cat ggt caa atg act    1200
Lys Ser Leu Val Val His Pro Ala Thr Thr Thr His Gly Gln Met Thr
385                 390                 395                 400 gaa gaa gat cta cga gct tgc ggt att gaa cct gag caa atc cgt gtt    1248
Glu Glu Asp Leu Arg Ala Cys Gly Ile Glu Pro Glu Gln Ile Arg Val
                405                 410                 415 tct att ggt ttg gaa aat gct gat gac tta atc gaa gat ttg cgc cta    1296
Ser Ile Gly Leu Glu Asn Ala Asp Asp Leu Ile Glu Asp Leu Arg Leu
            420                 425                 430 gca ctt gaa aaa ata taa                                            1314
Ala Leu Glu Lys Ile
                435

<210> SEQ ID NO 32
<211> LENGTH: 437
```

<212> TYPE: PRT
<213> ORGANISM: Streptococcus mutans

<400> SEQUENCE: 32

```
Met Glu Leu Ile Asn Asn Lys Arg Arg Ala Ser Met Thr Arg Glu Phe
1               5                   10                  15

Ser Phe Glu Thr Leu Gln Leu His Ala Gly Gln Ser Val Asp Pro Thr
            20                  25                  30

Thr Lys Ser Arg Ala Val Pro Ile Tyr Gln Thr Thr Ser Tyr Val Phe
        35                  40                  45

Asn Asp Ala Gln Asp Ala Glu Asp Ser Phe Ala Leu Arg Thr Pro Gly
50                  55                  60

Asn Ile Tyr Thr Arg Ile Thr Asn Pro Thr Thr Ala Val Phe Glu Glu
65                  70                  75                  80

Arg Met Ala Ala Leu Glu Gly Val Gly Ala Leu Ala Thr Ala Ser
                85                  90                  95

Gly Met Ala Ala Val Thr Tyr Ile Ala Leu Ala Leu Ala His Ala Gly
            100                 105                 110

Asp His Ile Val Ser Ala Ala Thr Val Tyr Gly Gly Thr Phe Asn Leu
        115                 120                 125

Leu Lys Glu Thr Leu Pro Arg Tyr Gly Ile Thr Thr Ser Phe Val Asp
130                 135                 140

Val Ala Asn Phe Ala Glu Ile Glu Ala Ala Ile Thr Asp Lys Thr Lys
145                 150                 155                 160

Phe Ile Ile Ala Glu Thr Leu Gly Asn Pro Leu Gly Asn Ile Ala Asp
                165                 170                 175

Leu Glu Lys Leu Ala Glu Ile Ala His Arg His Ala Ile Pro Leu Val
            180                 185                 190

Ile Asp Asn Thr Phe Gly Thr Pro Tyr Leu Leu Asn Val Phe Ser Tyr
        195                 200                 205

Gly Val Asp Ile Ala Val His Ser Ala Thr Lys Phe Ile Gly Gly His
210                 215                 220

Gly Thr Ser Ile Gly Gly Val Ile Val Asp Ser Gly Asn Phe Asp Trp
225                 230                 235                 240

Glu Lys Ser Gly Lys Phe Pro Gln Phe Val Glu Pro Asp Pro Ser Tyr
                245                 250                 255

His Asp Ile Ser Tyr Thr Arg Asp Ile Gly Lys Ala Ala Phe Val Thr
            260                 265                 270

Ala Val Arg Thr Gln Leu Leu Arg Asp Thr Gly Ala Cys Leu Ser Pro
        275                 280                 285

Phe Asn Ala Phe Leu Leu Leu Gln Gly Leu Glu Thr Leu Ser Leu Arg
290                 295                 300

Val Glu Arg His Val Glu Asn Ala Lys Lys Ile Ala Tyr Tyr Leu Glu
305                 310                 315                 320

Asn His Pro Lys Val Thr Lys Val Asn Tyr Ala Ser Leu Pro Ser Ser
                325                 330                 335

Pro Tyr Tyr Asp Leu Ala Gln Lys Tyr Leu Pro Lys Gly Ala Ser Ser
            340                 345                 350

Ile Phe Thr Phe Asn Val Ala Gly Ser Ala Lys Ala Ala Arg Glu Val
        355                 360                 365

Ile Asp Ser Leu Glu Ile Phe Ser Asp Leu Ala Asn Val Ala Asp Ala
370                 375                 380

Lys Ser Leu Val Val His Pro Ala Thr Thr Thr His Gly Gln Met Thr
385                 390                 395                 400
```

```
Glu Glu Asp Leu Arg Ala Cys Gly Ile Glu Pro Glu Gln Ile Arg Val
                405                 410                 415

Ser Ile Gly Leu Glu Asn Ala Asp Asp Leu Ile Glu Asp Leu Arg Leu
            420                 425                 430

Ala Leu Glu Lys Ile
        435

<210> SEQ ID NO 33
<211> LENGTH: 1431
<212> TYPE: DNA
<213> ORGANISM: Burkholderia cepacia
<220> FEATURE:
<221> NAME/KEY: CDS
<222> LOCATION: (1)..(1431)

<400> SEQUENCE: 33
```

| | | | | | | | | | | | | | | | | |
|---|---|---|---|---|---|---|---|---|---|---|---|---|---|---|---|---|
| ttg | aag | cgc | cgc | acg | ccg | gtg | ata | gga | tgg | ccg | cca | ctt | tca | cct | ttc | 48 |
| Leu | Lys | Arg | Arg | Thr | Pro | Val | Ile | Gly | Trp | Pro | Pro | Leu | Ser | Pro | Phe | |
| 1 | | | 5 | | | | | 10 | | | | | 15 | | | |
| gcg | agg | ccg | tcc | gtg | gcc | ccg | ccg | ccc | agc | atg | tcc | gcg | aac | cgt | ttc | 96 |
| Ala | Arg | Pro | Ser | Val | Ala | Pro | Pro | Pro | Ser | Met | Ser | Ala | Asn | Arg | Phe | |
| | | | 20 | | | | | 25 | | | | | 30 | | | |
| gac | acg | ctt | gcg | ctg | cac | gcc | ggc | gct | gct | ccc | gac | ccg | acc | acc | ggc | 144 |
| Asp | Thr | Leu | Ala | Leu | His | Ala | Gly | Ala | Ala | Pro | Asp | Pro | Thr | Thr | Gly | |
| | | 35 | | | | | 40 | | | | | 45 | | | | |
| gcg | cgc | gcc | acg | ccg | att | tac | cag | act | acc | tcg | ttt | tcg | ttc | cgc | gat | 192 |
| Ala | Arg | Ala | Thr | Pro | Ile | Tyr | Gln | Thr | Thr | Ser | Phe | Ser | Phe | Arg | Asp | |
| | 50 | | | | | 55 | | | | | 60 | | | | | |
| tcc | gac | cac | gcc | gcg | gcg | ctc | ttc | aat | atg | gag | cgc | gcc | ggt | cat | gtt | 240 |
| Ser | Asp | His | Ala | Ala | Ala | Leu | Phe | Asn | Met | Glu | Arg | Ala | Gly | His | Val | |
| 65 | | | | | 70 | | | | | 75 | | | | | 80 | |
| tat | tcg | cgc | att | tcg | aac | ccg | acc | gtg | gcc | gtg | ttc | gag | gaa | cgc | gtg | 288 |
| Tyr | Ser | Arg | Ile | Ser | Asn | Pro | Thr | Val | Ala | Val | Phe | Glu | Glu | Arg | Val | |
| | | | | 85 | | | | | 90 | | | | | 95 | | |
| gcc | gcg | ctg | gaa | aac | ggc | gcg | ggc | gcg | atc | ggc | acg | gca | agc | ggc | cag | 336 |
| Ala | Ala | Leu | Glu | Asn | Gly | Ala | Gly | Ala | Ile | Gly | Thr | Ala | Ser | Gly | Gln | |
| | | | 100 | | | | | 105 | | | | | 110 | | | |
| gcg | gcc | ctg | cat | ctg | gcc | att | gcc | acg | ctg | atg | ggc | gcg | ggt | tcg | cat | 384 |
| Ala | Ala | Leu | His | Leu | Ala | Ile | Ala | Thr | Leu | Met | Gly | Ala | Gly | Ser | His | |
| | | 115 | | | | | 120 | | | | | 125 | | | | |
| atc | gtc | gcc | tcc | agc | gcg | ctg | tac | ggc | ggc | tcg | cac | aat | ctg | ctg | cac | 432 |
| Ile | Val | Ala | Ser | Ser | Ala | Leu | Tyr | Gly | Gly | Ser | His | Asn | Leu | Leu | His | |
| | 130 | | | | | 135 | | | | | 140 | | | | | |
| tac | acg | ttg | cgg | cgc | ttc | ggc | atc | gag | acg | act | ttc | gtc | aaa | ccc | ggc | 480 |
| Tyr | Thr | Leu | Arg | Arg | Phe | Gly | Ile | Glu | Thr | Thr | Phe | Val | Lys | Pro | Gly | |
| 145 | | | | | 150 | | | | | 155 | | | | | 160 | |
| gac | ctg | gac | gcg | tgg | cgc | gcc | gcg | ctg | cgc | cca | aac | acg | cgg | ctg | ctg | 528 |
| Asp | Leu | Asp | Ala | Trp | Arg | Ala | Ala | Leu | Arg | Pro | Asn | Thr | Arg | Leu | Leu | |
| | | | | 165 | | | | | 170 | | | | | 175 | | |
| ttc | ggc | gag | acg | ctc | ggc | aat | ccg | ggg | ctc | gac | gtg | ctc | gat | atc | gcc | 576 |
| Phe | Gly | Glu | Thr | Leu | Gly | Asn | Pro | Gly | Leu | Asp | Val | Leu | Asp | Ile | Ala | |
| | | | 180 | | | | | 185 | | | | | 190 | | | |
| gcc | gtc | gcg | cag | atc | gcg | cat | gag | cac | cgc | gtg | ccg | ctg | ctg | gtc | gac | 624 |
| Ala | Val | Ala | Gln | Ile | Ala | His | Glu | His | Arg | Val | Pro | Leu | Leu | Val | Asp | |
| | | 195 | | | | | 200 | | | | | 205 | | | | |
| tcg | acc | ttc | acc | aca | cct | tac | ctg | ctc | aaa | ccg | ttc | gaa | cat | ggc | gcg | 672 |
| Ser | Thr | Phe | Thr | Thr | Pro | Tyr | Leu | Leu | Lys | Pro | Phe | Glu | His | Gly | Ala | |
| | 210 | | | | | 215 | | | | | 220 | | | | | |
| gac | ttc | gtc | tat | cac | tcg | gcc | acc | aaa | ttc | ctc | ggc | ggc | cac | ggc | acg | 720 |
| Asp | Phe | Val | Tyr | His | Ser | Ala | Thr | Lys | Phe | Leu | Gly | Gly | His | Gly | Thr | |

```
                 225                 230                 235                 240 acg atc ggc ggc gtg ctg gtg gac ggc ggc acg ttc gac ttc gac gcc        768
Thr Ile Gly Gly Val Leu Val Asp Gly Gly Thr Phe Asp Phe Asp Ala
                    245                 250                 255 tcg ggg cgc ttc ccc gaa ttc acc gaa cct tac gac ggc ttt cac ggc        816
Ser Gly Arg Phe Pro Glu Phe Thr Glu Pro Tyr Asp Gly Phe His Gly
                260                 265                 270 atg gtg ttc gcc gag gag agc acc gtc gcg ccg ttt ctg ctg cga gca        864
Met Val Phe Ala Glu Glu Ser Thr Val Ala Pro Phe Leu Leu Arg Ala
            275                 280                 285 cgc cgc gag ggg ctg cgc gac ttc ggc gca tgc ctg cat ccg caa gcc        912
Arg Arg Glu Gly Leu Arg Asp Phe Gly Ala Cys Leu His Pro Gln Ala
        290                 295                 300 gca tgg caa ctg ctg caa ggc atc gag acg ctg ccg ttg cga atg gaa        960
Ala Trp Gln Leu Leu Gln Gly Ile Glu Thr Leu Pro Leu Arg Met Glu
305                 310                 315                 320 cgg cac gtt gcc aac acg cgc cgg gtg gtc gag ttc ctc gcc ggt cac       1008
Arg His Val Ala Asn Thr Arg Arg Val Val Glu Phe Leu Ala Gly His
                    325                 330                 335 gcc gcg gtc ggg gcc gtc gcc tat ccg gaa ctg ccc acg cac ccc gac       1056
Ala Ala Val Gly Ala Val Ala Tyr Pro Glu Leu Pro Thr His Pro Asp
                340                 345                 350 cac gcg ctc gcg aag cgg ctg ctg ccg cgc ggc gcc ggt gcc gtg ttc       1104
His Ala Leu Ala Lys Arg Leu Leu Pro Arg Gly Ala Gly Ala Val Phe
            355                 360                 365 agc ttc gat ctg cgc ggc gac cgc gcc gcc gga cgc agc ttt atc gaa       1152
Ser Phe Asp Leu Arg Gly Asp Arg Ala Ala Gly Arg Ser Phe Ile Glu
        370                 375                 380 gcg ctc tcg ctg ttc tcg cat ctc gcg aac gtg ggc gac gcg cgc tcg       1200
Ala Leu Ser Leu Phe Ser His Leu Ala Asn Val Gly Asp Ala Arg Ser
385                 390                 395                 400 ctc gtg atc cat ccc gcc tcg acc acc cac ttt cgc atg gac gcc gct       1248
Leu Val Ile His Pro Ala Ser Thr Thr His Phe Arg Met Asp Ala Ala
                    405                 410                 415 gcc ctt gcc gcg gcc ggt atc gcc gaa ggc acg atc cgc ctc tcg atc       1296
Ala Leu Ala Ala Ala Gly Ile Ala Glu Gly Thr Ile Arg Leu Ser Ile
                420                 425                 430 ggc ctc gaa gat ccc gac gat ctg atc gac gat ctc aag cgc gcg cta       1344
Gly Leu Glu Asp Pro Asp Asp Leu Ile Asp Asp Leu Lys Arg Ala Leu
            435                 440                 445 aag gcc gca cag aaa gcg ggc agt tcg agc gca gcg cac ggc ggc gca       1392
Lys Ala Ala Gln Lys Ala Gly Ser Ser Ser Ala Ala His Gly Gly Ala
        450                 455                 460 tcc ggc agt gcc gcc caa ccc cgc ccg gag tcc gca tga                   1431
Ser Gly Ser Ala Ala Gln Pro Arg Pro Glu Ser Ala
465                 470                 475

<210> SEQ ID NO 34
<211> LENGTH: 476
<212> TYPE: PRT
<213> ORGANISM: Burkholderia cepacia

<400> SEQUENCE: 34

Leu Lys Arg Arg Thr Pro Val Ile Gly Trp Pro Pro Leu Ser Pro Phe
1               5                   10                  15

Ala Arg Pro Ser Val Ala Pro Pro Ser Met Ser Ala Asn Arg Phe
                20                  25                  30

Asp Thr

```
Ala Arg Ala Thr Pro Ile Tyr Gln Thr Thr Ser Phe Ser Phe Arg Asp
     50                  55                  60

Ser Asp His Ala Ala Ala Leu Phe Asn Met Glu Arg Ala Gly His Val
 65                  70                  75                  80

Tyr Ser Arg Ile Ser Asn Pro Thr Val Ala Val Phe Glu Glu Arg Val
                 85                  90                  95

Ala Ala Leu Glu Asn Gly Ala Gly Ala Ile Gly Thr Ala Ser Gly Gln
            100                 105                 110

Ala Ala Leu His Leu Ala Ile Ala Thr Leu Met Gly Ala Gly Ser His
            115                 120                 125

Ile Val Ala Ser Ser Ala Leu Tyr Gly Gly Ser His Asn Leu Leu His
    130                 135                 140

Tyr Thr Leu Arg Arg Phe Gly Ile Glu Thr Thr Phe Val Lys Pro Gly
145                 150                 155                 160

Asp Leu Asp Ala Trp Arg Ala Ala Leu Arg Pro Asn Thr Arg Leu Leu
                165                 170                 175

Phe Gly Glu Thr Leu Gly Asn Pro Gly Leu Asp Val Leu Asp Ile Ala
            180                 185                 190

Ala Val Ala Gln Ile Ala His Glu His Arg Val Pro Leu Leu Val Asp
            195                 200                 205

Ser Thr Phe Thr Thr Pro Tyr Leu Leu Lys Pro Phe Glu His Gly Ala
210                 215                 220

Asp Phe Val Tyr His Ser Ala Thr Lys Phe Leu Gly Gly His Gly Thr
225                 230                 235                 240

Thr Ile Gly Gly Val Leu Val Asp Gly Gly Thr Phe Asp Phe Asp Ala
                245                 250                 255

Ser Gly Arg Phe Pro Glu Phe Thr Glu Pro Tyr Asp Gly Phe His Gly
            260                 265                 270

Met Val Phe Ala Glu Glu Ser Thr Val Ala Pro Phe Leu Leu Arg Ala
            275                 280                 285

Arg Arg Glu Gly Leu Arg Asp Phe Gly Ala Cys Leu His Pro Gln Ala
            290                 295                 300

Ala Trp Gln Leu Leu Gln Gly Ile Glu Thr Leu Pro Leu Arg Met Glu
305                 310                 315                 320

Arg His Val Ala Asn Thr Arg Arg Val Val Glu Phe Leu Ala Gly His
                325                 330                 335

Ala Ala Val Gly Ala Val Ala Tyr Pro Glu Leu Pro Thr His Pro Asp
            340                 345                 350

His Ala Leu Ala Lys Arg Leu Leu Pro Arg Gly Ala Gly Ala Val Phe
            355                 360                 365

Ser Phe Asp Leu Arg Gly Asp Arg Ala Ala Gly Arg Ser Phe Ile Glu
370                 375                 380

Ala Leu Ser Leu Phe Ser His Leu Ala Asn Val Gly Asp Ala Arg Ser
385                 390                 395                 400

Leu Val Ile His Pro Ala Ser Thr Thr His Phe Arg Met Asp Ala Ala
                405                 410                 415

Ala Leu Ala Ala Ala Gly Ile Ala Glu Gly Thr Ile Arg Leu Ser Ile
            420                 425                 430

Gly Leu Glu Asp Pro Asp Asp Leu Ile Asp Asp Leu Lys Arg Ala Leu
            435                 440                 445

Lys Ala Ala Gln Lys Ala Gly Ser Ser Ala Ala His Gly Gly Ala
450                 455                 460

Ser Gly Ser Ala Ala Gln Pro Arg Pro Glu Ser Ala
```

<210> SEQ ID NO 35
<211> LENGTH: 1722
<212> TYPE: DNA
<213> ORGANISM: Deinococcus radiodurans
<220> FEATURE:
<221> NAME/KEY: CDS
<222> LOCATION: (1)..(1722)

<400> SEQUENCE: 35

| | | | | | | | | | | | | | | | | |
|---|---|---|---|---|---|---|---|---|---|---|---|---|---|---|---|---|
| gtg | gcc | ttc | ccg | tgc | ggt | cag | gcg | ggg | aac | aag | ata | aca | agg | ccg | ggc | 48 |
| Val | Ala | Phe | Pro | Cys | Gly | Gln | Ala | Gly | Asn | Lys | Ile | Thr | Arg | Pro | Gly | |
| 1 | | | 5 | | | | | 10 | | | | | 15 | | | |
| caa | tgt | gtc | aac | ggg | ggc | agg | gca | cgc | tca | gcc | ccg | tct | aag | ttt | cgc | 96 |
| Gln | Cys | Val | Asn | Gly | Gly | Arg | Ala | Arg | Ser | Ala | Pro | Ser | Lys | Phe | Arg | |
| | | | 20 | | | | | 25 | | | | | 30 | | | |
| ctt | gac | ccc | tta | ccc | gcc | tcc | gcg | cta | ctt | ttt | gag | gag | ctc | ccg | cag | 144 |
| Leu | Asp | Pro | Leu | Pro | Ala | Ser | Ala | Leu | Leu | Phe | Glu | Glu | Leu | Pro | Gln | |
| | | 35 | | | | | 40 | | | | | 45 | | | | |
| cag | gag | cca | ccc | act | tca | gag | cgc | ccg | aga | gac | ctg | gct | cga | cga | cgg | 192 |
| Gln | Glu | Pro | Pro | Thr | Ser | Glu | Arg | Pro | Arg | Asp | Leu | Ala | Arg | Arg | Arg | |
| 50 | | | | | 55 | | | | | 60 | | | | | | |
| cgc | ggc | aac | cgg | acc | cca | tca | cgt | cac | ggt | gcc | aag | gcc | agc | ccc | ctg | 240 |
| Arg | Gly | Asn | Arg | Thr | Pro | Ser | Arg | His | Gly | Ala | Lys | Ala | Ser | Pro | Leu | |
| 65 | | | | | 70 | | | | | 75 | | | | | 80 | |
| ggc | gtg | tca | acg | atg | agc | cgc | cgg | gcg | gga | cca | agc | ggg | aag | gcc | acg | 288 |
| Gly | Val | Ser | Thr | Met | Ser | Arg | Arg | Ala | Gly | Pro | Ser | Gly | Lys | Ala | Thr | |
| | | | | 85 | | | | | 90 | | | | | 95 | | |
| cgg | atg | acg | ata | ttc | aag | tgt | ccc | ttc | tcg | att | cac | agc | agg | cag | ggg | 336 |
| Arg | Met | Thr | Ile | Phe | Lys | Cys | Pro | Phe | Ser | Ile | His | Ser | Arg | Gln | Gly | |
| | | | 100 | | | | | 105 | | | | | 110 | | | |
| gag | tgc | cgt | gac | tgg | cgc | ccc | cga | acc | tgc | ttc | ccc | cga | gga | gcc | gcc | 384 |
| Glu | Cys | Arg | Asp | Trp | Arg | Pro | Arg | Thr | Cys | Phe | Pro | Arg | Gly | Ala | Ala | |
| | | 115 | | | | | 120 | | | | | 125 | | | | |
| acc | atg | acc | gat | acc | aaa | cag | ccg | cag | cct | ctg | cac | ttc | gag | acc | ttg | 432 |
| Thr | Met | Thr | Asp | Thr | Lys | Gln | Pro | Gln | Pro | Leu | His | Phe | Glu | Thr | Leu | |
| 130 | | | | | 135 | | | | | 140 | | | | | | |
| cag | gtg | cac | gcc | gga | caa | cgc | ccc | gac | ccc | gtg | acc | gga | gcg | cag | caa | 480 |
| Gln | Val | His | Ala | Gly | Gln | Arg | Pro | Asp | Pro | Val | Thr | Gly | Ala | Gln | Gln | |
| 145 | | | | | 150 | | | | | 155 | | | | | 160 | |
| acg | ccc | atc | tac | gcc | acc | aac | tcc | tac | gtg | ttc | gag | tcg | ccc | gag | cac | 528 |
| Thr | Pro | Ile | Tyr | Ala | Thr | Asn | Ser | Tyr | Val | Phe | Glu | Ser | Pro | Glu | His | |
| | | | | 165 | | | | | 170 | | | | | 175 | | |
| gcc | gcc | gac | ctc | ttc | ggg | ctg | cgg | caa | ttc | ggc | aac | atc | tac | agc | cgc | 576 |
| Ala | Ala | Asp | Leu | Phe | Gly | Leu | Arg | Gln | Phe | Gly | Asn | Ile | Tyr | Ser | Arg | |
| | | | 180 | | | | | 185 | | | | | 190 | | | |
| atc | atg | aac | ccc | acc | aac | gac | gtg | ttc | gag | cag | cgg | gtg | gcc | gcc | ctc | 624 |
| Ile | Met | Asn | Pro | Thr | Asn | Asp | Val | Phe | Glu | Gln | Arg | Val | Ala | Ala | Leu | |
| | | 195 | | | | | 200 | | | | | 205 | | | | |
| gaa | ggg | ggc | gtg | ggg | gcg | ctg | tcg | gtg | tcg | agc | ggg | cac | gcg | ggg | cag | 672 |
| Glu | Gly | Gly | Val | Gly | Ala | Leu | Ser | Val | Ser | Ser | Gly | His | Ala | Gly | Gln | |
| 210 | | | | | 215 | | | | | 220 | | | | | | |
| ctc | gtg | aca | ttg | ctc | acg | ctg | gcg | cag | gcg | gga | gac | aac | atc | gtc | tcg | 720 |
| Leu | Val | Thr | Leu | Leu | Thr | Leu | Ala | Gln | Ala | Gly | Asp | Asn | Ile | Val | Ser | |
| 225 | | | | | 230 | | | | | 235 | | | | | 240 | |
| tcg | ccc | aac | ctg | tac | ggc | ggc | acc | gtc | aac | cag | ttc | cgc | gtc | acg | ctc | 768 |
| Ser | Pro | Asn | Leu | Tyr | Gly | Gly | Thr | Val | Asn | Gln | Phe | Arg | Val | Thr | Leu | |
| | | | | 245 | | | | | 250 | | | | | 255 | | |
| aag | cgg | ctc | ggc | atc | gag | gtg | cgg | ttt | acc | agc | aaa | gac | gag | cgc | ccc | 816 |
| Lys | Arg | Leu | Gly | Ile | Glu | Val | Arg | Phe | Thr | Ser | Lys | Asp | Glu | Arg | Pro | |

-continued

```
                    260                 265                 270
gag gaa ttc gcc gcg ctg atc gac gag cgc acg cgg gcc gta tat ctg      864
Glu Glu Phe Ala Ala Leu Ile Asp Glu Arg Thr Arg Ala Val Tyr Leu
        275                 280                 285 gaa acc atc ggc aac ccg gcg ctg aac att ccc gat ttc gag ggc gtg      912
Glu Thr Ile Gly Asn Pro Ala Leu Asn Ile Pro Asp Phe Glu Gly Val
    290                 295                 300 gcg aaa gtc gcg cac gag cac ggc gtc gcg gtg gtc gtg gac aac acc      960
Ala Lys Val Ala His Glu His Gly Val Ala Val Val Val Asp Asn Thr
305                 310                 315                 320 ttc ggg gcc ggc gga tac tac tgc cag ccg ctg cgg cac ggc gcc aac     1008
Phe Gly Ala Gly Gly Tyr Tyr Cys Gln Pro Leu Arg His Gly Ala Asn
                325                 330                 335 atc gtg ctg cac tcg gcg agc aag tgg atc ggc ggg cac ggc aac ggc     1056
Ile Val Leu His Ser Ala Ser Lys Trp Ile Gly Gly His Gly Asn Gly
            340                 345                 350 atc ggc ggg gtc atc gtg gac ggc ggg aac ttc gac tgg ggc agc ggg     1104
Ile Gly Gly Val Ile Val Asp Gly Gly Asn Phe Asp Trp Gly Ser Gly
        355                 360                 365 cgg tat ccg ctg atg acc gag ccc tcg ccg agt tat cac ggg ctg aag     1152
Arg Tyr Pro Leu Met Thr Glu Pro Ser Pro Ser Tyr His Gly Leu Lys
    370                 375                 380 ttc tgg gag acg ttc ggg gaa ggc aac ggg ctg ggg ctg ccg aac atc     1200
Phe Trp Glu Thr Phe Gly Glu Gly Asn Gly Leu Gly Leu Pro Asn Ile
385                 390                 395                 400 gcc ttc atc acc cgc gcc cgc acc gag ggg ctg cgc gac ctg gga acg     1248
Ala Phe Ile Thr Arg Ala Arg Thr Glu Gly Leu Arg Asp Leu Gly Thr
                405                 410                 415 acc ctg gcg ccg cag cag gcg tgg cag ttt ctg caa ggc ctt gaa acc     1296
Thr Leu Ala Pro Gln Gln Ala Trp Gln Phe Leu Gln Gly Leu Glu Thr
            420                 425                 430 ctg agc ctg cgc gcc gag cgc cac gcc gag aac acc ctg gcg ctg gcg     1344
Leu Ser Leu Arg Ala Glu Arg His Ala Glu Asn Thr Leu Ala Leu Ala
        435                 440                 445 cac tgg ctc atc agc cac ccg gac gtg aag cag gtc act tac ccc ggc     1392
His Trp Leu Ile Ser His Pro Asp Val Lys Gln Val Thr Tyr Pro Gly
    450                 455                 460 ctg agc aac cac ccc cac tac gac cgg gcg cag acc tac ttg ccg cgc     1440
Leu Ser Asn His Pro His Tyr Asp Arg Ala Gln Thr Tyr Leu Pro Arg
465                 470                 475                 480 ggg gcg ggc gcg gtg ctc acc ttc gag ctg cgc ggg ggc cgg gcg gcg     1488
Gly Ala Gly Ala Val Leu Thr Phe Glu Leu Arg Gly Gly Arg Ala Ala
                485                 490                 495 ggc gaa gcg ttt att cgc tcg gtc aag ctc gcg cag cac gtc gcc aac     1536
Gly Glu Ala Phe Ile Arg Ser Val Lys Leu Ala Gln His Val Ala Asn
            500                 505                 510 gtg ggc gac acc cgc acg ctg gtc att cat ccg gcg agc acc acc cac     1584
Val Gly Asp Thr Arg Thr Leu Val Ile His Pro Ala Ser Thr Thr His
        515                 520                 525 agc cag ctc gac gag gtg acg cag acg aac gcc ggg gtc acg ccg ggc     1632
Ser Gln Leu Asp Glu Val Thr Gln Thr Asn Ala Gly Val Thr Pro Gly
    530                 535                 540 ctc atc cgg gtg tcg gtg ggc atc gag cac gta gac gac atc cgc gag     1680
Leu Ile Arg Val Ser Val Gly Ile Glu His Val Asp Asp Ile Arg Glu
545                 550                 555                 560 gac ttc gcg cag gcc ctg gcg agc gct ggg gag cgg gcg tga              1722
Asp Phe Ala Gln Ala Leu Ala Ser Ala Gly Glu Arg Ala
                565                 570
```

<210> SEQ ID NO 36
<211> LENGTH: 573
<212> TYPE: PRT
<213> ORGANISM: Deinococcus radiodurans

<400> SEQUENCE: 36

```
Val Ala Phe Pro Cys Gly Gln Ala Gly Asn Lys Ile Thr Arg Pro Gly
1               5                   10                  15

Gln Cys Val Asn Gly Gly Arg Ala Arg Ser Ala Pro Ser Lys Phe Arg
            20                  25                  30

Leu Asp Pro Leu Pro Ala Ser Ala Leu Leu Phe Glu Glu Leu Pro Gln
        35                  40                  45

Gln Glu Pro Pro Thr Ser Glu Arg Pro Arg Asp Leu Ala Arg Arg Arg
    50                  55                  60

Arg Gly Asn Arg Thr Pro Ser Arg His Gly Ala Lys Ala Ser Pro Leu
65                  70                  75                  80

Gly Val Ser Thr Met Ser Arg Arg Ala Gly Pro Ser Gly Lys Ala Thr
                85                  90                  95

Arg Met Thr Ile Phe Lys Cys Pro Phe Ser Ile His Ser Arg Gln Gly
            100                 105                 110

Glu Cys Arg Asp Trp Arg Pro Arg Thr Cys Phe Pro Arg Gly Ala Ala
        115                 120                 125

Thr Met Thr Asp Thr Lys Gln Pro Gln Pro Leu His Phe Glu Thr Leu
    130                 135                 140

Gln Val His Ala Gly Gln Arg Pro Asp Pro Val Thr Gly Ala Gln Gln
145                 150                 155                 160

Thr Pro Ile Tyr Ala Thr Asn Ser Tyr Val Phe Glu Ser Pro Glu His
                165                 170                 175

Ala Ala Asp Leu Phe Gly Leu Arg Gln Phe Gly Asn Ile Tyr Ser Arg
            180                 185                 190

Ile Met Asn Pro Thr Asn Asp Val Phe Glu Gln Arg Val Ala Ala Leu
        195                 200                 205

Glu Gly Gly Val Gly Ala Leu Ser Val Ser Gly His Ala Gly Gln
    210                 215                 220

Leu Val Thr Leu Leu Thr Leu Ala Gln Ala Gly Asp Asn Ile Val Ser
225                 230                 235                 240

Ser Pro Asn Leu Tyr Gly Gly Thr Val Asn Gln Phe Arg Val Thr Leu
                245                 250                 255

Lys Arg Leu Gly Ile Glu Val Arg Phe Thr Ser Lys Asp Glu Arg Pro
            260                 265                 270

Glu Glu Phe Ala Ala Leu Ile Asp Glu Arg Thr Arg Ala Val Tyr Leu
        275                 280                 285

Glu Thr Ile Gly Asn Pro Ala Leu Asn Ile Pro Asp Phe Glu Gly Val
    290                 295                 300

Ala Lys Val Ala His Glu His Gly Val Ala Val Val Asp Asn Thr
305                 310                 315                 320

Phe Gly Ala Gly Gly Tyr Tyr Cys Gln Pro Leu Arg His Gly Ala Asn
                325                 330                 335

Ile Val Leu His Ser Ala Ser Lys Trp Ile Gly Gly His Gly Asn Gly
            340                 345                 350

Ile Gly Gly Val Ile Val Asp Gly Gly Asn Phe Asp Trp Gly Ser Gly
        355                 360                 365

Arg Tyr Pro Leu Met Thr Glu Pro Ser Pro Ser Tyr His Gly Leu Lys
    370                 375                 380
```

```
Phe Trp Glu Thr Phe Gly Glu Gly Asn Gly Leu Gly Leu Pro Asn Ile
385                 390                 395                 400

Ala Phe Ile Thr Arg Ala Arg Thr Glu Gly Leu Arg Asp Leu Gly Thr
            405                 410                 415

Thr Leu Ala Pro Gln Gln Ala Trp Gln Phe Leu Gln Gly Leu Glu Thr
            420                 425                 430

Leu Ser Leu Arg Ala Glu Arg His Ala Glu Asn Thr Leu Ala Leu Ala
            435                 440                 445

His Trp Leu Ile Ser His Pro Asp Val Lys Gln Val Thr Tyr Pro Gly
            450                 455                 460

Leu Ser Asn His Pro His Tyr Asp Arg Ala Gln Thr Tyr Leu Pro Arg
465                 470                 475                 480

Gly Ala Gly Ala Val Leu Thr Phe Glu Leu Arg Gly Arg Ala Ala
                485                 490                 495

Gly Glu Ala Phe Ile Arg Ser Val Lys Leu Ala Gln His Val Ala Asn
                500                 505                 510

Val Gly Asp Thr Arg Thr Leu Val Ile His Pro Ala Ser Thr Thr His
                515                 520                 525

Ser Gln Leu Asp Glu Val Thr Gln Thr Asn Ala Gly Val Thr Pro Gly
            530                 535                 540

Leu Ile Arg Val Ser Val Gly Ile Glu His Val Asp Asp Ile Arg Glu
545                 550                 555                 560

Asp Phe Ala Gln Ala Leu Ala Ser Ala Gly Glu Arg Ala
                565                 570

<210> SEQ ID NO 37
<211> LENGTH: 1284
<212> TYPE: DNA
<213> ORGANISM: Rhodobacter capsulatus
<220> FEATURE:
<221> NAME/KEY: CDS
<222> LOCATION: (1)..(1284)

<400> SEQUENCE: 37 atg acc gac cag gcc ttt gac acg ctg caa att cac gcg ggc gcc gaa    48
Met Thr Asp Gln Ala Phe Asp Thr Leu Gln Ile His Ala Gly Ala Glu
1               5                   10                  15 ccc gat ccc gcg acg ggc gcg cgg cag gtg ccg att tac cag acc acc    96
Pro Asp Pro Ala Thr Gly Ala Arg Gln Val Pro Ile Tyr Gln Thr Thr
            20                  25                  30 tcc tat gtc ttc aag gac gcc gac cat gcc gcg cgc ctg ttc ggg ctg   144
Ser Tyr Val Phe Lys Asp Ala Asp His Ala Ala Arg Leu Phe Gly Leu
        35                  40                  45 cag gag gtg ggc tat atc tat tcc cgc ctg acc aac ccg acc gtt tcg   192
Gln Glu Val Gly Tyr Ile Tyr Ser Arg Leu Thr Asn Pro Thr Val Ser
    50                  55                  60 gca ctg gcc gcc cgc gtt gcg gcg ctt gaa ggc ggc gtg ggc gcg gtc   240
Ala Leu Ala Ala Arg Val Ala Ala Leu Glu Gly Gly Val Gly Ala Val
65                  70                  75                  80 tgc tgc tcg tcc ggc cat gcg gcg cag atc atg gcg ctg ttt ccg ctg   288
Cys Cys Ser Ser Gly His Ala Ala Gln Ile Met Ala Leu Phe Pro Leu
                85                  90                  95 atg ggg ccg ggg ctg aac atc gtc gcc tcg acc cgg ctt tac ggc ggc   336
Met Gly Pro Gly Leu Asn Ile Val Ala Ser Thr Arg Leu Tyr Gly Gly
            100                 105                 110 acg atc acc cag ttc agc cag acc atc aaa cgc ttc ggc tgg tcc tgc   384
Thr Ile Thr Gln Phe Ser Gln Thr Ile Lys Arg Phe Gly Trp Ser Cys
        115                 120                 125
```

```
acc ttt gtc gat ttc gac gat ctg gcg gcg ctc gag gcc gcg gtg gat      432
Thr Phe Val Asp Phe Asp Asp Leu Ala Ala Leu Glu Ala Ala Val Asp
    130             135                 140 gac aac acc cgg gcg atc ttt tgc gaa tcg atc tcg aac ccg ggc ggc      480
Asp Asn Thr Arg Ala Ile Phe Cys Glu Ser Ile Ser Asn Pro Gly Gly
145                 150                 155                 160 tac atc acc gac ctg ccc gcc gtc gcg gcg gtg gcg aac aag gtc ggc      528
Tyr Ile Thr Asp Leu Pro Ala Val Ala Ala Val Ala Asn Lys Val Gly
                165                 170                 175 ctg ccg ctc att gtc gac aac acg ctg gcc tcg cct tat ctc tgc cgc      576
Leu Pro Leu Ile Val Asp Asn Thr Leu Ala Ser Pro Tyr Leu Cys Arg
            180                 185                 190 ccg atc gag cat ggc gcg acg ctg gtt gtc cat tcc gcc acg aaa tac      624
Pro Ile Glu His Gly Ala Thr Leu Val Val His Ser Ala Thr Lys Tyr
        195                 200                 205 ctg acc ggc aac ggc acg gtg acg ggc ggg gtg atc gtc gat tcg ggc      672
Leu Thr Gly Asn Gly Thr Val Thr Gly Gly Val Ile Val Asp Ser Gly
    210                 215                 220 aag ttc gac tgg tcg gcc tcg ggc aag ttc ccc agc ctt tcg gcg ccc      720
Lys Phe Asp Trp Ser Ala Ser Gly Lys Phe Pro Ser Leu Ser Ala Pro
225                 230                 235                 240 gaa ccc gcc tat cac ggg ctg aag ttc cac gag gca ctc ggc ccg atg      768
Glu Pro Ala Tyr His Gly Leu Lys Phe His Glu Ala Leu Gly Pro Met
                245                 250                 255 gcc ttc acc ttc cat tcg atc gcc gtc ggg ctg cgc gat ctg ggc atg      816
Ala Phe Thr Phe His Ser Ile Ala Val Gly Leu Arg Asp Leu Gly Met
                260                 265                 270 acg atg aac ccg cag ggc gcg cat tac acg ctg atg ggg atc gag acg      864
Thr Met Asn Pro Gln Gly Ala His Tyr Thr Leu Met Gly Ile Glu Thr
            275                 280                 285 ctc agc ctg cgc atg gac aag cac gtc gcc aat gcg aag gcg gtg gcg      912
Leu Ser Leu Arg Met Asp Lys His Val Ala Asn Ala Lys Ala Val Ala
        290                 295                 300 gaa tgg ctg gcc aaa gac ccg cgc atc gac ttc gtc acc tgg gcc ggg      960
Glu Trp Leu Ala Lys Asp Pro Arg Ile Asp Phe Val Thr Trp Ala Gly
305                 310                 315                 320 ctg ccc tcc tcg ccc tgg cac gaa cgc gcc gag cgg ctt tgc ccg aag     1008
Leu Pro Ser Ser Pro Trp His Glu Arg Ala Glu Arg Leu Cys Pro Lys
                325                 330                 335 ggg gcg ggg gcg ctt ttc acc gtc gcg gtc aag ggc ggc tat gag gcc     1056
Gly Ala Gly Ala Leu Phe Thr Val Ala Val Lys Gly Gly Tyr Glu Ala
                340                 345                 350 tgc gtg aaa ttg gtc aac aat ctc aag ctg ttc agc cat gtg gca aac     1104
Cys Val Lys Leu Val Asn Asn Leu Lys Leu Phe Ser His Val Ala Asn
            355                 360                 365 ctg ggc gac gcg cgc tcg ctg atc atc cat tcg gcc tcg acc acg cac     1152
Leu Gly Asp Ala Arg Ser Leu Ile Ile His Ser Ala Ser Thr Thr His
    370                 375                 380 cgt cag ctg acc gag gaa cag cag atc aag gcg ggg gcg gcg ccg aat     1200
Arg Gln Leu Thr Glu Glu Gln Gln Ile Lys Ala Gly Ala Ala Pro Asn
385                 390                 395                 400 gtg gtg cgg ctc tcg atc ggg atc gag aat gcc gcc gat ctg atc gcc     1248
Val Val Arg Leu Ser Ile Gly Ile Glu Asn Ala Ala Asp Leu Ile Ala
                405                 410                 415 gat ctg gat cag gct ctg gcc gcc gcc acc gcc tga                     1284
Asp Leu Asp Gln Ala Leu Ala Ala Ala Thr Ala
                420                 425

<210> SEQ ID NO 38
<211> LENGTH: 427
```

```
<212> TYPE: PRT
<213> ORGANISM: Rhodobacter capsulatus

<400> SEQUENCE: 38

Met Thr Asp Gln Ala Phe Asp Thr Leu Gln Ile His Ala Gly Ala Glu
1               5                   10                  15

Pro Asp Pro Ala Thr Gly Ala Arg Gln Val Pro Ile Tyr Gln Thr Thr
            20                  25                  30

Ser Tyr Val Phe Lys Asp Ala Asp His Ala Ala Arg Leu Phe Gly Leu
        35                  40                  45

Gln Glu Val Gly Tyr Ile Tyr Ser Arg Leu Thr Asn Pro Thr Val Ser
    50                  55                  60

Ala Leu Ala Ala Arg Val Ala Ala Leu Glu Gly Val Gly Ala Val
65                  70                  75                  80

Cys Cys Ser Ser Gly His Ala Ala Gln Ile Met Ala Leu Phe Pro Leu
                85                  90                  95

Met Gly Pro Gly Leu Asn Ile Val Ala Ser Thr Arg Leu Tyr Gly Gly
            100                 105                 110

Thr Ile Thr Gln Phe Ser Gln Thr Ile Lys Arg Phe Gly Trp Ser Cys
        115                 120                 125

Thr Phe Val Asp Phe Asp Asp Leu Ala Ala Leu Glu Ala Ala Val Asp
    130                 135                 140

Asp Asn Thr Arg Ala Ile Phe Cys Glu Ser Ile Ser Asn Pro Gly Gly
145                 150                 155                 160

Tyr Ile Thr Asp Leu Pro Ala Val Ala Ala Val Ala Asn Lys Val Gly
            165                 170                 175

Leu Pro Leu Ile Val Asp Asn Thr Leu Ala Ser Pro Tyr Leu Cys Arg
        180                 185                 190

Pro Ile Glu His Gly Ala Thr Leu Val Val His Ser Ala Thr Lys Tyr
    195                 200                 205

Leu Thr Gly Asn Gly Thr Val Thr Gly Gly Val Ile Val Asp Ser Gly
    210                 215                 220

Lys Phe Asp Trp Ser Ala Ser Gly Lys Phe Pro Ser Leu Ser Ala Pro
225                 230                 235                 240

Glu Pro Ala Tyr His Gly Leu Lys Phe His Glu Ala Leu Gly Pro Met
            245                 250                 255

Ala Phe Thr Phe His Ser Ile Ala Val Gly Leu Arg Asp Leu Gly Met
        260                 265                 270

Thr Met Asn Pro Gln Gly Ala His Tyr Thr Leu Met Gly Ile Glu Thr
    275                 280                 285

Leu Ser Leu Arg Met Asp Lys His Val Ala Asn Ala Lys Ala Val Ala
    290                 295                 300

Glu Trp Leu Ala Lys Asp Pro Arg Ile Asp Phe Val Thr Trp Ala Gly
305                 310                 315                 320

Leu Pro Ser Ser Pro Trp His Glu Arg Ala Glu Arg Leu Cys Pro Lys
            325                 330                 335

Gly Ala Gly Ala Leu Phe Thr Val Ala Val Lys Gly Gly Tyr Glu Ala
        340                 345                 350

Cys Val Lys Leu Val Asn Asn Leu Lys Leu Phe Ser His Val Ala Asn
    355                 360                 365

Leu Gly Asp Ala Arg Ser Leu Ile Ile His Ser Ala Ser Thr Thr His
    370                 375                 380

Arg Gln Leu Thr Glu Glu Gln Gln Ile Lys Ala Gly Ala Ala Pro Asn
385                 390                 395                 400
```

Val Val Arg Leu Ser Ile Gly Ile Glu Asn Ala Ala Asp Leu Ile Ala
            405                 410                 415

Asp Leu Asp Gln Ala Leu Ala Ala Ala Thr Ala
            420                 425

<210> SEQ ID NO 39
<211> LENGTH: 1269
<212> TYPE: DNA
<213> ORGANISM: Pasteurella multocida
<220> FEATURE:
<221> NAME/KEY: CDS
<222> LOCATION: (1)..(1269)

<400> SEQUENCE: 39

```
atg gaa ttt gca aca aaa tgt cta cat gcc ggt tat aca ccg aaa aat      48
Met Glu Phe Ala Thr Lys Cys Leu His Ala Gly Tyr Thr Pro Lys Asn
1               5                   10                  15 ggt gag cct cgt gtt caa ccg atc gta caa agt acc act ttt acc tac      96
Gly Glu Pro Arg Val Gln Pro Ile Val Gln Ser Thr Thr Phe Thr Tyr
            20                  25                  30 gat tcc gcc gaa gaa att ggt aag tta ttt gat tta caa gcg gct ggc     144
Asp Ser Ala Glu Glu Ile Gly Lys Leu Phe Asp Leu Gln Ala Ala Gly
        35                  40                  45 tat ttt tac acc cgc ctt tca aat cct act acc aat gcg gca gaa gaa     192
Tyr Phe Tyr Thr Arg Leu Ser Asn Pro Thr Thr Asn Ala Ala Glu Glu
    50                  55                  60 aaa att acc gca ctt gaa ggc ggt gta gca acc atg tgt acc gca tca     240
Lys Ile Thr Ala Leu Glu Gly Gly Val Ala Thr Met Cys Thr Ala Ser
65                  70                  75                  80 ggg caa gcc gcc gtg ttt tac gcg atg ctc aat att tta caa gcc ggt     288
Gly Gln Ala Ala Val Phe Tyr Ala Met Leu Asn Ile Leu Gln Ala Gly
                85                  90                  95 gat cac ttt att tct tca tcg tat gtt tac ggt ggt agc tac aac tta     336
Asp His Phe Ile Ser Ser Ser Tyr Val Tyr Gly Gly Ser Tyr Asn Leu
            100                 105                 110 ttt gca cat acc ttc aaa aaa atg gga att gag gtc act ttt gtg gat     384
Phe Ala His Thr Phe Lys Lys Met Gly Ile Glu Val Thr Phe Val Asp
        115                 120                 125 caa gat tta cct ctt gag gaa tta aaa aaa gct att cgc cca aat acg     432
Gln Asp Leu Pro Leu Glu Glu Leu Lys Lys Ala Ile Arg Pro Asn Thr
    130                 135                 140 aaa gcc att ttt gcc gaa act att gcc aat ccc gca tta cgc gtg ttg     480
Lys Ala Ile Phe Ala Glu Thr Ile Ala Asn Pro Ala Leu Arg Val Leu
145                 150                 155                 160 gat att gaa aag ttt gtt gca ctt gcg aag gca gca caa gcc cct tta     528
Asp Ile Glu Lys Phe Val Ala Leu Ala Lys Ala Ala Gln Ala Pro Leu
                165                 170                 175 tta gtt gac aat act ttt gca acc ccg tat ttt tgt cgc cct atc gaa     576
Leu Val Asp Asn Thr Phe Ala Thr Pro Tyr Phe Cys Arg Pro Ile Glu
            180                 185                 190 ttt ggt gct aac gtg gta att cat agt acg tca aaa tat tta gat ggg     624
Phe Gly Ala Asn Val Val Ile His Ser Thr Ser Lys Tyr Leu Asp Gly
        195                 200                 205 cat gcg att gcg ttg gga ggt tcg atc aca gat ggc ggg aat ttt gat     672
His Ala Ile Ala Leu Gly Gly Ser Ile Thr Asp Gly Gly Asn Phe Asp
    210                 215                 220 tgg aat aat ggt aaa ttc cca caa tta agc aca cct gat caa act tat     720
Trp Asn Asn Gly Lys Phe Pro Gln Leu Ser Thr Pro Asp Gln Thr Tyr
225                 230                 235                 240 cac ggt tta gtt tat acc gaa acc ttt gtt cca gcc gct tat att gtc     768
```

```
His Gly Leu Val Tyr Thr Glu Thr Phe Val Pro Ala Ala Tyr Ile Val
            245                 250                 255 aaa gcc cgt gtg caa tta atg cgt gat tta ggt gcc aca cca gca cca      816
Lys Ala Arg Val Gln Leu Met Arg Asp Leu Gly Ala Thr Pro Ala Pro
            260                 265                 270 caa aat agt ttc ttg ctc aat gtg ggc atg gaa act ctt gca ctg cgt      864
Gln Asn Ser Phe Leu Leu Asn Val Gly Met Glu Thr Leu Ala Leu Arg
            275                 280                 285 atg caa cgt cat tat gaa aat gca caa gcg gtc gcc gaa ttt tta gaa      912
Met Gln Arg His Tyr Glu Asn Ala Gln Ala Val Ala Glu Phe Leu Glu
            290                 295                 300 aat cat cca caa gtg gca aaa gtg agt tat ccg ggc ttg gca agt tca      960
Asn His Pro Gln Val Ala Lys Val Ser Tyr Pro Gly Leu Ala Ser Ser
305                 310                 315                 320 cct gat cat gca cta aaa caa aaa tat tta cca aac ggt tta tgt ggt     1008
Pro Asp His Ala Leu Lys Gln Lys Tyr Leu Pro Asn Gly Leu Cys Gly
            325                 330                 335 gtg att tcc ttt gaa att aga ggg gga aga gaa act gca gca aaa tgg     1056
Val Ile Ser Phe Glu Ile Arg Gly Gly Arg Glu Thr Ala Ala Lys Trp
            340                 345                 350 ctg aat gcg cta caa ctg gct tct cgt gaa gtc cat gta gcg gat att     1104
Leu Asn Ala Leu Gln Leu Ala Ser Arg Glu Val His Val Ala Asp Ile
            355                 360                 365 cgc act tgt gct tta cat ccg gcg acg tca aca cac cgt caa tta agt     1152
Arg Thr Cys Ala Leu His Pro Ala Thr Ser Thr His Arg Gln Leu Ser
370                 375                 380 gag gct gaa tta gaa aaa gtg ggg att tct gcg ggt tta att cgt ctt     1200
Glu Ala Glu Leu Glu Lys Val Gly Ile Ser Ala Gly Leu Ile Arg Leu
385                 390                 395                 400 tct tgc ggt att gaa agt atc caa gat att ttg gct gac tta gaa caa     1248
Ser Cys Gly Ile Glu Ser Ile Gln Asp Ile Leu Ala Asp Leu Glu Gln
            405                 410                 415 gca ttc cac gcg gca aaa taa                                         1269
Ala Phe His Ala Ala Lys
            420
```

<210> SEQ ID NO 40
<211> LENGTH: 422
<212> TYPE: PRT
<213> ORGANISM: Pasteurella multocida

<400> SEQUENCE: 40

```
Met Glu Phe Ala Thr Lys Cys Leu His Ala Gly Tyr Thr Pro Lys Asn
1               5                   10                  15

Gly Glu Pro Arg Val Gln Pro Ile Val Gln Ser Thr Thr Phe Thr Tyr
            20                  25                  30

Asp Ser Ala Glu Glu Ile Gly Lys Leu Phe Asp Leu Gln Ala Ala Gly
        35                  40                  45

Tyr Phe Tyr Thr Arg Leu Ser Asn Pro Thr Thr Asn Ala Ala Glu Glu
    50                  55                  60

Lys Ile Thr Ala Leu Glu Gly Gly Val Ala Thr Met Cys Thr Ala Ser
65                  70                  75                  80

Gly Gln Ala Ala Val Phe Tyr Ala Met Leu Asn Ile Leu Gln Ala Gly
                85                  90                  95

Asp His Phe Ile Ser Ser Ser Tyr Val Tyr Gly Gly Ser Tyr Asn Leu
            100                 105                 110

Phe Ala His Thr Phe Lys Lys Met Gly Ile Glu Val Thr Phe Val Asp
        115                 120                 125
```

```
Gln Asp Leu Pro Leu Glu Glu Leu Lys Lys Ala Ile Arg Pro Asn Thr
    130                 135                 140
Lys Ala Ile Phe Ala Glu Thr Ile Ala Asn Pro Ala Leu Arg Val Leu
145                 150                 155                 160
Asp Ile Glu Lys Phe Val Ala Leu Ala Lys Ala Ala Gln Ala Pro Leu
                165                 170                 175
Leu Val Asp Asn Thr Phe Ala Thr Pro Tyr Phe Cys Arg Pro Ile Glu
                180                 185                 190
Phe Gly Ala Asn Val Val Ile His Ser Thr Ser Lys Tyr Leu Asp Gly
            195                 200                 205
His Ala Ile Ala Leu Gly Gly Ser Ile Thr Asp Gly Gly Asn Phe Asp
    210                 215                 220
Trp Asn Gly Lys Phe Pro Gln Leu Ser Thr Pro Asp Gln Thr Tyr
225                 230                 235                 240
His Gly Leu Val Tyr Thr Glu Thr Phe Val Pro Ala Ala Tyr Ile Val
                245                 250                 255
Lys Ala Arg Val Gln Leu Met Arg Asp Leu Gly Ala Thr Pro Ala Pro
                260                 265                 270
Gln Asn Ser Phe Leu Leu Asn Val Gly Met Glu Thr Leu Ala Leu Arg
            275                 280                 285
Met Gln Arg His Tyr Glu Asn Ala Gln Ala Val Ala Glu Phe Leu Glu
    290                 295                 300
Asn His Pro Gln Val Ala Lys Val Ser Tyr Pro Gly Leu Ala Ser Ser
305                 310                 315                 320
Pro Asp His Ala Leu Lys Gln Lys Tyr Leu Pro Asn Gly Leu Cys Gly
                325                 330                 335
Val Ile Ser Phe Glu Ile Arg Gly Gly Arg Glu Thr Ala Ala Lys Trp
            340                 345                 350
Leu Asn Ala Leu Gln Leu Ala Ser Arg Glu Val His Val Ala Asp Ile
        355                 360                 365
Arg Thr Cys Ala Leu His Pro Ala Thr Ser Thr His Arg Gln Leu Ser
    370                 375                 380
Glu Ala Glu Leu Glu Lys Val Gly Ile Ser Ala Gly Leu Ile Arg Leu
385                 390                 395                 400
Ser Cys Gly Ile Glu Ser Ile Gln Asp Ile Leu Ala Asp Leu Glu Gln
                405                 410                 415
Ala Phe His Ala Ala Lys
                420

<210> SEQ ID NO 41
<211> LENGTH: 1266
<212> TYPE: DNA
<213> ORGANISM: Clostridium difficile
<220> FEATURE:
<221> NAME/KEY: CDS
<222> LOCATION: (1)..(1266)

<400> SEQUENCE: 41 atg tat aat aaa ga

| | |
|---|---|
| gga cat ata tat tca aga ata agc aat cct act att caa gct ttt gaa<br>Gly His Ile Tyr Ser Arg Ile Ser Asn Pro Thr Ile Gln Ala Phe Glu<br>    50                  55                  60 | 192 |
| gaa aaa ata agt tta cta gag ggt gga gta tct tct gta gct gta tca<br>Glu Lys Ile Ser Leu Leu Glu Gly Gly Val Ser Ser Val Ala Val Ser<br>65                  70                  75                  80 | 240 |
| tca ggg caa tct gca aat atg ttg gca gtt tta aat ata tgt aaa tca<br>Ser Gly Gln Ser Ala Asn Met Leu Ala Val Leu Asn Ile Cys Lys Ser<br>                85                  90                  95 | 288 |
| gga gat agt ata ctt tgt tct tca aaa gta tat gga gga aca ttc aat<br>Gly Asp Ser Ile Leu Cys Ser Ser Lys Val Tyr Gly Gly Thr Phe Asn<br>           100                   105                 110 | 336 |
| tta cta gga cct agt ctt aaa aaa ttt ggt ata gat tta ata tcg ttt<br>Leu Leu Gly Pro Ser Leu Lys Lys Phe Gly Ile Asp Leu Ile Ser Phe<br>         115                   120                 125 | 384 |
| gac tta gat tca agt gaa gat gag ata gta gaa ctt gca aag gaa aat<br>Asp Leu Asp Ser Ser Glu Asp Glu Ile Val Glu Leu Ala Lys Glu Asn<br>130                  135                 140 | 432 |
| act aag gtt gtg ttt gca gaa aca ctt gca aat cca act ctt gaa gtc<br>Thr Lys Val Val Phe Ala Glu Thr Leu Ala Asn Pro Thr Leu Glu Val<br>145                  150                 155                160 | 480 |
| ata gat ttt gaa aaa ata gca aat gta gct aag aga att aat gtt cca<br>Ile Asp Phe Glu Lys Ile Ala Asn Val Ala Lys Arg Ile Asn Val Pro<br>           165                   170                 175 | 528 |
| ttt att gtt gat aat tca tta gca tct cca gtg ctt tgt aac cct tta<br>Phe Ile Val Asp Asn Ser Leu Ala Ser Pro Val Leu Cys Asn Pro Leu<br>         180                   185                 190 | 576 |
| aag tat gga gca aat ata gtt act cat tct acc aca aaa tat tta gat<br>Lys Tyr Gly Ala Asn Ile Val Thr His Ser Thr Thr Lys Tyr Leu Asp<br>         195                   200                 205 | 624 |
| ggg cat gct tca agt gtt gga gga att ata gtg gat ggt gga aac ttt<br>Gly His Ala Ser Ser Val Gly Gly Ile Ile Val Asp Gly Gly Asn Phe<br>         210                   215                 220 | 672 |
| aac tgg gat aat gga aaa ttt cca gaa tta gtt gag cca gac cca aca<br>Asn Trp Asp Asn Gly Lys Phe Pro Glu Leu Val Glu Pro Asp Pro Thr<br>225                  230                 235                240 | 720 |
| tat cat ggt ata agc tat act caa aaa ttt gga aat gcc gca tat gca<br>Tyr His Gly Ile Ser Tyr Thr Gln Lys Phe Gly Asn Ala Ala Tyr Ala<br>         245                   250                 255 | 768 |
| act aaa gca aga gtt cag ttg ctt aga gac tat gga aat tgt tta agc<br>Thr Lys Ala Arg Val Gln Leu Leu Arg Asp Tyr Gly Asn Cys Leu Ser<br>         260                   265                 270 | 816 |
| cca ttc aat gcg tat ctt act aat tta aat gtt gaa aca cta cat ctt<br>Pro Phe Asn Ala Tyr Leu Thr Asn Leu Asn Val Glu Thr Leu His Leu<br>         275                   280                 285 | 864 |
| aga atg gag aga cat agt gaa aat gca ctt aaa ata gct aga ttt tta<br>Arg Met Glu Arg His Ser Glu Asn Ala Leu Lys Ile Ala Arg Phe Leu<br>         290                   295                 300 | 912 |
| gaa aaa cat gaa aat gta gat tgg att aat tac cca gga ctt gaa gat<br>Glu Lys His Glu Asn Val Asp Trp Ile Asn Tyr Pro Gly Leu Glu Asp<br>305                  310                 315                320 | 960 |
| aac aag tat tat gag aat gcc aaa aag tat tta tca aga gga tgt agt<br>Asn Lys Tyr Tyr Glu Asn Ala Lys Lys Tyr Leu Ser Arg Gly Cys Ser<br>         325                   330                 335 | 1008 |
| ggt gtt tta tca ttt gga gta aga ggt ggg tta gaa aat gcc aaa aaa<br>Gly Val Leu Ser Phe Gly Val Arg Gly Gly Leu Glu Asn Ala Lys Lys<br>         340                   345                 350 | 1056 |
| ttt gtg gaa aaa tta cag ata gca tct ttg gtt aca cat gtt tca gat<br>Phe Val Glu Lys Leu Gln Ile Ala Ser Leu Val Thr His Val Ser Asp | 1104 |

-continued

```
                    355                 360                 365
gta aga act tgt gtt ata cat cca gct tca act act cat aga caa tta      1152
Val Arg Thr Cys Val Ile His Pro Ala Ser Thr Thr His Arg Gln Leu
    370                 375                 380 aca gaa gaa caa tta att gca tct gga gta ttg cct tca cta ata aga      1200
Thr Glu Glu Gln Leu Ile Ala Ser Gly Val Leu Pro Ser Leu Ile Arg
385                 390                 395                 400 tta tct gtt gga ata gaa aat gta gag gat tta ata gct gat tta aat      1248
Leu Ser Val Gly Ile Glu Asn Val Glu Asp Leu Ile Ala Asp Leu Asn
                405                 410                 415 caa gct tta aat ttc taa                                              1266
Gln Ala Leu Asn Phe
            420

<210> SEQ ID NO 42
<211> LENGTH: 421
<212> TYPE: PRT
<213> ORGANISM: Clostridium difficile

<400> SEQUENCE: 42

Met Tyr Asn Lys Glu Thr Ile Cys Val Gln Gly Asn Tyr Lys Pro Gly
1               5                   10                  15

Asn Gly Glu Pro Arg Val Leu Pro Leu Tyr Gln Ser Thr Thr Phe Lys
                20                  25                  30

Tyr Ser Ser Ile Asp Gln Leu Ala Glu Leu Phe Asp Leu Lys Val Asp
            35                  40                  45

Gly His Ile Tyr Ser Arg Ile Ser Asn Pro Thr Ile Gln Ala Phe Glu
        50                  55                  60

Glu Lys Ile Ser Leu Leu Glu Gly Gly Val Ser Ser Val Ala Val Ser
65                  70                  75                  80

Ser Gly Gln Ser Ala Asn Met Leu Ala Val Leu Asn Ile Cys Lys Ser
                85                  90                  95

Gly Asp Ser Ile Leu Cys Ser Ser Lys Val Tyr Gly Gly Thr Phe Asn
            100                 105                 110

Leu Leu Gly Pro Ser Leu Lys Lys Phe Gly Ile Asp Leu Ile Ser Phe
        115                 120                 125

Asp Leu Asp Ser Ser Glu Asp Glu Ile Val Glu Leu Ala Lys Glu Asn
    130                 135                 140

Thr Lys Val Val Phe Ala Glu Thr Leu Ala Asn Pro Thr Leu Glu Val
145                 150                 155                 160

Ile Asp Phe Glu Lys Ile Ala Asn Val Ala Lys Arg Ile Asn Val Pro
                165                 170                 175

Phe Ile Val Asp Asn Ser Leu Ala Ser Pro Val Leu Cys Asn Pro Leu
            180                 185                 190

Lys Tyr Gly Ala Asn Ile Val Thr His Ser Thr Thr Lys Tyr Leu Asp
        195                 200                 205

Gly His Ala Ser Ser Val Gly Gly Ile Ile Val Asp Gly Gly Asn Phe
    210                 215                 220

Asn Trp Asp Asn Gly Lys Phe Pro Glu Leu Val Glu Pro Asp Pro Thr
225                 230                 235                 240

Tyr His Gly Ile Ser Tyr Thr Gln Lys Phe Gly Asn Ala Ala Tyr Ala
                245                 250                 255

Thr Lys Ala Arg Val Gln Leu Leu Arg Asp Tyr Gly Asn Cys Leu Ser
            260                 265                 270

Pro Phe Asn Ala Tyr Leu Thr Asn Leu Asn Val Glu Thr Leu His Leu
        275                 280                 285
```

```
Arg Met Glu Arg His Ser Glu Asn Ala Leu Lys Ile Ala Arg Phe Leu
    290                 295                 300

Glu Lys His Glu Asn Val Asp Trp Ile Asn Tyr Pro Gly Leu Glu Asp
305                 310                 315                 320

Asn Lys Tyr Tyr Glu Asn Ala Lys Lys Tyr Leu Ser Arg Gly Cys Ser
                325                 330                 335

Gly Val Leu Ser Phe Gly Val Arg Gly Leu Glu Asn Ala Lys Lys
                340                 345                 350

Phe Val Glu Lys Leu Gln Ile Ala Ser Leu Val Thr His Val Ser Asp
            355                 360                 365

Val Arg Thr Cys Val Ile His Pro Ala Ser Thr Thr His Arg Gln Leu
        370                 375                 380

Thr Glu Glu Gln Leu Ile Ala Ser Gly Val Leu Pro Ser Leu Ile Arg
385                 390                 395                 400

Leu Ser Val Gly Ile Glu Asn Val Glu Asp Leu Ile Ala Asp Leu Asn
                405                 410                 415

Gln Ala Leu Asn Phe
            420

<210> SEQ ID NO 43
<211> LENGTH: 1272
<212> TYPE: DNA
<213> ORGANISM: Campylobacter jejuni
<220> FEATURE:
<221> NAME/KEY: CDS
<222> LOCATION: (1)..(1272)

<400> SEQUENCE: 43 atg aat ttc aat aaa gaa act tta gca tta cac gga gct tat aat ttt        48
Met Asn Phe Asn Lys Glu Thr Leu Ala Leu His Gly Ala Tyr Asn Phe
1               5                   10                  15 gat act caa aga agt att agt gtg cct ata tat caa aac act gcg tat        96
Asp Thr Gln Arg Ser Ile Ser Val Pro Ile Tyr Gln Asn Thr Ala Tyr
            20                  25                  30 aat ttt gaa aat ttg gat caa gct gca gca agg ttt aat ctt caa gaa       144
Asn Phe Glu Asn Leu Asp Gln Ala Ala Ala Arg Phe Asn Leu Gln Glu
        35                  40                  45 ctt ggc aat att tac tca aga ctt agc aat cct aca agc gat gtt tta       192
Leu Gly Asn Ile Tyr Ser Arg Leu Ser Asn Pro Thr Ser Asp Val Leu
    50                  55                  60 gga caa aga ctt gct aat gtc gaa gga ggg gct ttt gga att cct gtt       240
Gly Gln Arg Leu Ala Asn Val Glu Gly Gly Ala Phe Gly Ile Pro Val
65                  70                  75                  80 gct agc ggt atg gca gct tgt ttt tat gct ctt atc aat tta gca agt       288
Ala Ser Gly Met Ala Ala Cys Phe Tyr Ala Leu Ile Asn Leu Ala Ser
                85                  90                  95 tcg gga gat aat gtc gcg tat tcg aac aaa att tat ggt ggg act caa       336
Ser Gly Asp Asn Val Ala Tyr Ser Asn Lys Ile Tyr Gly Gly Thr Gln
            100                 105                 110 act tta att tct cac aca ctt aaa aat ttt ggc ata gaa gct agg gaa       384
Thr Leu Ile Ser His Thr Leu Lys Asn Phe Gly Ile Glu Ala Arg Glu
        115                 120                 125 ttt gat atc gat gat tta gat agc ttg gaa aaa gtt ata gat caa aac       432
Phe Asp Ile Asp Asp Leu Asp Ser Leu Glu Lys Val Ile Asp Gln Asn
    130                 135                 140 aca aaa gcg att ttt ttc gaa agt ctt tca aat cct caa att gcc ata       480
Thr Lys Ala Ile Phe Phe Glu Ser Leu Ser Asn Pro Gln Ile Ala Ile
145                 150                 155                 160
```

```
gct ata gaa aaa ata aac caa ata gca aaa aaa cat aaa atc gtt       528
Ala Asp Ile Glu Lys Ile Asn Gln Ile Ala Lys Lys His Lys Ile Val
            165                 170                 175 agc att tgt gat aat acc gtt gct act cct ttc tta ctc caa cct ttt   576
Ser Ile Cys Asp Asn Thr Val Ala Thr Pro Phe Leu Leu Gln Pro Phe
                180                 185                 190 aaa cat ggc gtg gat gta atc gtg cat agt tta agt aaa tat gta agc   624
Lys His Gly Val Asp Val Ile Val His Ser Leu Ser Lys Tyr Val Ser
            195                 200                 205 ggt caa ggc act gct ttg ggt gga gca ctt ata gaa aga aaa gat tta   672
Gly Gln Gly Thr Ala Leu Gly Gly Ala Leu Ile Glu Arg Lys Asp Leu
        210                 215                 220 aac gac ttg ctt aaa aat aac gat aga tat aaa gct ttt aac act cct   720
Asn Asp Leu Leu Lys Asn Asn Asp Arg Tyr Lys Ala Phe Asn Thr Pro
225                 230                 235                 240 gat cca agt tat cat gga ctg aat tta aat aca ctt gat ttg ccg att   768
Asp Pro Ser Tyr His Gly Leu Asn Leu Asn Thr Leu Asp Leu Pro Ile
                245                 250                 255 ttt agt att aga gtc atc atc act tgg ctt aga gat cta gga gct agc   816
Phe Ser Ile Arg Val Ile Ile Thr Trp Leu Arg Asp Leu Gly Ala Ser
            260                 265                 270 tta gca cct caa aat gct tgg tta ctt tta caa gga ctt gaa acc ttg   864
Leu Ala Pro Gln Asn Ala Trp Leu Leu Leu Gln Gly Leu Glu Thr Leu
        275                 280                 285 gca gtg cgt ata gaa aaa cac agt caa aat gct gaa aaa gtt gcg aat   912
Ala Val Arg Ile Glu Lys His Ser Gln Asn Ala Glu Lys Val Ala Asn
    290                 295                 300 ttt tta aat tct cat cct gat atc aag ggc gta aat tat cct act tta   960
Phe Leu Asn Ser His Pro Asp Ile Lys Gly Val Asn Tyr Pro Thr Leu
305                 310                 315                 320 gca agt aat gct tat cat aat tta ttt aaa aaa tat ttt gat aaa aat  1008
Ala Ser Asn Ala Tyr His Asn Leu Phe Lys Lys Tyr Phe Asp Lys Asn
                325                 330                 335 ttt gct agc ggg ctt tta agc ttt gaa gct aaa gat tat gag cat gct  1056
Phe Ala Ser Gly Leu Leu Ser Phe Glu Ala Lys Asp Tyr Glu His Ala
            340                 345                 350 aga aga att tgt gat aaa act caa ctt ttc tta ctt gct gca aat ttg  1104
Arg Arg Ile Cys Asp Lys Thr Gln Leu Phe Leu Leu Ala Ala Asn Leu
        355                 360                 365 ggt gat agc aag tct ttg atc atc cat cct gct tct act act cat tcg  1152
Gly Asp Ser Lys Ser Leu Ile Ile His Pro Ala Ser Thr Thr His Ser
    370                 375                 380 caa cta agc gaa gaa gaa ctc caa aaa gca ggc att acg aaa gct act  1200
Gln Leu Ser Glu Glu Glu Leu Gln Lys Ala Gly Ile Thr Lys Ala Thr
385                 390                 395                 400 ata cgc tta agc ata gga ctt gaa aat agc gat gat ttg ata gcg gat  1248
Ile Arg Leu Ser Ile Gly Leu Glu Asn Ser Asp Asp Leu Ile Ala Asp
                405                 410                 415 tta aaa caa gct ata gaa agt taa                                   1272
Leu Lys Gln Ala Ile Glu Ser
            420

<210> SEQ ID NO 44
<211> LENGTH: 423
<212> TYPE: PRT
<213> ORGANISM: Campylobacter jejuni

<400> SEQUENCE: 44

Met Asn Phe Asn Lys Glu Thr Leu Ala Leu His Gly Ala Tyr Asn Phe
1               5                   10                  15
```

-continued

```
Asp Thr Gln Arg Ser Ile Ser Val Pro Ile Tyr Gln Asn Thr Ala Tyr
            20                  25                  30

Asn Phe Glu Asn Leu Asp Gln Ala Ala Arg Phe Asn Leu Gln Glu
        35                  40                  45

Leu Gly Asn Ile Tyr Ser Arg Leu Ser Asn Pro Thr Ser Asp Val Leu
    50                  55                  60

Gly Gln Arg Leu Ala Asn Val Glu Gly Gly Ala Phe Gly Ile Pro Val
65                  70                  75                  80

Ala Ser Gly Met Ala Ala Cys Phe Tyr Ala Leu Ile Asn Leu Ala Ser
                85                  90                  95

Ser Gly Asp Asn Val Ala Tyr Ser Asn Lys Ile Tyr Gly Gly Thr Gln
                100                 105                 110

Thr Leu Ile Ser His Thr Leu Lys Asn Phe Gly Ile Glu Ala Arg Glu
                115                 120                 125

Phe Asp Ile Asp Asp Leu Asp Ser Leu Glu Lys Val Ile Asp Gln Asn
    130                 135                 140

Thr Lys Ala Ile Phe Phe Glu Ser Leu Ser Asn Pro Gln Ile Ala Ile
145                 150                 155                 160

Ala Asp Ile Glu Lys Ile Asn Gln Ile Ala Lys Lys His Lys Ile Val
                165                 170                 175

Ser Ile Cys Asp Asn Thr Val Ala Thr Pro Phe Leu Leu Gln Pro Phe
                180                 185                 190

Lys His Gly Val Asp Val Ile Val His Ser Leu Ser Lys Tyr Val Ser
            195                 200                 205

Gly Gln Gly Thr Ala Leu Gly Gly Ala Leu Ile Glu Arg Lys Asp Leu
210                 215                 220

Asn Asp Leu Leu Lys Asn Asn Asp Arg Tyr Lys Ala Phe Asn Thr Pro
225                 230                 235                 240

Asp Pro Ser Tyr His Gly Leu Asn Leu Asn Thr Leu Asp Leu Pro Ile
                245                 250                 255

Phe Ser Ile Arg Val Ile Ile Thr Trp Leu Arg Asp Leu Gly Ala Ser
                260                 265                 270

Leu Ala Pro Gln Asn Ala Trp Leu Leu Leu Gln Gly Leu Glu Thr Leu
                275                 280                 285

Ala Val Arg Ile Glu Lys His Ser Gln Asn Ala Glu Lys Val Ala Asn
                290                 295                 300

Phe Leu Asn Ser His Pro Asp Ile Lys Gly Val Asn Tyr Pro Thr Leu
305                 310                 315                 320

Ala Ser Asn Ala Tyr His Asn Leu Phe Lys Lys Tyr Phe Asp Lys Asn
                325                 330                 335

Phe Ala Ser Gly Leu Leu Ser Phe Glu Ala Lys Asp Tyr Glu His Ala
                340                 345                 350

Arg Arg Ile Cys Asp Lys Thr Gln Leu Phe Leu Leu Ala Ala Asn Leu
                355                 360                 365

Gly Asp Ser Lys Ser Leu Ile Ile His Pro Ala Ser Thr Thr His Ser
        370                 375                 380

Gln Leu Ser Glu Glu Leu Gln Lys Ala Gly Ile Thr Lys Ala Thr
385                 390                 395                 400

Ile Arg Leu Ser Ile Gly Leu Glu Asn Ser Asp Asp Leu Ile Ala Asp
                405                 410                 415

Leu Lys Gln Ala Ile Glu Ser
                420
```

<210> SEQ ID NO 45
<211> LENGTH: 1041
<212> TYPE: DNA
<213> ORGANISM: Streptococcus pneumoniae
<220> FEATURE:
<221> NAME/KEY: CDS
<222> LOCATION: (1)..(1041)

<400> SEQUENCE: 45

| | | | | | | | | | | | | | | | | |
|---|---|---|---|---|---|---|---|---|---|---|---|---|---|---|---|---|
| ttg | agg | aaa | cca | ggg | aac | att | tat | act | cgt | atc | acc | aat | cct | aca | aca | 48 |
| Leu | Arg | Lys | Pro | Gly | Asn | Ile | Tyr | Thr | Arg | Ile | Thr | Asn | Pro | Thr | Thr | |
| 1 | | | | 5 | | | | | 10 | | | | | 15 | | |
| gct | gcc | ctt | gaa | ggt | ggt | gtt | gaa | gcg | cta | gca | aca | gca | tca | ggt | atg | 96 |
| Ala | Ala | Leu | Glu | Gly | Gly | Val | Glu | Ala | Leu | Ala | Thr | Ala | Ser | Gly | Met | |
| | | | 20 | | | | | 25 | | | | | 30 | | | |
| act | gca | gtg | act | tat | acg | att | ttg | gcg | att | gcc | cat | gct | ggt | gac | cat | 144 |
| Thr | Ala | Val | Thr | Tyr | Thr | Ile | Leu | Ala | Ile | Ala | His | Ala | Gly | Asp | His | |
| | | 35 | | | | | 40 | | | | | 45 | | | | |
| gta | gtg | gct | gct | tcg | act | att | tac | ggt | gga | acc | ttc | aat | ctt | ttg | aaa | 192 |
| Val | Val | Ala | Ala | Ser | Thr | Ile | Tyr | Gly | Gly | Thr | Phe | Asn | Leu | Leu | Lys | |
| 50 | | | | | 55 | | | | | 60 | | | | | | |
| gaa | ccc | ctt | cct | cgt | tat | ggt | atc | aca | aca | acc | ttt | ttc | gat | att | gat | 240 |
| Glu | Pro | Leu | Pro | Arg | Tyr | Gly | Ile | Thr | Thr | Thr | Phe | Phe | Asp | Ile | Asp | |
| 65 | | | | | 70 | | | | | 75 | | | | | 80 | |
| aat | ttg | gag | gaa | gta | gaa | gca | gct | atc | aaa | gac | aat | acc | aag | ctt | gtc | 288 |
| Asn | Leu | Glu | Glu | Val | Glu | Ala | Ala | Ile | Lys | Asp | Asn | Thr | Lys | Leu | Val | |
| | | | | 85 | | | | | 90 | | | | | 95 | | |
| ttg | att | gaa | acc | ttg | ggt | aac | ccc | ttg | att | aat | att | cca | gac | ctg | gaa | 336 |
| Leu | Ile | Glu | Thr | Leu | Gly | Asn | Pro | Leu | Ile | Asn | Ile | Pro | Asp | Leu | Glu | |
| | | | 100 | | | | | 105 | | | | | 110 | | | |
| aaa | ctg | gca | gag | att | gct | cat | aaa | cat | caa | atc | cca | ctt | gtg | tca | gac | 384 |
| Lys | Leu | Ala | Glu | Ile | Ala | His | Lys | His | Gln | Ile | Pro | Leu | Val | Ser | Asp | |
| | | 115 | | | | | 120 | | | | | 125 | | | | |
| aat | act | ttt | gca | aca | cct | tat | ttg | att | aac | gtc | ttc | tct | cat | ggc | gtt | 432 |
| Asn | Thr | Phe | Ala | Thr | Pro | Tyr | Leu | Ile | Asn | Val | Phe | Ser | His | Gly | Val | |
| | | 130 | | | | | 135 | | | | | 140 | | | | |
| gac | att | gcc | att | cac | tct | gtg | act | aag | ttt | atc | ggt | ggg | cat | ggt | aca | 480 |
| Asp | Ile | Ala | Ile | His | Ser | Val | Thr | Lys | Phe | Ile | Gly | Gly | His | Gly | Thr | |
| 145 | | | | | 150 | | | | | 155 | | | | | 160 | |
| act | att | gga | gga | ata | att | gtc | gat | agt | ggt | cgt | ttt | gac | tgg | acg | gct | 528 |
| Thr | Ile | Gly | Gly | Ile | Ile | Val | Asp | Ser | Gly | Arg | Phe | Asp | Trp | Thr | Ala | |
| | | | 165 | | | | | 170 | | | | | 175 | | | |
| tca | ggg | aaa | ttc | cct | caa | ttt | gtt | gac | gag | ggt | cca | agc | tgc | cac | aat | 576 |
| Ser | Gly | Lys | Phe | Pro | Gln | Phe | Val | Asp | Glu | Gly | Pro | Ser | Cys | His | Asn | |
| | | 180 | | | | | 185 | | | | | 190 | | | | |
| ttg | agc | tat | act | cgt | gat | gtg | ggt | gca | gca | gcc | ttt | att | ata | gct | gtt | 624 |
| Leu | Ser | Tyr | Thr | Arg | Asp | Val | Gly | Ala | Ala | Ala | Phe | Ile | Ile | Ala | Val | |
| | | 195 | | | | | 200 | | | | | 205 | | | | |
| cga | gtt | caa | ttg | ctt | cgt | gat | aca | ggt | gca | gcc | ttg | tca | cca | ttc | aat | 672 |
| Arg | Val | Gln | Leu | Leu | Arg | Asp | Thr | Gly | Ala | Ala | Leu | Ser | Pro | Phe | Asn | |
| 210 | | | | | 215 | | | | | 220 | | | | | | |
| gct | ttc | ctc | ttg | cta | caa | aga | ctt | gaa | acc | tct | tca | ctt | cgt | gtg | aa | 720 |
| Ala | Phe | Leu | Leu | Leu | Gln | Arg | Leu | Glu | Thr | Ser | Ser | Leu | Arg | Val | Glu | |
| 225 | | | | | 230 | | | | | 235 | | | | | 240 | |
| cgc | cat | gta | caa | aat | gct | gag | aca | att | gtt | gat | ttt | ctt | gtc | aac | cat | 768 |
| Arg | His | Val | Gln | Asn | Ala | Glu | Thr | Ile | Val | Asp | Phe | Leu | Val | Asn | His | |
| | | | | 245 | | | | | 250 | | | | | 255 | | |
| cct | aag | gta | gaa | aag | gta | aat | tat | cca | aaa | ctt | gca | gat | agt | cct | tat | 816 |
| Pro | Lys | Val | Glu | Lys | Val | Asn | Tyr | Pro | Lys | Leu | Ala | Asp | Ser | Pro | Tyr | |
| | | | 260 | | | | | 265 | | | | | 270 | | | |
| cat | gcc | ttg | gct | gag | aaa | tac | ttg | cca | aaa | ggt | gtc | ggt | tca | atc | ttt | 864 |

```
His Ala Leu Ala Glu Lys Tyr Leu Pro Lys Gly Val Gly Ser Ile Phe
            275                 280                 285 acc ttc cac gtc aaa ggt ggc gag gaa gaa gca cgc aag gtc att gat       912
Thr Phe His Val Lys Gly Gly Glu Glu Glu Ala Arg Lys Val Ile Asp
        290                 295                 300 aat tta gaa atc ttt tct gac ctt gca aac gcg gca gat gct aaa tcg       960
Asn Leu Glu Ile Phe Ser Asp Leu Ala Asn Ala Ala Asp Ala Lys Ser
305                 310                 315                 320 ctt gtt gtc cat cca gca aca acc act cac ggt caa ttg tca gaa aaa      1008
Leu Val Val His Pro Ala Thr Thr Thr His Gly Gln Leu Ser Glu Lys
                325                 330                 335 gac cta gaa gca gca ggt gtc aca cca aac taa                          1041
Asp Leu Glu Ala Ala Gly Val Thr Pro Asn
                340                 345

<210> SEQ ID NO 46
<211> LENGTH: 346
<212> TYPE: PRT
<213> ORGANISM: Streptococcus pneumoniae

<400> SEQUENCE: 46

Leu Arg Lys Pro Gly Asn Ile Tyr Thr Arg Ile Thr Asn Pro Thr Thr
1               5                   10                  15

Ala Ala Leu Glu Gly Gly Val Glu Ala Leu Ala Thr Ala Ser Gly Met
            20                  25                  30

Thr Ala Val Thr Tyr Thr Ile Leu Ala Ile Ala His Ala Gly Asp His
        35                  40                  45

Val Val Ala Ala Ser Thr Ile Tyr Gly Gly Thr Phe Asn Leu Leu Lys
    50                  55                  60

Glu Pro Leu Pro Arg Tyr Gly Ile Thr Thr Thr Phe Phe Asp Ile Asp
65                  70                  75                  80

Asn Leu Glu Glu Val Glu Ala Ala Ile Lys Asp Asn Thr Lys Leu Val
                85                  90                  95

Leu Ile Glu Thr Leu Gly Asn Pro Leu Ile Asn Ile Pro Asp Leu Glu
            100                 105                 110

Lys Leu Ala Glu Ile Ala His Lys His Gln Ile Pro Leu Val Ser Asp
        115                 120                 125

Asn Thr Phe Ala Thr Pro Tyr Leu Ile Asn Val Phe Ser His Gly Val
    130                 135                 140

Asp Ile Ala Ile His Ser Val Thr Lys Phe Ile Gly Gly His Gly Thr
145                 150                 155                 160

Thr Ile Gly Gly Ile Ile Val Asp Ser Gly Arg Phe Asp Trp Thr Ala
                165                 170                 175

Ser Gly Lys Phe Pro Gln Phe Val Asp Glu Gly Pro Ser Cys His Asn
            180                 185                 190

Leu Ser Tyr Thr Arg Asp Val Gly Ala Ala Phe Ile Ile Ala Val
        195                 200                 205

Arg Val Gln Leu Leu Arg Asp Thr Gly Ala Ala Leu Ser Pro Phe Asn
    210                 215                 220

Ala Phe Leu Leu Leu Gln Arg Leu Glu Thr Ser Ser Leu Arg Val Glu
225                 230                 235                 240

Arg His Val Gln Asn Ala Glu Thr Ile Val Asp Phe Leu Val Asn His
                245                 250                 255

Pro Lys Val Glu Lys Val Asn Tyr Pro Lys Leu Ala Asp Ser Pro Tyr
            260                 265                 270

His Ala Leu Ala Glu Lys Tyr Leu Pro Lys Gly Val Gly Ser Ile Phe
```

```
                  275                 280                 285
Thr Phe His Val Lys Gly Gly Glu Glu Ala Arg Lys Val Ile Asp
    290                 295                 300

Asn Leu Glu Ile Phe Ser Asp Leu Ala Asn Ala Ala Asp Ala Lys Ser
305                 310                 315                 320

Leu Val Val His Pro Ala Thr Thr His Gly Gln Leu Ser Glu Lys
                325                 330                 335

Asp Leu Glu Ala Ala Gly Val Thr Pro Asn
                340                 345

<210> SEQ ID NO 47
<211> LENGTH: 1335
<212> TYPE: DNA
<213> ORGANISM: Saccharomyces cerevisiae
<220> FEATURE:
<221> NAME/KEY: CDS
<222> LOCATION: (1)..(1335)

<400> SEQUENCE: 47 atg cca tct cat ttc gat act gtt caa cta cac gcc ggc caa gag aac        48
Met Pro Ser His Phe Asp Thr Val Gln Leu His Ala Gly Gln Glu Asn
1               5                  10                  15 cct ggt gac aat gct cac aga tcc aga gct gta cca att tac gcc acc        96
Pro Gly Asp Asn Ala His Arg Ser Arg Ala Val Pro Ile Tyr Ala Thr
                20                  25                  30 act tct tat gtt ttc gaa aac tct aag cat ggt tcg caa ttg ttt ggt       144
Thr Ser Tyr Val Phe Glu Asn Ser Lys His Gly Ser Gln Leu Phe Gly
            35                  40                  45 cta gaa gtt cca ggt tac gtc tat tcc cgt ttc caa aac cca acc agt       192
Leu Glu Val Pro Gly Tyr Val Tyr Ser Arg Phe Gln Asn Pro Thr Ser
        50                  55                  60 aat gtt ttg gaa gaa aga att gct gct tta gaa ggt ggt gct gct gct       240
Asn Val Leu Glu Glu Arg Ile Ala Ala Leu Glu Gly Gly Ala Ala Ala
65                  70                  75                  80 ttg gct gtt tcc tcc ggt caa gcc gct caa acc ctt gcc atc caa ggt       288
Leu Ala Val Ser Ser Gly Gln Ala Ala Gln Thr Leu Ala Ile Gln Gly
                85                  90                  95 ttg gca cac act ggt gac aac atc gtt tcc act tct tac tta tac ggt       336
Leu Ala His Thr Gly Asp Asn Ile Val Ser Thr Ser Tyr Leu Tyr Gly
            100                 105                 110 ggt act tat aac cag ttc aaa atc tcg ttc aaa aga ttt ggt atc gag       384
Gly Thr Tyr Asn Gln Phe Lys Ile Ser Phe Lys Arg Phe Gly Ile Glu
        115                 120                 125 gct aga ttt gtt gaa ggt gac aat cca gaa gaa ttc gaa aag gtc ttt       432
Ala Arg Phe Val Glu Gly Asp Asn Pro Glu Glu Phe Glu Lys Val Phe
    130                 135                 140 gat gaa aga acc aag gct gtt tat ttg gaa acc att ggt aat cca aag       480
Asp Glu Arg Thr Lys Ala Val Tyr Leu Glu Thr Ile Gly Asn Pro Lys
145                 150                 155                 160 tac aat gtt ccg gat ttt gaa aaa att gtt gca att gct cac aaa cac       528
Tyr Asn Val Pro Asp Phe Glu Lys Ile Val Ala Ile Ala His Lys His
                165                 170                 175 ggt att cca gtt gtc gtt gac aac aca ttt ggt gcc ggt ggt tac ttc       576
Gly Ile Pro Val Val Val Asp Asn Thr Phe Gly Ala Gly Gly Tyr Phe
            180                 185                 190 tgt cag cca att aaa tac ggt gct gat att gta aca cat tct gct acc       624
Cys Gln Pro Ile Lys Tyr Gly Ala Asp Ile Val Thr His Ser Ala Thr
        195                 200                 205 aaa tgg att ggt ggt cat ggt act act atc ggt ggt att att gtt gac       672
Lys Trp Ile Gly Gly His Gly Thr Thr Ile Gly Gly Ile Ile Val Asp
```

```
tct ggt aag ttc cca tgg aag gac tac cca gaa aag ttc cct caa ttc     720
Ser Gly Lys Phe Pro Trp Lys Asp Tyr Pro Glu Lys Phe Pro Gln Phe
225                 230                 235                 240 tct caa cct gcc gaa gga tat cac ggt act atc tac aat gaa gcc tac     768
Ser Gln Pro Ala Glu Gly Tyr His Gly Thr Ile Tyr Asn Glu Ala Tyr
                245                 250                 255 ggt aac ttg gca tac atc gtt cat gtt aga act gaa cta tta aga gat     816
Gly Asn Leu Ala Tyr Ile Val His Val Arg Thr Glu Leu Leu Arg Asp
            260                 265                 270 ttg ggt cca ttg atg aac cca ttt gcc tct ttc ttg cta cta caa ggt     864
Leu Gly Pro Leu Met Asn Pro Phe Ala Ser Phe Leu Leu Leu Gln Gly
        275                 280                 285 gtt gaa aca tta tct ttg aga gct gaa aga cac ggt gaa aat gca ttg     912
Val Glu Thr Leu Ser Leu Arg Ala Glu Arg His Gly Glu Asn Ala Leu
    290                 295                 300 aag tta gcc aaa tgg tta gaa caa tcc cca tac gta tct tgg gtt tca     960
Lys Leu Ala Lys Trp Leu Glu Gln Ser Pro Tyr Val Ser Trp Val Ser
305                 310                 315                 320 tac cct ggt tta gca tct cat tct cat cat gaa aat gct aag aag tat    1008
Tyr Pro Gly Leu Ala Ser His Ser His His Glu Asn Ala Lys Lys Tyr
                325                 330                 335 cta tct aac ggt ttc ggt ggt gtc tta tct ttc ggt gta aaa gac tta    1056
Leu Ser Asn Gly Phe Gly Gly Val Leu Ser Phe Gly Val Lys Asp Leu
            340                 345                 350 cca aat gcc gac aag gaa act gac cca ttc aaa ctt tct ggt gct caa    1104
Pro Asn Ala Asp Lys Glu Thr Asp Pro Phe Lys Leu Ser Gly Ala Gln
        355                 360                 365 gtt gtt gac aat tta aag ctt gcc tct aac ttg gcc aat gtt ggt gat    1152
Val Val Asp Asn Leu Lys Leu Ala Ser Asn Leu Ala Asn Val Gly Asp
    370                 375                 380 gcc aag acc tta gtc att gct cca tac ttc act acc cac aaa caa tta    1200
Ala Lys Thr Leu Val Ile Ala Pro Tyr Phe Thr Thr His Lys Gln Leu
385                 390                 395                 400 aat gac aaa gaa aag ttg gca tct ggt gtt acc aag gac tta att cgt    1248
Asn Asp Lys Glu Lys Leu Ala Ser Gly Val Thr Lys Asp Leu Ile Arg
                405                 410                 415 gtc tct gtt ggt atc gaa ttt att gat gac att att gca gac ttc cag    1296
Val Ser Val Gly Ile Glu Phe Ile Asp Asp Ile Ile Ala Asp Phe Gln
            420                 425                 430 caa tct ttt gaa act gtt ttc gct ggc caa aaa cca tga                1335
Gln Ser Phe Glu Thr Val Phe Ala Gly Gln Lys Pro
        435                 440

<210> SEQ ID NO 48
<211> LENGTH: 444
<212> TYPE: PRT
<213> ORGANISM: Saccharomyces cerevisiae

<400> SEQUENCE: 48

Met Pro Ser His Phe Asp Thr Val Gln Leu His Ala Gly Gln Glu Asn
1               5                   10                  15

Pro Gly Asp Asn Ala His Arg Ser Arg Ala Val Pro Ile Tyr Ala Thr
                20                  25                  30

Thr Ser Tyr Val Phe Glu Asn Ser Lys His Gly Ser Gln Leu Phe Gly
            35                  40                  45

Leu Glu Val Pro Gly Tyr Val Tyr Ser Arg Phe Gln Asn Pro Thr Ser
        50                  55                  60

Asn Val Leu Glu Glu Arg Ile Ala Ala Leu Glu Gly Gly Ala Ala Ala
```

```
              65                  70                  75                  80
Leu Ala Val Ser Ser Gly Gln Ala Gln Thr Leu Ala Ile Gln Gly
                85                  90                  95

Leu Ala His Thr Gly Asp Asn Ile Val Ser Thr Ser Tyr Leu Tyr Gly
                100                 105                 110

Gly Thr Tyr Asn Gln Phe Lys Ile Ser Phe Lys Arg Phe Gly Ile Glu
                115                 120                 125

Ala Arg Phe Val Glu Gly Asp Asn Pro Glu Glu Phe Glu Lys Val Phe
            130                 135                 140

Asp Glu Arg Thr Lys Ala Val Tyr Leu Glu Thr Ile Gly Asn Pro Lys
145                 150                 155                 160

Tyr Asn Val Pro Asp Phe Glu Lys Ile Val Ala Ile Ala His Lys His
                165                 170                 175

Gly Ile Pro Val Val Asp Asn Thr Phe Gly Ala Gly Tyr Phe
                180                 185                 190

Cys Gln Pro Ile Lys Tyr Gly Ala Asp Ile Val Thr His Ser Ala Thr
                195                 200                 205

Lys Trp Ile Gly Gly His Gly Thr Thr Ile Gly Ile Ile Val Asp
210                 215                 220

Ser Gly Lys Phe Pro Trp Lys Asp Tyr Pro Glu Lys Phe Pro Gln Phe
225                 230                 235                 240

Ser Gln Pro Ala Glu Gly Tyr His Gly Thr Ile Tyr Asn Glu Ala Tyr
                245                 250                 255

Gly Asn Leu Ala Tyr Ile Val His Val Arg Thr Glu Leu Leu Arg Asp
                260                 265                 270

Leu Gly Pro Leu Met Asn Pro Phe Ala Ser Phe Leu Leu Gln Gly
            275                 280                 285

Val Glu Thr Leu Ser Leu Arg Ala Glu Arg His Gly Glu Asn Ala Leu
            290                 295                 300

Lys Leu Ala Lys Trp Leu Glu Gln Ser Pro Tyr Val Ser Trp Val Ser
305                 310                 315                 320

Tyr Pro Gly Leu Ala Ser His Ser His His Glu Asn Ala Lys Lys Tyr
                325                 330                 335

Leu Ser Asn Gly Phe Gly Gly Val Leu Ser Phe Gly Val Lys Asp Leu
                340                 345                 350

Pro Asn Ala Asp Lys Glu Thr Asp Pro Phe Lys Leu Ser Gly Ala Gln
            355                 360                 365

Val Val Asp Asn Leu Lys Leu Ala Ser Asn Leu Ala Asn Val Gly Asp
            370                 375                 380

Ala Lys Thr Leu Val Ile Ala Pro Tyr Phe Thr Thr His Lys Gln Leu
385                 390                 395                 400

Asn Asp Lys Glu Lys Leu Ala Ser Gly Val Thr Lys Asp Leu Ile Arg
                405                 410                 415

Val Ser Val Gly Ile Glu Phe Ile Asp Asp Ile Ile Ala Asp Phe Gln
                420                 425                 430

Gln Ser Phe Glu Thr Val Phe Ala Gly Gln Lys Pro
            435                 440

<210> SEQ ID NO 49
<211> LENGTH: 1335
<212> TYPE: DNA
<213> ORGANISM: Kluyveromyces lactis
<220> FEATURE:
<221> NAME/KEY: CDS
<222> LOCATION: (1)..(1335)
```

<400> SEQUENCE: 49

```
atg cca tct cac ttc gat act ttg caa ttg cac gct ggt caa gaa aag      48
Met Pro Ser His Phe Asp Thr Leu Gln Leu His Ala Gly Gln Glu Lys
1               5                   10                  15 act gct gat gct cat aac cca aga gcc gtc cca att tac gct acc act      96
Thr Ala Asp Ala His Asn Pro Arg Ala Val Pro Ile Tyr Ala Thr Thr
            20                  25                  30 tct tac gtc ttc aac gac tct aag cat ggt gct caa ttg ttc ggt tta     144
Ser Tyr Val Phe Asn Asp Ser Lys His Gly Ala Gln Leu Phe Gly Leu
        35                  40                  45 gaa act cca ggt tac att tac tct cgt att atg aac cct act cta gac     192
Glu Thr Pro Gly Tyr Ile Tyr Ser Arg Ile Met Asn Pro Thr Leu Asp
    50                  55                  60 gtc ttg gaa aag aga ttg gca gcc tta gaa ggt ggt att gct gct ttg     240
Val Leu Glu Lys Arg Leu Ala Ala Leu Glu Gly Gly Ile Ala Ala Leu
65                  70                  75                  80 gct act tct tct ggc caa gct gct caa acc ttg gct gtc act ggt ttg     288
Ala Thr Ser Ser Gly Gln Ala Ala Gln Thr Leu Ala Val Thr Gly Leu
                85                  90                  95 gcc cac act ggt gac aat att gtc tct acc tct ttc tta tac ggt ggt     336
Ala His Thr Gly Asp Asn Ile Val Ser Thr Ser Phe Leu Tyr Gly Gly
            100                 105                 110 act tat aac caa ttc aag gtt gcc ttc aag aga tta gga att gaa gct     384
Thr Tyr Asn Gln Phe Lys Val Ala Phe Lys Arg Leu Gly Ile Glu Ala
        115                 120                 125 aga ttt gtc gat ggt gac aag cca gaa gac ttc gaa aag ttg ttc gat     432
Arg Phe Val Asp Gly Asp Lys Pro Glu Asp Phe Glu Lys Leu Phe Asp
    130                 135                 140 gaa aag act aag gct ctc tat ctg gaa tct atc ggt aat cct aag tac     480
Glu Lys Thr Lys Ala Leu Tyr Leu Glu Ser Ile Gly Asn Pro Lys Tyr
145                 150                 155                 160 aat gtc cca gac ttc gaa aag att gtt gct gtt gct cat aag cat ggt     528
Asn Val Pro Asp Phe Glu Lys Ile Val Ala Val Ala His Lys His Gly
                165                 170                 175 atc cca gtt gtt gtt gac aac act ttc ggt gcc ggt ggt ttc ttc tgc     576
Ile Pro Val Val Val Asp Asn Thr Phe Gly Ala Gly Gly Phe Phe Cys
            180                 185                 190 caa cct atc aaa tac ggt gct gat atc gtt act cac tct gct acc aag     624
Gln Pro Ile Lys Tyr Gly Ala Asp Ile Val Thr His Ser Ala Thr Lys
        195                 200                 205 tgg atc ggt ggt cat ggt gtc acc gtt ggt ggt gtc atc att gac tct     672
Trp Ile Gly Gly His Gly Val Thr Val Gly Gly Val Ile Ile Asp Ser
    210                 215                 220 ggt aag ttc cca tgg aag gat tac ccg gaa aag ttc cct caa ttc tct     720
Gly Lys Phe Pro Trp Lys Asp Tyr Pro Glu Lys Phe Pro Gln Phe Ser
225                 230                 235                 240 cag cca tct gaa ggt tat cat ggt ttg atc ttc aat gat gcc ttt ggt     768
Gln Pro Ser Glu Gly Tyr His Gly Leu Ile Phe Asn Asp Ala Phe Gly
                245                 250                 255 cca gct gct ttc att ggt cat gta aga acc gaa ttg cta aga gat tta     816
Pro Ala Ala Phe Ile Gly His Val Arg Thr Glu Leu Leu Arg Asp Leu
            260                 265                 270 ggt cca gtg ttg agt cca ttc gct ggt ttc ttg tta cag ggt ctt         864
Gly Pro Val Leu Ser Pro Phe Ala Gly Phe Leu Leu Gln Gly Leu
        275                 280                 285 gaa act ttg tct cta aga ggt gaa aga cac ggt tcc aac gct ttg aag     912
Glu Thr Leu Ser Leu Arg Gly Glu Arg His Gly Ser Asn Ala Leu Lys
    290                 295                 300
```

```
ttg gct caa tac ttg gaa agt tct cca tac gtt tca tgg gtc tct tac    960
Leu Ala Gln Tyr Leu Glu Ser Ser Pro Tyr Val Ser Trp Val Ser Tyr
305                 310                 315                 320 cca ggt ttg cca tct cac tct cac cac gaa aac gct aag aaa tac ttg   1008
Pro Gly Leu Pro Ser His Ser His His Glu Asn Ala Lys Lys Tyr Leu
                325                 330                 335 gaa aat ggt ttc ggt ggt gtt tta tcc ttc ggt gtc aaa gat ttg cct   1056
Glu Asn Gly Phe Gly Gly Val Leu Ser Phe Gly Val Lys Asp Leu Pro
            340                 345                 350 aac gct tcc gag gaa tct gat cca ttc aag gct tct ggt gcc caa gtt   1104
Asn Ala Ser Glu Glu Ser Asp Pro Phe Lys Ala Ser Gly Ala Gln Val
        355                 360                 365 gtt gac aac ttg aag ctg gct tct aac ttg gca aac gtt ggt gac tcc   1152
Val Asp Asn Leu Lys Leu Ala Ser Asn Leu Ala Asn Val Gly Asp Ser
370                 375                 380 aag acc ttg gtc att gct cca tac ttc act aca cat caa caa ttg acc   1200
Lys Thr Leu Val Ile Ala Pro Tyr Phe Thr Thr His Gln Gln Leu Thr
385                 390                 395                 400 gac gaa gaa aag tta gct tct ggt gtt acc aag gac ttg atc cgt gtt   1248
Asp Glu Glu Lys Leu Ala Ser Gly Val Thr Lys Asp Leu Ile Arg Val
                405                 410                 415 tct gtt ggt act gaa ttc att gac gac att att gct gac ttt gaa gca   1296
Ser Val Gly Thr Glu Phe Ile Asp Asp Ile Ile Ala Asp Phe Glu Ala
            420                 425                 430 tct ttc gct act gtc ttc aat ggc caa aaa cct gaa taa              1335
Ser Phe Ala Thr Val Phe Asn Gly Gln Lys Pro Glu
        435                 440

<210> SEQ ID NO 50
<211> LENGTH: 444
<212> TYPE: PRT
<213> ORGANISM: Kluyveromyces lactis

<400> SEQUENCE: 50

Met Pro Ser His Phe Asp Thr Leu Gln Leu His Ala Gly Gln Glu Lys
1               5                   10                  15

Thr Ala Asp Ala His Asn Pro Arg Ala Val Pro Ile Tyr Ala Thr Thr
            20                  25                  30

Ser Tyr Val Phe Asn Asp Ser Lys His Gly Ala Gln Leu Phe Gly Leu
        35                  40                  45

Glu Thr Pro Gly Tyr Ile Tyr Ser Arg Ile Met Asn Pro Thr Leu Asp
    50                  55                  60

Val Leu Glu Lys Arg Leu Ala Ala Leu Glu Gly Gly Ile Ala Ala Leu
65                  70                  75                  80

Ala Thr Ser Ser Gly Gln Ala Ala Gln Thr Leu Ala Val Thr Gly Leu
                85                  90                  95

Ala His Thr Gly Asp Asn Ile Val Ser Thr Ser Phe Leu Tyr Gly Gly
            100                 105                 110

Thr Tyr Asn Gln Phe Lys Val Ala Phe Lys Arg Leu Gly Ile Glu Ala
        115                 120                 125

Arg Phe Val Asp Gly Asp Lys Pro Glu Asp Phe Glu Lys Leu Phe Asp
    130                 135                 140

Glu Lys Thr Lys Ala Leu Tyr Leu Glu Ser Ile Gly Asn Pro Lys Tyr
145                 150                 155                 160

Asn Val Pro Asp Phe Glu Lys Ile Val Ala Val Ala His Lys His Gly
                165                 170                 175

Ile Pro Val Val Val Asp Asn Thr Phe Gly Ala Gly Gly Phe Phe Cys
            180                 185                 190
```

```
Gln Pro Ile Lys Tyr Gly Ala Asp Ile Val Thr His Ser Ala Thr Lys
            195                 200                 205

Trp Ile Gly Gly His Gly Val Thr Val Gly Gly Val Ile Ile Asp Ser
    210                 215                 220

Gly Lys Phe Pro Trp Lys Asp Tyr Pro Glu Lys Phe Pro Gln Phe Ser
225                 230                 235                 240

Gln Pro Ser Glu Gly Tyr His Gly Leu Ile Phe Asn Asp Ala Phe Gly
                245                 250                 255

Pro Ala Ala Phe Ile Gly His Val Arg Thr Glu Leu Leu Arg Asp Leu
            260                 265                 270

Gly Pro Val Leu Ser Pro Phe Ala Gly Phe Leu Leu Gln Gly Leu
        275                 280                 285

Glu Thr Leu Ser Leu Arg Gly Glu Arg His Gly Ser Asn Ala Leu Lys
    290                 295                 300

Leu Ala Gln Tyr Leu Glu Ser Ser Pro Tyr Val Ser Trp Val Ser Tyr
305                 310                 315                 320

Pro Gly Leu Pro Ser His Ser His His Glu Asn Ala Lys Lys Tyr Leu
                325                 330                 335

Glu Asn Gly Phe Gly Gly Val Leu Ser Phe Gly Val Lys Asp Leu Pro
            340                 345                 350

Asn Ala Ser Glu Glu Ser Asp Pro Phe Lys Ala Ser Gly Ala Gln Val
        355                 360                 365

Val Asp Asn Leu Lys Leu Ala Ser Asn Leu Ala Asn Val Gly Asp Ser
    370                 375                 380

Lys Thr Leu Val Ile Ala Pro Tyr Phe Thr Thr His Gln Gln Leu Thr
385                 390                 395                 400

Asp Glu Glu Lys Leu Ala Ser Gly Val Thr Lys Asp Leu Ile Arg Val
                405                 410                 415

Ser Val Gly Thr Glu Phe Ile Asp Asp Ile Ile Ala Asp Phe Glu Ala
            420                 425                 430

Ser Phe Ala Thr Val Phe Asn Gly Gln Lys Pro Glu
        435                 440

<210> SEQ ID NO 51
<211> LENGTH: 1323
<212> TYPE: DNA
<213> ORGANISM: Candida albicans
<220> FEATURE:
<221> NAME/KEY: CDS
<222> LOCATION: (1)..(1323)

<400> SEQUENCE: 51 atg cct tct cac ttt gat aca ctt caa tta cat gct ggt caa cca gtt      48
Met Pro Ser His Phe Asp Thr Leu Gln Leu His Ala Gly Gln Pro Val
1               5                   10                  15 gaa aaa cca cac caa cca aga gcc cca cca att tat gca acc acc tcc      96
Glu Lys Pro His Gln Pro Arg Ala Pro Pro Ile Tyr Ala Thr Thr Ser
                20                  25                  30 tat gtt ttc aat gac tct aaa cac ggt gct caa tta ttt ggt tta gaa     144
Tyr Val Phe Asn Asp Ser Lys His Gly Ala Gln Leu Phe Gly Leu Glu
            35                  40                  45 acc cca gga tac att tac tcc aga att atg aat cca aca aac gat gtg     192
Thr Pro Gly Tyr Ile Tyr Ser Arg Ile Met Asn Pro Thr Asn Asp Val
        50                  55                  60 ttt gaa caa aga att gct gcc ttg gaa ggt ggt att ggt gca ttg gcc     240
Phe Glu Gln Arg Ile Ala Ala Leu Glu Gly Gly Ile Gly Ala Leu Ala
65                  70                  75                  80
```

```
act tct tct ggt caa tca gct caa ttc ttg gcc att gct ggg ttg gct      288
Thr Ser Ser Gly Gln Ser Ala Gln Phe Leu Ala Ile Ala Gly Leu Ala
             85                  90                  95 cat gct ggt gat aac att atc agt aca tcc tac ttg tat ggt ggt act      336
His Ala Gly Asp Asn Ile Ile Ser Thr Ser Tyr Leu Tyr Gly Gly Thr
        100                 105                 110 tat aat caa ttc aaa gtt gct ttc aaa cgt ttg ggc att gaa acc aaa      384
Tyr Asn Gln Phe Lys Val Ala Phe Lys Arg Leu Gly Ile Glu Thr Lys
            115                 120                 125 ttc gtt aat ggt gac gcc gct gaa gat ttt gct aaa ttg att gac gac      432
Phe Val Asn Gly Asp Ala Ala Glu Asp Phe Ala Lys Leu Ile Asp Asp
130                 135                 140 aag aca aaa gct att tat att gaa acc att gga aac cct aaa tat aat      480
Lys Thr Lys Ala Ile Tyr Ile Glu Thr Ile Gly Asn Pro Lys Tyr Asn
145                 150                 155                 160 gtt ccg gac ttt gaa aaa atc acc aaa ttg gcc cat gaa cac ggt att      528
Val Pro Asp Phe Glu Lys Ile Thr Lys Leu Ala His Glu His Gly Ile
                165                 170                 175 cct gtt gtt gtc gac aac act ttt ggt gct ggt gga ttt tta gtt aac      576
Pro Val Val Val Asp Asn Thr Phe Gly Ala Gly Gly Phe Leu Val Asn
            180                 185                 190 cca att gcc cac ggt gct gat att gtt gtt cat tct gct act aaa tgg      624
Pro Ile Ala His Gly Ala Asp Ile Val Val His Ser Ala Thr Lys Trp
        195                 200                 205 att ggt ggt cac ggt act aca att gct ggt gtt att gtt gat tcc ggt      672
Ile Gly Gly His Gly Thr Thr Ile Ala Gly Val Ile Val Asp Ser Gly
    210                 215                 220 aac ttc cca tgg acc gag tac cca gaa aaa tac cca caa ttc tct aaa      720
Asn Phe Pro Trp Thr Glu Tyr Pro Glu Lys Tyr Pro Gln Phe Ser Lys
225                 230                 235                 240 cca tca gaa ggt tac cac ggg ttg atc ttg aat gat gct tta ggt aag      768
Pro Ser Glu Gly Tyr His Gly Leu Ile Leu Asn Asp Ala Leu Gly Lys
                245                 250                 255 gcc gca tac att ggt cac ttg aga att gaa ttg ttg aga gac ttg ggt      816
Ala Ala Tyr Ile Gly His Leu Arg Ile Glu Leu Leu Arg Asp Leu Gly
            260                 265                 270 cca gct ttg aat cca ttt gga agt ttt ttg ttg caa ggt tta gaa          864
Pro Ala Leu Asn Pro Phe Gly Ser Phe Leu Leu Gln Gly Leu Glu
        275                 280                 285 act ttg tct ttg aga gtt gaa aga caa tct gaa aat gct ttg aaa ttg      912
Thr Leu Ser Leu Arg Val Glu Arg Gln Ser Glu Asn Ala Leu Lys Leu
    290                 295                 300 gcc caa tgg ttg gaa aag aac cca aat gtt gag tct gtg tcc tat ttg      960
Ala Gln Trp Leu Glu Lys Asn Pro Asn Val Glu Ser Val Ser Tyr Leu
305                 310                 315                 320 gga ttg cca tct cac gaa tcc cac gaa ttg agt aaa aaa tac ttg aac     1008
Gly Leu Pro Ser His Glu Ser His Glu Leu Ser Lys Lys Tyr Leu Asn
                325                 330                 335 aat gac gct aag tac ttt ggt ggt gct tta gca ttt act gtc aag gac     1056
Asn Asp Ala Lys Tyr Phe Gly Gly Ala Leu Ala Phe Thr Val Lys Asp
            340                 345                 350 atc acc aac acc tcc agc gac cca ttc aat gaa gcc tca cca aag ttg     1104
Ile Thr Asn Thr Ser Ser Asp Pro Phe Asn Glu Ala Ser Pro Lys Leu
        355                 360                 365 gtt gac aat ttg gag att gct tca aac ttg gct aat gtg ggt gac tct     1152
Val Asp Asn Leu Glu Ile Ala Ser Asn Leu Ala Asn Val Gly Asp Ser
    370                 375                 380 aag act ttg gtt att gct cca tgg ttt act aca cat caa caa ttg tct     1200
Lys Thr Leu Val Ile Ala Pro Trp Phe Thr Thr His Gln Gln Leu Ser
```

```
                385                 390                 395                 400
gat gaa gaa aag ttg gct tct ggt gtt acc aag ggc tta atc aga gtt       1248
Asp Glu Glu Lys Leu Ala Ser Gly Val Thr Lys Gly Leu Ile Arg Val
                405                 410                 415 tct act ggt act gaa tat att gat gat att att aac gac ttt gaa caa       1296
Ser Thr Gly Thr Glu Tyr Ile Asp Asp Ile Ile Asn Asp Phe Glu Gln
            420                 425                 430 gca ttc aag aag gtt tat aac aac taa                                   1323
Ala Phe Lys Lys Val Tyr Asn Asn
        435                 440

<210> SEQ ID NO 52
<211> LENGTH: 440
<212> TYPE: PRT
<213> ORGANISM: Candida albicans

<400> SEQUENCE: 52

Met Pro Ser His Phe Asp Thr Leu Gln Leu His Ala Gly Gln Pro Val
1               5                   10                  15

Glu Lys Pro His Gln Pro Arg Ala Pro Pro Ile Tyr Ala Thr Thr Ser
                20                  25                  30

Tyr Val Phe Asn Asp Ser Lys His Gly Ala Gln Leu Phe Gly Leu Glu
            35                  40                  45

Thr Pro Gly Tyr Ile Tyr Ser Arg Ile Met Asn Pro Thr Asn Asp Val
        50                  55                  60

Phe Glu Gln Arg Ile Ala Ala Leu Glu Gly Gly Ile Gly Ala Leu Ala
65                  70                  75                  80

Thr Ser Ser Gly Gln Ser Ala Gln Phe Leu Ala Ile Ala Gly Leu Ala
                85                  90                  95

His Ala Gly Asp Asn Ile Ile Ser Thr Ser Tyr Leu Tyr Gly Gly Thr
                100                 105                 110

Tyr Asn Gln Phe Lys Val Ala Phe Lys Arg Leu Gly Ile Glu Thr Lys
            115                 120                 125

Phe Val Asn Gly Asp Ala Ala Glu Asp Phe Ala Lys Leu Ile Asp Asp
        130                 135                 140

Lys Thr Lys Ala Ile Tyr Ile Glu Thr Ile Gly Asn Pro Lys Tyr Asn
145                 150                 155                 160

Val Pro Asp Phe Glu Lys Ile Thr Lys Leu Ala His Glu His Gly Ile
                165                 170                 175

Pro Val Val Val Asp Asn Thr Phe Gly Ala Gly Gly Phe Leu Val Asn
            180                 185                 190

Pro Ile Ala His Gly Ala Asp Ile Val Val His Ser Ala Thr Lys Trp
        195                 200                 205

Ile Gly Gly His Gly Thr Thr Ile Ala Gly Val Ile Val Asp Ser Gly
210                 215                 220

Asn Phe Pro Trp Thr Glu Tyr Pro Glu Lys Tyr Pro Gln Phe Ser Lys
225                 230                 235                 240

Pro Ser Glu Gly Tyr His Gly Leu Ile Leu Asn Asp Ala Leu Gly Lys
                245                 250                 255

Ala Ala Tyr Ile Gly His Leu Arg Ile Glu Leu Leu Arg Asp Leu Gly
            260                 265                 270

Pro Ala Leu Asn Pro Phe Gly Ser Phe Leu Leu Gln Gly Leu Glu
        275                 280                 285

Thr Leu Ser Leu Arg Val Glu Arg Gln Ser Glu Asn Ala Leu Lys Leu
    290                 295                 300
```

-continued

```
Ala Gln Trp Leu Glu Lys Asn Pro Asn Val Glu Ser Val Ser Tyr Leu
305                 310                 315                 320

Gly Leu Pro Ser His Glu Ser His Glu Leu Ser Lys Lys Tyr Leu Asn
            325                 330                 335

Asn Asp Ala Lys Tyr Phe Gly Gly Ala Leu Ala Phe Thr Val Lys Asp
        340                 345                 350

Ile Thr Asn Thr Ser Ser Asp Pro Phe Asn Glu Ala Ser Pro Lys Leu
    355                 360                 365

Val Asp Asn Leu Glu Ile Ala Ser Asn Leu Ala Asn Val Gly Asp Ser
370                 375                 380

Lys Thr Leu Val Ile Ala Pro Trp Phe Thr Thr His Gln Gln Leu Ser
385                 390                 395                 400

Asp Glu Glu Lys Leu Ala Ser Gly Val Thr Lys Gly Leu Ile Arg Val
            405                 410                 415

Ser Thr Gly Thr Glu Tyr Ile Asp Asp Ile Ile Asn Asp Phe Glu Gln
        420                 425                 430

Ala Phe Lys Lys Val Tyr Asn Asn
    435                 440
```

<210> SEQ ID NO 53
<211> LENGTH: 1290
<212> TYPE: DNA
<213> ORGANISM: Schizosaccharomyces pombe
<220> FEATURE:
<221> NAME/KEY: CDS
<222> LOCATION: (1)..(1290)

<400> SEQUENCE: 53

```
atg cca gtc gag agt gaa cat ttc gaa act tta caa tta cat gct ggc      48
Met Pro Val Glu Ser Glu His Phe Glu Thr Leu Gln Leu His Ala Gly
1               5                   10                  15 caa gag cct gat gct gct acc agc tct cgt gcc gtt ccc atc tac gct      96
Gln Glu Pro Asp Ala Ala Thr Ser Ser Arg Ala Val Pro Ile Tyr Ala
            20                  25                  30 act act tcc tat gtt ttc cgt gat tgc gac cat ggc ggc cgc ttg ttc     144
Thr Thr Ser Tyr Val Phe Arg Asp Cys Asp His Gly Gly Arg Leu Phe
        35                  40                  45 gga tta cag gaa cca ggt tac atc tac tcg cgt atg atg aat ccc acc     192
Gly Leu Gln Glu Pro Gly Tyr Ile Tyr Ser Arg Met Met Asn Pro Thr
    50                  55                  60 gcc gac gtt ttt gag aaa cgt att gcc gcc ttg gag cat ggc gct gct     240
Ala Asp Val Phe Glu Lys Arg Ile Ala Ala Leu Glu His Gly Ala Ala
65                  70                  75                  80 gca atc gct act agt tcc ggt act tcc gct ctc ttc atg gct ttg acc     288
Ala Ile Ala Thr Ser Ser Gly Thr Ser Ala Leu Phe Met Ala Leu Thr
                85                  90                  95 acg ttg gct aag gcc ggt gat aac att gtc tcc act tct tac ctt tat     336
Thr Leu Ala Lys Ala Gly Asp Asn Ile Val Ser Thr Ser Tyr Leu Tyr
            100                 105                 110 ggt ggt act tac aac ctc ttc aag gtt acc ctg cct aga ttg gga att     384
Gly Gly Thr Tyr Asn Leu Phe Lys Val Thr Leu Pro Arg Leu Gly Ile
        115                 120                 125 act acc aag ttt gtc aat ggt gat gat cct aat gat ctt gca gct cag     432
Thr Thr Lys Phe Val Asn Gly Asp Asp Pro Asn Asp Leu Ala Ala Gln
    130                 135                 140 att gat gaa aac aca aag gct gtt tac gtt gag tcc atc ggc aat ccc     480
Ile Asp Glu Asn Thr Lys Ala Val Tyr Val Glu Ser Ile Gly Asn Pro
145                 150                 155                 160 atg tac aac gtt ccc gat ttt gag cgt atc gct gag gtt gct cat gcc     528
```

-continued

```
Met Tyr Asn Val Pro Asp Phe Glu Arg Ile Ala Glu Val Ala His Ala
                165                 170                 175 gct ggt gtg cct tta atg gtc gat aac act ttt ggc ggt ggt tat          576
Ala Gly Val Pro Leu Met Val Asp Asn Thr Phe Gly Gly Gly Tyr
        180                 185                 190 ttg gtt cgt ccc att gac cac ggt gcc gat atc gtt acc cac tct gcc      624
Leu Val Arg Pro Ile Asp His Gly Ala Asp Ile Val Thr His Ser Ala
    195                 200                 205 act aag tgg atc ggt ggt cat ggc act act att ggc ggt gtg att gtt      672
Thr Lys Trp Ile Gly Gly His Gly Thr Thr Ile Gly Gly Val Ile Val
210                 215                 220 gat agt ggt aag ttt gac tgg aag aag aac agc aag cgt ttc cct gaa      720
Asp Ser Gly Lys Phe Asp Trp Lys Lys Asn Ser Lys Arg Phe Pro Glu
225                 230                 235                 240 ttc aac gag cct cat ccc ggt tac cat ggc atg gtc ttt act gaa act      768
Phe Asn Glu Pro His Pro Gly Tyr His Gly Met Val Phe Thr Glu Thr
            245                 250                 255 ttt ggt aac ttg gca tat gct ttt gct tgc cgt act caa act ctc cgt      816
Phe Gly Asn Leu Ala Tyr Ala Phe Ala Cys Arg Thr Gln Thr Leu Arg
        260                 265                 270 gat gtt ggt ggc aat gcc aat cca ttc ggt gtc ttt ttg ctt ctt caa      864
Asp Val Gly Gly Asn Ala Asn Pro Phe Gly Val Phe Leu Leu Leu Gln
    275                 280                 285 ggt ctt gaa acg ctt tct ctt cgt atg gag cgt cac gtt caa aat gca      912
Gly Leu Glu Thr Leu Ser Leu Arg Met Glu Arg His Val Gln Asn Ala
290                 295                 300 ttt gct ctt gca aaa tat ttg gaa aag cac ccc aag gtt aac tgg gtt      960
Phe Ala Leu Ala Lys Tyr Leu Glu Lys His Pro Lys Val Asn Trp Val
305                 310                 315                 320 tct tac cct ggt ctt gaa tct cac gtc tct cac aaa ctt gcc aag aag     1008
Ser Tyr Pro Gly Leu Glu Ser His Val Ser His Lys Leu Ala Lys Lys
            325                 330                 335 tac ttg aaa aat ggt tac ggc gcc gtt ctc agc ttt ggc gct aaa ggt     1056
Tyr Leu Lys Asn Gly Tyr Gly Ala Val Leu Ser Phe Gly Ala Lys Gly
        340                 345                 350 ggc cct gat caa agt cgt aag gta gtc aat gcc tta aag ctt gct agt     1104
Gly Pro Asp Gln Ser Arg Lys Val Val Asn Ala Leu Lys Leu Ala Ser
    355                 360                 365 cag ttg gcc aat gtt ggt gat gcc aaa act ttg gtt atc gct cct gcc     1152
Gln Leu Ala Asn Val Gly Asp Ala Lys Thr Leu Val Ile Ala Pro Ala
370                 375                 380 tat acc act cat tta caa tta act gat gag gag caa att tct gcc ggt     1200
Tyr Thr Thr His Leu Gln Leu Thr Asp Glu Glu Gln Ile Ser Ala Gly
385                 390                 395                 400 gtc act aag gat ctt att cgt gtg gcc gtc ggt att gag cac atc gat     1248
Val Thr Lys Asp Leu Ile Arg Val Ala Val Gly Ile Glu His Ile Asp
            405                 410                 415 gat att atc gcc gac ttt gct caa gct ttg gaa gtt gcc taa             1290
Asp Ile Ile Ala Asp Phe Ala Gln Ala Leu Glu Val Ala
        420                 425

<210> SEQ ID NO 54
<211> LENGTH: 429
<212> TYPE: PRT
<213> ORGANISM: Schizosaccharomyces pombe

<400> SEQUENCE: 54

Met Pro Val Glu Ser Glu His Phe Glu Thr Leu Gln Leu His Ala Gly
1               5                   10                  15

Gln Glu Pro Asp Ala Ala Thr Ser Ser Arg Ala Val Pro Ile Tyr Ala
```

```
                   20                  25                  30
Thr Thr Ser Tyr Val Phe Arg Asp Cys Asp His Gly Gly Arg Leu Phe
             35                  40                  45
Gly Leu Gln Glu Pro Gly Tyr Ile Tyr Ser Arg Met Met Asn Pro Thr
 50                  55                  60
Ala Asp Val Phe Glu Lys Arg Ile Ala Ala Leu Glu His Gly Ala Ala
 65                  70                  75                  80
Ala Ile Ala Thr Ser Ser Gly Thr Ser Ala Leu Phe Met Ala Leu Thr
                 85                  90                  95
Thr Leu Ala Lys Ala Gly Asp Asn Ile Val Ser Thr Ser Tyr Leu Tyr
                100                 105                 110
Gly Gly Thr Tyr Asn Leu Phe Lys Val Thr Leu Pro Arg Leu Gly Ile
             115                 120                 125
Thr Thr Lys Phe Val Asn Gly Asp Pro Asn Asp Leu Ala Ala Gln
             130                 135                 140
Ile Asp Glu Asn Thr Lys Ala Val Tyr Val Glu Ser Ile Gly Asn Pro
145                 150                 155                 160
Met Tyr Asn Val Pro Asp Phe Glu Arg Ile Ala Glu Val Ala His Ala
                 165                 170                 175
Ala Gly Val Pro Leu Met Val Asp Asn Thr Phe Gly Gly Gly Tyr
             180                 185                 190
Leu Val Arg Pro Ile Asp His Gly Ala Asp Ile Val Thr His Ser Ala
             195                 200                 205
Thr Lys Trp Ile Gly Gly His Gly Thr Thr Ile Gly Val Ile Val
         210                 215                 220
Asp Ser Gly Lys Phe Asp Trp Lys Lys Asn Ser Lys Arg Phe Pro Glu
225                 230                 235                 240
Phe Asn Glu Pro His Pro Gly Tyr His Gly Met Val Phe Thr Glu Thr
                 245                 250                 255
Phe Gly Asn Leu Ala Tyr Ala Phe Ala Cys Arg Thr Gln Thr Leu Arg
             260                 265                 270
Asp Val Gly Gly Asn Ala Asn Pro Phe Gly Val Phe Leu Leu Leu Gln
             275                 280                 285
Gly Leu Glu Thr Leu Ser Leu Arg Met Glu Arg His Val Gln Asn Ala
         290                 295                 300
Phe Ala Leu Ala Lys Tyr Leu Glu Lys His Pro Lys Val Asn Trp Val
305                 310                 315                 320
Ser Tyr Pro Gly Leu Glu Ser His Val Ser His Lys Leu Ala Lys Lys
                 325                 330                 335
Tyr Leu Lys Asn Gly Tyr Gly Ala Val Leu Ser Phe Gly Ala Lys Gly
             340                 345                 350
Gly Pro Asp Gln Ser Arg Lys Val Val Asn Ala Leu Lys Leu Ala Ser
             355                 360                 365
Gln Leu Ala Asn Val Gly Asp Ala Lys Thr Leu Val Ile Ala Pro Ala
         370                 375                 380
Tyr Thr Thr His Leu Gln Leu Thr Asp Glu Glu Gln Ile Ser Ala Gly
385                 390                 395                 400
Val Thr Lys Asp Leu Ile Arg Val Ala Val Gly Ile Glu His Ile Asp
                 405                 410                 415
Asp Ile Ile Ala Asp Phe Ala Gln Ala Leu Glu Val Ala
             420                 425

<210> SEQ ID NO 55
```

```
<211> LENGTH: 52
<212> TYPE: DNA
<213> ORGANISM: Artificial sequence
<220> FEATURE:
<223> OTHER INFORMATION: Description of the artificial sequence:PCR
      primer

<400> SEQUENCE: 55
cccgggatcc gctagcggcg cgccggccgg cccggtgtga ataccgcac ag            52

<210> SEQ ID NO 56
<211> LENGTH: 53
<212> TYPE: DNA
<213> ORGANISM: Artificial sequence
<220> FEATURE:
<223> OTHER INFORMATION: Description of the artificial sequence:PCR
      primer

<400> SEQUENCE: 56
tctagactcg agcggccgcg gccggccttt aaattgaaga cgaaagggcc tcg          53

<210> SEQ ID NO 57
<211> LENGTH: 47
<212> TYPE: DNA
<213> ORGANISM: Artificial sequence
<220> FEATURE:
<223> OTHER INFORMATION: Description of the artificial sequence:PCR
      primer

<400> SEQUENCE: 57
gagatctaga cccggggatc cgctagcggg ctgctaaagg aagcgga                47

<210> SEQ ID NO 58
<211> LENGTH: 38
<212> TYPE: DNA
<213> ORGANISM: Artificial sequence
<220> FEATURE:
<223> OTHER INFORMATION: Description of the artificial sequence:PCR
      primer

<400> SEQUENCE: 58
gagaggcgcg ccgctagcgt gggcgaagaa ctccagca                          38

<210> SEQ ID NO 59
<211> LENGTH: 34
<212> TYPE: DNA
<213> ORGANISM: Artificial sequence
<220> FEATURE:
<223> OTHER INFORMATION: Description of the artificial sequence:PCR
      primer

<400> SEQUENCE: 59
gagagggcgg ccgcgcaaag tcccgcttcg tgaa                              34

<210> SEQ ID NO 60
<211> LENGTH: 34
<212> TYPE: DNA
<213> ORGANISM: Artificial sequence
<220> FEATURE:
<223> OTHER INFORMATION: Description of the artificial sequence:PCR
      primer

<400> SEQUENCE: 60
gagagggcgg ccgctcaagt cggtcaagcc acgc                              34

<210> SEQ ID NO 61
<211> LENGTH: 140
```

```
<212> TYPE: DNA
<213> ORGANISM: Artificial sequence
<220> FEATURE:
<223> OTHER INFORMATION: Description of the artificial sequence:PCR
      primer

<400> SEQUENCE: 61
tcgaatttaa atctcgagag gcctgacgtc gggcccggta ccacgcgtca tatgactagt     60
tcggacctag ggatatcgtc gacatcgatg ctcttctgcg ttaattaaca attgggatcc    120
tctagacccg ggatttaaat                                                140

<210> SEQ ID NO 62
<211> LENGTH: 140
<212> TYPE: DNA
<213> ORGANISM: Artificial sequence
<220> FEATURE:
<223> OTHER INFORMATION: Description of the artificial sequence:PCR
      primer

<400> SEQUENCE: 62
gatcatttaa atcccgggtc tagaggatcc caattgttaa ttaacgcaga agagcatcga     60
tgtcgacgat atccctaggt ccgaactagt catatgacgc gtggtaccgg gcccgacgtc    120
aggcctctcg agatttaaat                                                140

<210> SEQ ID NO 63
<211> LENGTH: 33
<212> TYPE: DNA
<213> ORGANISM: Artificial sequence
<220> FEATURE:
<223> OTHER INFORMATION: Description of the artificial sequence:PCR
      primer

<400> SEQUENCE: 63
gagagcggcc gccgatcctt tttaacccat cac                                  33

<210> SEQ ID NO 64
<211> LENGTH: 32
<212> TYPE: DNA
<213> ORGANISM: Artificial sequence
<220> FEATURE:
<223> OTHER INFORMATION: Description of the artificial sequence:PCR
      primer

<400> SEQUENCE: 64
aggagcggcc gccatcggca ttttcttttg cg                                   32

<210> SEQ ID NO 65
<211> LENGTH: 5091
<212> TYPE: DNA
<213> ORGANISM: Artificial sequence
<220> FEATURE:
<223> OTHER INFORMATION: Description of the artificial sequence:plasmid

<400> SEQUENCE: 65
gccgcgactg ccttcgcgaa gccttgcccc gcggaaattt cctccaccga gttcgtgcac     60
acccctatgc caagcttctt tcaccctaaa ttcgagagat tggattctta ccgtggaaat    120
tcttcgcaaa aatcgtcccc tgatcgccct tgcgacgttg gcgtcggtgc cgctggttgc    180
gcttggcttg accgacttga tcagcggccg ctcgatttaa atctcgagag gcctgacgtc    240
gggcccggta ccacgcgtca tatgactagt tcggacctag ggatatcgtc gacatcgatg    300
ctcttctgcg ttaattaaca attgggatcc tctagacccg ggatttaaat cgctagcggg    360
```

```
ctgctaaagg aagcggaaca cgtagaaagc cagtccgcag aaacggtgct gacccggat     420 gaatgtcagc tactgggcta tctggacaag ggaaaacgca agcgcaaaga gaaagcaggt    480
agcttgcagt gggcttacat ggcgatagct agactgggcg ttttatgga cagcaagcga     540 accggaattg ccagctgggg cgccctctgg taaggttggg aagccctgca aagtaaactg    600
gatggctttc ttgccgccaa ggatctgatg gcgcagggga tcaagatctg atcaagagac    660
aggatgagga tcgtttcgca tgattgaaca agatggattg cacgcaggtt ctccggccgc    720
ttgggtggag aggctattcg gctatgactg ggcacaacag acaatcggct gctctgatgc    780
cgccgtgttc cggctgtcag cgcaggggcg cccggttctt tttgtcaaga ccgacctgtc    840
cggtgccctg aatgaactgc aggacgaggc agcgcggcta tcgtggctgg ccacgacggg    900
cgttccttgc gcagctgtgc tcgacgttgt cactgaagcg ggaagggact ggctgctatt    960
gggcgaagtg ccggggcagg atctcctgtc atctcacctt gctcctgccg agaaagtatc    1020
catcatggct gatgcaatgc ggcggctgca tacgcttgat ccggctacct gcccattcga    1080
ccaccaagcg aaacatcgca tcgagcgagc acgtactcgg atggaagccg gtcttgtcga    1140
tcaggatgat ctggacgaag agcatcaggg gctcgcgcca gccgaactgt tcgccaggct    1200
caaggcgcgc atgcccgacg gcgaggatct cgtcgtgacc catggcgatg cctgcttgcc    1260
gaatatcatg gtgaaaatg gccgcttttc tggattcatc gactgtggcc ggctgggtgt    1320
ggcggaccgc tatcaggaca tagcgttggc tacccgtgat attgctgaag agcttggcgg    1380
cgaatgggct gaccgcttcc tcgtgcttta cggtatcgcc gctcccgatt cgcagcgcat    1440
cgccttctat cgccttcttg acgagttctt ctgagcggga ctctggggtt cgaaatgacc    1500
gaccaagcga cgcccaacct gccatcacga gatttcgatt ccaccgccgc cttctatgaa    1560
aggttgggct tcggaatcgt tttccgggac gccggctgga tgatcctcca gcgcgggat    1620 ctcatgctgg agttcttcgc ccacgctagc ggcgcgccgg ccggcccggt gtgaaatacc    1680
gcacagatgc gtaaggagaa aataccgcat caggcgctct ccgcttcct cgctcactga    1740 ctcgctgcgc tcggtcgttc ggctgcggcg agcggtatca gctcactcaa aggcggtaat    1800
acggttatcc acagaatcag gggataacgc aggaaagaac atgtgagcaa aaggccagca    1860
aaaggccagg aaccgtaaaa aggccgcgtt gctggcgttt ttccataggc tccgcccccc    1920
tgacgagcat cacaaaaatc gacgctcaag tcagaggtgg cgaaacccga caggactata    1980
aagataccag gcgtttcccc ctggaagctc cctcgtgcgc tctcctgttc cgaccctgcc    2040
gcttaccgga tacctgtccg cctttctccc ttcgggaagc gtggcgcttt ctcatagctc    2100
acgctgtagg tatctcagtt cggtgtaggt cgttcgctcc aagctgggct gtgtgcacga    2160
accccccgtt cagcccgacc gctgcgcctt atccggtaac tatcgtcttg agtccaaccc    2220
ggtaagacac gacttatcgc cactggcagc agccactggt aacaggatta gcagagcgag    2280
gtatgtaggc ggtgctacag agttcttgaa gtggtggcct aactacggct acactagaag    2340
gacagtattt ggtatctgcg ctctgctgaa gccagttacc ttcggaaaaa gagttggtag    2400
ctcttgatcc ggcaaacaaa ccaccgctgg tagcggtggt ttttttgttt gcaagcagca    2460
gattacgcgc agaaaaaaag gatctcaaga agatcctttg atcttttcta cggggtctga    2520
cgctcagtgg aacgaaaact cacgttaagg gattttggtc atgagattat caaaaaggat    2580
cttcacctag atccttttaa aggccggccg cggccgcgca aagtcccgct tcgtgaaaat    2640
tttcgtgccg cgtgattttc cgccaaaaac tttaacgaac gttcgttata atggtgtcat    2700
gaccttcacg acgaagtact aaaattggcc cgaatcatca gctatggatc tctctgatgt    2760
```

```
cgcgctggag tccgacgcgc tcgatgctgc cgtcgattta aaaacggtga tcggattttt    2820
ccgagctctc gatacgacgg acgcgccagc atcacgagac tgggccagtg ccgcgagcga    2880
cctagaaact ctcgtggcgg atcttgagga gctggctgac gagctgcgtg ctcggccagc    2940
gccaggagga cgcacagtag tggaggatgc aatcagttgc gcctactgcg gtggcctgat    3000
tcctccccgg cctgacccgc gaggacggcg cgcaaaatat tgctcagatg cgtgtcgtgc    3060
cgcagccagc cgcgagcgcg ccaacaaacg ccacgccgag gagctggagg cggctaggtc    3120
gcaaatggcg ctggaagtgc gtcccccgag cgaaattttg gccatggtcg tcacagagct    3180
ggaagcggca gcgagaatta tcgcgatcgt ggcggtgccc gcaggcatga caaacatcgt    3240
aaatgccgcg tttcgtgtgc cgtggccgcc caggacgtgt cagcgccgcc accacctgca    3300
ccgaatcggc agcagcgtcg cgcgtcgaaa aagcgcacag gcggcaagaa gcgataagct    3360
gcacgaatac ctgaaaaatg ttgaacgccc cgtgagcggt aactcacagg gcgtcggcta    3420 accccccagtc caaacctggg agaaagcgct caaaaatgac tctagcggat tcacgagaca    3480
ttgacacacc ggcctggaaa ttttccgctg atctgttcga cacccatccc gagctcgcgc    3540
tgcgatcacg tggctggacg agcgaagacc gccgcgaatt cctcgctcac ctgggcagag    3600
aaaatttcca gggcagcaag acccgcgact tcgccagcgc ttggatcaaa gacccggaca    3660
cggagaaaca cagccgaagt tataccgagt tggttcaaaa tcgcttgccc ggtgccagta    3720
tgttgctctg acgcacgcgc agcacgcagc cgtgcttgtc ctggacattg atgtgccgag    3780
ccaccaggcc ggcgggaaaa tcgagcacgt aaaccccgag gtctacgcga ttttggagcg    3840
ctgggcacgc ctggaaaaag cgccagcttg gatcggcgtg aatccactga gcgggaaatg    3900
ccagctcatc tggctcattg atccggtgta tgccgcagca ggcatgagca gcccgaatat    3960
gcgcctgctg gctgcaacga ccgaggaaat gacccgcgtt ttcggcgctg accaggcttt    4020
ttcacatagg ctgagccgtg gccactgcac tctccgacga tcccagccgt accgctggca    4080
tgcccagcac aatcgcgtgg atcgcctagc tgatcttatg gaggttgctc gcatgatctc    4140
aggcacagaa aaacctaaaa aacgctatga gcaggagttt tctagcggac gggcacgtat    4200
cgaagcggca agaaaagcca ctgcggaagc aaaagcactt gccacgcttg aagcaagcct    4260
gccgagcgcc gctgaagcgt ctggagagct gatcgacggc gtccgtgtcc tctggactgc    4320
tccagggcgt gccgcccgtg atgagacggc ttttcgccac gctttgactg tgggataccha    4380 gttaaaagcg gctggtgagc gcctaaaaga caccaagggt catcgagcct acgagcgtgc    4440
ctacaccgtc gctcaggcgg tcggaggagg ccgtgagcct gatctgccgc cggactgtga    4500
ccgccagacg gattggccgc gacgtgtgcg cggctacgtc gctaaaggcc agccagtcgt    4560
ccctgctcgt cagacagaga cgcagagcca gccgaggcga aaagctctgg ccactatggg    4620
aagacgtggc ggtaaaaagg ccgcagaacg ctggaaagac ccaaacagtg agtacgcccg    4680
agcacagcga gaaaaactag ctaagtccag tcaacgacaa gctaggaaag ctaaaggaaa    4740
tcgcttgacc attgcaggtt ggtttatgac tgttgaggga gagactggct cgtggccgac    4800
aatcaatgaa gctatgtctg aatttagcgt gtcacgtcag accgtgaata gagcacttaa    4860
ggtctgcggg cattgaactt ccacgaggac gccgaaagct tcccagtaaa tgtgccatct    4920
cgtaggcaga aaacggttcc cccgtagggt ctctctcttg gcctcctttc taggtcgggc    4980
tgattgctct tgaagctctc tagggggct cacaccatag gcagataacg ttccccaccg    5040
gctcgcctcg taagcgcaca aggactgctc ccaaagatct tcaaagccac t              5091
```

<210> SEQ ID NO 66
<211> LENGTH: 4323
<212> TYPE: DNA
<213> ORGANISM: Artificial sequence
<220> FEATURE:
<223> OTHER INFORMATION: Description of the artificial sequence:plasmid

<400> SEQUENCE: 66

| | | | | | |
|---|---|---|---|---|---|
| tctctcagcg | tatggttgtc | gcctgagctg | tagttgcctt | catcgatgaa | ctgctgtaca | 60 |
| ttttgatacg | tttttccgtc | accgtcaaag | attgatttat | aatcctctac | accgttgatg | 120 |
| ttcaaagagc | tgtctgatgc | tgatacgtta | acttgtgcag | ttgtcagtgt | ttgtttgccg | 180 |
| taatgtttac | cggagaaatc | agtgtagaat | aaacggattt | ttccgtcaga | tgtaaatgtg | 240 |
| gctgaacctg | accattcttg | tgtttggtct | tttaggatag | aatcatttgc | atcgaatttg | 300 |
| tcgctgtctt | taaagacgcg | gccagcgttt | ttccagctgt | caatagaagt | ttcgccgact | 360 |
| ttttgataga | acatgtaaat | cgatgtgtca | tccgcatttt | taggatctcc | ggctaatgca | 420 |
| aagacgatgt | ggtagccgtg | atagtttgcg | acagtgccgt | cagcgttttg | taatggccag | 480 |
| ctgtcccaaa | cgtccaggcc | ttttgcagaa | gagatatttt | taattgtgga | cgaatcaaat | 540 |
| tcagaaactt | gatattttc | attttttgc | tgttcaggga | tttgcagcat | atcatggcgt | 600 |
| gtaatatggg | aaatgccgta | tgtttcctta | tatggctttt | ggttcgtttc | tttcgcaaac | 660 |
| gcttgagttg | cgcctcctgc | cagcagtgcg | gtagtaaagg | ttaatactgt | tgcttgtttt | 720 |
| gcaaactttt | tgatgttcat | cgttcatgtc | tcctttttta | tgtactgtgt | tagcggtctg | 780 |
| cttcttccag | ccctcctgtt | tgaagatggc | aagttagtta | cgcacaataa | aaaaagacct | 840 |
| aaaatatgta | aggggtgacg | ccaaagtata | cactttgccc | tttacacatt | ttaggtcttg | 900 |
| cctgctttat | cagtaacaaa | cccgcgcgat | ttacttttcg | acctcattct | attagactct | 960 |
| cgtttggatt | gcaactggtc | tattttcctc | ttttgtttga | tagaaaatca | taaaggatt | 1020 |
| tgcagactac | gggcctaaag | aactaaaaaa | tctatctgtt | tcttttcatt | ctctgtattt | 1080 |
| tttatagttt | ctgttgcatg | gcataaaagt | tgccttttta | atcacaattc | agaaaatatc | 1140 |
| ataatatctc | atttcactaa | ataatagtga | acggcaggta | tatgtgatgg | gttaaaaagg | 1200 |
| atcggcggcc | gctcgattta | aatctcgaga | ggcctgacgt | cgggcccggt | accacgcgtc | 1260 |
| atatgactag | ttcggaccta | gggatatcgt | cgacatcgat | gctcttctgc | gttaattaac | 1320 |
| aattgggatc | ctctagaccc | gggatttaaa | tcgctagcgg | gctgctaaag | gaagcggaac | 1380 |
| acgtagaaag | ccagtccgca | gaaacggtgc | tgaccccgga | tgaatgtcag | ctactgggct | 1440 |
| atctggacaa | gggaaaacgc | aagcgcaaag | agaaagcagg | tagcttgcag | tgggcttaca | 1500 |
| tggcgatagc | tagactgggc | ggttttatgg | acagcaagcg | aaccggaatt | gccagctggg | 1560 |
| gcgccctctg | gtaaggttgg | gaagccctgc | aaagtaaact | ggatggcttt | cttgccgcca | 1620 |
| aggatctgat | ggcgcagggg | atcaagatct | gatcaagaga | caggatgagg | atcgtttcgc | 1680 |
| atgattgaac | aagatggatt | gcacgcaggt | tctccggccg | cttgggtgga | gaggctattc | 1740 |
| ggctatgact | gggcacaaca | gacaatcggc | tgctctgatg | ccgccgtgtt | ccggctgtca | 1800 |
| gcgcaggggc | gcccggttct | ttttgtcaag | accgacctgt | ccggtgccct | gaatgaactg | 1860 |
| caggacgagg | cagcgcggct | atcgtggctg | gccacgacgg | gcgttccttg | cgcagctgtg | 1920 |
| ctcgacgttg | tcactgaagc | gggaagggac | tggctgctat | gggcgaagt | gccggggcag | 1980 |
| gatctcctgt | catctcacct | tgctcctgcc | gagaaagtat | ccatcatggc | tgatgcaatg | 2040 |
| cggcggctgc | atacgcttga | tccggctacc | tgcccattcg | accaccaagc | gaaacatcgc | 2100 |

```
atcgagcgag cacgtactcg gatggaagcc ggtcttgtcg atcaggatga tctggacgaa    2160
gagcatcagg ggctcgcgcc agccgaactg ttcgccaggc tcaaggcgcg catgcccgac    2220
ggcgaggatc tcgtcgtgac ccatggcgat gcctgcttgc cgaatatcat ggtggaaaat    2280
ggccgctttt ctggattcat cgactgtggc cggctgggtg tggcggaccg ctatcaggac    2340
atagcgttgg ctacccgtga tattgctgaa gagcttggcg gcgaatgggc tgaccgcttc    2400
ctcgtgcttt acggtatcgc cgctcccgat tcgcagcgca tcgccttcta tcgccttctt    2460
gacgagttct tctgagcggg actctggggt tcgaaatgac cgaccaagcg acgcccaacc    2520
tgccatcacg agatttcgat tccaccgccg ccttctatga aaggttgggc ttcggaatcg    2580
ttttccggga cgccggctgg atgatcctcc agcgcgggga tctcatgctg gagttcttcg    2640
cccacgctag cggcgcgccg gccggcccgg tgtgaaatac cgcacagatg cgtaaggaga    2700
aaataccgca tcaggcgctc ttccgcttcc tcgctcactg actcgctgcg ctcggtcgtt    2760
cggctgcggc gagcggtatc agctcactca aaggcggtaa tacggttatc cacagaatca    2820
ggggataacg caggaaagaa catgtgagca aaaggccagc aaaaggccag gaaccgtaaa    2880
aaggccgcgt tgctggcgtt tttccatagg ctccgccccc ctgacgagca tcacaaaaat    2940
cgacgctcaa gtcagaggtg gcgaaacccg acaggactat aaagatacca ggcgtttccc    3000
cctggaagct ccctcgtgcg ctctcctgtt ccgaccctgc cgcttaccgg atacctgtcc    3060
gcctttctcc cttcgggaag cgtggcgctt tctcatagct cacgctgtag gtatctcagt    3120
tcggtgtagg tcgttcgctc caagctgggc tgtgtgcacg aaccccccgt tcagcccgac    3180
cgctgcgcct tatccggtaa ctatcgtctt gagtccaacc cggtaagaca cgacttatcg    3240
ccactggcag cagccactgg taacaggatt agcagagcga ggtatgtagg cggtgctaca    3300
gagttcttga agtggtggcc taactacggc tacactagaa ggacagtatt tggtatctgc    3360
gctctgctga agccagttac cttcggaaaa agagttggta gctcttgatc cggcaaacaa    3420
accaccgctg gtagcggtgg tttttttgtt tgcaagcagc agattacgcg cagaaaaaaa    3480
ggatctcaag aagatccttt gatcttttct acggggtctg acgctcagtg gaacgaaaac    3540
tcacgttaag ggattttggt catgagatta tcaaaaagga tcttcaccta gatccttta    3600 aaggccggcc gcggccgcca tcggcatttt cttttgcgtt tttatttgtt aactgttaat    3660
tgtccttgtt caaggatgct gtctttgaca acagatgttt tcttgccttt gatgttcagc    3720
aggaagctcg gcgcaaacgt tgattgtttg tctgcgtaga atcctctgtt tgtcatatag    3780
cttgtaatca cgacattgtt tcctttcgct tgaggtacag cgaagtgtga gtaagtaaag    3840
gttacatcgt taggatcaag atccattttt aacacaaggc cagttttgtt cagcggcttg    3900
tatgggccag ttaaagaatt agaaacataa ccaagcatgt aaatatcgtt agacgtaatg    3960
ccgtcaatcg tcattttga tccgcgggag tcagtgaaca ggtaccattt gccgttcatt    4020
ttaaagacgt tcgcgcgttc aatttcatct gttactgtgt tagatgcaat cagcggtttc    4080 atcactttt tcagtgtgta atcatcgttt agctcaatca taccgagagc gccgtttgct    4140
aactcagccg tgcgtttttt atcgctttgc agaagttttt gactttcttg acggaagaat    4200
gatgtgcttt tgccatagta tgcttttgtta aataaagatt cttcgccttg gtagccatct    4260
tcagttccag tgtttgcttc aaatactaag tatttgtggc ctttatcttc tacgtagtga    4320
gga                                                                  4323

<210> SEQ ID NO 67
```

```
<211> LENGTH: 35
<212> TYPE: DNA
<213> ORGANISM: Artificial sequence
<220> FEATURE:
<223> OTHER INFORMATION: Description of the artificial sequence: PCR
      primer

<400> SEQUENCE: 67
gagagagaga cgcgtcccag tggctgagac gcatc                               35

<210> SEQ ID NO 68
<211> LENGTH: 34
<212> TYPE: DNA
<213> ORGANISM: Artificial sequence
<220> FEATURE:
<223> OTHER INFORMATION: Description of the artificial sequence: PCR
      primer

<400> SEQUENCE: 68
ctctctctgt cgacgaattc aatcttacgg cctg                                34

<210> SEQ ID NO 69
<211> LENGTH: 5860
<212> TYPE: DNA
<213> ORGANISM: Artificial sequence
<220> FEATURE:
<223> OTHER INFORMATION: Description of the artificial sequence: plasmid

<400> SEQUENCE: 69
cccggtacca cgcgtcccag tggctgagac gcatccgcta aagccccagg aaccctgtgc    60
agaaagaaaa cactcctctg ctaggtagac acagtttat aaaggtagag ttgagcgggt    120
aactgtcagc acgtagatcg aaaggtgcac aaaggtggcc ctggtcgtac agaaatatgg    180
cggttcctcg cttgagagtg cggaacgcat tagaaacgtc gctgaacgga tcgttgccac    240
caagaaggct ggaaatgatg tcgtggttgt ctgctccgca atgggagaca ccacggatga    300
acttctagaa cttgcagcgg cagtgaatcc cgttccgcca gctcgtgaaa tggatatgct    360
cctgactgct ggtgagcgta tttctaacgc tctcgtcgcc atggctattg agtcccttgg    420
cgcagaagcc aatctttca cgggctctca ggctggtgtg ctcaccaccg agcgccacgg    480
aaacgcacgc attgttgatg tcactccagg tcgtgtgcgt gaagcactcg atgagggcaa    540
gatctgcatt gttgctggtt tccagggtgt taataaagaa acccgcgatg tcaccacgtt    600
gggtcgtggt ggttctgaca ccactgcagt tgcgttggca gctgctttga acgctgatgt    660
gtgtgagatt tactcggacg ttgacggtgt gtataccgct gacccgcgca tcgttcctaa    720
tgcacagaag ctggaaaagc tcagcttcga agaaatgctg gaacttgctg ctgttggctc    780
caagattttg gtgctgcgca gtgttgaata cgctcgtgca ttcaatgtgc acttcgcgt    840 acgctcgtct tatagtaatg atcccggcac tttgattgcc ggctctatgg aggatattcc    900
tgtggaagaa gcagtcctta ccggtgtcgc aaccgacaag tccgaagcca agtaaccgt    960 tctgggtatt tccgataagc caggcgaggc tgcgaaggtt ttccgtgcgt tggctgatgc   1020
agaaatcaac attgacatgg ttctgcagaa cgtctcttct gtagaagacg gcaccaccga   1080
catcaccttc acctgccctc gttccgacgg ccgccgcgcg atggagatct gaagaagct   1140 tcaggttcag ggcaactgga ccaatgtgct ttacgacgac caggtcggca agtctccct   1200 cgtgggtgct ggcatgaagt ctcacccagg tgttaccgca gagttcatgg aagctctgcg   1260
cgatgtcaac gtgaacatcg aattgatttc cacctctgag attcgtattt ccgtgctgat   1320
ccgtgaagat gatctggatg ctgctgcacg tgcattgcat gagcagttcc agctgggcgg   1380
```

```
cgaagacgaa gccgtcgttt atgcaggcac cggacgctaa agttttaaag gagtagtttt    1440
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aaggaagcgg aacacgtaga    1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg gcggttttta tggacagcaa gcgaaccgga attgccagct ggggcgccct    1860
ctggtaaggt tgggaagccc tgcaaagtaa actggatggc tttcttgccg ccaaggatct    1920
gatggcgcag gggatcaaga tctgatcaag agacaggatg aggatcgttt cgcatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tctttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa aatggccgct    2580
tttctggatt catcgactgt ggccggctgg gtgtggcgga ccgctatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg ggcttcggaa tcgttttccg    2880
ggacgccggc tggatgatcc tccagcgcgg ggatctcatg ctggagttct cgcccacgc    2940 tagcggcgcg ccggccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaggc caggaaccgt aaaaaggccg    3180
cgttgctggc gttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta agggacagt attggtatc tgcgctctgc    3660 tgaagccagt taccttcgga aaagagttg gtagctcttg atccggcaaa caaaccaccg    3720
```

```
ctggtagcgg tggttttttt gtttgcaagc agcagattac gcgcagaaaa aaaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
gccgcggccg ccatcggcat tttcttttgc gtttttattt gttaactgtt aattgtcctt    3960
gttcaaggat gctgtctttg acaacagatg ttttcttgcc tttgatgttc agcaggaagc    4020
tcggcgcaaa cgttgattgt ttgtctgcgt agaatcctct gtttgtcata tagcttgtaa    4080
tcacgacatt gtttcctttc gcttgaggta cagcgaagtg tgagtaagta aaggttacat    4140
cgttaggatc aagatccatt tttaacacaa ggccagtttt gttcagcggc ttgtatgggc    4200
cagttaaaga attagaaaca taaccaagca tgtaaatatc gttagacgta atgccgtcaa    4260
tcgtcatttt tgatccgcgg gagtcagtga acaggtacca tttgccgttc attttaaaga    4320
cgttcgcgcg ttcaatttca tctgttactg tgttagatgc aatcagcggt ttcatcactt    4380
ttttcagtgt gtaatcatcg tttagctcaa tcataccgag agcgccgttt gctaactcag    4440
ccgtgcgttt tttatcgctt tgcagaagtt tttgactttc ttgacggaag aatgatgtgc    4500
ttttgccata gtatgctttg ttaaataaag attcttcgcc ttggtagcca tcttcagttc    4560
cagtgtttgc ttcaaatact aagtatttgt ggcctttatc ttctacgtag tgaggatctc    4620
tcagcgtatg gttgtcgcct gagctgtagt tgccttcatc gatgaactgc tgtacatttt    4680
gatacgtttt tccgtcaccg tcaaagattg atttataatc ctctacaccg ttgatgttca    4740
aagagctgtc tgatgctgat acgttaactt gtgcagttgt cagtgtttgt ttgccgtaat    4800
gtttaccgga gaaatcagtg tagaataaac ggattttcc gtcagatgta aatgtggctg    4860
aacctgacca ttcttgtgtt tggtctttta ggatagaatc atttgcatcg aatttgtcgc    4920
tgtctttaaa gacgcggcca cgttttcc agctgtcaat agaagtttcg ccgacttttt    4980
gatagaacat gtaaatcgat gtgtcatccg catttttagg atctccggct aatgcaaaga    5040
cgatgtggta gccgtgatag tttgcgacag tgccgtcagc gttttgtaat ggccagctgt    5100
cccaaacgtc caggcctttt gcagaagaga tattttaat tgtggacgaa tcaaattcag    5160
aaacttgata tttttcattt ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340 acttttgat gttcatcgtt catgtctcct tttttatgta ctgtgttagc ggtctgcttc    5400
ttccagccct cctgtttgaa gatggcaagt tagttacgca caataaaaaa agacctaaaa    5460
tatgtaaggg gtgacgccaa agtatacact ttgccccttta cacattttag gtcttgcctg    5520
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtattttta    5700 tagtttctgt tgcatgggca taaagttgcc ttttaatca caattcagaa aatatcataa    5760 tatctcatt cactaaataa tagtgaacgg caggtatatg tgatgggtta aaaaggatcg    5820
gcggccgctc gatttaaatc tcgagaggcc tgacgtcggg                         5860
```

```
<210> SEQ ID NO 70
<211> LENGTH: 38
<212> TYPE: DNA
<213> ORGANISM: Artificial sequence
<220> FEATURE:
<223> OTHER INFORMATION: Description of the artificial sequence: PCR
```

-continued

```
      primer

<400> SEQUENCE: 70
cggcaccacc gacatcatct tcacctgccc tcgttccg                              38

<210> SEQ ID NO 71
<211> LENGTH: 38
<212> TYPE: DNA
<213> ORGANISM: Artificial sequence
<220> FEATURE:
<223> OTHER INFORMATION: Description of the artificial sequence: PCR
      primer

<400> SEQUENCE: 71
cggaacgagg gcaggtgaag atgatgtcgg tggtgccg                              38

<210> SEQ ID NO 72
<211> LENGTH: 1266
<212> TYPE: DNA
<213> ORGANISM: LysC mutant
<220> FEATURE:
<221> NAME/KEY: CDS
<222> LOCATION: (1)..(1266)

<400> SEQUENCE: 72
```

| | | | | | | | | | | | | | | | | |
|---|---|---|---|---|---|---|---|---|---|---|---|---|---|---|---|---|
| gtg | gcc | ctg | gtc | gta | cag | aaa | tat | ggc | ggt | tcc | tcg | ctt | gag | agt | gcg | 48 |
| Val | Ala | Leu | Val | Val | Gln | Lys | Tyr | Gly | Gly | Ser | Ser | Leu | Glu | Ser | Ala | |
| 1 | | | | 5 | | | | | 10 | | | | | 15 | | |
| gaa | cgc | att | aga | aac | gtc | gct | gaa | cgg | atc | gtt | gcc | acc | aag | aag | gct | 96 |
| Glu | Arg | Ile | Arg | Asn | Val | Ala | Glu | Arg | Ile | Val | Ala | Thr | Lys | Lys | Ala | |
| | | | 20 | | | | | 25 | | | | | 30 | | | |
| gga | aat | gat | gtc | gtg | gtt | gtc | tgc | tcc | gca | atg | gga | gac | acc | acg | gat | 144 |
| Gly | Asn | Asp | Val | Val | Val | Val | Cys | Ser | Ala | Met | Gly | Asp | Thr | Thr | Asp | |
| | | 35 | | | | | 40 | | | | | 45 | | | | |
| gaa | ctt | cta | gaa | ctt | gca | gcg | gca | gtg | aat | ccc | gtt | ccg | cca | gct | cgt | 192 |
| Glu | Leu | Leu | Glu | Leu | Ala | Ala | Ala | Val | Asn | Pro | Val | Pro | Pro | Ala | Arg | |
| | 50 | | | | | 55 | | | | | 60 | | | | | |
| gaa | atg | gat | atg | ctc | ctg | act | gct | ggt | gag | cgt | att | tct | aac | gct | ctc | 240 |
| Glu | Met | Asp | Met | Leu | Leu | Thr | Ala | Gly | Glu | Arg | Ile | Ser | Asn | Ala | Leu | |
| 65 | | | | | 70 | | | | | 75 | | | | | 80 | |
| gtc | gcc | atg | gct | att | gag | tcc | ctt | ggc | gca | gaa | gcc | caa | tct | ttc | acg | 288 |
| Val | Ala | Met | Ala | Ile | Glu | Ser | Leu | Gly | Ala | Glu | Ala | Gln | Ser | Phe | Thr | |
| | | | | 85 | | | | | 90 | | | | | 95 | | |
| ggc | tct | cag | gct | ggt | gtg | ctc | acc | acc | gag | cgc | cac | gga | aac | gca | cgc | 336 |
| Gly | Ser | Gln | Ala | Gly | Val | Leu | Thr | Thr | Glu | Arg | His | Gly | Asn | Ala | Arg | |
| | | | 100 | | | | | 105 | | | | | 110 | | | |
| att | gtt | gat | gtc | act | cca | ggt | cgt | gtg | cgt | gaa | gca | ctc | gat | gag | ggc | 384 |
| Ile | Val | Asp | Val | Thr | Pro | Gly | Arg | Val | Arg | Glu | Ala | Leu | Asp | Glu | Gly | |
| | | | 115 | | | | | 120 | | | | | 125 | | | |
| aag | atc | tgc | att | gtt | gct | ggt | ttc | cag | ggt | gtt | aat | aaa | gaa | acc | cgc | 432 |
| Lys | Ile | Cys | Ile | Val | Ala | Gly | Phe | Gln | Gly | Val | Asn | Lys | Glu | Thr | Arg | |
| | | 130 | | | | | 135 | | | | | 140 | | | | |
| gat | gtc | acc | acg | ttg | ggt | cgt | ggt | ggt | tct | gac | acc | act | gca | gtt | gcg | 480 |
| Asp | Val | Thr | Thr | Leu | Gly | Arg | Gly | Gly | Ser | Asp | Thr | Thr | Ala | Val | Ala | |
| 145 | | | | | 150 | | | | | 155 | | | | | 160 | |
| ttg | gca | gct | gct | ttg | aac | gct | gat | gtg | tgt | gag | att | tac | tcg | gac | gtt | 528 |
| Leu | Ala | Ala | Ala | Leu | Asn | Ala | Asp | Val | Cys | Glu | Ile | Tyr | Ser | Asp | Val | |
| | | | | 165 | | | | | 170 | | | | | 175 | | |
| gac | ggt | gtg | tat | acc | gct | gac | ccg | cgc | atc | gtt | cct | aat | gca | cag | aag | 576 |
| Asp | Gly | Val | Tyr | Thr | Ala | Asp | Pro | Arg | Ile | Val | Pro | Asn | Ala | Gln | Lys | |
| | | | 180 | | | | | 185 | | | | | 190 | | | |
| ctg | gaa | aag | ctc | agc | ttc | gaa | gaa | atg | ctg | gaa | ctt | gct | gct | gtt | ggc | 624 |

```
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat      672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg      720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc      768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat      864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa      912
Ala Glu Ile Asn Ile Asp Met Val Leu Gln Asn Val Ser Ser Val Glu
    290                 295                 300 gac ggc acc acc gac atc atc ttc acc tgc cct cgt tcc gac ggc cgc      960
Asp Gly Thr Thr Asp Ile Ile Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc taa                                             1266
Ala Gly Thr Gly Arg
            420

<210> SEQ ID NO 73
<211> LENGTH: 421
<212> TYPE: PRT
<213> ORGANISM: LysC mutant

<400> SEQUENCE: 73

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60
```

```
Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420
```

<210> SEQ ID NO 74
<211> LENGTH: 5860
<212> TYPE: DNA
<213> ORGANISM: Artificial sequence
<220> FEATURE:
<223> OTHER INFORMATION: Description of the artificial sequence: plasmid

<400> SEQUENCE: 74

```
cccggtacca cgcgtcccag tggctgagac gcatccgcta aagccccagg aaccctgtgc    60
agaaagaaaa cactcctctg gctaggtaga cacagtttat aaaggtagag ttgagcgggt   120
aactgtcagc acgtagatcg aaaggtgcac aaaggtggcc ctggtcgtac agaaatatgg   180
cggttcctcg cttgagagtg cggaacgcat tagaaacgtc gctgaacgga tcgttgccac   240
caagaaggct ggaaatgatg tcgtggttgt ctgctccgca atgggagaca ccacggatga   300
acttctagaa cttgcagcgg cagtgaatcc cgttccgcca gctcgtgaaa tggatatgct   360
cctgactgct ggtgagcgta tttctaacgc tctcgtcgcc atggctattg agtcccttgg   420
cgcagaagcc caatctttca cgggctctca ggctggtgtg ctcaccaccg agcgccacgg   480
aaacgcacgc attgttgatg tcactccagg tcgtgtgcgt gaagcactcg atgagggcaa   540
gatctgcatt gttgctggtt tccagggtgt taataaagaa acccgcgatg tcaccacgtt   600
gggtcgtggt ggttctgaca ccactgcagt tgcgttggca gctgctttga acgctgatgt   660
gtgtgagatt tactcggacg ttgacggtgt gtataccgct gacccgcgca tcgttcctaa   720
tgcacagaag ctggaaaagc tcagcttcga agaaatgctg gaacttgctg ctgttggctc   780
caagattttg gtgctgcgca gtgttgaata cgctcgtgca ttcaatgtgc acttcgcgt    840 acgctcgtct tatagtaatg atcccggcac tttgattgcc ggctctatgg aggatattcc   900
tgtggaagaa gcagtcctta ccggtgtcgc aaccgacaag tccgaagcca agtaaccgt    960 tctgggtatt ccgataagc caggcgaggc tgcgaaggtt ttccgtgcgt tggctgatgc   1020
agaaatcaac attgacatgg ttctgcagaa cgtctcttct gtagaagacg gcaccaccga   1080
catcatcttc acctgccctc gttccgacgg ccgccgcgcg atggagatct gaagaagct    1140 tcaggttcag ggcaactgga ccaatgtgct ttacgacgac caggtcggca aagtctccct   1200
cgtgggtgct ggcatgaagt ctcacccagg tgttaccgca gagttcatgg aagctctgcg   1260
cgatgtcaac gtgaacatcg aattgatttc cacctctgag attcgtattt ccgtgctgat   1320
ccgtgaagat gatctggatg ctgctgcacg tgcattgcat gagcagttcc agctgggcgg   1380
cgaagacgaa gccgtcgttt atgcaggcac cggacgctaa agttttaaag gagtagtttt   1440
acaatgacca ccatcgcagt tgttggtgca accggccagg tcggccaggt tatgcgcacc   1500
cttttggaag agcgcaattt cccagctgac actgttcgtt tctttgcttc cccacgttcc   1560
gcaggccgta agattgaatt cgtcgacatc gatgctcttc tgcgttaatt aacaattggg   1620
atcctctaga cccgggattt aaatcgctag cgggctgcta aaggaagcgg aacacgtaga   1680
aagccagtcc gcagaaacgg tgctgacccc ggatgaatgt cagctactgg gctatctgga   1740
caagggaaaa cgcaagcgca aagagaaagc aggtagcttg cagtgggctt acatggcgat   1800
agctagactg ggcggtttta tggacagcaa gcgaaccgga attgccagct ggggcgccct   1860
ctggtaaggt tgggaagccc tgcaaagtaa actggatggc tttcttgccg ccaaggatct   1920
gatggcgcag gggatcaaga tctgatcaag agacaggatg aggatcgttt cgcatgattg   1980
aacaagatgg attgcacgca ggttctccgg ccgcttgggt ggagaggcta ttcggctatg   2040
actgggcaca acagacaatc ggctgctctg atgccgccgt gttccggctg tcagcgcagg   2100
ggcgcccggt tctttttgtc aagaccgacc tgtccggtgc cctgaatgaa ctgcaggacg   2160
aggcagcgcg gctatcgtgg ctggccacga cgggcgttcc ttgcgcagct gtgctcgacg   2220
ttgtcactga agcgggaagg gactggctgc tattgggcga agtgccgggg caggatctcc   2280
tgtcatctca ccttgctcct gccgagaaag tatccatcat ggctgatgca atgcggcggc   2340
tgcatacgct tgatccggct acctgcccat tcgaccacca agcgaaacat cgcatcgagc   2400
```

```
gagcacgtac tcggatggaa gccggtcttg tcgatcagga tgatctggac gaagagcatc   2460
aggggctcgc gccagccgaa ctgttcgcca ggctcaaggc gcgcatgccc gacggcgagg   2520
atctcgtcgt gacccatggc gatgcctgct tgccgaatat catggtggaa aatggccgct   2580
tttctggatt catcgactgt ggccggctgg gtgtggcgga ccgctatcag gacatagcgt   2640
tggctacccg tgatattgct gaagagcttg cggcgaatg ggctgaccgc ttcctcgtgc   2700
tttacggtat cgccgctccc gattcgcagc gcatcgcctt ctatcgcctt cttgacgagt   2760
tcttctgagc gggactctgg ggttcgaaat gaccgaccaa gcgacgccca acctgccatc   2820
acgagatttc gattccaccg ccgccttcta tgaaaggttg ggcttcggaa tcgttttccg   2880
ggacgccggc tggatgatcc tccagcgcgg ggatctcatg ctggagttct cgcccacgc   2940 tagcggcgcg ccggccggcc cggtgtgaaa taccgcacag atgcgtaagg agaaaatacc   3000
gcatcaggcg ctcttccgct tcctcgctca ctgactcgct gcgctcggtc gttcggctgc   3060
ggcgagcggt atcagctcac tcaaaggcgg taatacggtt atccacagaa tcaggggata   3120
acgcaggaaa gaacatgtga gcaaaaggcc agcaaaaggc caggaaccgt aaaaaggccg   3180
cgttgctggc gtttttccat aggctccgcc cccctgacga gcatcacaaa aatcgacgct   3240
caagtcagag gtggcgaaac ccgacaggac tataaagata ccaggcgttt ccccctggaa   3300
gctccctcgt gcgctctcct gttccgaccc tgccgcttac cggatacctg tccgcctttc   3360
tcccttcggg aagcgtggcg ctttctcata gctcacgctg taggtatctc agttcggtgt   3420
aggtcgttcg ctccaagctg ggctgtgtgc acgaacccc cgttcagccc gaccgctgcg   3480
ccttatccgg taactatcgt cttgagtcca acccggtaag acacgactta tcgccactgg   3540
cagcagccac tggtaacagg attagcagag cgaggtatgt aggcggtgct acagagttct   3600
tgaagtggtg gcctaactac ggctacacta aggacagt atttggtatc tgcgctctgc   3660
tgaagccagt taccttcgga aaaagagttg gtagctcttg atccggcaaa caaaccaccg   3720
ctggtagcgg tggtttttt gtttgcaagc agcagattac gcgcagaaaa aaaggatctc   3780
aagaagatcc tttgatcttt tctacggggt ctgacgctca gtggaacgaa aactcacgtt   3840
aagggatttt ggtcatgaga ttatcaaaaa ggatcttcac ctagatcctt ttaaaggccg   3900
gccgcggccg ccatcggcat tttcttttgc gttttatt gttaactgtt aattgtcctt   3960
gttcaaggat gctgtctttg acaacagatg ttttcttgcc tttgatgttc agcaggaagc   4020
tcggcgcaaa cgttgattgt ttgtctgcgt agaatcctct gtttgtcata tagcttgtaa   4080
tcacgacatt gtttcctttc gcttgaggta cagcgaagtg tgagtaagta aaggttacat   4140
cgttaggatc aagatccatt tttaacacaa ggccagtttt gttcagcggc ttgtatgggc   4200
cagttaaaga attagaaaca taaccaagca tgtaaatatc gttagacgta atgccgtcaa   4260
tcgtcatttt tgatccgcgg gagtcagtga acaggtacca tttgccgttc attttaaaga   4320
cgttcgcgcg ttcaatttca tctgttactg tgttagatgc aatcagcggt ttcatcactt   4380
ttttcagtgt gtaatcatcg tttagctcaa tcataccgag agcgccgttt gctaactcag   4440
ccgtgcgttt tttatcgctt tgcagaagtt tttgactttc ttgacggaag aatgatgtgc   4500
ttttgccata gtatgctttg ttaaataaag attcttcgcc ttggtagcca tcttcagttc   4560
cagtgtttgc ttcaaatact aagtatttgt ggcctttatc ttctacgtag tgaggatctc   4620
tcagcgtatg gttgtcgcct gagctgtagt tgccttcatc gatgaactgc tgtacatttt   4680
gatacgtttt tccgtcaccg tcaaagattg atttataatc ctctacaccg ttgatgttca   4740
```

-continued

```
aagagctgtc tgatgctgat acgttaactt gtgcagttgt cagtgtttgt ttgccgtaat    4800
gtttaccgga gaaatcagtg tagaataaac ggatttttcc gtcagatgta aatgtggctg    4860
aacctgacca ttcttgtgtt tggtctttta ggatagaatc atttgcatcg aatttgtcgc    4920
tgtctttaaa gacgcggcca gcgttttttcc agctgtcaat agaagtttcg ccgactttttt   4980 gatagaacat gtaaatcgat gtgtcatccg cattttttagg atctccggct aatgcaaaga    5040
cgatgtggta gccgtgatag tttgcgacag tgccgtcagc gttttgtaat ggccagctgt    5100
cccaaacgtc caggccttttt gcagaagaga tatttttaat tgtggacgaa tcaaattcag    5160
aaacttgata tttttcattt ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340 acttttttgat gttcatcgtt catgtctcct ttttttatgta ctgtgttagc ggtctgcttc    5400
ttccagccct cctgtttgaa gatggcaagt tagttacgca caataaaaaa agacctaaaa    5460
tatgtaaggg gtgacgccaa agtatacact ttgccctttta cacattttag gtcttgcctg    5520
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtattttttta    5700 tagtttctgt tgcatgggca taaagttgcc tttttaatca caattcagaa aatatcataa    5760
tatctcattt cactaaataa tagtgaacgg caggtatatg tgatgggtta aaaaggatcg    5820
gcggccgctc gatttaaatc tcgagaggcc tgacgtcggg                          5860
```

<210> SEQ ID NO 75
<211> LENGTH: 31
<212> TYPE: DNA
<213> ORGANISM: Artificial sequence
<220> FEATURE:
<223> OTHER INFORMATION: Description of the artificial sequence: PCR
      primer

<400> SEQUENCE: 75
gagaggatcc ggaaggtgaa tcgaatttcg g                                   31

<210> SEQ ID NO 76
<211> LENGTH: 40
<212> TYPE: DNA
<213> ORGANISM: Artificial sequence
<220> FEATURE:
<223> OTHER INFORMATION: Description of the artificial sequence: PCR
      primer

<400> SEQUENCE: 76
ctattgctgt cggcgctcat gattctccaa aaataatcgc                          40

<210> SEQ ID NO 77
<211> LENGTH: 20
<212> TYPE: DNA
<213> ORGANISM: Artificial sequence
<220> FEATURE:
<223> OTHER INFORMATION: Description of the artificial sequence: PCR
      primer

<400> SEQUENCE: 77
atgagcgccg acagcaatag                                                20

<210> SEQ ID NO 78

```
<211> LENGTH: 29
<212> TYPE: DNA
<213> ORGANISM: Artificial sequence
<220> FEATURE:
<223> OTHER INFORMATION: Description of the artificial sequence: PCR
      primer

<400> SEQUENCE: 78
gaactctaga tcagaacgcc gccacggac                                    29

<210> SEQ ID NO 79
<211> LENGTH: 6591
<212> TYPE: DNA
<213> ORGANISM: Artificial sequence
<220> FEATURE:
<223> OTHER INFORMATION: Description of the artificial sequence: plasmid

<400> SEQUENCE: 79
gatccggaag gtgaatcgaa tttcggggct ttaaagcaaa aatgaacagc ttggtctata      60
gtggctaggt acccttttg ttttggacac atgtaggtg gccgaaacaa agtaatagga       120
caacaacgct cgaccgcgat tattttttgga gaatcatgag cgccgacagc aatagcaccg    180
acgccgatcc gaccgcgcat tggtcgttcg aaaccaaaca gatacacgct ggtcagcacc    240
ctgatccgac caccaacgcc cgggctctgc cgatctatgc gaccacgtcg tacaccttcg    300
acgacaccgc gcacgccgcc gccctgttcg gactggaaat tccgggcaat atctacaccc    360
ggatcggcaa ccccaccacc gacgtcgtcg agcagcgcat cgccgcgctc gagggcggtg    420
tggccgcgct gttcctgtcg tcggggcagg ccgcggagag gttcgccatc ttgaacctgg    480
ccggcgcggg cgatcacatc gtgtccagcc cgcgcctgta cggcggcacc tacaacctgt    540
tccactattc gctggccaag ctcggcatcg aggtcagctt cgtcgacgat ccggacgatc    600
tggacacctg gcaggcggcg gtacggccca acaccaaggc gttcttcgcc gagaccatct    660
ccaacccgca gatcgacctg ctggacaccc cggcggtttc cgaggtcgcc catcgcaacg    720
gggtgccgtt gatcgtcgac aacaccatcg ccacgccata cctgatccaa ccgttggccc    780
agggcgccga catcgtcgtg cattcggcca ccaagtacct gggcgggcac ggtgccgcca    840
tcgcgggtgt gatcgtcgac ggcggcaact tcgattggac ccagggccgc ttccccggct    900
tcaccacccc cgaccccagc taccacgcg tggtgttcgc cgagctgggt ccaccggcgt    960 tgcgctcaa agctcgagtg cagctgctcc gtgactacgg ctcggcggct tcgccgttca    1020
acgcgttctt ggtggcgcag ggtctggaaa cgctgagcct gcggatcgag cggcacgtcg    1080
ccaacgcgca gcgcgtcgcc gagttcctgg ccgcccgcga cgacgtgctt tcggtcaact    1140
atgcggggct gccctcctcg ccctggcatg agcgggccaa gaggctggcg cccaagggaa    1200
ccggggccgt gctgtccttc gagttggccg gcggcatcga ggccggcaag gcattcgtga    1260
acgcgttgaa gctgcacagc cacgtcgcca acatcggtga cgtgcgctcg ctggtgatcc    1320
acccggcatc gaccactcat gcccagctga gccggccga gcagctggcg accggggtca    1380
gcccgggcct ggtgcgtttg gctgtgggca tcgaaggtat cgacgatatc ctggccgacc    1440
tggagcttgg ctttgccgcg gccgcagat tcagcgccga cccgcagtcc gtggcggcgt    1500
tctgatctag acccgggatt taaatcgcta gcgggctgct aaaggaagcg gaacacgtag    1560
aaagccagtc cgcagaaacg gtgctgaccc cggatgaatg tcagctactg ggctatctgg    1620
acaagggaaa acgcaagcgc aaagagaaag caggtagctt gcagtgggct tacatggcga    1680
tagctagact gggcggtttt atggacagca agcgaaccgg aattgccagc tggggcgccc    1740
```

```
tctggtaagg ttgggaagcc ctgcaaagta aactggatgg ctttcttgcc gccaaggatc   1800
tgatggcgca ggggatcaag atctgatcaa gagacaggat gaggatcgtt tcgcatgatt   1860
gaacaagatg gattgcacgc aggttctccg gccgcttggg tggagaggct attcggctat   1920
gactgggcac aacagacaat cggctgctct gatgccgccg tgttccggct gtcagcgcag   1980
gggcgcccgg ttcttttttgt caagaccgac ctgtccggtg ccctgaatga actgcaggac   2040
gaggcagcgc ggctatcgtg gctggccacg acgggcgttc cttgcgcagc tgtgctcgac   2100
gttgtcactg aagcgggaag ggactggctg ctattgggcg aagtgccggg gcaggatctc   2160
ctgtcatctc accttgctcc tgccgagaaa gtatccatca tggctgatgc aatgcggcgg   2220
ctgcatacgc ttgatccggc tacctgccca ttcgaccacc aagcgaaaca tcgcatcgag   2280
cgagcacgta ctcggatgga agccggtctt gtcgatcagg atgatctgga cgaagagcat   2340
caggggctcg cgccagccga actgttcgcc aggctcaagg cgcgcatgcc cgacggcgag   2400
gatctcgtcg tgacccatgg cgatgcctgc ttgccgaata tcatggtgga aaatggccgc   2460
ttttctggat tcatcgactg tggccggctg ggtgtggcgg accgctatca ggacatagcg   2520
ttggctaccc gtgatattgc tgaagagctt ggcggcgaat gggctgaccg cttcctcgtg   2580
ctttacggta tcgccgctcc cgattcgcag cgcatcgcct tctatcgcct tcttgacgag   2640
ttcttctgag cgggactctg gggttcgaaa tgaccgacca agcgacgccc aacctgccat   2700
cacgagattt cgattccacc gccgccttct atgaaaggtt gggcttcgga atcgttttcc   2760
gggacgccgg ctggatgatc ctccagcgcg gggatctcat gctggagttc ttcgcccacg   2820
ctagcggcgc gccggccggc ccggtgtgaa ataccgcaca gatgcgtaag gagaaaatac   2880
cgcatcaggc gctcttccgc ttcctcgctc actgactcgc tgcgctcggt cgttcggctg   2940
cggcgagcgg tatcagctca ctcaaaggcg gtaatacggt tatccacaga atcaggggat   3000
aacgcaggaa agaacatgtg agcaaaaggc cagcaaaagg ccaggaaccg taaaaaggcc   3060
gcgttgctgg cgtttttcca taggctccgc cccctgacg agcatcacaa aaatcgacgc   3120
tcaagtcaga ggtggcgaaa cccgacagga ctataaagat accaggcgtt tcccctggaa   3180
agctccctcg tgcgctctcc tgttccgacc ctgccgctta ccggatacct gtccgccttt   3240
ctcccttcgg gaagcgtggc gctttctcat agctcacgct gtaggtatct cagttcggtg   3300
taggtcgttc gctccaagct gggctgtgtg cacgaacccc ccgttcagcc cgaccgctgc   3360
gccttatccg gtaactatcg tcttgagtcc aacccggtaa gacacgactt atcgccactg   3420
gcagcagcca ctggtaacag gattagcaga gcgaggtatg taggcggtgc tacagagttc   3480
ttgaagtggt ggcctaacta cggctacact agaaggacag tatttggtat ctgcgctctg   3540
ctgaagccag ttaccttcgg aaaaagagtt ggtagctctt gatccggcaa acaaaccacc   3600
gctggtagcg gtggtttttt tgtttgcaag cagcagatta cgcgcagaaa aaaaggatct   3660
caagaagatc ctttgatctt ttctacgggg tctgacgctc agtggaacga aaactcacgt   3720
taagggattt tggtcatgag attatcaaaa aggatcttca cctagatcct tttaaaggcc   3780
ggccgcggcc gcgcaaagtc ccgcttcgtg aaaattttcg tgccgcgtga ttttccgcca   3840
aaaactttaa cgaacgttcg ttataatggt gtcatgacct tcacgacgaa gtactaaaat   3900
tggcccgaat catcagctat ggatctctct gatgtcgcgc tggagtccga cgcgctcgat   3960
gctgccgtcg atttaaaaac ggtgatcgga ttttttccgag ctctcgatac gacggacgcg   4020
ccagcatcac gagactgggc cagtgccgcg agcgacctag aaactctcgt ggcggatctt   4080
gaggagctgg ctgacgagct gcgtgctcgg ccagcgccag gaggacgcac agtagtggag   4140
```

```
gatgcaatca gttgcgccta ctgcggtggc ctgattcctc cccggcctga cccgcgagga    4200
cggcgcgcaa atattgctc agatgcgtgt cgtgccgcag ccagccgcga gcgcgccaac     4260
aaacgccacg ccgaggagct ggaggcggct aggtcgcaaa tggcgctgga agtgcgtccc    4320
ccgagcgaaa ttttggccat ggtcgtcaca gagctggaag cggcagcgag aattatcgcg    4380
atcgtggcgg tgcccgcagg catgacaaac atcgtaaatg ccgcgtttcg tgtgccgtgg    4440
ccgcccagga cgtgtcagcg ccgccaccac ctgcaccgaa tcggcagcag cgtcgcgcgt    4500
cgaaaaagcg cacaggcggc aagaagcgat aagctgcacg aatacctgaa aaatgttgaa    4560
cgccccgtga gcggtaactc acagggcgtc ggctaacccc cagtccaaac ctgggagaaa    4620
gcgctcaaaa atgactctag cggattcacg agacattgac acaccggcct ggaaattttc    4680
cgctgatctg ttcgacaccc atcccgagct cgcgctgcga tcacgtggct ggacgagcga    4740
agaccgccgc gaattcctcg ctcacctggg cagagaaaat ttccagggca gcaagacccg    4800
cgacttcgcc agcgcttgga tcaaagaccc ggacacggag aaacacagcc gaagttatac    4860
cgagttggtt caaaatcgct tgcccggtgc cagtatgttg ctctgacgca cgcgcagcac    4920
gcagccgtgc ttgtcctgga cattgatgtg ccgagccacc aggccggcgg gaaaatcgag    4980
cacgtaaacc ccgaggtcta cgcgattttg gagcgctggg cacgcctgga aaaagcgcca    5040
gcttggatcg gcgtgaatcc actgagcggg aaatgccagc tcatctggct cattgatccg    5100
gtgtatgccg cagcaggcat gagcagcccg aatatgcgcc tgctggctgc aacgaccgag    5160
gaaatgaccc gcgttttcgg cgctgaccag gcttttcac ataggctgag ccgtggccac    5220
tgcactctcc gacgatccca gccgtaccgc tggcatgccc agcacaatcg cgtggatcgc    5280
ctagctgatc ttatgggagt tgctcgcatg atctcaggca cagaaaaacc taaaaaacgc    5340
tatgagcagg agttttctag cggacgggca cgtatcgaag cggcaagaaa agccactgcg    5400
gaagcaaaag cacttgccac gcttgaagca agcctgccga gcgccgctga agcgtctgga    5460
gagctgatcg acggcgtccg tgtcctctgg actgctccag ggcgtgccgc ccgtgatgag    5520
acggcttttc gccacgcttt gactgtggga taccagttaa aagcggctgg tgagcgccta    5580
aaagacacca agggtcatcg agcctacgag cgtgcctaca ccgtcgctca ggcggtcgga    5640
ggaggccgtg agcctgatct gccgccggac tgtgaccgcc agacggattg gccgcgacgt    5700
gtgcgcggct acgtcgctaa aggccagcca gtcgtccctg ctcgtcagac agagacgcag    5760
agccagccga ggcgaaaagc tctggccact atgggaagac gtggcggtaa aaaggccgca    5820
gaacgctgga agacccaaa cagtgagtac gcccgagcac agcgagaaaa actagctaag    5880
tccagtcaac gacaagctag gaaagctaaa ggaaatcgct tgaccattgc aggttggttt    5940
atgactgttg agggagagac tggctcgtgg ccgacaatca atgaagctat gtctgaattt    6000
agcgtgtcac gtcagaccgt gaatagagca cttaaggtct gcgggcattg aacttccacg    6060
aggacgccga agcttccca gtaaatgtgc catctcgtag gcagaaaacg gttcccccgt    6120
agggtctctc tcttggcctc ctttctaggt cgggctgatt gctcttgaag ctctctaggg    6180
gggctcacac cataggcaga taacgttccc caccggctcg cctcgtaagc gcacaaggac    6240
tgctcccaaa gatcttcaaa gccactgccg cgactgcctt cgcgaagcct tgccccgcgg    6300
aaatttcctc caccgagttc gtgcacaccc ctatgccaag cttctttcac cctaaattcg    6360
agagattgga ttcttaccgt ggaaattctt cgcaaaaatc gtcccctgat cgcccttgcg    6420
acgttggcgt cggtgccgct ggttgcgctt ggcttgaccg acttgatcag cggccgctcg    6480
```

-continued

```
atttaaatct cgagaggcct gacgtcgggc ccggtaccac gcgtcatatg actagttcgg    6540
acctagggat atcgtcgaca tcgatgctct tctgcgttaa ttaacaattg g             6591
```

METHOD FOR ZYMOTIC PRODUCTION OF FINE CHEMICALS (METY) CONTAINING SULPHUR

RELATED APPLICATIONS

This application is a national stage application (under 35 U.S.C. 371) of PCT/EP2003/009453 filed Aug. 26, 2003, which claims benefit of German application 102 39 082.7 filed Aug. 26, 2002.

DESCRIPTION

The invention relates to a method for the fermentative production of sulfur-containing fine chemicals, in particular L-methionine, by using bacteria which express a nucleotide sequence coding for an O-acetylhomoserine sulfhydrolase (metY) gene.

PRIOR ART

Sulfur-containing fine chemicals such as, for example, methionine, homocysteine, S-adenosylmethionine, glutathione, cysteine, biotin, thiamine, lipoic acid are produced in cells via natural metabolic processes and are used in many branches of industry, including the food, animal feed, cosmetics and pharmaceutical industries. These substances which are collectively referred to "sulfur-containing fine chemicals" include organic acids, both proteinogenic and nonproteinogenic amino acids, vitamins and cofactors. They are most expediently produced on a large scale by means of cultivating bacteria which have been developed in order to produce and secrete large amounts of the substance desired in each case. Organisms which are particularly suitable for this purpose are coryneform bacteria, Gram-positive nonpathogenic bacteria.

It is known that amino acids are produced by fermentation of strains of coryneform bacteria, in particular *Corynebacterium glutamicum*. Due to the great importance, the production processes are constantly improved. Process improvements can relate to measures regarding technical aspects of the fermentation, such as, for example, stirring and oxygen supply, or to the nutrient media composition such as, for example, sugar concentration during fermentation or to the work-up to give the product, for example by ion exchange chromatography, or to the intrinsic performance properties of the microorganism itself.

A number of mutant strains which produce an assortment of desirable compounds from the group of sulfur-containing fine chemicals have been developed via strain selection. The performance properties of said microorganisms are improved with respect to the production of a particular molecule by applying methods of mutagenesis, selection and mutant selection. However, this is a time-consuming and difficult process. In this way strains are obtained, for example, which are resistant to antimetabolites such as, for example, the methionine analogs α-methylmethionine, ethionine, norleucine, n-acetylnorleucine, S-trifluoromethylhomocysteine, 2-amino-5-heprenoitic acid, selenomethionine, methioninesulfoximine, methoxine, 1-aminocyclopentanecarboxylic acid or which are auxotrophic for metabolites important for regulation and which produce sulfur-containing fine chemicals such as, for example, L-methionine.

Methods of recombinant DNA technology have also been used for some years to improve *Corynebacterium* strains producing L-amino acids by amplifying individual amino-acid biosynthesis genes and investigating the effect on amino acid production.

WO-A-02/18613 describes the nucleic acid sequence and the amino acid sequence for metY from *C. glutamicum* and its use for the production of L-lysine.

BRIEF DESCRIPTION OF THE INVENTION

It is an object of the present invention to provide a novel method for the improved fermentative production of sulfur-containing fine chemicals, in particular L-methionine.

We have found that this object is achieved by providing a method for the fermentative production of a sulfur-containing fine chemical, comprising the expression of a heterologous nucleotide sequence coding for a protein with metY activity in a coryneform bacterium.

The invention firstly relates to a method for the fermentative production of at least one sulfur-containing fine chemical, which comprises the following steps:

a) fermentation of a coryneform bacteria culture producing the desired sulfur-containing fine chemical, the coryneform bacteria expressing at least one heterologous nucleotide sequence which codes for a protein with O-acetylhomoserine sulfhydrolase (metY) activity;

b) concentration of the sulfur-containing fine chemical in the medium or in the bacterial cells, and c) isolation of the sulfur-containing fine chemical, which preferably comprises L-methionine.

The above heterologous metY-encoding nucleotide sequence is preferably less than 100%, such as, for example, more than 70%, such as 75, 80, 85, 90 or 95%, or less than 70%, such as, for example, up to 60, 50, 40, 30, 20 or 10% homologous to the metY-encoding sequence from *Corynebacterium glutamicum* ATCC 13032. The metY-encoding sequence is derived preferably from any of the following organisms of list I:

| List I | |
|---|---|
| *Corynebacterium diphteriae* | ATCC 14779 |
| *Mycobacterium tuberculosis* CDC1551 | ATCC 25584 |
| *Clostridium acetobutylicum* | ATCC 824 |
| *Bacillus halodurans* | ATCC21591 |
| *Bacillus stearothermophilus* | ATCC 12980 |
| *Chlorobium tepidum* | ATCC 49652 |
| *Synechococcus* sp. | ATCC27104 |
| *Emericella nidulans* | ATCC 36104 |
| *Bacteroides fragilis* | ATCC 25285 |
| *Lactococcus lactis* | ATCC 7962 |
| *Bordetella bronchiseptica* | ATCC 19395 |
| *Pseudomonas aeruginosa* | ATCC 17933 |
| *Nitrosomonas europaea* | ATCC 19718 |
| *Sinorhizobium meliloti* | ATCC 4399 |
| *Thermotoga maritima* | ATCC 43589 |
| *Streptococcus mutans* | ATCC 25175 |
| *Burkholderia cepacia* | ATCC 25416 |
| *Deinococcus radiodurans* | ATCC 13939 |
| *Rhodobacter capsulatus* | ATCC 11166 |
| *Pasteurella multocida* | ATCC 6530 |
| *Clostridium difficile* | ATCC 9689 |
| *Campylobacter jejuni* | ATCC 33560 |
| *Streptococcus pneumoniae* | ATCC 6308 |
| *Saccharomyces cerevisiae* | ATCC 2704 |
| *Kluyveromyces lactis* | ATCC 8585 |
| *Candida albicans* | ATCC 10231 |
| *Schizosaccharomyces pombe* | ATCC 24969 |

ATCC: American Type Culture Collection, Rockville, MD, USA

The metY-encoding sequence used according to the invention preferably comprises a coding sequence according to SEQ ID NO:1, 3, 5, 7, 9, 11, 13, 15, 17, 19, 21, 23, 25, 27, 29, 31, 33, 35, 37, 39, 41, 43, 45, 47, 49, 51 and 53 or a nucleotide sequence homologous thereto which codes for a protein with metY activity.

Moreover, the metY-encoding sequence used according to the invention preferably codes for a protein with metY activity, said protein comprising an amino acid sequence according to SEQ ID NO:2, 4, 6, 8, 10, 12, 14, 16, 18, 20, 22, 24, 26, 28, 30, 32, 34, 36, 38, 40, 42, 44, 46, 48, 50, 52 and 54 or an amino acid sequence homologous thereto which represents a protein with metY activity.

The coding metY sequence is preferably a DNA or an RNA which can be replicated in coryneform bacteria or is stably integrated into the chromosome.

According to a preferred embodiment, the method of the invention is carried out by
a) using a bacterial strain transformed with a plasmid vector which carries at least one copy of the coding metY sequence under the control of regulatory sequences or
b) using a strain in which the coding metY sequence has been integrated into the bacterial chromosome.

Furthermore, preference is given to overexpressing the coding metY sequence for the fermentation.

It may also be desirable to ferment bacteria in which additionally at least one further gene of the biosynthetic pathway of the desired sulfur-containing fine chemical has been amplified; and/or in which at least one metabolic pathway, which reduces production of the desired sulfur-containing fine chemical has, at least partially, been switched off.

It may also be desirable to ferment bacteria in which additionally the activity of at least one further gene of the biosynthetic pathway of the desired sulfur-containing fine chemical is not undesirably influenced by metabolic metabolites.

Therefore, according to another embodiment of the method of the invention, coryneform bacteria are fermented in which, at the same time, at least one of the genes selected from among
a) the gene lysC, which encodes an aspartate kinase,
b) the gene asd, which encodes an aspartate-semialdehyde dehydrogenase,
c) the glyceraldehyde-3-phosphate dehydrogenase-encoding gene gap,
d) the 3-phosphoglycerate kinase-encoding gene pgk,
e) the pyruvate carboxylase-encoding gene pyc,
f) the triose phosphate isomerase-encoding gene tpi,
g) the homoserine O-acetyltransferase-encoding gene metA,
h) the cystathionine gamma-synthase-encoding gene metB,
i) the cystathionine gamma-lyase-encoding gene metC,
j) the serine hydroxymethyltransferase-encoding gene glyA,
k) the methionine synthase-encoding gene metH,
l) the methylene tetrahydrofolate reductase-encoding gene metF,
m) the phosphoserine aminotransferase-encoding gene serC,
n) the phosphoserine phosphatase-encoding gene serB,
o) the serine acetyl transferase-encoding gene cysE,
p) the homoserine dehydrogenase-encoding gene hom is overexpressed.

According to another embodiment of the method of the invention, coryneform bacteria are fermented in which, at the same time, at least one of the genes selected from among genes of the abovementioned group a) to p) is mutated in such a way that the activity of the corresponding proteins is influenced by metabolic metabolites to a smaller extent, if at all, compared to nonmutated proteins and that in particular the inventive production of the fine chemical is not adversely affected.

According to another embodiment of the method of the invention, coryneform bacteria are fermented in which, at the same time, at least one of the genes selected from among
q) the homoserine kinase-encoding gene thrB,
r) the threonine dehydratase-encoding gene ilvA,
s) the threonine synthase-encoding gene thrC,
t) the meso-diaminopimelate D-dehydrogenase-encoding gene ddh,
u) the phosphoenolpyruvate carboxykinase-encoding gene pck,
v) the glucose-6-phosphate 6-isomerase-encoding gene pgi,
w) the pyruvate oxidase-encoding gene poxB,
x) the dihydrodipicolinate synthase-encoding gene dapA,
y) the dihydrodipicolinate reductase-encoding gene dapB; or
z) the diaminopicolinate decarboxylase-encoding gene lysA is attenuated, in particular by reducing the rate of expression of the corresponding gene.

According to another embodiment of the method of the invention, coryneform bacteria are fermented in which, at the same time, at least one of the genes of the above groups q) to z) is mutated in such a way that the enzymic activity of the corresponding protein is partially or completely reduced.

Preference is given to using, in the method of the invention, microorganisms of the species *Corynebacterium glutamicum*.

The invention further relates to a method for producing an L-methionine-containing animal feed additive from fermentation broths, which comprises the following steps:
a) culturing and fermentation of an L-methionine-producing microorganism in a fermentation medium;
b) removal of water from the L-methionine-containing fermentation broth;
c) removal of from 0 to 100% by weight of the biomass formed during fermentation; and
d) drying of the fermentation broth obtained according to b) and/or c), in order to obtain the animal feed additive in the desired powder or granule form.

The invention likewise relates to the coding metY sequences isolated from the above microorganisms for the first time, to the O-acetylhomoserine sulfhydrolases encoded thereby and to the functional homologs of these polynucleotides and proteins, respectively.

Figure 1:
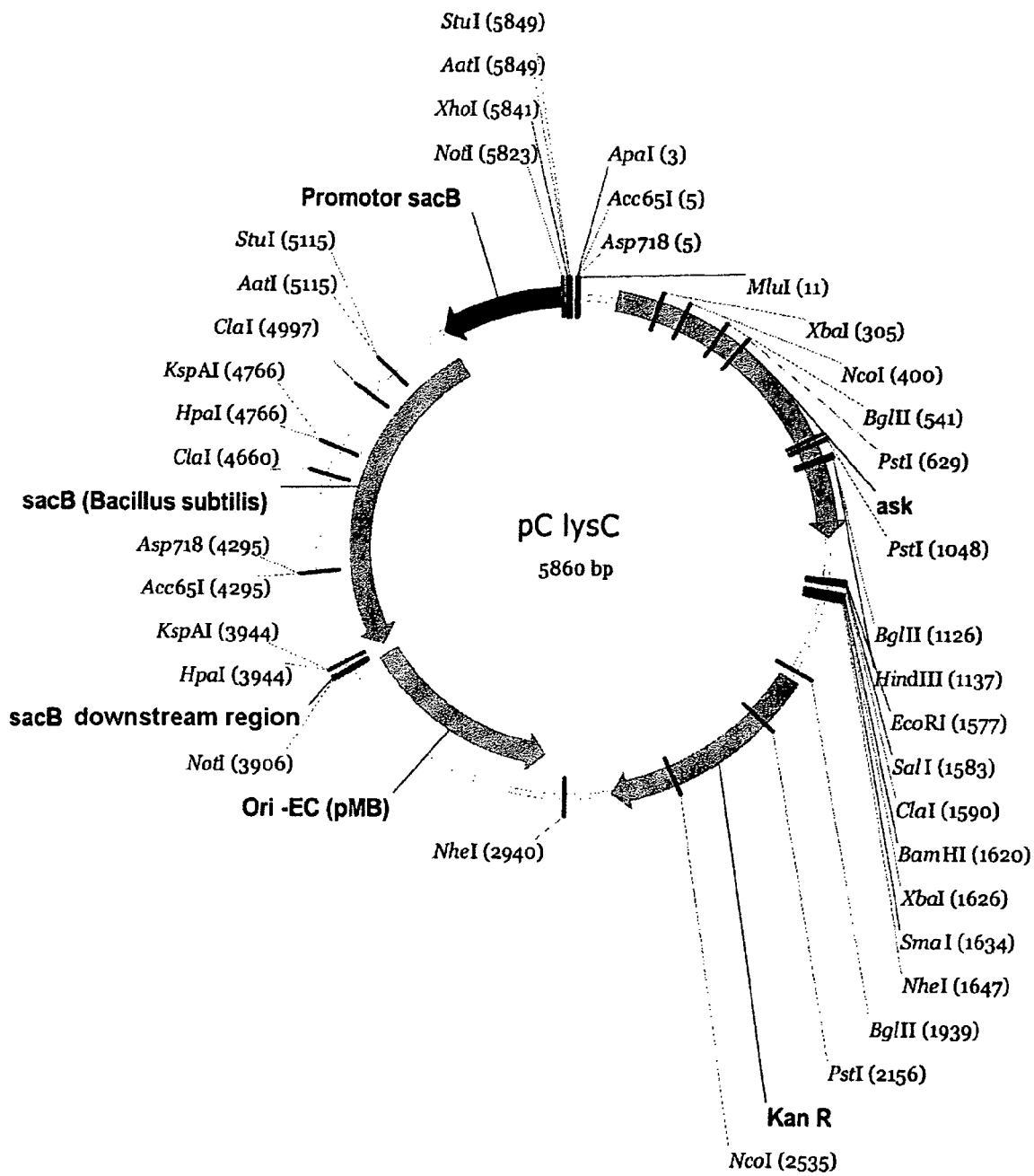
FIG. 1 shows the plasmid map for plasmid pC lysC.

DETAILED DESCRIPTION OF THE INVENTION a) General Terms

Proteins with O-acetylhomoserine sulfhydrolase activity, also referred to as metY (EC 4.2.99.10), are described as being proteins which are capable of converting O-acetylhomoserine and sulfide into homocystein, using the cofactor pyrodoxal phosphate. The skilled worker distinguishes between the activity of O-acetylhomoserine sulfhydrolase and that of O-succinylhomoserine sulfhydrolase, also referred to as metz. In the latter enzyme, O-succinylhomoserine and not O-acetylhomoserine acts as the substrate for the reaction. The skilled worker can detect the enzymatic activity of mety by means of enzyme assays, protocols for which may be: Shimizu H. Yamagata S. Masui R. Inoue Y. Shibata T. Yokoyama S. Kuramitsu S. Iwama T. Biochimica et Biophysica Acta. 1549(1):61-72, 2001, Yamagata S. Isaji M. Nakamura K. Fujisaki S. Doi K. Bawden S. D'Andrea R. Applied Microbiology & Biotechnology. 42(1):92-9, 1994.

Within the scope of the present invention, the term "sulfur-containing fine chemical" includes any chemical compound which contains at least one covalently bound sulfur atom and is accessible by a fermentation method of the invention. Nonlimiting examples thereof are methionine, homocysteine, S-adenosylmethionine, in particular methionine and S-adenosylmethionine.

Within the scope of the present invention, the terms "L-methionine", "methionine", homocysteine and S-adenosylmethionine also include the corresponding salts such as, for example, methionine hydrochloride or methionine sulfate.

"Polynucleotides" in general refers to polyribonucleotides (RNA) and polydeoxynbonucleotides (DNA) which may be unmodified RNA and DNA respectively, or modified RNA and DNA, respectively.

According to the invention, "polypeptides" means peptides or proteins which contain two or more amino acids linked via peptide bonds.

The term "metabolic metabolite" refers to chemical compounds which occur in the metabolism of organisms as intermediates or else final products and which, apart from their property as chemical building blocks, may also have a modulating effect on enzymes and on their catalytic activity. It is known from the literature that such metabolic metabolites may act on the activity of enzymes in both an inhibiting and a stimulating manner (Biochemistry, Stryer, Lubert, 1995 W. H. Freeman & Company, New York, N.Y.). The possibility of producing in organisms enzymes in which the influence of metabolic metabolites has been modified by measures such as mutation of the genomic DNA by UV radiation, ionizing radiation or mutagenic substances and subsequent selection for particular phenotypes has also been described in the literature (Sahm H., Eggeling L., de Graaf A A., Biological Chemistry 381(9-10):899-910, 2000; Eikmanns B J., Eggeling L., Sahm H., Antonie van Leeuwenhoek., 64:145-63, 1993-94). These altered properties may also be achieved by specific measurements. The skilled worker knows that it is possible specifically to modify in enzyme genes particular nucleotides of the DNA coding for the protein that the protein resulting from the expressed DNA sequence has certain new properties, in such a way for example that the modulating effect of metabolic metabolites on the unmodified protein has changed.

The activity of enzymes may be influenced in such a way that the reaction rate is reduced or the affinity for the substrate is modified or the reaction rates are changed.

The terms "express" and "amplification" or "overexpression" describe in the context of the invention the production of or increase in intracellular activity of one or more enzymes encoded by the corresponding DNA in a microorganism. For this purpose, for example, it is possible to introduce a gene into an organism, to replace an existing gene by another gene, to increase the copy number of the gene or genes, to use a strong promoter or to use a gene which codes for a corresponding enzyme having a high activity, and these measures can be combined, where appropriate.

b) MetY Proteins of the Invention

The invention likewise includes "functional equivalents" of the specifically disclosed metY enzymes of organisms in the above list I.

Within the scope of the present invention, "functional equivalents" or analogs of the specifically disclosed polypeptides are polypeptides different therefrom, which furthermore have the desired biological activity such as, for example, substrate specificity.

According to the invention, "functional equivalents" means in particular mutants which have in at least one of the abovementioned sequence positions an amino acid other than the specifically mentioned amino acid, but which have nevertheless one of the abovementioned biological activities. "Functional equivalents" thus also include the mutants obtainable by one or more amino acid additions, substitutions, deletions and/or inversions, it being possible for said modifications to occur at any position in the sequence as long as they result in a mutant having the property profile of the invention. There is functional equivalence in particular also when the reaction patterns of mutant and unmodified polypeptide match qualitatively, i.e. identical substrates are converted with different rates, for example.

"Functional equivalents" naturally also comprise polypeptides which are obtainable from other organisms, and naturally occurring variants. For example, homologous sequence regions can be found by sequence comparison, and equivalent enzymes can be established following the specific guidelines of the invention.

"Functional equivalents" likewise comprise fragments, preferably individual domains or sequence motifs, of the polypeptides of the invention, which have the desired biological function, for example.

"Functional equivalents" are also fusion proteins which have one of the abovementioned polypeptide sequences or functional equivalents derived therefrom and at least one further heterologous sequence functionally different therefrom in functional N- or C-terminal linkage (i.e. with negligible functional impairment of the functions of the fusion protein parts). Nonlimiting examples of such heterologous sequences are, for example, signal peptides, enzymes, immunoglobulins, surface antigens, receptors or receptor ligands.

According to the invention, "functional equivalents" include homologs of the specifically disclosed proteins. These have at least 30%, or about 40%, 50%, preferably at least about 60%, 65%, 70%, or 75%, in particular at least 85%, such as, for example, 90%, 95% or 99%, homology to one of the specifically disclosed sequences, calculated by the algorithm of Pearson and Lipman, Proc. Natl. Acad., Sci. (USA) 85(8), 1988, 2444-2448.

Homologs of the proteins or polypeptides of the invention can be generated by mutagenesis, for example by point mutation or truncation of the protein. The term "homolog", as used herein, relates to a variant form of the protein, which acts as agonist or antagonist of the protein activity.

Homologs of the proteins of the invention can be identified by screening combinatorial libraries of mutants such as, for example, truncation mutants. It is possible, for example, to generate a variegated library of protein variants by combinatory mutagenesis at the nucleic acid level, for example by enzymatic ligation of a mixture of synthetic oligonucleotides. There is a multiplicity of methods which can be used for preparing libraries of potential homologs from a degenerate oligonucleotide sequence. Chemical synthesis of a degenerate gene sequence can be carried out in an automatic DNA synthesizer, and the synthetic gene can then be ligated into a suitable expression vector. The use of a degenerate set of genes makes it possible to provide whole sequences which encode the desired set of potential protein sequences in one mixture. Methods for synthesizing degenerate oligonucleotides are known to the skilled worker (for example, Narang, S. A., (1983) Tetrahedron 39:3; Itakura et al., (1984) Annu. Rev. Biochem. 53:323; Itakura et al., (1984) Science 198:1056; Ike et al., (1983) Nucleic Acids Res. 11:477).

In addition, libraries of fragments of the protein codon can be used to generate a variegated population of protein fragments for screening and for subsequent selection of homologs of a protein of the invention. In one embodiment, a library of coding sequence fragments can be generated by treating a double-stranded PCR fragment of a coding sequence with a nuclease under conditions under which nicking occurs only about once per molecule, denaturing the double-stranded DNA, renaturing the DNA to form double-stranded DNA which may comprise sense/antisense pairs of various nicked products, removing single-stranded sections from newly formed duplexes by treatment with S1 nuclease and ligating the resulting fragment library into an expression vector. It is possible by this method to devise an expression library which encodes N-terminal, C-terminal and internal fragments of the protein of the invention, which has different sizes.

Several techniques are known in the prior art for screening gene products from combinatorial libraries which have been produced by point mutations or truncation and for screening cDNA libraries for gene products with a selected property. These techniques can be adapted to rapid screening of gene libraries which have been generated by combinatorial mutagenesis of homologs of the invention. The most frequently used techniques for screening large gene libraries undergoing high-throughput analysis comprise the cloning of the gene library into replicable expression vectors, transformation of suitable cells with the resulting vector library and expression of the combinatorial genes under conditions under which detection of the desired activity facilitates isolation of the vector encoding the gene whose product has been detected. Recursive ensemble mutagenesis (REM), a technique which increases the frequency of functional mutants in the libraries, can be used in combination with the screening tests in order to identify homologs (Arkin und Yourvan (1992) PNAS 89:7811-7815; Delgrave et al. (1993) Protein Engineering 6(3):327-331 c) Polynucleotides of the Invention

The invention also relates to nucleic acid sequences (single- and double-stranded DNA and RNA sequences such as, for example cDNA and mRNA) coding for one of the above metY enzymes and the functional equivalents thereof which are obtainable, for example, also by use of artificial nucleotide analogs.

The invention relates both to isolated nucleic acid molecules which code for polypeptides or proteins of the invention or for biologically active sections thereof, and to nucleic acid fragments which can be used, for example, for use as hybridization probes or primers for identifying or amplifying coding nucleic acids of the invention.

Moreover, the nucleic acid molecules of the invention may contain untranslated sequences from the 3' and/or 5' ends of the coding region of the gene.

An "isolated" nucleic acid molecule is separated from other nucleic acid molecules which are present in the natural source of the nucleic acid and may moreover be essentially free of other cellular material or culture medium if it is prepared by recombinant techniques, or free of chemical precursors or other chemicals if it is chemically synthesized.

The invention furthermore comprises the nucleic acid molecules complementary to the specifically described nucleotide sequences or a section thereof.

The nucleotide sequences of the invention make it possible to generate probes and primers which can be used for identifying and/or cloning homologous sequences in other cell types and organisms. Such probes and primers usually complete a nucleotide sequence region which hybridizes under stringent conditions to at least about 12, preferably at least about 25, such as, for example 40, 50 or 75, consecutive nucleotides of a sense strand of a nucleic acid sequence of the invention or of a corresponding antisense strand.

Further nucleic acid sequences of the invention are derived from SEQ ID NO:1, 3, 5, 7, 9, 11, 13, 15, 17, 19, 21, 23, 25, 27, 29, 31, 33, 35, 37, 39, 41, 43, 45, 47, 49, 51 or 53 and differ therefrom through addition, substitution, insertion or deletion of one or more nucleotides, but still code for polypeptides having the desired profile of properties. These may be polynucleotides which are identical to above sequences in at least about 50%, 55%, 60%, 65%, 70%, 80% or 90%, preferably in at least about 95%, 96%, 97%, 98% or 99%, of the sequence positions.

The invention also includes those nucleic acid sequences which comprise "silent" mutations or are modified, by comparison with a specifically mentioned sequence, in accordance with the codon usage of a specific source or host organism, as well as naturally occurring variants such as, for example, splice variants or allelic variants. The invention likewise relates to sequences which are obtainable by conservative nucleotide substitutions (i.e. the relevant amino acid is replaced by an amino acid of the same charge, size, polarity and/or solubility).

The invention also relates to molecules derived from specifically disclosed nucleic acids through sequence polymorphisms. These genetic polymorphisms may exist because of the natural variation between individuals within a population. These natural variations usually result in a variance of from 1 to 5% in the nucleotide sequence of a gene.

The invention furthermore also comprises nucleic acid sequences which hybridize with or are complementary to the abovementioned coding sequences. These polynucleotides can be found on screening of genomic or cDNA libraries, and where appropriate, be amplified therefrom by means of PCR using suitable primers, and then, for example, be isolated with suitable probes. Another possibility is to transform suitable microorganisms with polynucleotides or vectors of the invention, multiply the microorganisms and thus the polynucleotides, and then isolate them. An additional possibility is to synthesize polynucleotides of the invention by chemical routes.

The property of being able to "hybridize" to polynucleotides means the ability of a polynucleotide or oligonucleotide to bind under stringent conditions to an almost complementary sequence, while there are no unspecific bindings between noncomplementary partners under these conditions. For this purpose, the sequences should be 70-100%, preferably 90-100%, complementary. The property of complementary sequences being able to bind specifically to one another is made use of, for example, in the Northern or Southern blot technique or in PCR or RT-PCR in the case of primer binding. Oligonucleotides with a length of 30 base pairs or more are usually employed for this purpose. Stringent conditions means, for example, in the Northern blot technique the use of a washing solution at 50-70° C., preferably 60-65° C., for example 0.1×SSC buffer with 0.1% SDS (20×SSC; 3M NaCl, 0.3M Na citrate, pH 7.0) for eluting nonspecifically hybridized cDNA probes or oligonucleotides. In this case, as mentioned above, only nucleic acids with a high degree of complementarity remain bound to one another. The setting up of stringent conditions is known to the skilled worker and is described, for example, in Ausubel et al., Current Protocols in Molecular Biology, John Wiley & Sons, N.Y. (1989), 6.3.1-6.3.6.

c) Isolation of the Coding MetY Gene

The metY genes coding for the enzyme O-acetylhomoserine sulfhydrolase can be isolated from the organisms of the above list I in a manner known per se.

In order to isolate the metY genes or else other genes of the organisms of the above list I, first a gene library of this organism is generated in *Escherichia coli* (*E. coli*). The generation of gene libraries is described in detail in generally known textbooks and manuals. Examples which may be mentioned are the textbook by Winnacker: Gene und Klone, Eine Einfuhrung in die Gentechnologie (Vertag Chemie, Weinheim, Germany, 1990), and the manual by Sambrook et al.: Molecular Cloning, A Laboratory Manual (Cold Spring Harbor Laboratory Press, 1989). A very well-known gene library is that of *E. coli* K-12 strain W3110, which was generated in λ vectors by Kohara et al. (Cell 50, 495-508 (1980).

In order to produce a gene library from organisms of list I in *E. coli*, cosmids such as the cosmid vector SuperCos I (Wahl et al., 1987, Proceedings of the National Academy of Sciences USA, 84: 2160-2164), or else plasmids such as pBR322 (BoliVal; Life Sciences, 25, 807-818 (1979)) or pUC9 (Vieira et al., 1982, Gene, 19: 259-268) can be used. Suitable hosts are in particular those *E. coli* strains which are restriction and recombination defective. An example of this is the strain DH5αmcr which has been described by Grant et al. (Proceedings of the National Academy of Sciences USA, 87 (1990) 4645-4649). The long DNA fragments cloned with the aid of cosmids may then in turn be subcloned into common vectors suitable for sequencing and subsequently be sequenced, as described, for example, in Sanger et al. (proceedings of the National Academy of Sciences of the United States of America, 74: 5463-5467, 1977).

The DNA sequences obtained can then be studied using known algorithms or sequence analysis programs such as, for example, those by Staden (Nucleic Acids Research 14, 217-232(1986)), by Marck (Nucleic Acids Research 16, 1829-1836 (1988)) or the GCG program by Butler (Methods of Biochemical Analysis 39, 74-97 (1998)).

The metY-encoding DNA sequences from organisms according to the above list I were found. In particular, DNA sequences according to SEQ ID NO:1, 3, 5, 7, 9, 11, 13, 15, 17, 19, 21, 23, 25, 27, 29, 31, 33, 35, 37, 39, 41, 43, 45, 47, 49, 51 and 53 were found. Furthermore, the amino acid sequences of the corresponding proteins were derived from said DNA sequences present, using the above-described methods. SEQ ID NO:2, 4, 6, 8, 10, 12, 14, 16, 18, 20, 22, 24, 26, 28, 30, 32, 34, 36, 38, 40, 42, 44, 46, 48, 50, 52 and 54 depict the resulting amino acid sequences of the metY gene products.

Coding DNA sequences which result from the sequences according to SEQ ID NO:1, 3, 5, 7, 9, 11, 13, 15, 17, 19, 21, 23, 25, 27, 29, 31, 33, 35, 37, 39, 41, 43, 45, 47, 49, 51 and 53 due to the degeneracy of the genetic code are likewise subject of the invention. In the same way, the invention relates to DNA sequences which hybridize with said sequences or parts of sequences derived therefrom.

Instructions for identifying DNA sequences by means of hybridization can be found by the skilled worker, inter alia, in the manual "The DIG System Users Guide fur Filter Hybridization" from Boehringer Mannheim GmbH (Mannheim, Germany, 1993) and in Liebl et al. (International Journal of Systematic Bacteriology (1991) 41: 255-260). Instructions for amplifying DNA sequences with the aid of the polymerase chain reaction (PCR) can be found by the skilled worker, inter alia, in the manual by Gait: Oligonucleotide synthesis: A Practical Approach (IRL Press, Oxford, UK, 1984) and in Newton and Graham: PCR (Spektrum Akademischer Verlag, Heidelberg, Germany, 1994).

It is furthermore known that changes at the N- and/or C-terminus of a protein do not substantially impair its function or may even stabilize said function. Information on this can be found by the skilled worker, inter alia, in Ben-Bassat et al. (Journal of Bacteriology 169: 751-757 (1987)), in O'Regan et al. (Gene 77: 237-251 (1989), in Sahin-Toth et al. (Protein Sciences 3: 240-247 (1994)), in Hochuli et al. (Biotechnology 6: 1321-1325 (1988)) and in known textbooks of genetics and molecular biology.

Amino acid sequences which result accordingly from SEQ ID NO:2, 4, 6, 8, 10, 12, 14, 16, 18, 20, 22, 24, 26, 28, 30, 32, 34, 36, 38, 40, 42, 44, 46, 48, 50, 52 and 54 are likewise part of the invention.

d) Host Cells Used According to the Invention

The invention further relates to microorganisms serving as host cells, in particular coryneform bacteria, which contain a vector, in particular a shuttle vector or plasmid vector, carrying at least one metY gene as defined by the invention or in which a metY gene of the invention is expressed or amplified.

These microorganisms can produce sulfur-containing fine chemicals, in particular L-methionine, from glucose, sucrose, lactose, fructose, maltose, molasses, starch, cellulose or from glycerol and ethanol. Said microorganisms are preferably coryneform bacteria, in particular of the genus *Corynebacterium*. Of the genus *Corynebacterium*, mention must be made in particular of the species *Corynebacterium glutamicum* which is known in the art for its ability to produce L-amino acids.

Examples of suitable strains of coryneform bacteria, which may be mentioned, are those of the genus *Corynebacterium*, in particular of the species *Corynebacterium glutamicum* (*C. glutamicum*), such as

*Corynebacterium glutamicum* ATCC 13032,
*Corynebacterium acetoglutamicum* ATCC 15806,
*Corynebacterium acetoacidophilum* ATCC 13870,
*Corynebacterium thermoaminogenes* FERM BP-1539,
*Corynebacterium melassecola* ATCC 17965 or
of the genus *Brevibacterium*, such as
*Brevibacterium flavum* ATCC 14067
*Brevibacterium lactofermentum* ATCC 13869 and
*Brevibacterium divaricatum* ATCC 14020;

Or strains derived therefrom such as
*Corynebacterium glutamicum* KFCC10065
*Corynebacterium glutamicum* ATCC21608
which likewise produce the desired fine chemical or the precursor(s) thereof.

The abbreviation KFCC means the Korean Federation of Culture Collection, the abbreviation ATCC means the American Type Strain Culture Collection, and the abbreviation FERM means the collection of the National Institute of Bioscience and Human Technology, Agency of Industrial Science and Technology, Japan.

e) Carrying out the Fermentation of the Invention

According to the invention, it was found that coryneform bacteria, after overexpression of a metY gene from organisms of the list I, produce sulfur-containing fine chemicals, in particular L-methionine, in an advantageous manner.

To achieve overexpression, the skilled worker can take different measures individually or in combination. Thus it is possible to increase the copy number of the appropriate genes or to mutate the promoter and regulatory region or the ribosomal binding site which is located upstream of the structural gene. Expression cassettes which are incorporated upstream of the structural gene act in the same way. Inducible promoters make it additionally possible to increase expression during the course of the fermentative L-methionine production. Expression is likewise improved by measures which extend the life span of the mRNA. Furthermore, the enzymic activity is likewise enhanced by preventing degradation of the enzyme protein. The genes or gene constructs may be either present in plasmids with varying copy number or integrated and amplified in the chromosome. A further possible alternative is to achieve overexpression of the relevant genes by changing the media composition and management of the culture. Instructions for this can be found by the skilled worker, inter alia, in Martin et al. (Biontechnology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in the European patent 0472869, in U.S. Pat. No. 4,601,893, in Schwarzer and Pühler (Biotechnology 9, 84-87 (1991), in Remscheid et al. (Applied and Environmental Microbiology 60, 126-132 (1994), in LaBarre et al. (Journal of Bacteriology 175, 1001-1007 (1993)), in the patent application WO 96/15246, in Malumbres et al. (Gene 134, 15-24 (1993)), in the Japanese published specification JP-A-10-229891, in Jensen und Hammer (Biotechnology and Bioengineering 58,191-195 (1998)), in Makrides (Microbiological Reviews 60: 512-538 (1996) and in known textbooks of genetics and molecular biology.

The invention therefore also relates to expression constructs comprising a nucleic acid sequence coding for a polypeptide of the invention under the genetic control of regulatory nucleic acid sequences; and to vectors comprising at least one of said expression constructs. Such constructs of the invention preferably include a promoter 5' upstream of the particular coding sequence and a terminator sequence 3' downstream and also, where appropriate, further regulatory elements, in each case operatively linked to the coding sequence. An "operative linkage" means the sequential arrangement of promoter, coding sequence, terminator and, where appropriate, further regulatory elements such that each of the regulatory elements can properly carry out its function in the expression of the coding sequence. Examples of operatively linkable sequences are activating sequences and enhancers and the like. Further regulatory elements include selectable markers, amplification signals, origins of replication and the like. Suitable regulatory sequences are described, for example in Goeddel, Gene Expression Technology: Methods in Enzymology 185, Academic Press, San Diego, Calif. (1990).

In addition to the artificial regulatory sequences, the natural regulatory sequence may still be present upstream of the actual structural gene. Genetic modification can, where appropriate, switch off this natural regulation and increase or decrease expression of the genes. However, the gene construct may also have a simpler design, i.e. no additional regulatory signals are inserted upstream of the structural gene and the natural promoter with its regulation is not removed. Instead, the natural regulatory sequence is mutated such that regulation no longer takes place and gene expression is increased or reduced. The gene construct may contain one or more copies of the nucleic acid sequences.

Examples of useful promoters are: ddh, amy, lysC, dapA, lysA from *Corynebacterium glutamicum* promoters, but also Gram-positive promoters SPO02, as are described in *Bacillus Subtilis* and Its Closest Relatives, Sonenshein, Abraham L., Hoch, James A., Losick, Richard; ASM Press, District of Columbia, Washington and Patek M. Eikmanns B J., Patek J., Sahm H., Microbiology. 142 1297-309, 1996 or else the cos, tac, trp, tet, trp-tet, Ipp, lac, lpp-lac, laclq, T7, T5, T3, gal, trc, ara, SP6, $\lambda$-PR and $\lambda$-PL promoters which are advantageously applied in Gram-negative bacteria. Preference is also give to using inducible promoters such as, for example light- and, in particular, temperature-inducible promoters such as the $P_rP_l$ promoter. It is in principle possible to use all natural promoters with their regulatory sequences. In addition, it is also possible to use advantageously synthetic promoters.

The regulatory sequences mentioned are intended to make specific expression of the nucleic acid sequences possible. Depending on the host organism, this may mean, for example, that the gene is expressed or overexpressed only after induction, or that it is immediately expressed and/or overexpressed.

In this connection, the regulatory sequences and factors may preferably have a beneficial effect on, and thus increase or decrease, expression. Thus, it is possible and advantageous to enhance the regulatory elements at the transcriptional level by using strong transcription signals such as promoters and/or enhancers. However, it is also possible besides this to enhance translation by, for example, improving the stability of the mRNA.

An expression cassette is prepared by fusing a suitable promoter, a suitable Shine-Dalgarno sequence, to a metY nucleotide sequence and a suitable termination signal. For this purpose, common recombination and cloning techniques are used, such as those described, for example, in Current Protocols in Molecular Biology, 1993, John Wiley & Sons, Incorporated, New York, New York, PCR Methods, Gelfand, David H., Innis, Michael A., Sninsky, John J., 1999, Academic Press, Incorporated, California, San Diego, PCR Cloning Protocols, Methods in Molecular Biology Ser., Vol. 192, 2nd ed., Humana Press, New Jersey, Totowa. T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman und L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is expressed in a suitable host organism by inserting it advantageously into a host-specific vector which makes optimal expression of the genes in the host possible. Vectors are well known to the skilled worker and can be found, for example, in "Cloning Vectors" (Pouwels P. H. et al., Hrsg, Elsevier, Amsterdam-New York-Oxford, 1985). The term "vectors" means, apart from plasmids, also all other vectors known to the skilled worker, such as, for example, phages, transposons, IS elements, plasmids, cosmids and linear or circular DNA. These vectors can replicate autonomously in the host organism or are replicated chromosomally.

MetY genes of the invention were amplified by overexpressing them by way of example with the aid of episomal plasmids. Suitable plasmids are those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107: 69-74 (1991)) are based on the cryptic plasmids pHM1519, pBL1 or pGA1. Other plasmid vectors such as, for example, pCLiK5MCS, or those based on pCG4 (U.S. Pat. No. 4,489,160) or pNG2 (Serwold-Davis et al., FEMS Microbiology Letters 66, 119-124 (1990)) or pAG1 (U.S. Pat. No. 5,158,891) may be used in the same way.

Suitable plasmid vectors are furthermore also those with the aid of which it is possible to apply the method of gene amplification by integration into the chromosome, as has been described, for example, by Remscheid et al. (Applied and Environmental Microbiology 60,126-132 (1994)) for the duplication and amplification of the hom-thrB operon. In this method, the complete gene is cloned into a plasmid vector which can replicate in a host (typically *E. coli*) but not in *C. glutamicum*. Suitable vectors are, for example, pSUP301 (Simon et al., Bio/Technology 1, 784-791 (1983)), pK18mob or pK19mob (Schafer et al., Gene 145, 69-73 (1994)), Bernard et al., Journal of Molecular Biology, 234: 534-541 (1993)), pEM1 (Schrumpf et al., 1991, Journal of Bacteriology 173: 4510-4516) or pBGS8 (Spratt et al., 1986, Gene 41: 337-342). The plasmid vector containing the gene to be amplified is then transferred into the desired *C. glutamicum* strain via transformation. Methods for transformation are described, for example, in Thierbach et al. (Applied Microbiology and Biotechnology 29, 356-362 (1988)), Dunican and Shivnan (Biotechnology 7, 1067-1070 (1989)) and Tauch et al. (FEMS Microbiological Letters 123, 343-347 (1994)).

The activity of enzymes can be influenced by mutations in the corresponding genes in such a way that the rate of the enzymic reaction is partly or completely reduced. Examples of such mutations are known to the skilled worker (Motoyama H., Yano H., Terasaki Y., Anazawa H., Applied & Environmental Microbiology. 67:3064-70, 2001, Eikmanns B J., Eggeling L., Sahm H., Antonie van Leeuwenhoek. 64:145-63, 1993-94.)

Additionally, it may be advantageous for the production of sulfur-containing fine chemicals, in particular L-methionine, to amplify, in addition to expression and amplification of a metY gene of the invention, one or more enzymes of the respective biosynthetic pathway, the cysteine pathway, of aspartate-semialdehyde synthesis, of glycolysis, of anaplerosis, of the pentose phosphate metabolism, the citrate acid cycle or the amino acid export.

Thus, one or more of the following genes can be amplified to produce sulfur-containing fine chemicals, in particular L-methionine:

the gene lysC, which encodes an aspartate kinase (EP 1 108 790 A2; DNA-SEQ NO. 281), the gene asd which encodes an aspartate-semialdehyde dehydrogenase (EP 1 108 790 A2; DNA-SEQ NO. 282), the glyceraldehyde-3-phosphate dehydrogenase-encoding gene gap (Eikmanns (1992), Journal of Bacteriology 174: 6076-6086), the 3-phosphoglycerate kinase-encoding gene pgk (Eikmanns (1992), Journal of Bacteriology 174: 6076-6086), the pyruvate carboxylase-encoding gene pyc (Eikmanns (1992), Journal of Bacteriology 174: 6076-6086), the triose phosphate isomerase-encoding gene tpi (Eikmanns (1992), Journal of Bacteriology 174: 6076-6086), the homoserine O-acetyltransferase-encoding gene metA (EP 1 108 790 A2; DNA-SEQ NO. 725), the cystathionine gamma-synthase-encoding gene metB (EP 1 108 790 A2; DNA-SEQ NO. 3491), the cystathionine gamma-lyase-encoding gene metC (EP 1 108 790 A2; DNA-SEQ NO. 3061), the serine hydroxymethyltransferase-encoding gene glyA (EP 1 108 790 A2; DNA-SEQ NO. 1110), the methionine synthase-encoding gene metH (EP 1 108 790 A2), the methylene tetrahydrofolate reductase-encoding gene metF (EP 1 108 790 A2; DNA-SEQ NO. 2379), the phosphoserine aminotransferase-encoding gene serC (EP 1 108 790 A2; DNA-SEQ NO. 928), a phosphoserine phosphatase-encoding gene serB (EP 1 108 790 A2; DNA-SEQ NO. 334, DNA-SEQ NO. 467, DNA-SEQ NO. 2767), the gene cysE, which encodes a serine acetyl transferase (EP 1 108 790 A2; DNA-SEQ NO. 2818), the gene hom, which encodes a homoserine dehydrogenase (EP 1 108 790 A2; DNA-SEQ NO. 1306)

Thus, it may be advantageous for the production of sulfur-containing fine chemicals, in particular L-methionine, in coryneform bacteria to mutate, at the same time, at least one of the genes below, so that the activity of the corresponding proteins, compared to that of unmutated proteins, is influenced by a metabolic metabolite to a lesser extent or not at all:

the gene lysC, which encodes an aspartate kinase (EP 1 108 790 A2; DNA-SEQ NO. 281), the pyruvate carboxylase-encoding gene pyc (Eikmanns (1992), Journal of Bacteriology 174: 6076-6086), the homoserine O-acetyltransferase-encoding gene metA (EP 1 108 790 A2; DNA-SEQ NO. 725), the cystathionine gamma-synthase-encoding gene metB (EP 1 108 790 A2; DNA-SEQ NO. 3491), the cystathionine gamma-lyase-encoding gene metC (EP 1 108 790 A2; DNA-SEQ NO. 3061), the serine hydroxymethyltransferase-encoding gene glyA (EP 1 108 790 A2; DNA-SEQ NO. 1110), the methionine synthase-encoding gene metH (EP 1 108 790 A2), the methylene tetrahydrofolate reductase-encoding gene metF (EP 1 108 790 A2; DNA-SEQ NO. 2379), the phosphoserine aminotransferase-encoding gene serC (EP 1 108 790 A2; DNA-SEQ NO. 928), a phosphoserine phosphatase-encoding gene serB (EP 1 108 790 A2; DNA-SEQ NO. 334, DNA-SEQ NO. 467, DNA-SEQ NO. 2767), the serine acetyl transferase-encoding gene cysE (EP 1 108 790 A2; DNA-SEQ NO. 2818), the gene hom, which encodes a homoserine dehydrogenase (EP 1 108 790 A2; DNA-SEQ NO. 1306)

It may be furthermore advantageous for the production of sulfur-containing fine chemicals, in particular L-methionine, in addition to expression and amplification of one of the metY genes of the invention, to attenuate one or more of the following genes, in particular to reduce expression thereof, or to switch them off:

the homoserine kinase-encoding gene thrB (EP 1 108 790 A2; DNA-SEQ NO. 3453), the threonine dehydratase-encoding gene ilvA (EP 1 108 790 A2; DNA-SEQ NO. 2328), the threonine synthase-encoding gene thrC (EP 1 108 790 A2; DNA-SEQ NO. 3486), the meso-diaminopimelate D-dehydrogenase-encoding gene ddh (EP 1 108 790 A2; DNA-SEQ NO. 3494), the phosphoenolpyruvate carboxykinase-encoding gene pck (EP 1 108 790 A2; DNA-SEQ NO. 3157), the glucose-6-phosphate 6-isomerase-encoding gene pgi (EP 1 108 790 A2; DNA-SEQ NO. 950), the pyruvate oxidase-encoding gene poxB (EP 1 108 790 A2; DNA-SEQ NO. 2873), the dihydrodipicolinate synthase-encoding gene dapA (EP 1 108 790 A2; DNA-SEQ NO. 3476), the dihydrodipicolinate reductase-encoding gene dapB (EP 1 108 790 A2; DNA-SEQ NO. 3477)

the diaminopicolinate decarboxylase-encoding gene lysA (EP 1 108 790 A2; DNA-SEQ NO. 3451)

It may be furthermore advantageous for the production of sulfur-containing fine chemicals, in particular L-methionine, in addition to expression and amplification of one of the metY genes of the invention in coryneform bacteria, to mutate, at the same time, at least one of the following genes in such a way that the enzymic activity of the corresponding protein is partly or completely reduced:

the homoserine kinase-encoding gene thrB (EP 1 108 790 A2; DNA-SEQ NO. 3453), the threonine dehydratase-encoding gene ilvA (EP 1 108 790 A2; DNA-SEQ NO. 2328), the threonine synthase-encoding gene thrC (EP 1 108 790 A2; DNA-SEQ NO. 3486), the meso-diaminopimelate D-dehydrogenase-encoding gene ddh (EP 1 108 790 A2; DNA-SEQ NO. 3494), the phosphoenolpyruvate carboxykinase-encoding gene pck (EP 1 108 790 A2; DNA-SEQ NO. 3157), the glucose-6-phosphate 6-isomerase-encoding gene pgi (EP 1 108 790 A2; DNA-SEQ NO. 950), the pyruvate oxidase-encoding gene poxB (EP 1 108 790 A2; DNA-SEQ NO. 2873), the dihydrodipicolinate synthase-encoding gene dapA (EP 1 108 790 A2; DNA-SEQ NO.3476), the dihydrodipicolinate reductase-encoding gene dapB (EP 1 108 790 A2; DNA-SEQ NO. 3477)

the diaminopicolinate decarboxylase-encoding gene lysA (EP 1 108 790 A2; DNA-SEQ NO. 3451)

It may be furthermore advantageous for the production of sulfur-containing fine chemicals, in particular L-methionine, apart from expression and amplification of a metY gene of the invention, to eliminate unwanted secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention may be cultured continuously or batchwise or in a fed batch or repeated fed batch process to produce sulfur-containing fine chemicals, in particular L-methionine. An overview of known cultivation methods can be found in the textbook by Chmiel (Bioprozeβtechnik 1. Einfuhrung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy the demands of the particular strains in a suitable manner. The textbook "Manual of Methods fur General Bacteriology" by the American Society for Bacteriology (Washington D.C., USA, 1981) contains descriptions of culture media for various microorganisms.

Said media which can be used according to the invention usually comprise one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch and cellulose. Sugars may also be added to the media via complex compounds such as molasses or other byproducts of sugar refining. It may also be advantageous to add mixtures of different carbon sources. Other possible carbon sources are oils and fats such as, for example, soybean oil, sunflower oil, peanut oil and coconut fat, fatty acids such as, for example, palmitic acid, stearic acid and linoleic acid, alcohols such as, for example, glycerol, methanol and ethanol and organic acids such as, for example acetic acid and lactic acid.

Nitrogen sources are usually organic or inorganic hydrogen compounds or materials containing said compounds. Examples of nitrogen sources include ammonia gas or ammonium salts such as ammonium sulfate, ammonium chloride, ammonium phosphate, ammonium carbonate and ammonium nitrate, nitrates, urea, amino acids and complex nitrogen sources such as cornsteep liquor, soybean flour, soybean protein, yeast extract, meat extract and others. The nitrogen sources may be used singly or as mixture.

Inorganic salt compounds which may be included in the media comprise the chloride, phosphorus or sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention usually also contain other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media heavily depends on the particular experiment and is decided upon individually for each specific case. Information on the optimization of media can be found in the textbook "Applied Microbiol. Physiology, A Practical Approach" (Editors. P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by sterile filtration. The components may be sterilized either together or, if required, separately. All media components may be present at the start of the cultivation or added continuously or batchwise, as desired.

The culture temperature is normally between 15° C. and 45° C., preferably at from 25° C. to 40° and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, air into the culture. The temperature of the culture is normally 20° C. to 45° C. The culture is continued until formation of the desired product is at a maximum. This aim is normally achieved within 10 to 160 hours.

The fermentation broths obtained in this way, in particular those containing L-methionine, usually contain a dry biomass of from 7.5 to 25% by weight.

An additional advantage is to carry out the fermentation under sugar limitation, at least at the end, but in particular over at least 30% of the fermentation period. This means that during this time the concentration of utilizable sugar in the fermentation medium is maintained at or reduced to ≧0 to 3 g/l.

The fermentation broth is then processed further. The biomass may, according to requirement, be removed completely or partially from the fermentation broth by separation methods such as, for example, centrifugation, filtration, decanting or a combination of these methods or be left completely in said broth.

Subsequently, the fermentation broth may be thickened or concentrated using known methods such as, for example, with the aid of a rotary evaporator, thin film evaporator, falling film evaporator, by reverse osmosis, or by nanofiltration. This concentrated fermentation broth can then be worked up by freeze drying, spray drying, spray granulation or by other methods.

However, it is also possible to further purify the sulfur-containing fine chemicals, in particular L-methionine. To this end, the product-containing broth, after removing the biomass, is subjected to a chromatography using a suitable resin, the desired product or the contaminations being retained completely or partially on the chromatographic resin. These chromatographic steps can be repeated, if necessary, using the same or different chromatographic resin. The skilled worker is familiar with the selection of suitable chromatographic resins and their most effective application. The purified product can be concentrated by filtration or ultrafiltration and stored at a temperature at which the stability of the product is greatest.

The identity and purity of the isolated compound(s) can be determined by techniques of the art. These include high performance liquid chromatography (HPLC), spectroscopic methods, staining methods, thin-layer chromatography, NIRS, enzyme assay or microbiological assays. These analytic methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ulmann's Encyclopedia of Industrial Chemistry (1996) Bd. A27, VCH: Weinheim, pp. 89-90, pp. 521-540, pp. 540-547, pp. 559-566, 575-581 and pp. 581-587; Michal, G., (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Volume 17.

Figure 2:
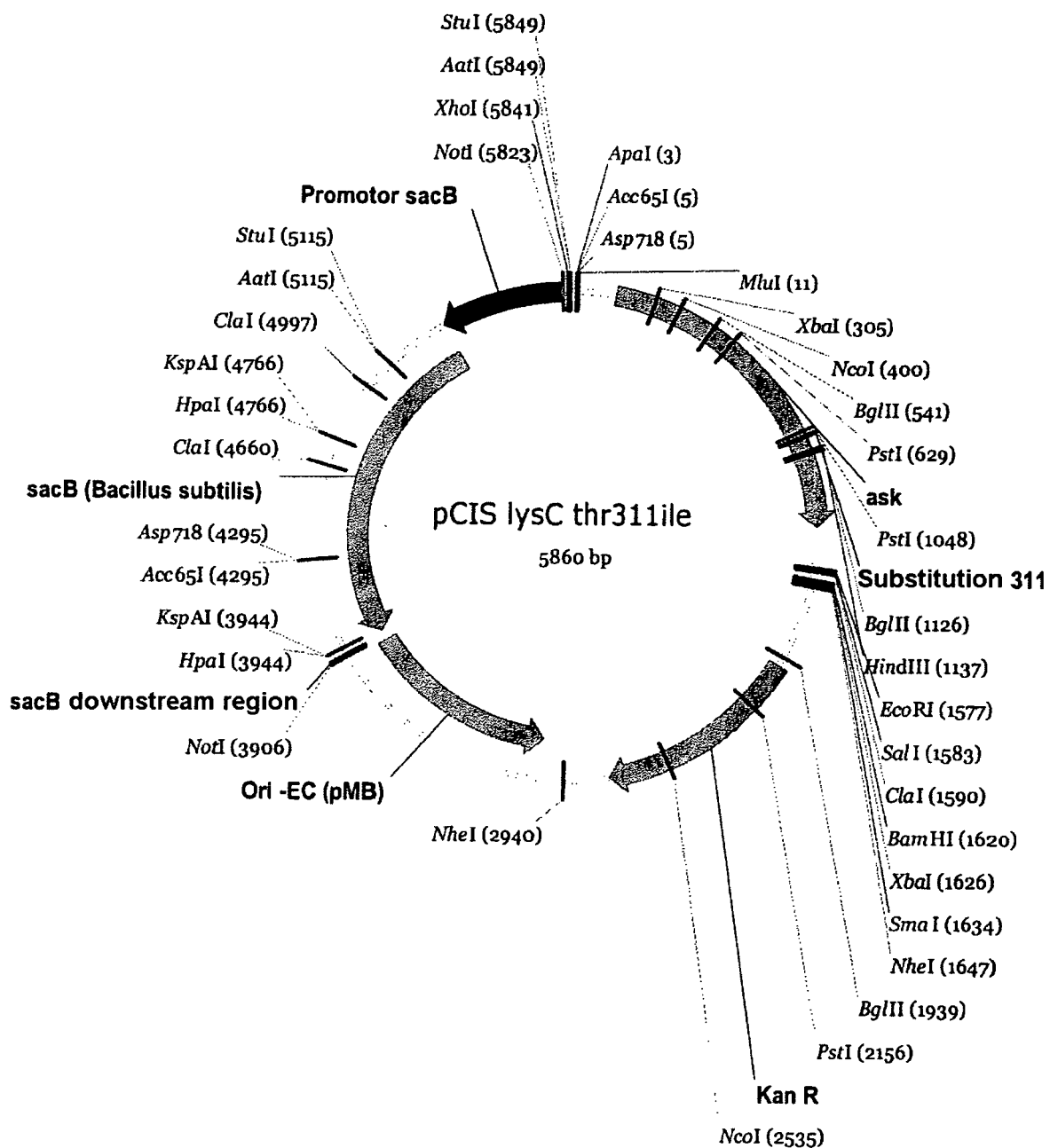
FIG. 2 shows the plasmid map for plasmid pCIS lysC thr311ile.
Figure 3:
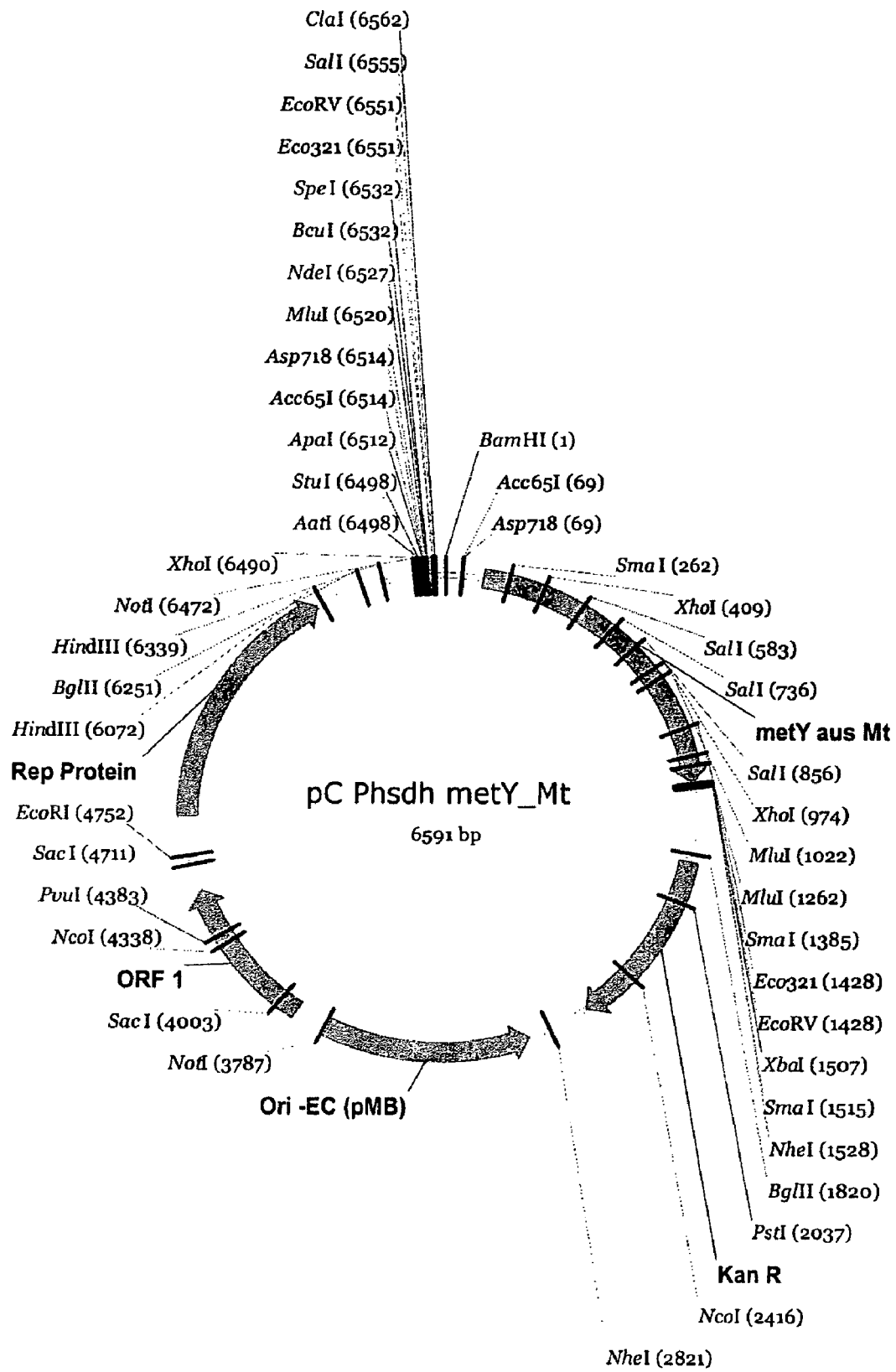
FIG. 3 shows the plasmid map for plasmid pG Phsdh metY_Mt (*Mycobacterium tuberculosis*).

The invention is now described in greater detail with reference to the following nonlimiting examples and with reference to the appended figures, in which FIG. 1 shows the plasmid map for plasmid pClysC;

FIG. 2 the plasmid map for plasmid pClSlysCthr311ile;

FIG. 3 the plasmid map for plasmid pCPhsdhmetY_Mt.

Restriction cleavage sites with the corresponding indication of their position in brackets are shown in the plasmid maps. Essential sequence segments are described in bold. KanR means kanamycin resistance gene; ask means aspartate kinase gene.

EXAMPLE 1

Construction of pCLiK5MCS

First, ampicillin resistance and origin of replication of the vector pBR322 were amplified using the oligonucleotides p1.3 (SEQ ID NO:55) and p2.3 (SEQ ID NO:56) with the aid of the polymerase chain reaction (PCR).

```
p1.3
                                              (SEQ ID NO:55)
5'-CCCGGGATCCGCTAGCGGCGCGCCGGCCGGCCCGGTGTGAAATACCG

CACAG-3' p2.3
                                              (SEQ ID NO:56)
5'-TCTAGACTCGAGCGGCCGCGGCCGGCCTTTAAATTGAAGACGAAAGG

GCCTCG-3'
```

In addition to sequences complementary to pBR322, the oligonucleotide p1.3 (SEQ ID NO:55) contains in 5'-3' direction the cleavage sites for the restriction nucleases SmaI, BamHI, NheI and AscI and the oligonucleotide p2.3 (SEQ ID NO:56) contains in 5'-3' direction the cleavage sites for the restriction endonucleases XbaI, XhoI, NotI and DraI. The PCR reaction was carried out according to a standard method such as that by Innis et al. (PCR Protocols. A Guide to Methods and Applications, Academic Press (1990)) using PfuTurbo polymerase (Stratagene, La Jolla, USA). The DNA fragment obtained of approximately 2.1 kb in size was purified using the GFX™PCR, DNA and gel band purification kit (Amersham Pharmacia, Freiburg) according to the manufacturer's instructions. The blunt ends of the DNA fragment were ligated to one another using the rapid DNA ligation kit (Roche Diagnostics, Mannheim) according to the manufacturer's instructions and the ligation mixture was transformed into competent E. coli XL-1Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto ampicillin (50 μg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK1.

Starting from plasmid pWLT1 (Liebl et al., 1992) as template for a PCR reaction, a kanamycin resistance cassette was amplified using the oligonucleotides neo1 (SEQ ID NO:57) and neo2 (SEQ ID NO:58).

neo1
(SEQ ID NO:57)
5'-GAGATCTAGACCCGGGGATCCGCTAGCGGGCTGCTAAAGGAAGCGGA-3':
neo2
(SEQ ID NO:58)
5'-GAGAGGCGCGCCGCTAGCGTGGGCGAAGAACTCCAGCA-3':

Apart from the sequences complementary to pWLT1, the oligonucleotide neo1 contains in 5'-3' direction the cleavage sites for the restriction endonucleases XbaI, SmaI, BamHI, NheI and the oligonucleotide neo2 (SEQ ID NO:58) contains in 5'-3' direction the cleavage sites for the restriction endonucleases AscI and NheI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained was approximately 1.3 kb in size was purified using the GFX™PCR, DNA and gel band purification kit (Amersham Pharmacia, Freiburg) according to the manufacturer's instructions. The DNA fragment was cleaved with restriction endonucleases XbaI and AscI (New England Biolabs, Beverly, USA) and, following that, again purified using the GFX™PCR, DNA and gel band purification kit (Amersham Pharmacia, Freiburg) according to the manufacturer's instructions. The vector pCLiK1 was likewise cleaved with the restriction endonucleases XbaI and AscI and dephosphorylated using alkaline phosphatase (Roche Diagnostics, Mannheim) according to the manufacturer's instructions. After electrophoresis in a 0.8% strength agarose gel, the linearized vector (approx. 2.1 kb) was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent E. coli XL-1Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto ampicillin (50 µg/ml)- and kanamycin (20 µg/ml)-containing LB agar (Lennox, 1955, Virology, 1: 190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK2.

The vector pCLiK2 was cleaved with the restriction endonuclease DraI (New England Biolabs, Beverly, USA). After electrophoresis in 0.8% strength agarose gel, an approx. 2.3 kb vector fragment was isolated using the GFX™PCR, DNA and gel band purification kit (Amersham Pharmacia, Freiburg) according to the manufacturer's instructions. This vector fragment was religated with the aid of the rapid DNA ligation kit (Roche Diagnostics, Mannheim) according to the manufacturer's instructions and the ligation mixture was transformed into competent E. coli XL-1Blue (Stratagene, La Jolla, USA) according to standard methods, as described in Sambrook et al. (Molecular Cloning. A Laboratory Manual, Cold Spring Harbor, (1989)).

Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK3.

Starting from plasmid pWLQ2 (Liebl et al., 1992) as template for a PCR reaction, the origin of replication pHM1519 was amplified using the oligonucleotides cg1 (SEQ ID NO:59) and cg2 (SEQ ID NO:60).

cg1
(SEQ ID NO:59)
5'-GAGAGGGCGGCCGCGCAAAGTCCCGCTTCGTGAA-3':

cg2
(SEQ ID NO:60)
5'-GAGAGGGCGGCCGCTCAAGTCGGTCAAGCCACGC-3':

Apart from the sequences complementary to pWLQ2, the oligonucleotides cg1 (SEQ ID NO:59) and cg2 (SEQ ID NO:60) contain cleavage sites for the restriction endonuclease NotI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained was approximately 2.7 kb in size and was purified using the GFX™PCR, DNA and gel band purification kit (Amersham Pharmacia, Freiburg) according to the manufacturer's instructions. The DNA fragment was cleaved with restriction endonuclease NotI (New England Biolabs, Beverly, USA) and, following that, again purified using the GFX™PCR, DNA and gel band purification kit (Amersham Pharmacia, Freiburg) according to the manufacturer's instructions. The vector pCLiK3 was likewise cleaved with the restriction endonuclease NotI and dephosphorylated using alkaline phosphatase (Roche Diagnostics, Mannheim) according to the manufacturer's instructions. After electrophoresis in a 0.8% strength agarose gel, the linearized vector (approx. 2.3 kb) was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent E. coli XL-1Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5.

PCLik5 was extended by a multiple cloning site (MCS) by combining the two synthetic essentially complementary oligonucleotides HS445 ((SEQ ID NO:61) and HS446 (SEQ ID NO:62)) which contain cleavage sites for the restriction endonucleases SwaI, XhoI, AatI, ApaI, Asp718, MluI, NdeI, SpeI, EcoRV, SalI, ClaI, BamHI, XbaI and SmaI to give a double-stranded DNA fragment by heating them together to 95° C. followed by slow cooling.

HS445
(SEQ ID NO:61)
5'-TCGAATTTAAATCTCGAGAGGCCTGACGTCGGGCCCGGTACCACGCG

TCATATGACTAGTTCGGACCTAGGGATATCGTCGACATCGATGCTCTTCT

GCGTTAATTAACAATTGGGATCCTCTAGACCCGGGATTTAAAT-3':

HS446
(SEQ ID NO:62)
5'-GATCATTTAAATCCCGGGTCTAGAGGATCCCAATTGTTAATTAACGC

AGAAGAGCATCGATGTCGACGATATCCCTAGGTCCGAACTAGTCATATGA

CGCGTGGTACCGGGCCCGACGTCAGGCCTCTCGAGATTTAAAT-3'

The vector pCLiK5 was cleaved with the restriction endonucleases XhoI and BamHI (New England Biolabs, Beverly, USA) and dephosphorylated using alkaline phosphatase (I (Roche Diagnostics, Mannheim)) according to the manufacturer's instructions. After electrophoresis in a 0.8% strength agarose gel, the linearized vector (approx. 5.0 kb) was isolated using the GFX™PCR, DNA and gel band purification kit (Amersham Pharmacia, Freiburg) according to the manufacturer's instructions. This vector fragment was ligated with the synthetic double-stranded DNA fragment with the aid of the rapid DNA ligation kit (Roche Diagnostics, Mannheim) according to the manufacturer's instructions and the ligation mixture was transformed into competent E. coli XL-1Blue (Stratagene, La Jolla, USA) according to standard methods as described Sambrook et al. (Molecular Cloning. A Laboratory Manual, Cold Spring Harbor (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturers instructions and checked by restriction digests. The plasmid obtained in this way is denoted pCLiK5MCS.

Sequencing reactions were carried out according to Sanger et al. (1977) Proceedings of the National Academy of Sciences USA 74:5463-5467. The sequencing reactions were fractionated and analyzed by means of ABI Prism 377 (PE Applied Biosystems, Weiterstadt).

The resultant plasmid pCLiK5MCS is listed as SEQ ID NO: 65.

EXAMPLE 2

Construction of pCLiK5MCS Integrativ SacB

Starting from the plasmid pK19mob (Schäfer et al., Gene 145,69-73(1994)) as template for a PCR reaction, the *Bacillus subtilis* sacB gene (coding for levan sucrase) was amplified using the oligonucleotides BK1732 and BK1733.

BK1732
(SEQ ID NO:63)
5'-GAGAGCGGCCGCCGATCCTTTTTAACCCATCAC-3':

BK1733
(SEQ ID NO:64)
5'-AGGAGCGGCCGCCATCGGCATTTTCTTTTGCG-3':

Apart from the sequences complementary to pEK19mobsac, the oligonucleotides BK1732 and BK1733 contain cleavage sites for the restriction endonuclease NotI. The PCR reaction was carried out using PfuTurbo polymerase (Stratagene, La Jolla, USA) using a standard method like that of Innis et al. (PCR Protocols. A Guide to Methods and Applications, Academic Press (1990)). The DNA fragment obtained of approximately 1.9 kb in size was purified using the GFX™PCR, DNA and gel band purification kit (Amersham Pharmacia, Freiburg) according to the manufacturer's instructions. The DNA fragment was cleaved with the restriction endonuclease NotI (New England Biolabs, Beverly, USA) and, following that, again purified using the GFX™PCR, DNA and gel band purification kit (Amersham Pharmacia, Freiburg) according to the manufacturer's instructions.

The vector pCLiK5MCS (prepared according to example 1) was likewise cleaved with the restriction endonuclease NotI and dephosphorylated using alkali phosphatase (I (Roche Diagnostics, Mannheim)) according to the manufacturer's instructions. After electrophoresis in a 0.8% strength agarose gel, an approximately 2.4 kb in size vector fragment was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent E. coli XL-1Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5MCS integrativ sacB.

Sequencing reactions were carried out according to Sanger et al. (1977) Proceedings of the National Academy of Sciences USA 74:5463-5467. The sequencing reactions were fractionated and analyzed by means of ABI Prism 377 (PE Applied Biosystems, Weiterstadt).

The resultant plasmid pCLiK5MCS integrativ sacB is listed as SEQ ID NO: 66.

It is possible to prepare in an analog manner further vectors which are suitable for the inventive expression or overproduction of metY genes.

EXAMPLE 3

Isolation of the lysC Gene from the *C. glutamicum* Strain LU1479

In the first step of the strain construction, it is intended to carry out an allelic substitution of the lysC wild-type gene encoding the enzyme aspartate kinase in *C. glutamicum* ATCC13032, hereinbelow referred to as LU1479. It is intended to carry out a nucleotide substitution in the LysC gene so that the amino acid Ile is substituted for the amino acid Thr at position 311 in the resulting protein.

Starting from the chromosomal DNA of LU1479 as template for a PCR reaction, an amplification was carried out with the oligonucleotide primers SEQ ID NO:67 and SEQ ID NO:68 lysC with the aid of the Pfu-Turbo PCR system (Stratagene USA) following the manufacture's instructions. Chromosomal DNA from *C. glutamicum* ATCC 13032 was prepared as described by Tauch et al. (1995) Plasmid 33:168-179 or Eikmanns et al. (1994)

Microbiology 140:1817-1828. The amplified fragment is flanked at its 5' end by a SalI restriction cleavage and at its 3' end by an MluI restriction cleavage. Prior to the cloning step, the amplified fragment was restricted by these two restriction enzymes and purified using GFX™PCR, DNA and gel band purification kit (Amersham Pharmacia, Freiburg).

SEQ ID NO:67
5'-GAGAGAGAGACGCGTCCCAGTGGCTGAGACGCATC-3'

SEQ ID NO:68
5'-CTCTCTCTGTCGACGAATTCAATCTTACGGCCTG-3'

The resulting polynucleotide was cloned into pCLIK5 MCS integrativ SacB (hereinbelow referred to as pCIS; SEQ ID NO: 66 of Example 2) via the SalI and MluI restriction cleavages and transformed into E. coli XL-1 blue. A selection for plasmid-bearing cells was achieved by plating onto kanamycin (20 µg/ml)-containing LB agar (Lennox, 1955, Virology, 1:190). The plasmid was isolated and the expected nucleotide sequence was verified by sequencing. The plasmid DNA preparation was carried out by methods of, and using material from, Quiagen. Sequencing reactions were carried out as described by Sanger et al. (1977) Proceedings of the National Academy of Sciences USA 74:5463-5467. The sequencing reactions were separated by means of ABI Prism 377 (PE Applied Biosystems, Weiterstadt) and evaluated. The resulting plasmid pCIS lysC is shown as SEQ ID NO:69. The corresponding plasmid map is shown in FIG. 1.

The sequence SEQ ID NO:69 encompasses the following essential part-regions:

| LOCUS | pCIS\lysC 5860 bp DNA circular |
|---|---|
| FEATURES | Location/Qualifiers |
| CDS[1] | 155 . . . 1420 |
| | /vntifkey = "4" |
| | /label = lysC |
| CDS | complement[2](3935 . . . 5356) |
| | /vntifkey = "4" |
| | /label = sacB\(Bacillus\subtilis) |
| promoter | complement(5357 . . . 5819) |
| | /vntifkey = "30" |
| | /label = Promotor\sacB |
| C_region | complement(3913 . . . 3934) |
| | /vntifkey = "2" |
| | /label = sacB\downstream region |
| CDS | 1974 . . . 2765 |
| | /vntifkey = "4" |
| | /label = Kan\R |
| CDS | complement(3032 . . . 3892) |
| | /vntifkey = "4" |
| | /label = Ori\-EC\(pMB) |

[1]coding sequence
[2]on the complementary strand

EXAMPLE 4

Mutagenesis of the C. glutamicum LysC Gene

The site-directed mutagenesis of the C. glutamicum lysC gene (Example 3) was carried out with the QuickChange Kit (Stratagene/USA) following the manufacturer's instructions. The mutagenesis was carried out in the plasmid pCIS lysC, SEQ ID NO:69. The following oligonucleotide primers were synthesized for the substitution of thr311 for 311ile with the aid of the Quickchange method (Stratagene):

SEQ ID NO:70
5'-CGGCACCACCGACATCATCTTCACCTGCCCTCGTTCCG-3'

SEQ ID NO:71
5'-CGGAACGAGGGCAGGTGAAGATGATGTCGGTGGTGCCG-3'

The use of these oligonucleotide primers in the Quickchange reaction brings about a substitution of the nucleotide in position 932 (T for C) in the lysC gene (cf. SEQ ID NO:72) and an amino acid substitution in position 311 (Thr→Ile) (cf. SEQ ID NO:73) in the corresponding enzyme. The resulting amino acid substitution Thr311Ile in the lysC gene was confirmed by sequencing following transformation into E. coli XL1-blue and plasmid preparation. The plasmid was named pCIS lysC thr311ile and is listed as SEQ ID NO:74. The corresponding plasmid map is shown in FIG. 2.

The sequence SEQ ID NO:74 encompasses the following essential part-regions:

| LOCUS | pCIS\lysC\thr311ile 5860 bp DNA circular |
|---|---|
| FEATURES | Location/Qualifiers |
| CDS[1] | 155 . . . 1420 |
| | /vntifkey = "4" |
| | /label = lysC |
| CDS | complement[2](3935 . . . 5356) |
| | /vntifkey = "4" |
| | /label = sacB\(Bacillus\subtilis) |
| promoter | complement(5357 . . . 5819) |
| | /vntifkey = "30" |
| | /label = Promotor\sacB |
| C_region | complement(3913 . . . 3934) |
| | /vntifkey = "2" |
| | /label = sacB\downstream region |
| CDS | 1974 . . . 2765 |
| | /vntifkey = "4" |
| | /label = Kan\R |
| CDS | complement(3032 . . . 3892) |
| | /vntifkey = "4" |
| | /label = Ori\-EC\(pMB) |

[1]coding sequence
[2]on the complementary strand

The plasmid pCIS lysC thr311ile was transformed into C. glutamicum LU1479 by means of electroporation as described by Liebl, et al. (1989) FEMS Microbiology Letters 53:299-303. Modifications of the protocol are described in DE-A-10046870. The chromosomal arrangement of the lysC locus of individual transformants was verified using standard methods by means of Southern blotting and hybridization as described in Sambrook et al. (1989), Molecular Cloning. A Laboratory Manual, Cold Spring Harbor. It was thus ensured that the transformants were transformants which have the transformed plasmid integrated at the lysC locus by homologous recombination. After such colonies were grown overnight in media without antibiotic, the cells were plated onto a sucrose CM agar medium (10% sucrose) and incubated for 24 hours at 30° C.

Since the sacB gene which is present in the vector pCIS lysC thr311ile converts sucrose into a toxic product, only those colonies are capable of growing which have the sacB gene deleted between the wild-type lysC gene and the mutated gene lysC thr311ile by a second homologous recombination step. During the homologous recombination, either the wild-type gene or the mutated gene can be deleted together with the sacB gene. If the sacB gene is removed together with the wild-type gene, the result is a mutated transformant.

Growing colonies were picked and examined for a kanamycin-sensitive phenotype. Clones with deleted SacB gene must simultaneously show kanamycin-sensitive growth behavior. Such Kan-sensitive clones were examined for their lysine productivity in a shaker flask (see Example 6). For comparison, the untreated strain LU1479 was cultured. Clones whose lysine production was increased in comparison with the control were selected, chromosomal DNA was obtained, and the corresponding region of the lysC gene was amplified by a PCR reaction and sequenced. Such a clone with the characteristic of an increased lysine synthesis and a confirmed mutation in lysC at position 932 was termed LU1479 lysC 311 ile).

EXAMPLE 5

Generation of Ethionine-resistant *C. Glutamicum* Strains

In the second step of the strain construction, the resulting strain LU1479 lysC 311ile (Example 4) was treated in order to induce ethionine resistance (Kase, H. Nakayama K. Agr. Biol. Chem. 39 153-106 1975 L-methionine production by methionine analog-resistant mutants of *Corynebacterium glutamicum*). An overnight culture in BHI medium (Difco) was washed in citrate buffer (50 mM pH 5.5) and treated for 20 minutes at 30° C. with N-methylnitrosoguanidine (10 mg/ml in 50 mM citrate pH5.5). After treatment with the chemical mutagen N-methyl-nitrosoguanidine, nitrosoguanidine ,the cells were washed (citrate buffer 50 mM pH 5.5) and plated onto a medium composed of the following components, based on 500 ml: 10 g $(NH_4)_2SO_4$, 0.5 g $KH_2PO_4$, 0.5 g $K_2HPO_4$, 0.125 g $MgSO_4.7H_2O$, 21 g MOPS, 50 mg $CaCl_2$, 15 mg proteocatechuate, 0.5 mg biotin, 1 mg thiamine, 5 g/l D,L-ethionine (Sigma Chemicals Deutschland), pH 7.0. The medium additionally comprised 0.5 ml of a microsalt solution of: 10 g/l $FeSO_4.7H_2O$, 1 g/l $MnSO_4*H_2O$, 0.1 g/l $ZnSO_4*7H_2O$, 0.02 g/l $CuSO_4$, 0.002 g/l $NiCl_2*6H_2O$. All salts were dissolved in 0.1M HCl. The finished medium was filter-sterilized and, after addition of 40 ml sterile 50% glucose solution, treated with liquid sterile agar in a final concentration of 1.5% agar and poured into culture dishes.

Mutagen-treated cells were placed onto plates containing the above-described medium and incubated for 3-7 days at 30° C. Resulting clones were isolated, isolated individually at least once on the selection medium and then examined for their methionine productivity in medium II in a shake flask (see Example 6).

EXAMPLE 6

Methionine Production with Strain LU1479 LysC311ile ET-16

The strains produced in Example 5 were grown for 2 days at 30° C. on an agar plate with CM medium.
CM agar:
10.0 g/l D-glucose, 2.5 g/l NaCl, 2.0 g/l urea, 10.0 g/l Bacto peptone (Difco), 5.0 g/l yeast extract (Difco), 5.0 g/l beef extract (Difco), 22.0 g/l agar (Difco), autoclaved (20 min., 121° C.)

The cells were subsequently scraped off the plate and resuspended in saline. For the main culture, 10 ml of medium II and 0.5 g autoclaved $CaCO_3$ (Riedel de Haen) in a 100 ml Erlenmeyer flask were inoculated with the cell suspension until an OD600 nm of 1.5 was reached and incubated for 72 hours at 30° C. on an orbital shaker at 200 rpm.

Medium II:

| | |
|---|---|
| 40 g/l | Sucrose |
| 60 g/l | Molasses (based on 100% sugar content) |
| 10 g/l | $(NH_4)_2SO_4$ |
| 0.4 g/l | $MgSO_4*7H_2O$ |
| 0.6 g/l | $KH_2PO_4$ |
| 0.3 mg/l | Thiamine*HCl |
| 1 mg/l | Biotin (from a 1 mg/ml filter-sterilized stock solution which had been brought to pH 8.0 with $NH_4OH$) |
| 2 mg/l | $FeSO_4$ |
| 2 mg/l | $MnSO_4$ | brought to pH 7.8 with $NH_4OH$, autoclaved (121° C., 20 min). In addition, vitamin B12 (hydroxycobalamine Sigma Chemicals) from a stock solution (200 µg/ml, filter-sterilized) was added to a final concentration of 100 µg/l.

The methionine formed, and other amino acids in the culture broth, were [lacuna] with the aid of the amino acid determination method from Agilent using a Agilent 1100 Series LC System HPLC. Derivatization before the column separation with ortho-phthalaldehyde enabled the quantification of the amino acids formed. The amino acid mixture was separated on a Hypersil AA column (Agilent).

Those clones whose methionine productivity was at least twice as high as that of the original strain LU1479 lysC 311ile were isolated. Such a clone was employed for the further experiments and was named LU1479 lysC 311ile ET-16.

EXAMPLE 7

Cloning MetY from *Mycobacterium tuberculosis* and Cloning into the Plasmid pC Phsdh MetY_Mt Chromosomal DNA of *Mycobacterium tuberculosis* was obtained from the American Type Strain Culture Collection (ATCC, Atlanta-USA) from strain ATCC 25584. Chromosomal DNA from *C. glutamicum* ATCC 13032 was prepared by the method described by Tauch et al. (1995) Plasmid 33:168-179 or Eikmanns et al. (1994) Microbiology 140:1817-1828.

Using the oligonucleotide primers SEQ ID NO:75 and SEQ ID NO:76, the chromosomal DNA from *C. glutamicum* as template and Pfu Turbo polymerase (Stratagene), an approx. 180 base pair DNA fragment was amplified from the noncoding 5' region (promoter region) of homoserine dehydrogenase (HsDH) with the aid of the polymerase chain reaction (PCR) following standard methods, such as Innis et al. (1990) PCR Protocols. A Guide to Methods and Applications, Academic Press. The amplified fragment is flanked at its 5' end by a BamHI restriction cleavage site and at its 3' end by a region which is homologous to metY from *Mycobacterum tuberculosis* and has been introduced via the oligo.

SEQ ID NO:75
5'-GAGAGGATCCGGAAGGTGAATCGAATTTCGG-3'
and

SEQ ID NO:76
5'-CTATTGCTGTCGGCGCTCATGATTCTCCAAAAATAATCGC-3'

The resulting DNA fragment was purified using the GFX™PCR, DNA and gel band purification kit (Amersham Pharmacia, Freiburg) following the manufacturer's instructions.

Starting from the chromosomal DNA from *Mycobacterium tuberculosis* as template for a PCR reaction, metY was amplified with the aid of the GC-rich PCR system (Roche Diagnostics, Mannheim) following the manufacturer's instructions, using the oligonucleotide primers SEQ ID NO:77 and SEQ ID NO:78. The amplified fragment is flanked at its 3' end by an XbaI restriction cleavage site which has been introduced via the oligo.

SEQ ID NO:77
5'-ATGAGCGCCGACAGCAATAG-3'
and

SEQ ID NO:78
5'-GAACTCTAGATCAGAACGCCGCCACGGAC-3'

The approximately 1.4 kb DNA fragment which was obtained was purified with the GFX™PCR, DNA and gel band purification kit (Amersham Pharmacia, Freiburg) following the manufacturer's instructions.

In a further PCR reaction, the two fragments obtained above were employed jointly as template. Owing to the regions which are homologous to the metY fragment and which have been introduced with the oligonucleotide primer SEQ ID NO:76, the two fragments anneal with one another during the PCR reaction and are elongated to a continuous DNA strand by the polymerase employed. The standard method was modified inasfar as the oligonucleotide primers used, SEQ ID NO:75 and SEQ ID NO:78, were only added to the reaction at the beginning of the 2nd cycle.

The amplified DNA fragment, which was approximately 1.6 kb in size, was purified with the GFX™PCR, DNA and gel band purification kit following the manufacturer's instructions. Thereafter, it was cleaved with the restriction enzymes BamHI and XbaI (Roche Diagnostics, Mannheim) and separated by gel electrophoresis. The approximately 1.6 kb DNA fragment was subsequently isolated from the agarose using the GFX™PCR, DNA and gel band purification kit (Amersham Pharmacia, Freiburg).

The vector pClik5MCS SEQ ID NO:65, hereinbelow referred to as pC, was cleaved with the restriction enzymes BamHI and XbaI (Roche Diagnostics, Mannheim), and, after separation by electrophoresis, a 5 kb fragment was isolated with the GFX™PCR, DNA and gel band purification kit.

The vector fragment together with the cleaved and isolated PCR fragment were ligated with the aid of the Rapid DNA ligation kit (Roche Diagnostics, Mannheim) following the manufacturer's instructions and the ligation reaction was transformed into competent *E. coli* XL-1Blue (Stratagene, La Jolla, USA) by standard methods as described in Sambrook et al. (Molecular Cloning. A Laboratory Manual, Cold Spring Harbor, (1989)). Selection for plasmid-bearing cells was achieved by plating on kanamycin (20 µg/ml)—containing LB agar (Lennox, 1955, Virology, 1:190).

The plasmid DNA preparation was carried out by methods of, and using materials from, Quiagen. Sequencing reactions were carried out as described by Sanger et al. (1977) Proceedings of the National Academy of Sciences USA 74:5463-5467. The sequencing reactions were separated and evaluated by means of ABI Prism 377 (PE Applied Biosystems, Weiterstadt).

The resulting plasmid pC Phsdh metY_Mt (*Mycobacterium tuberculosis*) is listed as SEQ ID NO:79. The corresponding plasmid map is shown in FIG. 3.

The sequence SEQ ID NO:79 encompasses the following essential part-regions:

| LOCUS | pC\Phsdh\metY_Mt 6591 bp DNA circular 21-JUL-2003 |
|---|---|
| FEATURES | Location/Qualifiers |
| CDS | 156 . . . 1505 |
| | /vntifkey = "4" |
| | /label = metY\aus\M\*tuberculosis* |
| CDS | 1855 . . . 2646 |
| | /vntifkey = "4" |
| | /label = Kan\R |
| CDS | 4927 . . . 6048 |
| | /vntifkey = "4" |
| | /label = Rep\Protein |
| CDS | 3919 . . . 4593 |
| | /vntifkey = "4" |
| | /label = ORF\1 |
| CDS | complement(2913 . . . 3773) |
| | /vntifkey = "4" |
| | /label = Ori\-EC\(pMB) |

EXAMPLE 8

Transformation of the Strain LU1479 LysC 311ile ET-16 With the Plasmid pC Phsdh MetY_Mt The strain LU1479 lysC 311ile ET-16 was transformed with the plasmid pC Phsdh metY_Mt by the above-described method (Liebl, et al. (1989) FEMS Microbiology Letters 53:299-303). The transformation mixture was plated onto CM plates which additionally comprised 20 mg/l kanamycin in order to achieve a selection for plasmid-containing cells. Resulting kanamycin-resistant clones were picked and isolated individually. The methionine productivity of the clones was examined in a shake-flask experiment (see Example 6). The strain LU1479 lysC 311ile ET-16 pC Phsdh metY_Mt produced significantly more methionine in comparison with LU1479 lysC 311ile ET-16.

We claim:

1. A method for the fermentative production of L-methionine, which comprises the following steps:
   a) fermenting in a medium cells of a coryneform *bacterium* for producing L-methionine, the coryneform bacteria expressing at least one heterologous nucleotide sequence which codes for a protein with O-acetylhomoserine sulfhydrolase (metY) activity, wherein the heterologous nucleotide sequence comprises a nucleotide sequence encoding a metY protein having an amino acid sequence as set forth in SEQ ID NO: 4 or comprises a nucleotide sequence encoding a metY protein having an amino acid sequence with 95% homology or more to the sequence as set forth in SEQ ID NO: 4;
   b) concentrating L-methionine in the medium or in the bacterial cells, and
   c) isolating L-methionine.

2. The method as claimed in claim 1, wherein the metY-encoding nucleotide sequence comprises a coding sequence as set forth in SEQ ID NO: 3.

3. The method as claimed in claim 1, wherein the metY-encoding sequence codes for a protein with metY activity, the protein comprising an amino acid sequence as set forth in SEQ ID NO: 4.

4. The method as claimed in claim 1, wherein the coding metY sequence is a DNA or RNA which can be replicated in *coryneform bacteria* or is stably integrated into the chromosome.

5. The method as claimed in claim 4, wherein the bacteria is
   a) a bacteria strain transformed with a plasmid vector carrying at least one copy of the coding metY sequence under the control of regulatory sequences, or
   b) a strain in which the coding metY sequence has been integrated into the bacteria chromosome.

6. The method as claimed in claim 1, wherein the coding metY sequence is overexpressed.

7. The method as claimed in claim 1, wherein the bacteria are fermented in which additionally at least one further gene of the biosynthetic pathway of L-metlaionine has been overexpressed.

8. The method as claimed in claim 1, wherein the coryneform bacteria are fermented in which, at the same time, at least one of the genes selected from among
   a) the gene lysC, which encodes an aspartate kinase,
   b) the glyceraldehyde-3-phosphate dehydrogenase-encoding gene gap,
   c) the 3-phosphoglycerate kinase-encoding gene pgk,
   d) the pyruvate carboxylase-encoding gene pyc,
   e) the triose phosphate isomerase-encoding gene tpi,
   f) the homoserine O-acetyltransferase-encoding gene metA,
   g) the cystathionine gamma-synthase-encoding gene metB,
   h) the cystathionine gamma-lyase-encoding gene metC,
   i) serine hydroxymethyltransferase-encoding gene glyA,
   j) the methylene tetrahydrofolate reductase-encoding gene metF,
   k) the vitamin B 12-dependent methionine synthase-encoding gene metH,
   l) the phophoserine aminotransferase-encoding gene serC,
   m) the phosphoserine phosphatase-encoding gene serB,
   n) the serine acetyltransferase-encoding gene cysE, and
   o) the gene hom, which encodes a homoserine dehydrogenase,
is overexpressed.

9. The method as claimed in claim 1, wherein the coryneform bacteria are fermented in which, at the same time, at least one of the genes selected from among
   a) the homoserine kinase-encoding gene thrB,
   b) the threonine dehydratase-encoding gene ilvA,
   c) the threonine synthase-encoding gene thrC,
   d) the meso-diaminopimelato D-dchydrogenase-encoding gene ddh,
   e) the phosphoenolpyruvate carboxykinase-encoding gene pck,
   f) the glucose-6-phosphate 6-isomerase-encoding gene pgi,
   g) the pyruvate oxidase-encoding gene poxB,
   h) the dihydrodipicolinate synthase-encoding gene dapA,
   i) the dihydrodipicolinate reductase-encoding gene dapB; and
   j) the diaminopicolinate decarboxylase-encoding gene,
is attenuated by changing the rate of expression.

10. The method as claimed in claim 1, wherein the coryneform *bacterium* is of the species *Corynebacterium glutamicum*.

11. A method for producing an L-methionine-containing animal feed additive from fermentation broths, which comprises the following steps:
   a) culturing and fermenting L-methionine-producing cells of a coryneform *bacterium* in a fermentation medium;
   b) removing water from the L-methionine-containing fermentation broth;
   c) removing from 0 to 100% by weight of the biomass formed during fermentation; and
   d) drying the fermentation broth obtained according to b) and/or c), in order to obtain the animal feed additive in the desired powder or granule form; wherein the coryneform bacteria express at least one heterologous nucleotide sequence which codes for a protein with O-acetylhomoserine sulfhdrolase (metY) activity, where the heterologous nucleotide sequence comprises a nucleotide sequence encoding a metY protein having an amino acid sequence as set forth in SEQ ID NO: 4 or comprises a nucleotide sequence encoding a metY protein having an amino acid sequence with 95% homology or more to the sequence as set forth in SEQ ID NO: 4.

12. The method of claim 1, wherein the metY-encoding sequence is derived from *Mycobacterium tuberculosis*.

13. The method of claim 1, wherein the *coryneform bacteria* are fermented in which, at the same time, a gene lysC derived from a *coryneform bacteria*, which encodes an aspartate kinase, is overexpressed.

14. The method of claim 13, wherein the lysC gene is derived from *Corynebacterium glutamicum*.

15. A method for the production of L-methionine, which comprises the following steps:
 a) fermenting in a medium cells of a coryneform *bacterium* for producing of L-methionine, the coryneform bacteria expressing at least one heterologous nucleotide sequence which codes for a protein with O-acetylhomoserine sulfhydrolase (metY) activity, wherein the heterologous nucleotide sequence comprises a nucleotide sequence having 95% identity or more to the sequence as set forth in SEQ ID NO: 3;
 b) concentrating L-methionine in the medium or in the bacterial cells; and
 c) isolating L-metbionine.

16. The method of claim 15, wherein the coding metY sequence is a DNA or RNA which can be replicated in coryneform bacteria or is stably integrated into the chromosome.

17. The method of claim 15, wherein
 a) a bacteria strain transformed with a plasmid vector carrying at least one copy of the coding metY sequence under the control of regulatory sequences is used, or
 b) a strain in which the coding metY sequence has been integrated into the bacteria chromosome is used.

18. The method of claim 15, wherein the coding metY sequence is overexpressed.

19. The method of claim 15, wherein the *coryneform bacterium* is of the species *Corynebacterium glutamicum*.

20. The method of claim 15, wherein bacteria are fermented in which additionally at least one further gene of the biosynthetic pathway of L-methionine is overexpressed.

21. The method of claim 20, wherein the at least one further gene is a gene lysC derived from a coryneform bacteria, which encodes an aspartate kinase.

* * * * *